(12) United States Patent
Koerber et al.

(10) Patent No.: US 8,653,000 B2
(45) Date of Patent: Feb. 18, 2014

(54) IMINE SUBSTITUTED 2,4-DIARYL-PYRROLINE DERIVATIVES AS PESTICIDES

(75) Inventors: Karsten Koerber, Eppelheim (DE); Florian Kaiser, Mannheim (DE); Wolfgang Von Deyn, Neustadt (DE); Prashant Deshmukh, Mannheim (DE); Arun Narine, Mannheim (DE); Joachim Dickhaut, Heidelberg (DE); Nina Gertrud Bandur, Mannheim (DE); Deborah L. Culbertson, Fuquay Varina, NC (US); Douglas D. Anspaugh, Apex, NC (US); Franz Josef Braun, Durham, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/876,317

(22) PCT Filed: Sep. 30, 2011

(86) PCT No.: PCT/EP2011/067088
§ 371 (c)(1),
(2), (4) Date: Mar. 27, 2013

(87) PCT Pub. No.: WO2012/042007
PCT Pub. Date: Apr. 5, 2012

(65) Prior Publication Data
US 2013/0190378 A1    Jul. 25, 2013

Related U.S. Application Data

(60) Provisional application No. 61/388,636, filed on Oct. 1, 2010, provisional application No. 61/429,216, filed on Jan. 3, 2011.

(51) Int. Cl.
*A01N 43/40*    (2006.01)
*A01N 43/36*    (2006.01)
*A61K 31/40*    (2006.01)
*A61K 31/4439*    (2006.01)
*C07D 207/20*    (2006.01)
*C07D 401/04*    (2006.01)
*C07D 401/14*    (2006.01)

(52) U.S. Cl.
USPC ........... 504/191; 514/333; 514/343; 514/429; 548/565; 546/256; 546/276.4

(58) Field of Classification Search
None
See application file for complete search history.

(56) References Cited

U.S. PATENT DOCUMENTS

2011/0269804 A1 *  11/2011  Cassayre et al. ............ 514/362

FOREIGN PATENT DOCUMENTS

| WO | WO 2008/122375 | 10/2008 |
|----|----------------|---------|
| WO | WO 2009/097992 | 8/2009 |
| WO | WO 2010/020522 | 2/2010 |
| WO | WO 2010/072602 | 7/2010 |
| WO | WO 2010/072781 | 7/2010 |
| WO | WO 2011/073444 | 6/2011 |
| WO | WO 2011/092287 | 8/2011 |
| WO | WO 2012/042006 | 4/2012 |

OTHER PUBLICATIONS

International Search Report dated Nov. 9, 2011, prepared in International Application No. PCT/EP2011/067088.
International Preliminary Report on Patentability dated Apr. 2, 2013, prepared in International Application No. PCT/EP2011/067088.

* cited by examiner

*Primary Examiner* — Michael Barker
(74) *Attorney, Agent, or Firm* — Brinks Gilson & Lione

(57) ABSTRACT

The present invention relates to imine compounds which are useful for combating or controlling invertebrate pests, in particular arthropod pests and nematodes. The invention also relates to a method for controlling invertebrate pests by using these compounds and to plant propagation material and to an agricultural and a veterinary composition comprising said compounds.

35 Claims, No Drawings

IMINE SUBSTITUTED 2,4-DIARYL-PYRROLINE DERIVATIVES AS PESTICIDES

This application is a National Stage application of International Application No. PCT/EP2011/067088 filed Sep. 30, 2011, which claims the benefit of U.S. Provisional Application No. 61/388,636, filed Oct. 1, 2010, and U.S. Provisional Application No. 61/429,216, filed Jan. 3, 2011, the entire contents of which are hereby incorporated herein by reference.

The present invention relates to imine compounds which are useful for combating or controlling invertebrate pests, in particular arthropod pests and nematodes. The invention also relates to a method for controlling invertebrate pests by using these compounds and to plant propagation material and to an agricultural and a veterinary composition comprising said compounds.

Invertebrate pests and in particular arthropods and nematodes destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating invertebrate pests, in particular insects, arachnids and nematodes.

WO 2010/072781 relates to isoxazoline compounds of formula

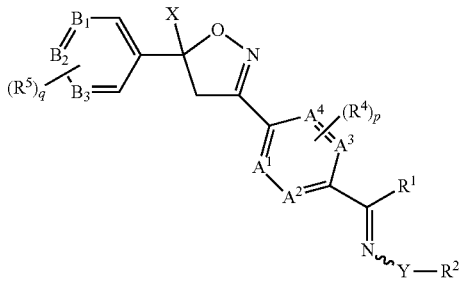

wherein, inter alia, $A^1$, $A^2$, $A^3$, $A^4$, $B^1$, $B^2$ and $B^3$ are independently carbon or nitrogen atoms. This document does not disclose imine compounds comprising the azolinyl or azolidinyl rings of the present invention.

It was an object of the present invention to provide compounds that have a good pesticidal activity, in particular insecticidal activity, and show a broad activity spectrum against a large number of different invertebrate pests, especially against difficult to control arthropod pests and/or nematodes.

It has been found that these objectives can be achieved by imine compounds of the formula I below, by their stereoisomers and by their salts, in particular their agriculturally or veterinarily acceptable salts.

Therefore, in a first aspect, the invention relates to imine compounds of formula I

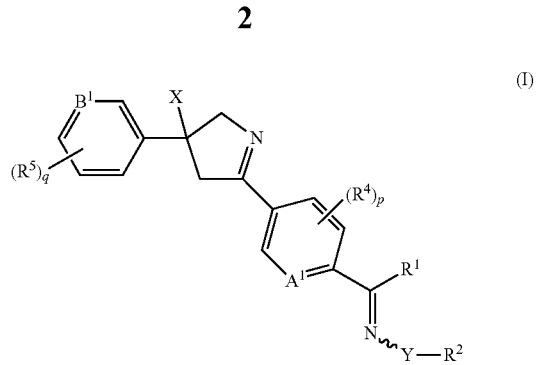

wherein
$A^1$ is N or CH;
$B^1$ is N or CH;
X is selected from the group consisting of $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl and $C_3$-$C_6$-halocycloalkyl;
Y is O, N—$R^3$, S(O)$_n$ or a chemical bond;
$R^1$ is selected from the group consisting of hydrogen; cyano; $C_1$-$C_{10}$-alkyl which may be partially or fully halogenated and/or may be substituted by one or more radicals $R^6$; $C_1$-$C_{10}$-alkoxy; $C_1$-$C_{10}$-haloalkoxy; $C_1$-$C_{10}$-alkylthio; $C_1$-$C_{10}$-haloalkylthio; $C_1$-$C_{10}$-alkylsulfinyl; $C_1$-$C_{10}$-haloalkylsulfinyl; $C_1$-$C_{10}$-alkylsulfonyl; $C_1$-$C_{10}$-haloalkylsulfonyl; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; phenyl which may be substituted by 1, 2, 3, 4 or 5 radicals $R^{10}$; and a C-bound 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals $R^{10}$;
$R^2$ is selected from the group consisting of hydrogen; cyano; $C_1$-$C_{10}$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —N($R^8$)$R^9$; —N($R^8$)C(=O)$R^6$; —Si($R^{14}$)$_2$$R^{13}$; —O$R^7$; —S$R^7$; —S(O)$_m$$R^7$; —S(O)$_n$N($R^8$)$R^9$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; —C(=N$R^8$)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals $R^{10}$; with the proviso that $R^2$ is not —O$R^7$ if Y is O;
$R^3$ is selected from the group consisting of hydrogen; cyano; $C_1$-$C_{10}$-alkyl which may be partially or fully halogenated and/or may be substituted by one or more radicals $R^6$;

$C_3$-$C_8$-cycloalkyl which may be partially or fully halogenated and/or may be substituted by one or more radicals $R^6$;
$C_2$-$C_{10}$-alkenyl which may be partially or fully halogenated and/or may be substituted by one or more radicals $R^6$;
$C_2$-$C_{10}$-alkynyl which may be partially or fully halogenated and/or may be substituted by one or more radicals $R^6$; —N($R^8$)$R^9$; —Si($R^{14}$)$_2$$R^{13}$; —O$R^7$; —S$R^7$; —S(O)$_m$$R^7$; —S(O)$_n$N($R^8$)$R^9$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; —C(=N$R^8$)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals $R^{10}$;

or $R^2$ and $R^3$ together form a group =C$R^{11}$$R^{12}$; =S(O)$_m$$R^7$; =S(O)$_m$N($R^8$)$R^9$; =N$R^8$; or =NO$R^7$;

or $R^2$ and $R^3$ together form a $C_2$-$C_7$ alkylene chain, thus forming, together with the nitrogen atom to which they are bound, a 3-, 4-, 5-, 6-, 7- or 8-membered ring, where the alkylene chain may be interrupted by 1 or 2 O, S and/or N$R^{18}$ and/or 1 or 2 of the CH$_2$ groups of the alkylene chain may be replaced by a group C=O, C=S and/or C=N$R^{18}$; and/or the alkylene chain may be substituted by one or more radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals $R^{10}$;

each $R^4$ is independently selected from the group consisting of halogen; cyano; azido; nitro; —SCN; SF$_5$; $C_1$-$C_6$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_6$-alkenyl which may be partially or fully halogenated and/or may be substituted by one or more radicals $R^6$; $C_2$-$C_6$-alkynyl which may be partially or fully halogenated and/or may be substituted by one or more radicals $R^6$; —Si($R^{14}$)$_2$$R^{13}$; —O$R^7$; —OS(O)$_n$$R^7$; —S$R^7$; —S(O)$_m$$R^7$; —S(O)$_n$N($R^8$)$R^9$; —N($R^8$)$R^9$; —N($R^8$)C(=O)$R^6$; —C(=O)$R^6$; —C(=O)O$R^7$; —C(=N$R^8$)H; —C(=N$R^8$)$R^6$; —C(=O)N($R^8$)$R^9$; C(=S)N($R^8$)$R^9$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals $R^{10}$;

or two radicals $R^4$ bound on adjacent carbon atoms may be together a group selected from —CH$_2$CH$_2$CH$_2$CH$_2$—, —CH=CH—CH=CH—, —N=CH—CH=CH—, —CH=N—CH=CH—, —N=CH—N=CH—, —OCH$_2$CH$_2$CH$_2$—, —OCH=CHCH$_2$—, —CH$_2$OCH$_2$CH$_2$—, —OCH$_2$CH$_2$O—, —OCH$_2$OCH$_2$—, —CH$_2$CH$_2$CH$_2$—, —CH=CHCH$_2$—, —CH$_2$CH$_2$O—, —CH=CHO—, —CH$_2$OCH$_2$—, —CH$_2$C(=O)O—, —C(=O)OCH$_2$—, —O(CH$_2$)O—, —SCH$_2$CH$_2$CH$_2$—, —SCH=CHCH$_2$—, —CH$_2$SCH$_2$CH$_2$—, —SCH$_2$CH$_2$S—, —SCH$_2$SCH$_2$—, —CH$_2$CH$_2$S—, —CH=CHS—, —CH$_2$SCH$_2$—, —CH$_2$C(=S)S—, —C(=S)SCH$_2$—, —S(CH$_2$)S—, —CH$_2$CH$_2$N$R^8$—, —CH$_2$CH=N—, —CH=CH—N$R^8$—, —OCH=N— and —SCH=N—, thus forming, together with the carbon atoms to which they are bound, a 5- or 6-membered ring, where the hydrogen atoms of the above groups may be replaced by one or more substituents selected from halogen, methyl, halomethyl, hydroxyl, methoxy and halomethoxy or one or more CH$_2$ groups of the above groups may be replaced by a C=O group;

each $R^5$ is independently selected from the group consisting of halogen, cyano, azido, nitro, —SCN, SF$_5$, $C_1$-$C_6$-alkyl which may be partially or fully halogenated and/or may be substituted by one or more radicals $R^6$, $C_3$-$C_8$-cycloalkyl which may be partially or fully halogenated and/or may be substituted by one or more radicals $R^6$, $C_2$-$C_6$-alkenyl which may be partially or fully halogenated and/or may be substituted by one or more radicals $R^6$, $C_2$-$C_6$-alkynyl which may be partially or fully halogenated and/or may be substituted by one or more radicals $R^6$, —Si($R^{14}$)$_2$$R^{13}$, —O$R^7$, —OS(O)$_n$$R^7$, —S$R^7$, —S(O)$_m$$R^7$, —S(O)$_n$N($R^8$)$R^9$, —N($R^8$)$R^9$, N($R^8$)C(=O)$R^6$, —C(=O)$R^6$, —C(=O)O$R^7$, —C(=S)$R^6$, —C(=S)O$R^7$, —C(=N$R^8$)$R^6$, —C(=O)N($R^8$)$R^9$, —C(=S)N($R^8$)$R^9$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals $R^{10}$;

each $R^6$ is independently selected from the group consisting of cyano, azido, nitro, —SCN, SF$_5$, $C_3$-$C_8$-cycloalkyl, $C_3$-$C_8$-halocycloalkyl, —Si($R^{14}$)$_2$$R^{13}$, —OSO$_2$$R^7$, —S$R^7$S(O)$_m$$R^7$, —S(O)$_n$N($R^8$)$R^9$, —N($R^8$)$R^9$, —C(=O)N($R^8$)$R^9$, —C(=S)N($R^8$)$R^9$, —C(=O)O$R^7$, —C(=O)$R^{19}$, —C(=N$R^8$)$R^{19}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals $R^{10}$;

and, in case $R^6$ is bound to a cycloalkyl group, $R^6$ may additionally be selected from the group consisting of $C_1$-$C_6$-alkyl, $C_1$-$C_6$-haloalkyl, $C_1$-$C_6$-alkoxy-$C_1$-$C_6$alkyl, $C_2$-$C_6$-alkenyl, $C_2$-$C_6$-haloalkenyl, $C_2$-$C_6$-alkynyl, $C_2$-$C_6$-haloalkynyl and benzyl which may be substituted by 1, 2, 3, 4 or 5 radicals $R^{10}$;

and in groups —C(=O)$R^6$, —C(=S)$R^6$, —C(=N$R^8$)$R^6$ and —N($R^8$)C(=O)$R^6$, $R^6$ may additionally be selected from hydrogen, halogen, $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl and benzyl which may be substituted by 1, 2, 3, 4 or 5 radicals $R^{10}$;

or two geminally bound radicals $R^6$ together form a group selected from =C$R^{11}$$R^{12}$, =S(O)$_m$$R^7$, =S(O)$_m$N($R^8$)$R^9$, =N$R^8$, =NO$R^7$ and =NN$R^8$;

or two radicals $R^6$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and SO$_2$, as ring members;

each $R^7$ is independently selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si($R^{14}$)$_2$$R^{13}$, —$SR^8$, —$S(O)_m$$R^7$, —$S(O)_n$N($R^8$)$R^9$, —N($R^8$)$R^9$, —N=$CR^{15}$$R^{16}$, —C(=O)$R^{17}$, —C(=O)N($R^8$)$R^9$, —C(=S)N($R^8$)$R^9$, —C(=O)O$R^{17}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;
with the proviso that $R^7$ is not $C_1$-$C_6$-alkoxy or $C_1$-$C_6$-haloalkoxy if it is bound to an oxygen atom;

each $R^8$ is independently selected from the group consisting of hydrogen, cyano, $C_1$-$C_6$-alkyl which may be partially or fully halogenated and/or may be substituted by one or more radicals $R^{19}$, $C_1$-$C_6$-alkoxy, $C_1$-$C_6$-haloalkoxy, $C_1$-$C_6$-alkylthio, $C_1$-$C_6$-haloalkylthio, where the alkyl moiety in the four last-mentioned radicals may be substituted by one or more radicals $R^{19}$, $C_3$-$C_8$-cycloalkyl which may be partially or fully halogenated and/or may be substituted by one or more radicals $R^{19}$, $C_3$-$C_8$-cycloalkyl-$C_1$-$C_4$-alkyl where the cycloalkyl moiety may be partially or fully halogenated and/or may be substituted by one or more radicals $R^{19}$, $C_2$-$C_6$-alkenyl which may be partially or fully halogenated and/or may be substituted by one or more radicals $R^{19}$, $C_2$-$C_6$-alkynyl which may be partially or fully halogenated and/or may be substituted by one or more radicals $R^{19}$, —$S(O)_m$$R^{20}$, —$S(O)_n$N($R^{21}$)$R^{22}$, phenyl which may be substituted by 1, 2, 3, 4 or 5 radicals $R^{10}$, benzyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

each $R^9$ is independently selected from the group consisting of hydrogen, cyano, $C_1$-$C_6$-alkyl which may be partially or fully halogenated and/or may be substituted by one or more radicals $R^{19}$, $C_1$-$C_6$-alkoxy, $C_1$-$C_6$-haloalkoxy, $C_1$-$C_6$-alkylthio, $C_1$-$C_6$-haloalkylthio, where the alkyl moiety in the four last-mentioned radicals may be substituted by one or more radicals $R^{19}$, $C_3$-$C_8$-cycloalkyl which may be partially or fully halogenated and/or may be substituted by one or more radicals $R^{19}$, $C_3$-$C_8$-cycloalkyl-$C_1$-$C_4$-alkyl where the cycloalkyl moiety may be partially or fully halogenated and/or may be substituted by one or more radicals $R^{19}$, $C_2$-$C_6$-alkenyl which may be partially or fully halogenated and/or may be substituted by one or more radicals $R^{19}$, $C_2$-$C_6$-alkynyl which may be partially or fully halogenated and/or may be substituted by one or more radicals $R^{19}$, —$S(O)_m$$R^{20}$, —$S(O)_n$N($R^{21}$)$R^{22}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

or $R^8$ and $R^9$ together form a group =$CR^{11}$$R^{12}$;
or $R^8$ and $R^9$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from N, O, S, NO, SO and $SO_2$, as ring members, where the heterocyclic ring may be substituted by one or more radicals $R^{10}$;

each $R^{10}$ is independently selected from the group consisting of halogen, cyano, azido, nitro, —SCN, $SF_5$, $C_1$-$C_{10}$-alkyl which may be partially or fully halogenated and/or may be substituted by one or more radicals $R^{19}$, $C_3$-$C_8$-cycloalkyl which may be partially or fully halogenated and/or may be substituted by one or more radicals $R^{19}$, $C_2$-$C_{10}$-alkenyl which may be partially or fully halogenated and/or may be substituted by one or more radicals $R^{19}$, $C_2$-$C_{10}$-alkynyl which may be partially or fully halogenated and/or may be substituted by one or more radicals $R^{19}$, —Si($R^{14}$)$_2$$R^{13}$, —$OR^{20}$, —$OS(O)_n$$R^{20}$, —$R^{20}$, —$S(O)_m$$R^{20}$, —$S(O)_n$N($R^{21}$)$R^{22}$, —N($R^{21}$)$R^{22}$, C(=O)$R^{19}$, —C(=O)O$R^{20}$, —C(=N$R^{21}$)$R^{22}$, —C(=O)N($R^{21}$)$R^{22}$, —C(=S)N($R^{21}$)$R^{22}$, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy; and a 3-, 4-, 5-, 6- or 7-membered saturated or unsaturated heterocyclic ring containing 1, 2 or 3 heteroatoms or heteroatom groups selected from N, O, S, NO, SO and $SO_2$, as ring members, which may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

or two radicals $R^{10}$ bound on adjacent atoms together form a group selected from —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C$(=O)O—, —C(=O)$OCH_2$—, —O($CH_2$)O—, —$SCH_2CH_2CH_2$—, —SCH=$CHCH_2$—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C$(=S)S—, —C(=S)$SCH_2$—, —S($CH_2$)S—, —$CH_2CH_2NR^{21}$—, —$CH_2CH$=N—, —CH=CH—$NR^{21}$—, —OCH=N— and —SCH=N—, thus forming, together with the atoms to which they are bound, a 5- or 6-membered ring, where the hydrogen atoms of the above groups may be replaced by one or more substituents selected from halogen, methyl, halomethyl, hydroxyl, methoxy and halomethoxy or one or more $CH_2$ groups of the above groups may be replaced by a C=O group;

$R^{11}$, $R^{12}$ are, independently of each other and independently of each occurrence, selected from the group consisting of hydrogen, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy, $C_1$-$C_6$-haloalkoxy, —C(=O)$R^{19}$, —C(=O)O$R^{20}$, —C(=$NR^{21}$)$R^{22}$, —C(=O)N($R^{21}$)$R^{22}$, —C(=S)N($R^{21}$)$R^{22}$, phenyl which may be substituted by 1, 2, 3, 4, or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, which may be substituted by one or more radicals $R^{10}$;

$R^{13}$, $R^{14}$ are, independently of each other and independently of each occurrence, selected from the group consisting of $C_1$-$C_4$-alkyl, $C_3$-$C_6$-cycloalkyl, $C_1$-$C_4$-alkoxy-$C_1$-$C_4$-alkyl, phenyl and benzyl;

$R^{15}$, $R^{16}$ are, independently of each other and independently of each occurrence, selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, phenyl which may be substituted by 1, 2, 3, 4, or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, which may be substituted by one or more radicals $R^{10}$;

each $R^{17}$ is independently selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, phenyl and benzyl;

each $R^{18}$ is independently defined like $R^3$;

each $R^{19}$ is independently selected from the group consisting of cyano, azido, nitro, —SCN, $SF_5$, $C_3$-$C_8$-cycloalkyl, $C_3$-$C_8$-halocycloalkyl, —Si($R^{14}$)$_2R^{13}$, —$OR^{20}$, —$OSO_2R^{20}$, —$SR^{20}$, —S(O)$_mR^{20}$, —S(O)$_n$N($R^{21}$)$R^{22}$, —N($R^{21}$)$R^{22}$, —C(=O)N($R^{21}$)$R^{22}$, —C(=S)N($R^{21}$)$R^{22}$, —C(=O)$OR^{20}$, —C(=O)$R^{20}$, —C(=$NR^{21}$)$R^{20}$, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

and, in case $R^{19}$ is bound to a cycloalkyl group, $R^{19}$ may additionally be selected from the group consisting of $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl and $C_2$-$C_6$-haloalkynyl; and in groups —C(=O)$R^{19}$, $R^{19}$ may additionally be selected from hydrogen, halogen, $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, and $C_2$-$C_6$-haloalkynyl;

or two geminally bound radicals $R^{19}$ together form a group selected from =$CR^{11}R^{12}$, =S(O)$_mR^{20}$, =S(O)$_m$N($R^{21}$)$R^{22}$, =$NR^{21}$, =$NOR^{20}$ and =$NNR^{21}$;

or two radicals $R^{19}$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members;

each $R^{20}$ is independently selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si($R^{14}$)$_2R^{13}$, $C_1$-$C_6$-alkylaminosulfonyl, amino, $C_1$-$C_6$-alkylamino, di-($C_1$-$C_6$-alkyl)-amino, $C_1$-$C_6$-alkylcarbonyl, $C_1$-$C_6$-haloalkylcarbonyl, aminocarbonyl, $C_1$-$C_6$-alkylaminocarbonyl, di-($C_1$-$C_6$-alkyl)-aminocarbonyl, $C_1$-$C_6$-alkoxycarbonyl, $C_1$-$C_6$-haloalkoxycarbonyl, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

with the proviso that $R^{20}$ is not $C_1$-$C_6$-alkoxy or $C_1$-$C_6$-haloalkoxy if it is bound to an oxygen atom;

$R^{21}$ and $R^{22}$ are independently of each other and independently of each occurence selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_3$-$C_8$-cycloalkyl-$C_1$-$C_4$-alkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

or $R^{21}$ and $R^{22}$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from N, O, S, NO, SO and $SO_2$, as ring members, where the heterocyclic ring may be substituted by one or more radicals selected from halogen, $C_1$-$C_6$-alkyl, $C_1$-$C_6$-haloalkyl, $C_1$-$C_6$-alkoxy and $C_1$-$C_6$-haloalkoxy;

each m is independently 1 or 2;
each n is independently 0, 1 or 2;
p is 0, 1, 2, 3 or 4; and
q is 0, 1, 2, 3, 4 or 5;

and the stereoisomers and agriculturally or veterinarily acceptable salts thereof.

The present invention also provides an agricultural composition comprising at least one compound of the formula I as defined herein and/or an agriculturally acceptable salt thereof and at least one liquid or solid carrier.

The present invention also provides a veterinary composition comprising at least one compound of the formula I as defined herein and/or a veterinarily acceptable salt thereof and at least one liquid or solid carrier.

The present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formula I or a salt thereof as defined herein.

The present invention also relates to plant propagation material, in particular seed, comprising at least one compound of formula I and/or an agriculturally acceptable salt thereof as defined herein.

The present invention further relates to a method for treating or protecting an animal from infestation or infection by parasites which comprises bringing the animal in contact with a parasiticidally effective amount of a compound of the formula I or a veterinarily acceptable salt thereof as defined herein. Bringing the animal in contact with the compound I, its salt or the veterinary composition of the invention means applying or administering it to the animal.

The term "steroisomers" encompasses both optical isomers, such as enantiomers or diastereomers, the latter existing due to more than one center of chirality in the molecule, as well as geometrical isomers (cis/trans isomers).

Depending on the substitution pattern, the compounds of the formula I may have one or more centers of chirality, in which case they are present as mixtures of enantiomers or diastereomers. One center of chirality is the carbon ring atom of the pyrroline ring carrying radical X. The invention provides both the pure enantiomers or diastereomers and their mixtures and the use according to the invention of the pure enantiomers or diastereomers of the compound I or its mixtures. Enantiomers with respect to the position of the group X and the ring containing $B^1$ as ring member on the pyrroline ring may be represented by following formulae I-A and I-B

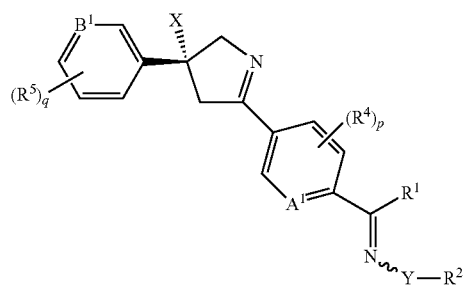

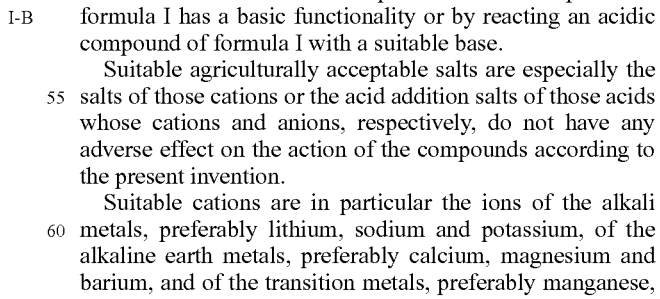

Among these, preference is given to enantiomer I-A, especially if X is $CF_3$. Thus, a preferred embodiment of the invention relates to compounds of formula I-A

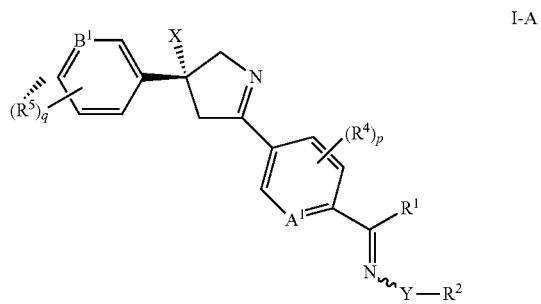

wherein the variables have one of the above-given general, or in particular one of the below-given preferred meanings. Preferably, X in compounds I-A is $CF_3$.

Suitable compounds of the formula I also include all possible geometrical stereoisomers (cis/trans isomers) and mixtures thereof. Cis/trans isomers may be present with respect to the imine group. Preference is given to compounds wherein the group —Y—$R^2$ is trans with respect to the ring containing $A^1$ as ring member, i.e. to compounds of formula trans-I

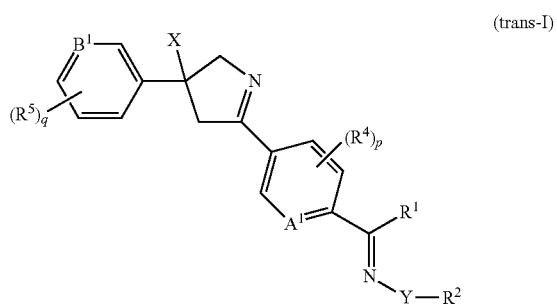

The compounds of the present invention may be amorphous or may exist in one or more different crystalline states (polymorphs) which may have a different macroscopic properties such as stability or show different biological properties such as activities.

The present invention includes both amorphous and crystalline compounds of the formula I, mixtures of different crystalline states of the respective compound I, as well as amorphous or crystalline salts thereof.

Salts of the compounds of the formula I are preferably agriculturally and veterinarily acceptable salts. They can be formed in a customary method, e.g. by reacting the compound with an acid of the anion in question if the compound of formula I has a basic functionality or by reacting an acidic compound of formula I with a suitable base.

Suitable agriculturally acceptable salts are especially the salts of those cations or the acid addition salts of those acids whose cations and anions, respectively, do not have any adverse effect on the action of the compounds according to the present invention.

Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formulae I with an acid of the corresponding anion, preferably of hydrochloric acid, hydrobromic acid, sulfuric acid, phosphoric acid or nitric acid.

By the term "veterinarily acceptable salts" is meant salts of those cations or anions which are known and accepted in the art for the formation of salts for veterinary use. Suitable acid addition salts, e.g. formed by compounds of formula I containing a basic nitrogen atom, e.g. an amino group, include salts with inorganic acids, for example hydrochlorids, sulphates, phosphates, and nitrates and salts of organic acids for example acetic acid, maleic acid, dimaleic acid, fumaric acid, difumaric acid, methane sulfenic acid, methane sulfonic acid, and succinic acid.

The term "invertebrate pest" as used herein encompasses animal populations, such as insects, arachnids and nematodes, which may attack plants, thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" as used herein includes all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "plants" comprises any types of plants including "non-cultivated plants" and in particular "cultivated plants".

The term "non-cultivated plants" refers to any wild type species or related species or related genera of a cultivated plant.

The term "cultivated plants" as used herein includes plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8, Protein Eng Des Sel. 2004 January; 17(1):57-66, Nat. Protoc. 2007; 2(5):1225-35, Curr. Opin. Chem. Biol. 2006 October; 10(5): 487-91. Epub 2006 August 28, Biomaterials. 2001 March; 22(5):405-17, Bioconjug Chem. 2005 January-February; 16(1):113-21).

The term "cultivated plants" as used herein further includes plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" as used herein further includes plants that are by the use of recombinant DNA techniques capable to synthesize one or more insecticidal proteins, especially those known from the bacterial genus *bacillus*, particularly from bacillus thuringiensis, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are dis-closed, for example, in EP-A 374 753, WO 93/007278, WO 95/34656, EP-A 427 529, EP-A 451 878, WO 03/018810 und WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods insects, particularly to beetles (Coleoptera), flies (Diptera), and butterflies and moths (Lepidoptera) and to plant parasitic nematodes (Nematoda).

The term "cultivated plants" as used herein further includes plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lyso-zym (e.g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" as used herein further includes plants that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" as used herein further includes plants that contain by the use of recombinant DNA techniques a modified amount of substances of content or new substances of content, specifically to improve human or animal nutrition, for ex-ample oil crops that produce health-promoting long-chain omega-3 fatty acids or unsaturated omega-9 fatty acids (e.g. Nexera® rape).

The term "cultivated plants" as used herein further includes plants that contain by the use of recombinant DNA techniques a modified amount of substances of content or new substances of content, specifically to improve raw material production, for example potatoes that produce increased amounts of amylopectin (e.g. Amflora® potato).

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "$C_1$-$C_{10}$-alkyl" as used herein and in the alkyl moieties of alkoxy, alkylthio, alkylsulfinyl, alkylsulfonyl, alkylcarbonyl, alkoxycarbonyl and the like refers to saturated straight-chain or branched hydrocarbon radicals having 1 to 2 ("$C_1$-$C_2$-alkyl"), 1 to 4 ("$C_1$-$C_4$-alkyl"), 1 to 6 ("$C_1$-$C_6$-alkyl"), 1 to 8 ("$C_1$-$C_8$-alkyl") or 1 to 10 ("$C_1$-$C_{10}$-alkyl") carbon atoms. $C_1$-$C_2$-Alkyl is methyl or ethyl. $C_1$-$C_4$-Alkyl is additionally propyl, isopropyl, butyl, 1-methylpropyl(sec-butyl), 2-methylpropyl(isobutyl) or 1,1-dimethylethyl(tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl. $C_1$-$C_8$-Alkyl is additionally also, for example, heptyl, octyl, 2-ethylhexyl and positional isomers thereof. $C_1$-$C_{10}$-Alkyl is additionally also, for example, nonyl, decyl and positional isomers thereof.

The term "$C_1$-$C_{10}$-haloalkyl" as used herein, which is also expressed as "C1-$C_{10}$-alkyl which is partially or fully halogenated", refers to straight-chain or branched alkyl groups having 1 to 2 ("$C_1$-$C_2$-haloalkyl"), 1 to 4 ("$C_1$-$C_4$-haloalkyl"), 1 to 6 ("$C_1$-$C_6$-haloalkyl"), 1 to 8 ("$C_1$-$C_8$-haloalkyl") or 1 to 10 ("$C_1$-$C_{10}$-haloalkyl") carbon atoms (as mentioned above), where some or all of the hydrogen atoms in these groups are replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl.

"Halomethyl" is methyl in which 1, 2 or 3 of the hydrogen atoms are replaced by halogen atoms. Examples are bromomethyl, chloromethyl, fluoromethyl, dichloromethyl, trichloromethyl, difluoromethyl, trifluoromethyl, chlorofluoromethyl, dichlorofluoromethyl, chlorodifluoromethyl and the like.

The term "$C_2$-$C_{10}$-alkenyl" as used herein and in the alkenyl moiety of alkenyloxy and the like refers to monounsaturated straight-chain or branched hydrocarbon radicals having 2 to 4 ("$C_2$-$C_4$-alkenyl"), 2 to 6 ("$C_2$-$C_6$-alkenyl"), 2 to 8 ("$C_2$-$C_8$-alkenyl"), 3 to 8 ("$C_3$-$C_8$-alkenyl"), 2 to 10 ("$C_2$-$C_{10}$-alkenyl") or 3 to 10 ("$C_3$-$C_{10}$-alkenyl") carbon atoms and a double bond in any position, for example $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like, or $C_2$-$C_{10}$-alkenyl, such as the radicals mentioned for $C_2$-$C_6$-alkenyl and additionally 1-heptenyl, 2-heptenyl, 3-heptenyl, 1-octenyl, 2-octenyl, 3-octenyl, 4-octenyl, 1-nonenyl, 2-nonenyl, 3-nonenyl, 4-nonenyl, 1-decenyl, 2-decenyl, 3-decenyl, 4-decenyl, 5-decenyl and the positional isomers thereof.

The term "$C_2$-$C_{10}$-haloalkenyl" as used herein, which is also expressed as "$C_1$-$C_{10}$-alkenyl which is partially or fully halogenated", and the haloalkenyl moieties in haloalkenyloxy, haloalkenylcarbonyl and the like refers to unsaturated straight-chain or branched hydrocarbon radicals having 2 to 4 ("$C_2$-$C_4$-haloalkenyl"), 2 to 6 ("$C_2$-$C_6$-haloalkenyl"), 2 to 8 ("$C_2$-$C_6$-haloalkenyl") or 2 to 10 ("$C_2$-$C_{10}$-haloalkenyl") carbon atoms and a double bond in any position (as mentioned above), where some or all of the hydrogen atoms in these groups are replaced by halogen atoms as mentioned above, in particular fluorine, chlorine and bromine, for example chlorovinyl, chloroallyl and the like.

The term "$C_2$-$C_{10}$-alkynyl" as used herein and the alkynyl moieties in alkynyloxy, alkynylcarbonyl and the like refers to straight-chain or branched hydrocarbon groups having 2 to 4 ("$C_2$-$C_4$-alkynyl"), 2 to 6 ("$C_2$-$C_6$-alkynyl"), 2 to 8 ("$C_2$-$C_8$-alkynyl"), 3 to 8 ("$C_3$-$C_8$-alkynyl"), 2 to 10 ("$C_2$-$C_{10}$-alkynyl") or 3 to 10 ("$C_3$-$C_8$-alkynyl") carbon atoms and one or two triple bonds in any position, for example $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

The term "$C_2$-$C_{10}$-haloalkynyl" as used herein, which is also expressed as "$C_1$-$C_{10}$-alkynyl which is partially or fully halogenated", and the haloalkynyl moieties in haloalkynyloxy, haloalkynylcarbonyl and the like refers to unsaturated straight-chain or branched hydrocarbon radicals having 2 to 4 ("$C_2$-$C_4$-haloalkynyl"), 3 to 4 ("$C_3$-$C_4$-haloalkynyl"), 2 to 6 ("$C_2$-$C_6$-haloalkynyl"), 3 to 6 ("$C_3$-$C_6$-haloalkynyl"), 2 to 8 ("$C_2$-$C_8$-haloalkynyl"), 3 to 8 ("$C_3$-$C_8$-haloalkynyl"), 2 to 10 ("$C_2$-$C_{10}$-haloalkynyl") or 3 to 10 ("$C_3$-$C_{10}$-haloalkynyl") carbon atoms and one or two triple bonds in any position (as mentioned above), where some or all of the hydrogen atoms in these groups are replaced by halogen atoms as mentioned above, in particular fluorine, chlorine and bromine;

The term "$C_3$-$C_8$-cycloalkyl" as used herein refers to mono- or bi- or polycyclic saturated hydrocarbon radicals having 3 to 8, in particular 3 to 6 carbon atoms ("$C_3$-$C_6$-cycloalkyl"). Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 or 8 carbon atoms comprise bicyclo[2.2.1]heptyl, bicyclo[3.1.1]heptyl, bicyclo[2.2.2]octyl and bicyclo[3.2.1]octyl.

The term "$C_3$-$C_8$-halocycloalkyl" as used herein, which is also expressed as "$C_3$-$C_8$-cycloalkyl which is partially or fully halogenated", and the halocycloalkyl moieties in halocycloalkoxy, halocycloalkylcarbonyl and the like refers to mono- or bi- or polycyclic saturated hydrocarbon groups having 3 to 8 ("$C_3$-$C_8$-halocycloalkyl") or preferably 3 to 6 ("$C_3$-$C_6$-halocycloalkyl") carbon ring members (as mentioned above) in which some or all of the hydrogen atoms are replaced by halogen atoms as mentioned above, in particular fluorine, chlorine and bromine.

The term "$C_3$-$C_8$-cycloalkyl-$C_1$-$C_4$-alkyl" refers to a $C_3$-$C_8$-cycloalkyl group as defined above which is bound to the remainder of the molecule via a $C_1$-$C_4$-alkyl group, as defined above. Examples are cyclopropylmethyl, cyclopropylethyl, cyclopropylpropyl, cyclobutylmethyl, cyclobutylethyl, cyclobutylpropyl, cyclopentylmethyl, cycloppentylethyl, cyclopentylpropyl, cyclohexylmethyl, cyclohexylethyl, cyclohexylpropyl, and the like.

The term "$C_1$-$C_2$-alkoxy" is a $C_1$-$C_2$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. The term "$C_1$-$C_{10}$-alkoxy" is a $C_1$-$C_{10}$-alkyl group, as defined above, attached via an oxygen atom. $C_1$-$C_2$-Alkoxy is methoxy or ethoxy. $C_1$-$C_4$-Alkoxy is additionally, for example, n-propoxy, 1-methylethoxy(isopropoxy), butoxy, 1-methylpropoxy(sec-butoxy), 2-methylpropoxy(isobutoxy) or 1,1-dimethylethoxy(tertbutoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof. $C_1$-$C_{10}$-Alkoxy is additionally, for example, nonyloxy, decyloxy and positional isomers thereof.

The term "$C_1$-$C_2$-haloalkoxy" is a $C_1$-$C_2$-haloalkyl group, as defined above, attached via an oxygen atom. The term "$C_1$-$C_4$-haloalkoxy" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. The term "$C_1$-$C_{10}$-haloalkoxy" is a $C_1$-$C_{10}$-haloalkyl group, as defined above, attached via an oxygen atom. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_4$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

The term "$C_1$-$C_2$-alkylthio" is a $C_1$-$C_2$-alkyl group, as defined above, attached via a sulfur atom. The term "$C_1$-$C_4$-alkylthio" is a $C_1$-$C_4$-alkyl group, as defined above, attached via a sulfur atom. The term "$C_1$-$C_6$-alkylthio" is a $C_1$-$C_6$- alkyl group, as defined above, attached via a sulfur atom. The term "$C_1$-$C_{10}$-alkylthio" is a $C_1$-$C_{10}$-alkyl group, as defined above, attached via a sulfur atom. $C_1$-$C_2$-Alkylthio is methylthio or ethylthio. $C_1$-$C_4$-Alkylthio is additionally, for example, n-propylthio, 1-methylethylthio(isopropylthio), butylthio, 1-methylpropylthio(sec-butylthio), 2-methylpropylthio(isobutylthio) or 1,1-dimethylethylthio(tert-butylthio). $C_1$-$C_6$-Alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio. $C_1$-$C_8$-Alkylthio is additionally, for example, heptylthio, octylthio, 2-ethylhexylthio and positional isomers thereof. $C_1$-$C_{10}$-Alkylthio is additionally, for example, nonylthio, decylthio and positional isomers thereof.

The term "$C_1$-$C_2$-haloalkylthio" is a $C_1$-$C_2$-haloalkyl group, as defined above, attached via a sulfur atom. The term "$C_1$-$C_4$-haloalkylthio" is a $C_1$-$C_4$-haloalkyl group, as defined above, attached via a sulfur atom. The term "$C_1$-$C_6$-haloalkylthio" is a $C_1$-$C_6$-haloalkyl group, as defined above, attached via a sulfur atom. The term "$C_1$-$C_{10}$-haloalkylthio" is a $C_1$-$C_{10}$-haloalkyl group, as defined above, attached via a sulfur atom. $C_1$-$C_2$-Haloalkylthio is, for example, $SCH_2F$, $SCHF_2$, $SCF_3$, $SCH_2Cl$, $SCHC_2$, $SCC_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_4$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio.

The term "$C_1$-$C_2$-alkylsulfinyl" is a $C_1$-$C_2$-alkyl group, as defined above, attached via a sulfinyl [S(O)] group. The term "$C_1$-$C_4$-alkylsulfinyl" is a $C_1$-$C_4$-alkyl group, as defined above, attached via a sulfinyl [S(O)] group. The term "$C_1$-$C_6$-alkylsulfinyl" is a $C_1$-$C_6$-alkyl group, as defined above, attached via a sulfinyl [S(O)] group. The term "$C_1$-$C_{10}$-alkylsulfinyl" is a $C_1$-$C_{10}$-alkyl group, as defined above, attached via a sulfinyl [S(O)] group. $C_1$-$C_2$-Alkylsulfinyl is methylsulfinyl or ethylsulfinyl. $C_1$-$C_4$-Alkylsulfinyl is additionally, for example, n-propylsulfinyl, 1-methylethylsulfinyl(isopropylsulfinyl), butylsulfinyl, 1-methylpropylsulfinyl(sec-butylsulfinyl), 2-methylpropylsulfinyl(isobutylsulfinyl) or 1,1-dimethylethylsulfinyl(tert-butylsulfinyl). $C_1$-$C_6$-Alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl. $C_1$-$C_8$-Alkylsulfinyl is additionally, for example, heptylsulfinyl, octylsulfinyl, 2-ethylhexylsulfinyl and positional isomers thereof. $C_1$-$C_{10}$-Alkylsulfinyl is additionally, for example, nonylsulfinyl, decylsulfinyl and positional isomers thereof.

The term "$C_1$-$C_2$-haloalkylsulfinyl" is a $C_1$-$C_2$-haloalkyl group, as defined above, attached via a sulfinyl [S(O)] group. The term "$C_1$-$C_4$-haloalkylsulfinyl" is a $C_1$-$C_4$-haloalkyl group, as defined above, attached via a sulfinyl [S(O)] group. The term "$C_1$-$C_6$-haloalkylsulfinyl" is a $C_1$-$C_6$-haloalkyl group, as defined above, attached via a sulfinyl [S(O)] group. The term "$C_1$-$C_{10}$-haloalkylsulfinyl" is a $C_1$-$C_{10}$-haloalkyl group, as defined above, attached via a sulfinyl [S(O)] group. $C_1$-$C_2$-Haloalkylsulfinyl is, for example, $S(O)CH_2F$, $S(O)CHF_2$, $S(O)CF_3$, $S(O)CH_2Cl$, $S(O)CHCl_2$, $S(O)CCl_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl or $S(O)C_2F_5$. $C_1$-$C_4$-Haloalkylsulfinyl is additionally, for example, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, $S(O)CH_2$—$C_2F_5$, $S(O)CF_2$—$C_2F_5$, 1-($CH_2F$)-2-fluoroethylsulfinyl, 1-($CH_2Cl$)-2-chloroethylsulfinyl, 1-($CH_2Br$)-2-bromoethylsulfinyl, 4-fluorobutylsulfinyl, 4-chlorobutylsulfinyl, 4-bromobutylsulfinyl or nonafluorobutylsulfinyl. $C_1$-$C_6$-Haloalkylsulfinyl is additionally, for example, 5-fluoropentylsulfinyl, 5-chloropentylsulfinyl, 5-brompentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl.

The term "$C_1$-$C_2$-alkylsulfonyl" is a $C_1$-$C_2$-alkyl group, as defined above, attached via a sulfonyl[$S(O)_2$] group. The term "$C_1$-$C_4$-alkylsulfonyl" is a $C_1$-$C_4$-alkyl group, as defined above, attached via a sulfonyl[$S(O)_2$] group. The term "$C_1$-$C_6$-alkylsulfonyl" is a $C_1$-$C_6$-alkyl group, as defined above, attached via a sulfonyl[$S(O)_2$] group. The term "$C_1$-$C_{10}$-alkylsulfonyl" is a $C_1$-$C_{10}$-alkyl group, as defined above, attached via a sulfonyl[$S(O)_2$]group. $C_1$-$C_2$-Alkylsulfonyl is methylsulfonyl or ethylsulfonyl. $C_1$-$C_4$-Alkylsulfonyl is additionally, for example, n-propylsulfonyl, 1-methylethylsulfonyl(isopropylsulfonyl), butylsulfonyl, 1-methylpropylsulfonyl(sec-butylsulfonyl), 2-methylpropylsulfonyl(isobutylsulfonyl) or 1,1-dimethylethylsulfonyl(tert-butylsulfonyl). $C_1$-$C_6$-Alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl. $C_1$-$C_8$-Alkylsulfonyl is additionally, for example, heptylsulfonyl, octylsulfonyl, 2-ethylhexylsulfonyl and positional isomers thereof. $C_1$-$C_{10}$-Alkylsulfonyl is additionally, for example, nonylsulfonyl, decylsulfonyl and positional isomers thereof.

The term "$C_1$-$C_2$-haloalkylsulfonyl" is a $C_1$-$C_2$-haloalkyl group, as defined above, attached via a sulfonyl[$S(O)_2$] group. The term "$C_1$-$C_4$-haloalkylsulfonyl" is a $C_1$-$C_4$-haloalkyl group, as defined above, attached via a sulfonyl [$S(O)_2$] group. The term "$C_1$-$C_6$-haloalkylsulfonyl" is a $C_1$-$C_6$-haloalkyl group, as defined above, attached via a sulfonyl [$S(O)_2$] group. The term "$C_1$-$C_{10}$-haloalkylsulfonyl" is a $C_1$-$C_{10}$-haloalkyl group, as defined above, attached via a sulfonyl[$S(O)_2$] group. $C_1$-$C_2$-Haloalkylsulfonyl is, for example, $S(O)_2CH_2F$, $S(O)_2CHF_2$, $S(O)_2CF_3$, $S(O)_2CH_2Cl$, $S(O)_2CHCl_2$, $S(O)_2CCO_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl or $S(O)_2C2F_5$. $C_1$-$C_4$-Haloalkylsulfonyl is additionally, for example, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, $S(O)_2CH_2$—$C_2F_5$, $S(O)_2CF_2$—$C_2F_5$, 1-($CH_2F$)-2-fluoroethylsulfonyl, 1-($CH_2Cl$)-2-chloroethylsulfonyl, 1-($CH_2Br$)-2-bromoethylsulfonyl, 4-fluorobutylsulfonyl, 4-chlorobutylsulfonyl, 4-bromobutylsulfonyl or nonafluorobutylsulfonyl. $C_1$-$C_6$-Haloalkylsulfonyl is additionally, for example, 5-fluoropentylsulfonyl, 5-chloropentylsulfonyl, 5-brompentylsulfonyl, 5-iodopentylsulfonyl, undecafluoropentylsulfonyl, 6-fluorohexylsulfonyl, 6-chlorohexylsulfonyl, 6-bromohexylsulfonyl, 6-iodohexylsulfonyl or dodecafluorohexylsulfonyl.

The term "3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members" as used herein refers to monocyclic radicals, the monocyclic radicals being saturated, partially unsaturated or aromatic. The heterocyclic radical may be attached to the remainder of the molecule via a carbon ring member or via a nitrogen ring member.

Examples of 3-, 4-, 5-, 6- or 7-membered saturated heterocyclyl include:

Oxiranyl, aziridinyl, oxetidinyl (radical of trimethylene oxide), thietidinyl (radical of trimethylene sulfide), azetidinyl, 2-tetrahydrofuranyl, 3-tetrahydrofuranyl, 1,3-dioxolane-2-yl, 1,3-dioxolane-4-yl, 2-tetrahydrothienyl, 3-tetrahydrothienyl, 1,3-thiolane-2-yl, 1,3-dithiolane-4-yl, 1-thia-3-oxolan-2-yl, 1-thia-3-oxolan-4-yl, 1-thia-3-oxolan-5-yl, 2-pyrrolidinyl, 3-pyrrolidinyl, 3-pyrazolidinyl, 4-pyrazolidinyl, 5-pyrazolidinyl, 2-imidazolidinyl, 4-imidazolidinyl, 2-oxazolidinyl, 4-oxazolidinyl, 5-oxazolidinyl, 3-isoxazolidinyl, 4-isoxazolidinyl, 5-isoxazolidinyl, 2-thiazolidinyl, 4-thiazolidinyl, 5-thiazolidinyl, 3-isothiazolidinyl, 4-isothiazolidinyl, 5-isothiazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2-tetrahydropyranyl, 3-tetrahydropyranyl, 4-tetrahydropyranyl, 1,3-dioxan-2-yl, 1,3-dioxan-4-yl, 1,3-dioxan-5-yl, 1,4-dioxan-2-yl, 2-thianyl, 3-thianyl, 4-thianyl, 1,3-dithian-2-yl, 1,3-dithian-4-yl, 1,3-dithian-5-yl, 1,4-dithian-2-yl, 1-oxa-3-thian-2-yl, 1-oxa-3-thian-4-yl, 1-oxa-3-thian-5-yl, 1-oxa-3-thian-6-yl, 1-oxa-4-thian-2-yl, 1-oxa-4-thian-3-yl, 2-piperidinyl, 3-piperidinyl, 4-piperidinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclyl include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

3-, 4-, 5-, 6- or 7-membered aromatic heterocyclyl is 5- or 6-membered aromatic heterocyclyl(hetaryl). Examples are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

$C_2$-$C_7$-alkylene is divalent branched or preferably unbranched saturated aliphatic chain having 2 to 7 carbon atoms, for example $CH_2CH_2$, —$CH(CH_3)$—, $CH_2CH_2CH_2$, $CH(CH_3)CH_2$, $CH_2CH(CH_3)$, $CH_2CH_2CH_2CH_2$, $CH_2CH_2CH_2CH_2CH_2$, $CH_2CH_2CH_2CH_2CH_2CH_2$, and $CH_2CH_2CH_2CH_2CH_2CH_2CH_2$ The remarks made below concerning preferred embodiments of the variables of the compounds of formula I, especially with respect to their substituents X, Y, $A^1$, $B^1$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, m, n, p and q, the features of the use and method according to the invention and of the composition of the invention are valid both on their own and, in particular, in every possible combination with each other.

As a matter of course, the q radicals $R^5$ replace a hydrogen atom on a carbon ring atom. For instance, if $B^1$ is defined to be CH and if this position is to be substituted by a radical $R^5$, then $B^1$ is of course C—$R^5$. If there is more than one radical $R^5$, these can be the same or different.

As a matter of course, the p radicals $R^4$ replace a hydrogen atom on a carbon ring atom. For instance, if $A^1$ is defined to be CH and if this position is to be substituted by a radical $R^4$, then $A^1$ is of course C—$R^4$. If there is more than one radical $R^4$, these can be the same or different.

Preferably, $A^1$ is CH.

In a preferred embodiment, the ring comprising the group $A^1$ as ring member carries 0, 1 or 2, preferably 0 or 1 and in particular 1 substituent $R^4$. In other words, p is preferably 0, 1 or 2, more preferably 0 or 1 and in particular 1. In case $A^1$ is CH and p is 1, the substituent $R^4$ is preferably bound on the position of $A^1$. In other words, $A^1$ is in this case preferably C—$R^4$.

In case p is 2, two substituents $R^4$ bound on adjacent carbon atoms preferably form together a group selected from —$CH_2CH_2CH_2CH_2$— and —CH=CH—CH=CH— and more preferably —CH=CH—CH=CH—, thus yielding a fused phenyl ring.

Preferably, $B^1$ is CH.

q is preferably 0, 1, 2 or 3, more preferably 1, 2 or 3, even more preferably 2 or 3 and in particular 2. If q is 3 and $B^1$ is CH, then the three substituents $R^5$ are preferably bound in the positions 3, 4 and 5 (relative to the 1-position of the attachment point of this ring to the remainder of the molecule), $B^1$ thus being C—$R^5$. If q is 2 and $B^1$ is CH, then the two substituents $R^5$ are preferably bound in the positions 3 and 5, $B^1$ thus being C—$R^5$.

X is preferably selected from the group consisting of $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_3$-$C_6$-cycloalkyl and $C_3$-$C_6$-halocycloalkyl. More preferably, X is selected from the group consisting of $C_1$-$C_4$-alkyl, $C_1$-$C_4$-haloalkyl, $C_3$-$C_6$-cycloalkyl and $C_3$-$C_6$-halocycloalkyl. Even more preferably, X is selected from the group consisting of $C_1$-$C_4$-alkyl and $C_1$-$C_4$-haloalkyl. In particular, X is $C_1$-$C_4$-haloalkyl, specifically $C_1$-$C_2$-haloalkyl and more specifically halomethyl, in particular fluoromethyl, such as fluoromethyl, difluoromethyl and trifluoromethyl, or fluorochloromethyl, such as chlorodifluoromethyl or dichlorofluoromethyl. Specifically, X is selected from $CF_3$, $CHF_2$ and $CF_2Cl$ and is very specifically trifluoromethyl.

Y is preferably a chemical bond, O or $NR^3$. $R^3$ has one of the meanings given above or preferably one of the preferred meanings given below. More preferably, Y is O or $NR^3$. In particular, Y is $NR^3$.

Preferably, $R^1$ is selected from the group consisting of hydrogen; cyano; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_1$-$C_{10}$-alkoxy; $C_1$-$C_{10}$-haloalkoxy; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_{10}$-alkenyl which may be partially or fully halogenated and/or may be substituted by one or more, e.g. 1, 2, 3 or 4, preferably 1 or 2, more preferably 1, radicals $R^6$; $C_2$-$C_{10}$-alkynyl which may be partially or fully halogenated and/or may be substituted by one or more, e.g. 1, 2, 3 or 4, preferably 1 or 2, more preferably 1, radicals $R^6$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; phenyl which may be substituted by 1, 2, 3, 4 or 5, preferably 1 or 2, more preferably 1, radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$;

where $R^7$, $R^8$, $R^9$ and $R^{10}$ have one of the meanings given above or in particular one of the preferred meanings given below.

More preferably, $R^1$ is selected from the group consisting of hydrogen; cyano; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_1$-$C_{10}$-alkoxy; $C_1$-$C_{10}$-haloalkoxy; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_{10}$-alkenyl which may be partially or fully halogenated and/or may be substituted by one or more, e.g. 1, 2, 3 or 4, preferably 1 or 2, more preferably 1, radicals $R^6$; $C_2$-$C_{10}$-alkynyl which may be partially or fully halogenated and/or may be substituted by one or more, e.g. 1, 2, 3 or 4, preferably 1 or 2, more preferably 1, radicals $R^6$; —C(=O)$R^6$; phenyl which may be substituted by 1, 2, 3, 4 or 5, preferably 1 or 2, more preferably 1, radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$ and $R^{10}$ have one of the meanings given above or in particular one of the preferred meanings given below.

Even more preferably, $R^1$ is selected from the group consisting of hydrogen; cyano; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_1$-$C_{10}$-alkoxy; $C_1$-$C_{10}$-haloalkoxy; $C_3$-$C_8$-cycloalkyl which may be partially or fully halogenated and/or may be substituted by one or more, e.g. 1, 2, 3 or 4, preferably 1 or 2, more preferably 1, radicals $R^6$, and —C(=O)$R^6$; where $R^6$ has one of the meanings given above or in particular one of the preferred meanings given below.

In particular, $R^1$ is selected from the group consisting of hydrogen, cyano, $C_1$-$C_{10}$-alkyl, preferably $C_1$-$C_6$-alkyl, more preferably $C_1$-$C_4$-alkyl, which may be partially or fully halogenated and/or may be substituted by one or more, e.g. 1, 2, 3 or 4, preferably 1 or 2, more preferably 1, radicals $R^6$; cyclopropyl; $C_1$-$C_4$-alkoxy; $C_1$-$C_4$-haloalkoxy, and —C(=O)$R^6$; where $R^6$ has one of the meanings given above or in particular one of the preferred meanings given below.

Specifically, $R^1$ is selected from the group consisting of hydrogen; cyano; $C_1$-$C_6$-alkyl; $C_1$-$C_4$-haloalkyl, specifically $C_1$-$C_4$-fluoroalkyl; $C_1$-$C_4$-alkoxy; $C_1$-$C_4$-haloalkoxy, specifically $C_1$-$C_4$-fluoroalkoxy; and —C(=O)$R^6$; where $R^6$ has one of the meanings given above or preferably one of the preferred meanings given below. More specifically, $R^1$ is hydrogen.

In case $R^1$ is selected from $C_1$-$C_{10}$-alkyl, preferably $C_1$-$C_6$-alkyl, more preferably $C_1$-$C_4$-alkyl, which is substituted by one or more, e.g. 1, 2, 3 or 4, preferably 1 or 2, more preferably 1, radicals $R^6$, $R^6$ is preferably selected from $C_3$-$C_6$-cycloalkyl, $C_3$-$C_6$-halocycloalkyl, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, more preferably from a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, even more preferably from a 5- or 6-membered saturated, partially unsaturated or aromatic heterocyclic ring containing 1, 2 or 3 heteroatoms selected from N, O and S, as ring members, where the heterocyclic ring may be substituted by one or more, e.g. 1, 2 or 3, preferably 1 or 2, more preferably 1, radicals $R^{10}$, in particular from a 5- or 6-membered heteroaromatic ring containing 1 heteroatom selected from N, O and S and optionally 1 or two further N atoms, as ring members, where the heteroaromatic ring may be substituted by one or more, e.g. 1, 2 or 3, preferably 1 or 2, more preferably 1, radicals $R^{10}$, and is specifically 6-membered heteroaromatic ring selected from pyridinyl, pyridazinyl, pyrimidinyl, pyrazinyl and 1,3,5-triazinyl, preferably from pyridyl and pyrimidinyl, where the heteroaromatic ring may be substituted by one or more, e.g. 1, 2 or 3, preferably 1 or 2, more preferably 1, radicals $R^{10}$, where $R^{10}$ has one of the meanings given above or in particular one of the preferred meanings given below.

$R^2$ is preferably selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_{10}$-alkenyl which may be partially or fully halogenated and/or may be substituted by one or more, e.g. 1, 2, 3 or 4, preferably 1 or 2, more preferably 1, radicals $R^6$; $C_2$-$C_{10}$-alkynyl which may be partially or fully halogenated and/or may be substituted by one or more, e.g. 1, 2, 3 or 4, preferably 1 or 2, more preferably 1, radicals $R^6$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; —C(=N$R^8$)$R^6$, phenyl which may be substituted by 1, 2, 3, 4 or 5, preferably 1 or 2, more preferably 1, radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, or $R^2$ and $R^3$ together form a group =C$R^{11}R^{12}$; =S(O)$_m R^7$; =S(O)$_m$N($R^8$)$R^9$; =N$R^8$; or =NO$R^7$;

or $R^2$ and $R^3$ together form a $C_2$-$C_7$ alkylene chain, thus forming, together with the nitrogen atom to which they are bound, a 3-, 4-, 5-, 6-, 7- or 8-membered ring, where the alkylene chain may be interrupted by 1 or 2 O, S and/or N$R^{18}$ and/or 1 or 2 of the $CH_2$ groups of the alkylene chain may be replaced by a group C=O, C=S and/or C=N$R^{18}$; and/or the alkylene chain may be substituted by one or more, e.g. 1, 2, 3 or 4, preferably 1 or 2, more preferably 1, radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5, preferably 1 or 2, more preferably 1, radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$, $R^{10}$, $R^{11}$, $R^{12}$ and $R^{18}$ have one of the meanings given above or in particular one of the preferred meanings given below.

More preferably, $R^2$ is selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_{10}$-alkenyl which may be partially or fully halogenated and/or may be substituted by one or more, e.g. 1, 2, 3 or 4, preferably 1 or 2, more preferably 1, radicals $R^6$; $C_2$-$C_{10}$-alkynyl which may be partially or fully halogenated and/or may be substituted by one or more, e.g. 1, 2, 3 or 4, preferably 1 or 2, more preferably 1, radicals $R^6$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; —C(=N$R^8$)$R^6$, phenyl which may be substituted by 1, 2, 3, 4 or 5, preferably 1 or 2, more preferably 1, radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$ and $R^{10}$ have one of the meanings given above or in particular one of the preferred meanings given below.

In case Y is a chemical bond, $R^2$ is more preferably selected from a substituent bound via a heteroatom, such as —N($R^8$)$R^9$; —N($R^8$)C(=O)$R^6$; —O$R^7$; —S$R^7$; —S(O)$_m R^7$; —S(O)$_n$N($R^8$)$R^9$ and an N-bound 3-, 4-, 5-, 6- or 7-membered saturated, partially unsaturated or aromatic heterocyclic ring containing 1 N atom as ring member and optionally 1 or 2 further heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$ and $R^{10}$ have one of the meanings given above or in particular one of the preferred meanings given below.

In case Y is a chemical bond, $R^2$ is even more preferably selected from —N($R^8$)$R^9$; —N($R^8$)C(=O)$R^6$; —O$R^7$; —S$R^7$; —S(O)$_m R^7$ and S(O)$_n$N($R^8$)$R^9$, in particular from —N($R^8$)$R^9$; —N($R^8$)C(=O)$R^6$; —O$R^7$ and —S$R^7$, and specifically from —N($R^8$)$R^9$; —N($R^8$)C(=O)$R^6$ and —O$R^7$, where $R^6$, $R^7$, $R^8$ and $R^9$ have one of the meanings given above or in particular one of the preferred meanings given below.

In case Y is not a chemical bond, $R^2$ is preferably selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_{10}$-alkenyl which may be partially or fully halogenated and/or may be substituted by one or more, e.g. 1, 2, 3 or 4, preferably 1 or 2, more preferably 1, radicals $R^6$; $C_2$-$C_{10}$-alkynyl which may be partially or fully halogenated and/or may be substituted by one or more, e.g. 1, 2, 3 or 4, preferably 1 or 2, more preferably 1, radicals $R^6$; —C(=O) $R^6$; —C(=O)O$R^7$; —C(=O)N($R^8$)$R^9$; —C(=S)$R^6$; —C(=S)O$R^7$, —C(=S)N($R^8$)$R^9$; —C(=N$R^8$)$R^6$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$ and $R^{10}$ have one of the meanings given above or in particular one of the preferred meanings given below.

In case Y is not a chemical bond, $R^2$ is more preferably selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; —C(=O)$R^6$; —C(=O)O$R^7$; —C(=O)N($R^8$)$R^9$; —C(=S)$R^6$; —C(=S)O$R^7$, —C(=S)N($R^8$)$R^9$; —C(=N$R^8$)$R^6$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$ and $R^{10}$ have one of the meanings given above or in particular one of the preferred meanings given below.

Independently from the meaning of Y, $R^2$ is even more preferably selected from the group consisting of $C_1$-$C_4$-alkyl; $C_1$-$C_4$-haloalkyl; a methyl group substituted by a radical $R^6$; —C(=O)$R^6$; —C(=O)N($R^8$)$R^9$; —C(=O)O$R^7$; —C(=S) $R^6$; —C(=S)N($R^8$)$R^9$; —C(=S)O$R^7$; and —C(=N$R^8$)$R^6$; and specifically from —C(=O)N($R^8$)$R^9$ and —C(=S)N($R^8$)$R^9$; where $R^6$, $R^7$, $R^8$ and $R^9$ have one of the meanings given above or in particular one of the preferred meanings given below. It is however preferred that $R^2$ has these meanings if Y is not a chemical bond and is preferably O or N$R^3$, specifically N$R^3$.

Independently from the meaning of Y, $R^2$ is particularly preferably selected from the group consisting of $C_1$-$C_4$-alkyl; $C_1$-$C_4$-haloalkyl; a methyl group substituted by a radical $R^{6a}$; —C(=O)$R^{6c}$; —C(=O)N($R^8$)$R^9$; —C(=O)O$R^7$; —C(=S)$R^{6c}$; —C(=S)N($R^8$)$R^9$; —C(=S)O$R^7$; and —C(=N$R^8$)$R^{6d}$; and specifically from —C(=O)N($R^8$)$R^9$ and —C(=S)N($R^8$)$R^9$;

where $R^{6a}$ is selected from CN, phenyl which may carry 1, 2 or 3, preferably 1 or 2, more preferably 1, substituents $R^{10}$, —C(=O)$R^{6b}$; —C(=O)N($R^8$)$R^9$ and —C(=O)O$R^7$;

$R^{6b}$ and $R^{6c}$ are independently selected from $C_1$-$C_4$-alkyl, $C_1$-$C_4$-haloalkyl, phenyl, benzyl and a 5- or 6-membered saturated, partially unsaturated or aromatic heterocyclic ring containing 1, 2 or 3 heteroatoms or heteroatom groups selected from N, O, S, NO, SO and $SO_2$, as ring members, where the phenyl or heterocyclyl rings in the three last-mentioned radicals may carry 1, 2 or 3, preferably 1 or 2, more preferably 1, substituents selected from halogen, CN, $C_1$-$C_4$-alkyl, $C_1$-$C_4$-haloalkyl, $C_1$-$C_4$-alkoxy and $C_1$-$C_4$-haloalkoxy;

$R^{6d}$ is selected from N($R^8$)$R^9$;

$R^7$ is selected from hydrogen, $C_1$-$C_4$-alkyl, $C_1$-$C_4$-haloalkyl, phenyl, benzyl and a 5- or 6-membered saturated, partially unsaturated or aromatic heterocyclic ring containing 1, 2 or 3 heteroatoms or heteroatom groups selected from N, O, S, NO, SO and $SO_2$, as ring members, where the phenyl or heterocyclyl rings in the three last-mentioned radicals may carry 1, 2 or 3, preferably 1 or 2, more preferably 1, substituents selected from halogen, CN, $C_1$-$C_4$-alkyl, $C_1$-$C_4$-haloalkyl, $C_1$-$C_4$-alkoxy and $C_1$-$C_4$-haloalkoxy;

each $R^8$ is independently selected from hydrogen, cyano, $C_1$-$C_6$-alkyl which may be partially or fully halogenated and/or may be substituted by one or more radicals $R^{19}$, $C_2$-$C_4$-alkenyl which may be partially or fully halogenated and/or may be substituted by one or more radicals $R^{19}$, $C_3$-$C_6$-cycloalkyl, $C_3$-$C_6$-halocycloalkyl, $C_3$-$C_6$-cycloalkyl-$C_1$-$C_4$-alkyl, $C_3$-$C_6$-halocycloalkyl-$C_1$-$C_4$-alkyl, —S(O)$_m$$R^{20}$, —S(O)$_n$N($R^{21}$)$R^{22}$, phenyl, benzyl and a 5- or 6-membered saturated, partially unsaturated or aromatic heterocyclic ring containing 1, 2 or 3 heteroatoms or heteroatom groups selected from N, O, S, NO, SO and $SO_2$, as ring members, where the phenyl or heterocyclyl rings in the three last-mentioned radicals may carry 1, 2 or 3, preferably 1 or 2, more preferably 1, substituents selected from halogen, CN, $C_1$-$C_4$-alkyl, $C_1$-$C_4$-haloalkyl, $C_1$-$C_4$-alkoxy and $C_1$-$C_4$-haloalkoxy;

each $R^9$ is independently selected from hydrogen, cyano, $C_1$-$C_6$-alkyl which may be partially or fully halogenated and/or may be substituted by one or more radicals $R^{19}$, $C_2$-$C_4$-alkenyl which may be partially or fully halogenated and/or may be substituted by one or more radicals $R^{19}$, $C_3$-$C_6$-cycloalkyl, $C_3$-$C_6$-halocycloalkyl, $C_3$-$C_6$-cycloalkyl-$C_1$-$C_4$-alkyl, $C_3$-$C_6$-halocycloalkyl-$C_1$-$C_4$-alkyl, —S(O)$_m$$R^{20}$, —S(O)$_n$N($R^{21}$)$R^{22}$, phenyl, benzyl and a 5- or 6-membered saturated, partially unsaturated or aromatic heterocyclic ring containing 1, 2 or 3 heteroatoms or heteroatom groups selected from N, O, S, NO, SO and $SO_2$, as ring members, where the phenyl or heterocyclyl rings in the three last-mentioned radicals may carry 1, 2 or 3, preferably 1 or 2, more preferably 1, substituents selected from halogen, CN, $C_1$-$C_4$-alkyl, $C_1$-$C_4$-haloalkyl, $C_1$-$C_4$-alkoxy and $C_1$-$C_4$-haloalkoxy; and $R^{10}$ is selected from halogen, CN, $C_1$-$C_4$-alkyl, $C_1$-$C_4$-haloalkyl, $C_1$-$C_4$-alkoxy and $C_1$-$C_4$-haloalkoxy;

where $R^{19}$ has one of the meanings given above or in particular one of the preferred meanings given below; or $R^8$ and $R^9$ together form a group =C$R^{11}$$R^{12}$; or $R^8$ and $R^9$, together with the nitrogen atom to which they are bound, form a 3-, 4-, 5-, 6- or 7-membered saturated, partially unsaturated or aromatic heterocyclic ring which may additionally containing 1 or 2 further heteroatoms or heteroatom groups selected from N, O, S, NO, SO and $SO_2$, as ring members, where the heterocyclic ring may be substituted by one or more radicals $R^{10}$.

It is however preferred that $R^2$ has these meanings if Y is not a chemical bond and is preferably O or N$R^3$, specifically N$R^3$.

In particular, $R^2$ is selected from —C(=O)N($R^8$)$R^9$ and —C(=S)N($R^8$)$R^9$, where $R^8$ and $R^9$ have one of the meanings given above or in particular one of the preferred meanings given below. More preferably, $R^2$ is selected from —C(=O)N($R^8$)$R^9$ and —C(=S)N($R^8$)$R^9$, where $R^8$ is selected from hydrogen and $C_1$-$C_6$-alkyl which may be partially or fully halogenated and/or may be substituted by one or more radicals $R^{19}$;

$R^9$ is selected from hydrogen, $C_1$-$C_6$-alkyl which may be partially or fully halogenated and/or may be substituted by one or more radicals $R^{19}$, $C_3$-$C_6$-cycloalkyl, $C_3$-$C_6$-halocycloalkyl, $C_3$-$C_6$-cycloalkyl-$C_1$-$C_4$-alkyl and $C_3$-$C_6$-halocycloalkyl-$C_1$-$C_4$-alkyl; and $R^{19}$ has one of the meanings given above or in particular one of the preferred meanings given below.

It is preferred that $R^2$ has these meanings if Y is not a chemical bond and is preferably O or $NR^3$, specifically $NR^3$.

Specifically, $R^2$ is selected from —C(=O)N($R^8$)$R^9$ and —C(=S)N($R^8$)$R^9$, where $R^8$ is hydrogen; and $R^9$ is selected from hydrogen, $C_1$-$C_6$-alkyl; $C_1$-$C_6$-haloalkyl, $C_3$-$C_6$-cycloalkyl, $C_3$-$C_6$-halocycloalkyl, $C_3$-$C_6$-cycloalkyl-$C_1$-$C_4$-alkyl and $C_3$-$C_6$-halocycloalkyl-$C_1$-$C_4$-alkyl.

It is preferred that $R^2$ has these meanings if Y is not a chemical bond and is preferably O or $NR^3$, specifically $NR^3$.

$R^3$ is preferably selected from the group consisting of hydrogen; cyano; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_{10}$-alkenyl which may be partially or fully halogenated and/or may be substituted by one or more, e.g. 1, 2, 3 or 4, preferably 1 or 2, more preferably 1, radicals $R^6$; $C_2$-$C_{10}$-alkynyl which may be partially or fully halogenated and/or may be substituted by one or more, e.g. 1, 2, 3 or 4, preferably 1 or 2, more preferably 1, radicals $R^6$; —N($R^8$)$R^9$; —Si($R^{14}$)$_2$$R^{13}$; —$OR^7$; —$SR^7$; —S(O)$_m$$R^7$; —S(O)$_n$N($R^8$)$R^9$; —C(=O)$R^6$; —C(=O)$OR^7$; —C(=O)N($R^8$)$R^9$; —C(=S)$R^6$; —C(=S)$OR^7$; —C(=S)N($R^8$)$R^9$; —C(=$NR^8$)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

or $R^2$ and $R^3$ together form a group =$CR^{11}$$R^{12}$; =S(O)$_m$$R^7$; =S(O)$_m$N($R^8$)$R^9$; =$NR^8$; or =$NOR^7$;

or $R^2$ and $R^3$ together form a $C_2$-$C_7$ alkylene chain, thus forming, together with the nitrogen atom to which they are bound, a 3-, 4-, 5-, 6-, 7- or 8-membered ring, where the alkylene chain may be interrupted by 1 or 2 O, S and/or $NR^{18}$ and/or 1 or 2 of the $CH_2$ groups of the alkylene chain may be replaced by a group C=O, C=S and/or C=$NR^{18}$; and/or the alkylene chain may be substituted by one or more, e.g. 1, 2, 3 or 4, preferably 1 or 2, more preferably 1, radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5, preferably 1 or 2, more preferably 1, radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$, $R^{10}$, $R^{11}$, $R^{12}$, $R^{13}$, $R^{14}$ and $R^{18}$ have one of the meanings given above or in particular one of the preferred meanings given below.

More preferably, $R^3$ is selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_{10}$-alkenyl which may be partially or fully halogenated and/or may be substituted by one or more, e.g. 1, 2, 3 or 4, preferably 1 or 2, more preferably 1, radicals $R^6$; $C_2$-$C_{10}$-alkynyl which may be partially or fully halogenated and/or may be substituted by one or more, e.g. 1, 2, 3 or 4, preferably 1 or 2, more preferably 1, radicals $R^6$; —C(=O)$R^6$; —C(=O)$OR^7$; —C(=O)N($R^8$)$R^9$; —C(=S)$R^6$; —C(=S)$OR^7$; —C(=S) N($R^8$)$R^9$; —C(=$NR^8$)$R^6$; phenyl which may be substituted by 1, 2, 3, 4 or 5, preferably 1 or 2, more preferably 1, radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$ and $R^{10}$ have one of the meanings given above or in particular one of the preferred meanings given below.

Even more preferably, $R^3$ is selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; —C(=O)$R^6$; —C(=O)$OR^7$; —C(=O)N($R^8$)$R^9$; —C(=S)$R^6$; —C(=S)$OR^7$; —C(=S)N($R^8$)$R^9$ and —C(=$NR^8$)$R^6$; where $R^6$, $R^7$, $R^8$ and $R^9$ have one of the meanings given above and in particular one of the preferred meanings given below. Preferably, in this case, $R^6$ as a $C_1$-$C_6$-alkyl substituent, is selected from CN, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio and a 5- or 6-membered hetaryl ring containing 1, 2 or 3 heteroatoms selected from N, O and S as ring members and being optionally substituted by 1, 2 or 3 radicals $R^{10}$. In this case, $R^6$ as a CO substituent, is preferably selected from $C_1$-$C_6$-alkyl, $C_1$-$C_6$-haloalkyl, $C_1$-$C_6$-alkoxy and $C_1$-$C_6$-haloalkoxy. In this case, $R^8$ and $R^9$ are preferably selected from hydrogen and $C_1$-$C_6$-alkyl.

In particular, $R^3$ is selected from the group consisting of hydrogen; $C_1$-$C_6$-alkyl and $C_1$-$C_4$-haloalkyl and is specifically hydrogen.

Preferably, each $R^4$ is independently selected from halogen; cyano; nitro; —SCN; $SF_5$; $C_1$-$C_6$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_6$-alkenyl which may be partially or fully halogenated and/or may be substituted by one or more, e.g. 1, 2, 3 or 4, preferably 1 or 2, more preferably 1, radicals $R^6$; $C_2$-$C_6$-alkynyl which may be partially or fully halogenated and/or may be substituted by one or more, e.g. 1, 2, 3 or 4, preferably 1 or 2, more preferably 1, radicals $R^6$; —Si($R^{14}$)$_2$$R^{13}$; —$OR^7$; —OS(O)$_n$$R^7$; —$SR^7$; —S(O)$_m$$R^7$; —S(O)$_n$N $(R^8)R^9$; —$N(R^8)R^9$; —$N(R^8)C(=O)R^6$; $C(=O)R^6$; —$C(=O)OR^7$; —$C(=NR^8)H$; —$C(=NR^8)R^6$; —$C(=O)N(R^8)R^9$; $C(=S)N(R^8)R^9$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$;

or two radicals $R^4$ bound on adjacent carbon atoms may be together a group selected from —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$— —$CH_2OCH_2CH_2$—, —$CH_2CH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C(=O)O$—, —$C(=O)OCH_2$—, —$O(CH_2)O$—, —$SCH_2CH_2CH_2$—, —SCH=$CHCH_2$—, —$CH_2SCH_2CH_2$—, —$SCH_2CH_2$—, —$SCH_2SCH_2$— —$CH_2CH_2S$—, —CH=CHS—, —$CH_2SCH_2$—, —$CH_2C(=S)S$—, —$C(=S)SCH_2$—, —$S(CH_2)S$—, —$CH_2CH_2NR^8$—, —$CH_2CH=N$—, —CH=CH—$NR^8$—, —OCH=N—, and —SCH=N—, thus forming, together with the carbon atoms to which they are bound, a 5- or 6-membered ring, where the hydrogen atoms of the above groups may be replaced by one or more, e.g. 1, 2, 3 or 4, preferably 1 or 2, more preferably 1, substituents selected from halogen, methyl, halomethyl, hydroxyl, methoxy and halomethoxy or one or more, e.g. 1 or 2, $CH_2$ groups of the above groups may be replaced by a C=O group, where $R^6$, $R^7$, $R^8$, $R^9$, $R^{10}$, $R^{13}$ and $R^{14}$ have one of the meanings given above or in particular one of the preferred meanings given below.

More preferably, each $R^4$ is independently selected from halogen; cyano; nitro; —SCN; $C_1$-$C_6$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; —$OR^7$; —$OS(O)_nR^7$; —$SR^7$; —$S(O)_mR^7$; —$S(O)_nN(R^8)R^9$; —$N(R^8)R^9$; —$N(R^8)C(=O)R^6$; $C(=O)R^6$; —$C(=O)OR^7$; —$C(=NR^8)R^6$; —$C(=O)N(R^8)R^9$; —$C(=S)N(R^8)R^9$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$;

or two radicals $R^4$ bound on adjacent carbon atoms may be together a group selected from —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C(=O)O$—, —$C(=O)OCH_2$—, —$O(CH_2)O$—, —$SCH_2CH_2CH_2$—, —SCH=$CHCH_2$—, —$CH_2SCH_2CH_2$—, —$CH_2CH_2S$—, —CH=CHS—, —$CH_2SCH_2$—, —$CH_2SCH_2$—, —$CH_2CH_2NR^8$—, —$CH_2CH=N$—, —OCH=N—, and —SCH=N—, thus forming, together with the carbon atoms to which they are bound, a 5- or 6-membered ring, where the hydrogen atoms of the above groups may be replaced by one or more, e.g. 1, 2, 3 or 4, preferably 1 or 2, more preferably 1, substituents selected from halogen, methyl, halomethyl, hydroxyl, methoxy and halomethoxy or one or more, e.g. 1 or 2, $CH_2$ groups of the above groups may be replaced by a C=O group, where $R^6$, $R^7$, $R^8$, $R^9$ and $R^{10}$ have one of the meanings given above or in particular one of the preferred meanings given below.

Even more preferably, each $R^4$ is independently selected from halogen; cyano; nitro; —SCN; $C_1$-$C_6$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; —$OR^7$; —$OS(O)_nR^7$; —$SR^7$; —$S(O)_mR^7$; —$S(O)_nN(R^8)R^9$; —$N(R^8)R^9$; $C(=O)R^6$; —$C(=O)OR^7$; —$C(=NR^8)R^6$; —$C(=O)N(R^8)R^9$; —$C(=S)N(R^8)R^9$ and phenyl which may be substituted by 1, 2, 3, 4 or 5 radicals $R^{10}$ where $R^6$, $R^7$, $R^8$, $R^9$ and $R^{10}$ have one of the meanings given above or in particular one of the preferred meanings given below.

In particular, each $R^4$ is independently selected from halogen; cyano; nitro; $C_1$-$C_6$-alkyl; $C_1$-$C_6$-haloalkyl; $C_1$-$C_6$-alkoxy; $C_1$-$C_6$-haloalkoxy; and phenyl which may be substituted by 1, 2, 3, 4 or 5 radicals $R^{10}$;

or two radicals $R^4$ bound on adjacent carbon atoms may be together a group selected from —$CH_2CH_2CH_2CH_2$— and —CH=CH—CH=CH— and preferably —CH=CH—CH=CH—, where $R^{10}$ has one of the meanings given above or in particular one of the preferred meanings given below.

More particularly, each $R^4$ is independently selected from halogen, cyano, $C_1$-$C_6$-alkyl, preferably $C_1$-$C_4$-alkyl, more preferably methyl, and $C_1$-$C_4$-haloalkyl, preferably $C_1$-$C_2$-haloalkyl. Specifically, each $R^4$ is independently selected from halogen and $C_1$-$C_4$-alkyl and is very specifically chlorine or methyl.

Preferably, each $R^5$ is independently selected from the group consisting of halogen, cyano, nitro, —SCN, $SF_5$, $C_1$-$C_6$-alkyl, $C_1$-$C_6$-alkyl which may be partially or fully halogenated and/or may be substituted by one or more, e.g. 1, 2, 3 or 4, preferably 1 or 2, more preferably 1, radicals $R^6$, $C_3$-$C_8$-cycloalkyl which may be partially or fully halogenated and/or may be substituted by one or more, e.g. 1, 2, 3 or 4, preferably 1 or 2, more preferably 1, radicals $R^6$, $C_2$-$C_6$-alkenyl which may be partially or fully halogenated and/or may be substituted by one or more, e.g. 1, 2, 3 or 4, preferably 1 or 2, more preferably 1, radicals $R^6$, $C_2$-$C_6$-alkynyl which may be partially or fully halogenated and/or may be substituted by one or more, e.g. 1, 2, 3 or 4, preferably 1 or 2, more preferably 1, radicals $R^6$, $Si(R^{14})_2R^{13}$, $OR^7$, $OS(O)_nR^7$, $S(O)_mR^7$, $NR^8R^9$, $N(R^8)C(=O)R^6$, $C(=O)R^6$, $C(=O)OR^7$, $C(=NR^8)R^6$, $C(=S)NR^6$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$, $R^{10}$, $R^{13}$ and $R^{14}$ have one of the meanings given above or in particular one of the preferred meanings given below.

More preferably, each $R^5$ is independently selected from the group consisting of halogen, cyano, nitro, $C_1$-$C_6$-alkyl, $C_1$-$C_6$-alkyl which may be partially or fully halogenated and/or may be substituted by one or more, e.g. 1, 2, 3 or 4, preferably 1 or 2, more preferably 1, radicals $R^6$, $OR^7$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$,
where $R^6$, $R^7$ and $R^{10}$ have one of the meanings given above or in particular one of the preferred meanings given below.

Even more preferably, each $R^5$ is independently selected from the group consisting of halogen, $C_1$-$C_6$-alkyl, $C_1$-$C_6$-haloalkyl, $C_1$-$C_6$-alkoxy and $C_1$-$C_6$-haloalkoxy, in particular from halogen, $C_1$-$C_4$-alkyl and $C_1$-$C_2$-haloalkyl and is specifically halogen, more specifically chlorine, or $C_1$-$C_2$-haloalkyl, specifically $CF_3$.

In case $R^6$ is a substituent on an alkyl, alkenyl or alkynyl group, it is preferably selected from the group consisting of cyano, azido, nitro, —SCN, $SF_5$, $C_3$-$C_8$-cycloalkyl, $C_3$-$C_8$-halocycloalkyl, —Si($R^{14}$)$_2R^{13}$, —$OR^7$, —$OSO_2R^7$, —$SR^7$, —S(O)$_mR^7$, —S(O)$_nN(R^8)R^9$, —$N(R^8)R^9$, —C(=O)N($R^8$)$R^9$, —C(=S)N($R^8$)$R^9$, —C(=O)$OR^7$, —C(=O)$R^{19}$, —C(=$NR^8$)$R^{19}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$; or two geminally bound radicals $R^6$ together form a group selected from =$CR^{11}R^{12}$, =S(O)$_mR^7$, =S(O)$_mN(R^8)R^9$, =$NR^8$, =$NOR^7$ and =$NNR^8$; or two radicals $R^6$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members,
where $R^7$, $R^8$, $R^9$, $R^{10}$, $R^{11}$, $R^{12}$, $R^{13}$, $R^{14}$ and $R^{19}$ have one of the meanings given above or in particular one of the preferred meanings given below.

In case $R^6$ is a substituent on an alkyl, alkenyl or alkynyl group, it is more preferably selected from the group consisting of cyano, $C_3$-$C_8$-cycloalkyl, $C_3$-$C_8$-halocycloalkyl, —$OR^7$, —$SR^7$, —C(=O)N($R^8$)$R^9$, —C(=S)N($R^8$)$R^9$, —C(=O)$OR^7$, —C(=O)$R^{19}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;
where $R^7$, $R^8$, $R^9$ and $R^{10}$ have one of the meanings given above or in particular one of the preferred meanings given below.

In case $R^6$ is a substituent on an alkyl, alkenyl or alkynyl group, it is even more preferably selected from the group consisting of cyano, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-haloalkylthio, —C(=O)N($R^8$)$R^9$, —C(=S)N($R^8$) $R^9$, —C(=O)$OR^7$, —C(=O)$R^{19}$, phenyl which may be substituted by 1, 2, 3, 4 or 6 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;
where $R^{10}$ has one of the meanings given above or in particular one of the preferred meanings given below.

In case $R^6$ is a substituent on an alkyl, alkenyl or alkynyl group, it is in particular selected from the group consisting of cyano, $C_3$-$C_6$-cycloalkyl, $C_3$-$C_6$-halocycloalkyl, —C(=O)N ($R^8$)$R^9$, —C(=S)N($R^8$)$R^9$, —C(=O)$OR^7$, —C(=O)$R^{19}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;
where $R^{10}$ has one of the meanings given above or in particular one of the preferred meanings given below.

In case $R^6$ is a substituent on a cycloalkyl group, it is preferably selected from the group consisting of cyano, azido, nitro, —SCN, $SF_5$, $C_1$-$C_6$-alkyl, $C_1$-$C_6$-haloalkyl, $C_1$-$C_6$-alkoxy-$C_1$-$C_6$-alkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si($R^{14}$)$_2R^{13}$, —$OR^7$, —$OSO_2R^7$, —$SR^7$, —S(O)$_mR^7$, —S(O)$_nN(R^8)R^9$, —$N(R^8)R^9$, —C(=O)N($R^8$)$R^9$, —C(=S)N($R^8$)$R^9$, —C(=O)$OR^7$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;
or two geminally bound radicals $R^6$ together form a group selected from =$CR^{11}R^{12}$, =S(O)$_mR^7$, =S(O)$_mN(R^8)R^9$, =$NR^8$, =$NOR^7$ and =$NNR^8$;
or two radicals $R^6$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members,
where $R^7$, $R^8$, $R^9$, $R^{10}$, $R^{11}$, $R^{12}$, $R^{13}$ and $R^{14}$ have one of the meanings given above or in particular one of the preferred meanings given below.

In case $R^6$ is a substituent on a cycloalkyl group, it is more preferably selected from the group consisting of halogen, cyano, $C_1$-$C_6$-alkyl, $C_1$-$C_6$-haloalkyl, $C_1$-$C_6$-alkoxy-$C_1$-$C_6$-alkyl, —$OR^7$, —$OSO_2R^7$, —$SR^7$, —S(O)$_mR^7$, —S(O)$_nN(R^8)R^9$, —$N(R^8)R^9$, —C(=O)N($R^8$)$R^9$, —C(=S)N($R^8$)$R^9$, —C(=O)$OR^7$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;
where $R^7$, $R^8$, $R^9$ and $R^{10}$ have one of the meanings given above or in particular one of the preferred meanings given below.

In case $R^6$ is a substituent on a cycloalkyl group, it is even more preferably selected from the group consisting of halogen, $C_1$-$C_4$-alkyl, $C_1$-$C_3$-haloalkyl, $C_1$-$C_4$-alkoxy and $C_1$-$C_3$-haloalkoxy. In particular, $R^6$ as a substituent on a cycloalkyl group is selected from halogen, $C_1$-$C_4$-alkyl and $C_1$-$C_3$-haloalkyl.

In case $R^6$ is a substituent on C(=O), C(=S) or C(=$NR^8$), it is preferably selected from the group consisting of hydrogen, $C_1$-$C_6$-alkyl, $C_1$-$C_6$-haloalkyl, $C_1$-$C_6$-alkoxy-$C_1$-$C_6$-alkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —$OR^7$, —$SR^7$, —$N(R^8)R^9$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

where $R^7$, $R^8$, $R^9$ and $R^{10}$ have one of the meanings given above or in particular one of the preferred meanings given below.

In case $R^6$ is a substituent on C(=O), C(=S) or C(=$NR^8$), it is more preferably selected from the group consisting of $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

where $R^{10}$ has one of the meanings given above or in particular one of the preferred meanings given below.

In case $R^6$ is a substituent on C(=O), C(=S) or C(=$NR^8$), it is more preferably selected from the group consisting of $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

where $R^{10}$ has one of the meanings given above or in particular one of the preferred meanings given below.

In case $R^6$ is a substituent on C(=O), C(=S) or C(=$NR^8$), it is even more preferably selected from the group consisting of $C_1$-$C_4$-alkyl, $C_1$-$C_3$-haloalkyl, $C_3$-$C_6$-cycloalkyl, $C_3$-$C_6$-halocycloalkyl, $C_1$-$C_4$-alkoxy, $C_1$-$C_3$-haloalkoxy, phenyl which may be substituted by 1, 2, 3, 4 or 5 radicals $R^{10}$, and a 5- or 6-membered heteroaromatic ring containing 1, 2 or 3 heteroatoms selected from N, O and S, as ring members, where the heteroaromatic ring may be substituted by one or more radicals $R^{10}$;

where $R^{10}$ has one of the meanings given above or in particular one of the preferred meanings given below.

Preferably, each $R^7$ is independently selected from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl$C_1$-$C_4$-alkyl, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^{10}$ has one of the meanings given above or in particular one of the preferred meanings given below.

More preferably, each $R^7$ is independently selected from the group consisting of hydrogen, $C_1$-$C_6$-alkyl, $C_1$-$C_6$-haloalkyl, phenyl which may be substituted by 1, 2, 3, 4 or 5 radicals $R^{10}$; and a 5- or 6-membered heteroaromatic ring containing 1, 2 or 3 heteroatoms selected from N, O and S, as ring members, where the heteroaromatic ring may be substituted by one or more radicals $R^{10}$; where $R^{10}$ has one of the meanings given above or in particular one of the preferred meanings given below.

$R^8$ and $R^9$ are independently of each other and independently of each occurrence preferably selected from the group consisting of hydrogen, cyano, $C_1$-$C_6$-alkyl which may be partially or fully halogenated and/or may be substituted by one or more radicals $R^{19}$, $C_2$-$C_6$-alkenyl which may be partially or fully halogenated and/or may be substituted by one or more radicals $R^{19}$, $C_2$-$C_6$-alkynyl which may be partially or fully halogenated and/or may be substituted by one or more radicals $R^{19}$, $C_3$-$C_8$-cycloalkyl, $C_3$-$C_8$-halocycloalkyl, $C_3$-$C_8$-cycloalkyl-$C_1$-$C_6$-alkyl, $S(O)_mR^{20}$, $S(O)_nNR^{21}R^{22}$, phenyl which may be substituted by 1, 2, 3, 4 or 5 radicals $R^{10}$, benzyl wherein the phenyl moiety may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$; where $R^{10}$ has one of the meanings given above or in particular one of the preferred meanings given below; or $R^8$ and $R^9$ together form a group =$CR^{11}R^{12}$; or $R^8$ and $R^9$, together with the nitrogen atom to which they are bound, form a 3-, 4-, 5-, 6- or 7-membered saturated, partially unsaturated or aromatic, preferably a saturated, heterocyclic ring which may additionally containing 1 or 2 further heteroatoms or heteroatom groups selected from N, O, S, NO, SO and $SO_2$, as ring members, where the heterocyclic ring may be substituted by one or more radicals $R^{10}$.

In the above preferred embodiment of $R^8$ and $R^9$, $R^{11}$ is preferably hydrogen or methyl and $R^{12}$ is preferably $C_1$-$C_6$-alkoxy, $C_1$-$C_6$-haloalkoxy, —C(=O)$R^{19}$, —C(=O)O$R^{20}$, or —C(=O)N($R^{21}$)$R^{22}$.

In the above preferred embodiment of $R^8$ and $R^9$, $R^9$, if it does not form together with $R^8$ a group =$CR^{11}R^{12}$ or together with $R^8$ and the N atom to which they are bound a heterocyclic ring, is preferably selected from hydrogen, cyano, $C_1$-$C_4$-alkyl, $C_1$-$C_4$-haloalkyl, cyclopropyl, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl and is more preferably hydrogen or $C_1$-$C_4$-alkyl.

In the above preferred embodiment of $R^8$ and $R^9$, $R^8$, if it does not form together with $R^9$ a group =$CR^{11}R^{12}$ or together with $R^9$ and the N atom to which they are bound a heterocyclic ring, is preferably selected from CN, $C_1$-$C_6$-alkyl; $C_1$-$C_6$-haloalkyl; $C_1$-$C_4$-alkyl which carries one radical $R^{19}$; $C_2$-$C_6$-alkenyl; $C_2$-$C_6$-haloalkenyl; $C_2$-$C_4$-alkenyl which is substituted by one radical $R^{19}$; $C_3$-$C_6$-cycloalkyl; $C_3$-$C_6$-halocycloalkyl; $C_3$-$C_6$-cycloalkyl$C_1$-$C_4$-alkyl; $C_3$-$C_6$-halocycloalkyl-$C_1$-$C_4$-alkyl; —$S(O)_mR^{20}$; —$S(O)_nN(R^{21})R^{22}$; phenyl; benzyl and a 5- or 6-membered saturated, partially unsaturated or aromatic heterocyclic ring containing 1, 2 or 3 heteroatoms or heteroatom groups selected from N, O, S, NO, SO and $SO_2$, as ring members, where the phenyl or heterocyclyl rings in the three last-mentioned radicals may carry 1, 2 or 3 substituents selected from halogen, CN, $C_1$-$C_4$-alkyl, $C_1$-$C_4$-haloalkyl, $C_1$-$C_4$-alkoxy and $C_1$-$C_4$-haloalkoxy.

If $R^8$ and $R^9$, together with the nitrogen atom to which they are bound, form a 3-, 4-, 5-, 6- or 7-membered saturated, partially unsaturated or aromatic heterocyclic ring which may additionally contain 1 or 2 further heteroatoms or heteroatom groups selected from N, O, S, NO, SO and $SO_2$, as ring members, this is preferably a 3, 5 or 6-membered saturated heterocyclic ring which may additionally contain 1 further heteroatom or heteroatom group selected from N, O, S, NO, SO and $SO_2$, as ring member.

Specifically, $R^8$ and $R^9$ are independently of each other and independently of each occurrence selected from the group consisting of hydrogen, $C_1$-$C_6$-alkyl, $C_1$-$C_6$-haloalkyl, $C_2$-$C_6$-alkynyl, $C_3$-$C_8$-cycloalkyl-$C_1$-$C_6$-alkyl, benzyl wherein the phenyl moiety may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$. More specifically, $R^9$ is hydrogen or $C_1$-$C_4$-alkyl and $R^8$ has one of the meanings specified above.

Preferably, each $R^{10}$ is independently selected from the group consisting of halogen, cyano, $C_1$-$C_{10}$-alkyl which may be partially or fully halogenated and/or may be substituted by one or more radicals $R^{19}$, $C_3$-$C_8$-cycloalkyl which may be partially or fully halogenated and/or may be substituted by one or more radicals $R^{19}$, —$OR^{20}$, —$OS(O)_nR^{20}$, —$SR^{20}$, —$S(O)_mR^{20}$, —$S(O)_nN(R^{21})R^{22}$, —$N(R^{21})R^{22}$, $C(\!\!=\!\!O)R^{19}$, —$C(\!\!=\!\!O)OR^{20}$, —$C(\!\!=\!\!O)N(R^{21})R^{21}$, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy; and a 3-, 4-, 5-, 6- or 7-membered saturated or unsaturated heterocyclic ring containing 1, 2 or 3 heteroatoms or heteroatom groups selected from N, O, S, NO, SO and $SO_2$, as ring members, which may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy;

or two radicals $R^{10}$ bound on adjacent atoms together form a group selected from —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C(\!\!=\!\!O)O$—, —$C(\!\!=\!\!O)OCH_2$—, and —$O(CH_2)O$—, thus forming, together with the atoms to which they are bound, a 5- or 6-membered ring, where the hydrogen atoms of the above groups may be replaced by one or more substituents selected from halogen, methyl, halomethyl, hydroxyl, methoxy and halomethoxy or one or more $CH_2$ groups of the above groups may be replaced by a C=O group, where $R^{19}$, $R^{20}$, $R^{21}$ and $R^{22}$ have one of the general or in particular one of the preferred meanings given above.

More preferably, each $R^{10}$ is independently selected from the group consisting of halogen, cyano, $C_1$-$C_{10}$-alkyl which may be partially or fully halogenated and/or may be substituted by one or more radicals $R^{19}$, —$OR^{20}$, —$N(R^{21})R^{22}$, $C(\!\!=\!\!O)R^{19}$, —$C(\!\!=\!\!O)OR^{20}$, —$C(\!\!=\!\!O)N(R^{21})R^{22}$, phenyl which may be substituted by 1, 2, 3, 4 or 5 radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy; and a 3-, 4-, 5-, 6- or 7-membered saturated or unsaturated heterocyclic ring containing 1, 2 or 3 heteroatoms or heteroatom groups selected from N, O, S, NO, SO and $SO_2$, as ring members, which may be substituted by one or more radicals independently selected from halogen, cyano, nitro, $C_1$-$C_6$-alkyl, $C_1$-$C_6$-haloalkyl, $C_1$-$C_6$-alkoxy and $C_1$-$C_6$-haloalkoxy; where $R^{19}$, $R^{20}$, $R^{21}$ and $R^{22}$ have one of the general or in particular one of the preferred meanings given above.

Even more preferably, each $R^{10}$ is independently selected from the group consisting of halogen, $C_1$-$C_4$-alkyl, $C_1$-$C_4$-haloalkyl, $C_1$-$C_4$-alkoxy and $C_1$-$C_4$-haloalkoxy. In particular, each $R^{10}$ is independently selected from the group consisting of halogen, $C_1$-$C_4$-alkyl and $C_1$-$C_4$-haloalkyl and is specifically halogen, more specifically chlorine.

Preferably, $R^{11}$ and $R^{12}$ are, independently of each other and independently of each occurrence, selected from the group consisting of hydrogen, halogen, $C_1$-$C_6$-alkyl and $C_1$-$C_6$-haloalkyl. More preferably, $R^{11}$ and $R^{12}$ are, independently of each other and independently of each occurrence, selected from the group consisting of hydrogen, halogen and $C_1$-$C_6$-alkyl and in particular from the group consisting of hydrogen and halogen. Specifically, they are hydrogen.

Preferably, $R^{13}$ and $R^{14}$ are, independently of each other and independently of each occurrence, selected from $C_1$-$C_4$-alkyl and are in particular methyl.

Preferably, $R^{15}$ and $R^{16}$ are, independently of each other and independently of each occurrence, selected from the group consisting of $C_1$-$C_6$-alkyl, $C_1$-$C_6$-haloalkyl and phenyl which may be substituted by 1, 2, 3, 4, or 5 radicals $R^{10}$; where $R^{10}$ has one of the general or in particular one of the preferred meanings given above.

Preferably, each $R^{17}$ is independently selected from the group consisting of $C_1$-$C_6$-alkyl, $C_1$-$C_6$-haloalkyl, $C_3$-$C_8$-cycloalkyl, $C_3$-$C_8$-halocycloalkyl, phenyl and benzyl. More preferably, each $R^{17}$ is independently selected from the group consisting of $C_1$-$C_6$-alkyl, $C_1$-$C_6$-haloalkyl and phenyl and is in particular $C_1$-$C_4$-alkyl or $C_1$-$C_3$-haloalkyl.

Preferably, each $R^{18}$ is independently selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; —$C(\!\!=\!\!O)R^6$; —$C(\!\!=\!\!O)OR^7$; —$C(\!\!=\!\!O)N(R^8)R^9$; —$C(\!\!=\!\!S)R^6$; —$C(\!\!=\!\!S)OR^7$; —$C(\!\!=\!\!S)N(R^8)R^9$ and —$C(\!\!=\!\!NR^8)R^6$; where $R^6$, $R^7$, $R^8$ and $R^9$ have one of the general or in particular one of the preferred meanings given above.

More preferably, each $R^{18}$ is selected from the group consisting of hydrogen; $C_1$-$C_6$-alkyl which may be partially or fully halogenated and/or may be substituted by one or more, e.g. 1, 2, 3 or 4, preferably 1 or 2, more preferably 1, radicals $R^6$; —$C(\!\!=\!\!O)R^6$ and —$C(\!\!=\!\!O)N(R^8)R^9$; where $R^6$, $R^8$ and $R^9$ have one of the general or in particular one of the preferred meanings given above. Preferably, in this case, $R^6$ as a $C_1$-$C_6$-alkyl substituent, is selected from CN, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio and a 5- or 6-membered hetaryl ring containing 1, 2 or 3 heteroatoms selected from N, O and S as ring members and being optionally substituted by 1, 2 or 3 radicals $R^{10}$. In this case, $R^6$ as a CO substituent, is preferably selected from $C_1$-$C_6$-alkyl, $C_1$-$C_6$-haloalkyl, $C_1$-$C_6$-alkoxy and $C_1$-$C_6$-haloalkoxy. In this case, $R^8$ and $R^9$ are preferably selected from hydrogen and $C_1$-$C_6$-alkyl.

In particular, each $R^{18}$ is selected from the group consisting of hydrogen, $C_1$-$C_4$-alkyl, $C_1$-$C_4$-haloalkyl and —$C(\!\!=\!\!O)R^6$, and is specifically selected from the group consisting of hydrogen, $C_1$-$C_4$-alkyl and —$C(\!\!=\!\!O)R^6$, where $R^6$ has one of the general or in particular one of the preferred meanings given above and is specifically $C_1$-$C_4$-alkyl.

In case $R^{19}$ is a substituent on an alkyl, alkenyl or alkynyl group, it is preferably selected from the group consisting of cyano, $C_3$-$C_6$-cycloalkyl, $C_3$-$C_6$-halocycloalkyl, —$OR^{20}$, —$C(\!\!=\!\!O)N(R^{21})R^{22}$, —$C(\!\!=\!\!S)N(R^{21})R^{22}$, —$C(\!\!=\!\!O)OR^{20}$, —$C(\!\!=\!\!O)R^{20}$, phenyl which may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$; where $R^{10}$ is selected from halogen, cyano, $C_1$-$C_4$-alkyl, $C_1$-$C_4$-haloalkyl, $C_1$-$C_4$-alkoxy and $C_1$-$C_4$-haloalkoxy;

$R^{20}$ is selected from hydrogen, $C_1$-$C_4$-alkyl, $C_1$-$C_4$-haloalkyl, phenyl, benzyl, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$; and $R^{21}$ and $R^{22}$, independently of each other and independently of each occurrence, are selected from hydrogen, $C_1$-$C_4$-alkyl, $C_1$-$C_4$-haloalkyl, phenyl, benzyl, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$.

In case $R^{19}$ is a substituent on a cycloalkyl group, it is preferably selected from the group consisting of cyano, $C_1$-$C_4$-alkyl, $C_1$-$C_4$-haloalkyl, $C_3$-$C_6$-cycloalkyl, $C_3$-$C_6$-halocycloalkyl, —C(=O)N($R^{21}$)$R^{22}$, —C(=S)N($R^{21}$)$R^{22}$, —C(=O)O$R^{20}$, —C(=O)$R^{20}$, phenyl which may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$; where $R^{10}$ is selected from halogen, cyano, $C_1$-$C_4$-alkyl, $C_1$-$C_4$-haloalkyl, $C_1$-$C_4$-alkoxy and $C_1$-$C_4$-haloalkoxy;

$R^{20}$ is selected from hydrogen, $C_1$-$C_4$-alkyl, $C_1$-$C_4$-haloalkyl, phenyl, benzyl, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$; and $R^{21}$ and $R^{22}$, independently of each other and independently of each occurrence, are selected from hydrogen, $C_1$-$C_4$-alkyl, $C_1$-$C_4$-haloalkyl, phenyl, benzyl, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$.

In case $R^{19}$ is a substituent on a C(=O) group, it is preferably selected from the group consisting of hydrogen, $C_1$-$C_4$-alkyl, $C_1$-$C_4$-haloalkyl, $C_3$-$C_6$-cycloalkyl, $C_3$-$C_6$-halocycloalkyl, $C_3$-$C_6$-cycloalkyl-$C_1$-$C_4$-alkyl, phenyl which may be substituted by 1, 2, 3, 4 or 5 radicals $R^{10}$, benzyl which may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$; where $R^{10}$ is selected from halogen, cyano, $C_1$-$C_4$-alkyl, $C_1$-$C_4$-haloalkyl, $C_1$-$C_4$-alkoxy and $C_1$-$C_4$-haloalkoxy.

$R^{20}$ is preferably selected from the group consisting of hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_3$-$C_6$-cycloalkyl-$C_1$-$C_4$-alkyl, phenyl which may be substituted by 1, 2, 3, 4 or 5 radicals $R^{10}$, benzyl which may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$; where $R^{10}$ is selected from halogen, cyano, $C_1$-$C_4$-alkyl, $C_1$-$C_4$-haloalkyl, $C_1$-$C_4$-alkoxy and $C_1$-$C_4$-haloalkoxy.

$R^{21}$ and $R^{22}$, independently of each other and independently of each occurrence, are preferably selected from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_4$-alkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{10}$, benzyl which may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$; where $R^{10}$ is selected from halogen, cyano, $C_1$-$C_4$-alkyl, $C_1$-$C_4$-haloalkyl, $C_1$-$C_4$-alkoxy and $C_1$-$C_4$-haloalkoxy;

or $R^{21}$ and $R^{22}$, together with the nitrogen atom to which they are bound, may form a 5- or 6-membered saturated, partially unsaturated or aromatic heterocyclic ring which may additionally containing 1 or 2 further heteroatoms or heteroatom groups selected from N, O, S, NO, SO and $SO_2$, as ring members, where the heterocyclic ring may be substituted by one or more radicals selected from halogen, $C_1$-$C_6$-alkyl, $C_1$-$C_6$-haloalkyl, $C_1$-$C_6$-alkoxy and $C_1$-$C_6$-haloalkoxy.

One particularly preferred embodiment of the invention refers to compounds of the formula I-1

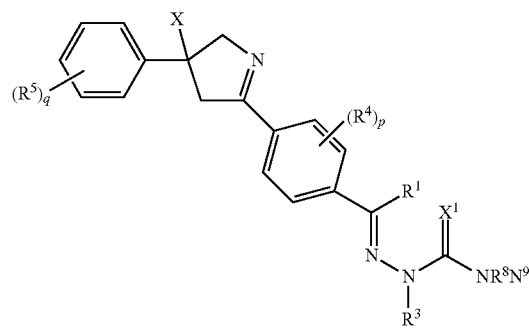

(I-1)

where $X^1$ is O or S and X, $R^1$, $R^3$, $R^4$, $R^5$, $R^8$, $R^9$, p and q have one of the above-given general or, in particular, one of the above-given preferred meanings.

In particular, the invention relates to compounds I-1, where $X^1$ is O or S;

p is 0, 1 or 2;

q is 0, 1, 2 or 3; and

X, $R^1$, $R^3$, $R^4$, $R^5$, $R^8$ and $R^9$ have one of the above-given general or, in particular, one of the above-given preferred meanings.

In compounds of the formula I-1, $R^1$ is preferably hydrogen.

In compounds of the formula I-1, $R^3$ is preferably hydrogen.

In compounds of the formula I-1, $R^4$ is preferably halogen, cyano, $C_1$-$C_4$-alkyl or $C_1$-$C_4$-haloalkyl, more preferably halogen or $C_1$-$C_4$-alkyl and specifically chlorine or methyl.

In compounds of the formula I-1, $R^5$ is preferably halogen or $C_1$-$C_4$-haloalkyl, more preferably chlorine or $CF_3$ and specifically chlorine.

In compounds of the formula I-1, $R^8$ is preferably selected from hydrogen and $C_1$-$C_6$-alkyl which may be partially or fully halogenated and/or may be substituted by one or more radicals $R^{19}$, where $R^{19}$ has one of the above-given general or, in particular, one of the above-given preferred meanings; $R^8$ is specifically hydrogen.

In compounds of the formula I-1, $R^9$ is preferably is selected from hydrogen, $C_1$-$C_6$-alkyl which may be partially or fully halogenated and/or may be substituted by one or more radicals $R^{19}$, $C_3$-$C_6$-cycloalkyl, $C_3$-$C_6$-halocycloalkyl, $C_3$-$C_6$-cycloalkyl-$C_1$-$C_4$-alkyl and $C_3$-$C_6$-halocycloalkyl-$C_1$-$C_4$-alkyl, and more preferably from hydrogen, $C_1$-$C_6$-alkyl, $C_1$-$C_4$-haloalkyl, $C_3$-$C_6$-cycloalkyl and $C_3$-$C_6$-cycloalkyl-methyl.

In compounds of the formula I-1, X is preferably selected from $CF_3$, $CHF_2$ and $CF_2Cl$ and is more preferably $CF_3$.

Particularly preferably, in compounds I-1X $X^1$ is O or S;
X is $CF_3$;
$R^1$ is hydrogen;
$R^3$ is hydrogen;
$R^4$ is halogen or $C_1$-$C_4$-alkyl, preferably chlorine or methyl;
$R^5$ is chlorine or $CF_3$, preferably chlorine;
$R^8$ is hydrogen;
$R^9$ is selected from hydrogen, $C_1$-$C_6$-alkyl which may be partially or fully halogenated and/or may be substituted by one or more radicals $R^{19}$, $C_3$-$C_6$-cycloalkyl, $C_3$-$C_6$-halocycloalkyl, $C_3$-$C_6$-cycloalkyl-$C_1$-$C_4$-alkyl and $C_3$-$C_6$-halocycloalkyl-$C_1$-$C_4$-alkyl, preferably from hydrogen, $C_1$-$C_6$-alkyl, $C_1$-$C_4$-haloalkyl, $C_3$-$C_6$-cycloalkyl and $C_3$-$C_6$-cycloalkyl-methyl;
p is 0, 1 or 2, preferably 1; and
q is 0, 1, 2 or 3, preferably 2.

As already mentioned, a preferred embodiment of the compounds of the present invention is enantiomer I-A

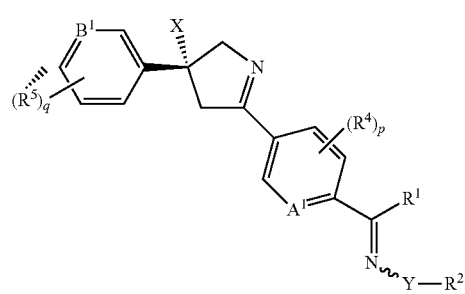

I-A wherein the variables have one of the above-given general, or in particular one of the above-given preferred meanings. Preferably, X in compounds I-A is $CF_3$.

A more preferred embodiment relates to compounds I-A.1

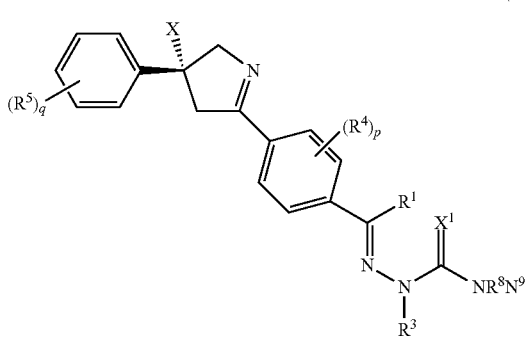

(I-A.1)

where
$X^1$ is O or S;
p is 0, 1 or 2;
q is 0, 1, 2 or 3; and

X, $R^1$, $R^3$, $R^4$, $R^5$, $R^8$ and $R^9$ have one of the above-given general or, in particular, one of the above-given preferred meanings.

In compounds of the formula I-A.1, $R^1$ is preferably hydrogen.

In compounds of the formula I-A.1, $R^3$ is preferably hydrogen.

In compounds of the formula I-A.1, $R^4$ is preferably halogen, cyano, $C_1$-$C_4$-alkyl or $C_1$-$C_4$-haloalkyl, more preferably halogen or $C_1$-$C_4$-alkyl and specifically chlorine or methyl.

In compounds of the formula I-A.1, $R^5$ is preferably halogen or $C_1$-$C_4$-haloalkyl, more preferably chlorine or $CF_3$ and specifically chlorine.

In compounds of the formula I-A.1, $R^8$ is preferably selected from hydrogen and $C_1$-$C_6$-alkyl which may be partially or fully halogenated and/or may be substituted by one or more radicals $R^{19}$, where $R^{19}$ has one of the above-given general or, in particular, one of the above-given preferred meanings; $R^8$ is specifically hydrogen.

In compounds of the formula I-A.1, $R^9$ is preferably is selected from hydrogen, $C_1$-$C_6$-alkyl which may be partially or fully halogenated and/or may be substituted by one or more radicals $R^{19}$, $C_3$-$C_6$-cycloalkyl, $C_3$-$C_6$-halocycloalkyl, $C_3$-$C_6$-cycloalkyl-$C_1$-$C_4$-alkyl and $C_3$-$C_6$-halocycloalkyl-$C_1$-$C_4$-alkyl, and more preferably from hydrogen, $C_1$-$C_6$-alkyl, $C_1$-$C_4$-haloalkyl, $C_3$-$C_6$-cycloalkyl and $C_3$-$C_6$-cycloalkyl-methyl.

In compounds of the formula I-A.1, X is preferably selected from $CF_3$, $CHF_2$ and $CF_2Cl$ and is more preferably $CF_3$.

Particularly preferably, in compounds I-A.1

$X^1$ is O or S;
X is $CF_3$;
$R^1$ is hydrogen;
$R^3$ is hydrogen;
$R^4$ is halogen or $C_1$-$C_4$-alkyl, preferably chlorine or methyl;
$R^5$ is chlorine or $CF_3$, preferably chlorine;
$R^8$ is hydrogen;
$R^9$ is selected from hydrogen, $C_1$-$C_6$-alkyl which may be partially or fully halogenated and/or may be substituted by one or more radicals $R^{19}$, $C_3$-$C_6$-cycloalkyl, $C_3$-$C_6$-halocycloalkyl, $C_3$-$C_6$-cycloalkyl-$C_1$-$C_4$-alkyl and $C_3$-$C_6$-halocycloalkyl-$C_1$-$C_4$-alkyl, preferably from hydrogen, $C_1$-$C_6$-alkyl, $C_1$-$C_4$-haloalkyl, $C_3$-$C_6$-cycloalkyl and $C_3$-$C_6$-cycloalkyl-methyl;
p is 0, 1 or 2, preferably 1; and
q is 0, 1, 2 or 3, preferably 2.

Examples of preferred compounds are compounds of the following formulae I.1 to I.66, where the variables have one of the general or preferred meanings given above. Examples of preferred compounds which are represented by the formulae I.1 to I.66 are the individual compounds compiled in the tables 1 to 24420 below, where the variables Y and $R^2$ have the meanings given in one row of table A. Moreover, the meanings mentioned for the individual variables in the tables are per se, independently of the combination in which they are mentioned, a particularly preferred embodiment of the substituents in question.

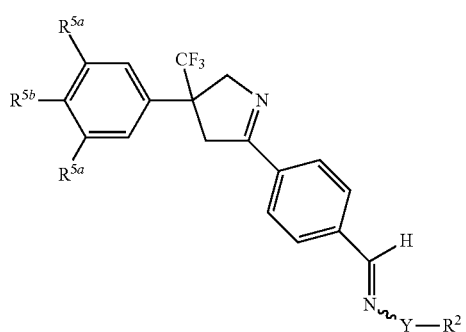 I.1
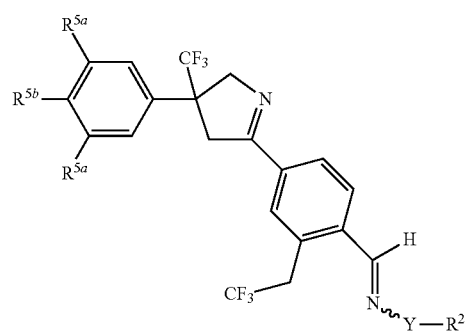 I.6
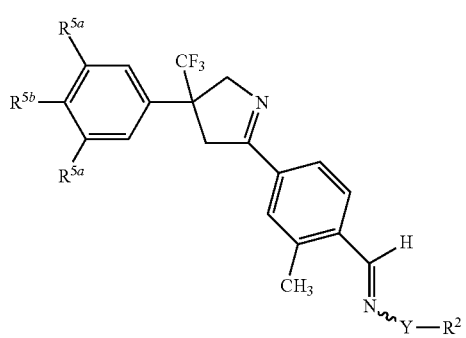 I.2
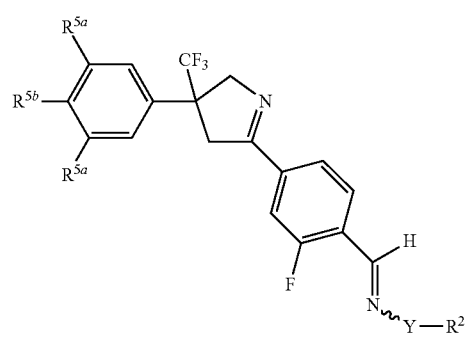 I.7
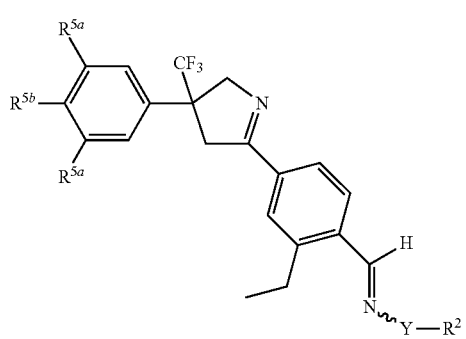 I.3
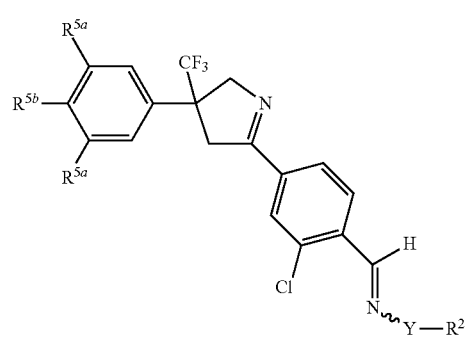 I.8
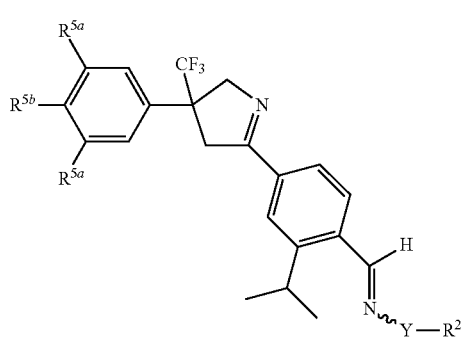 I.4
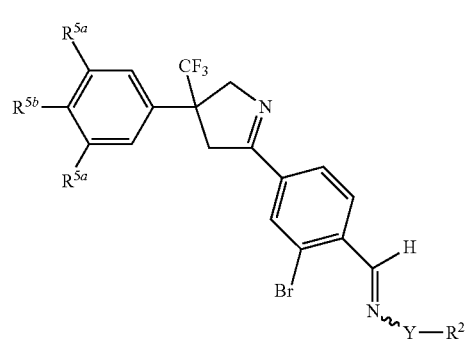 I.9
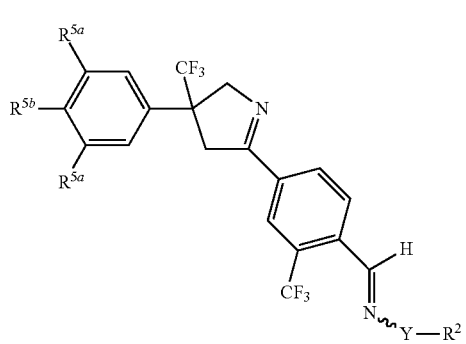 I.5
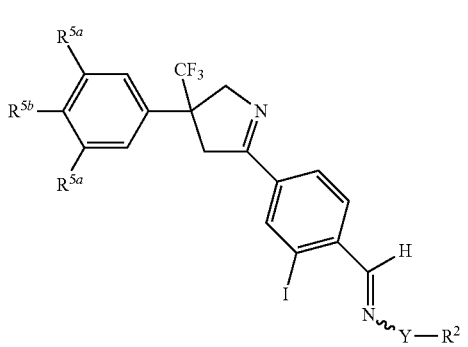 I.10

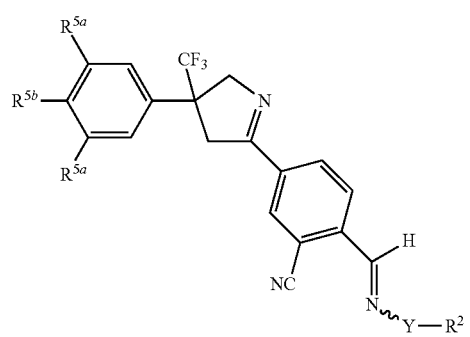
I.11
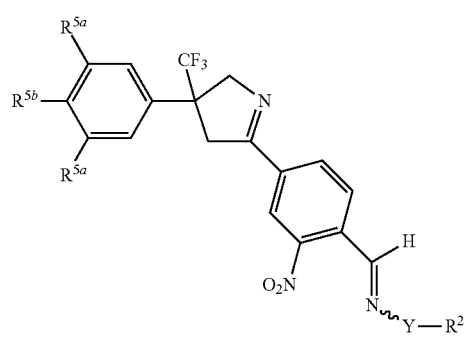
I.12
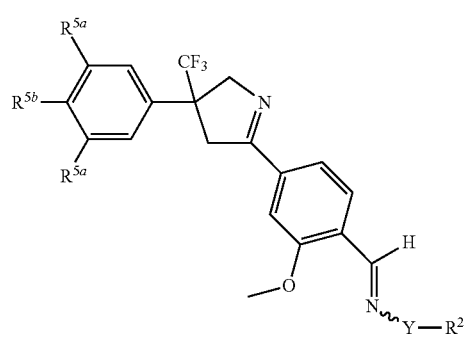
I.13
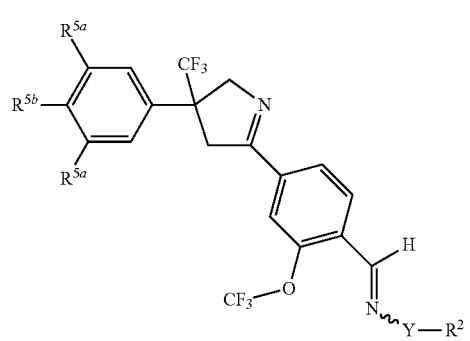
I.14
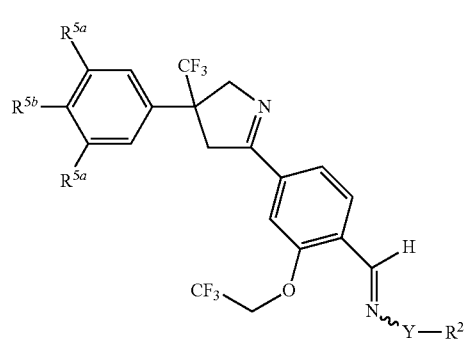
I.15
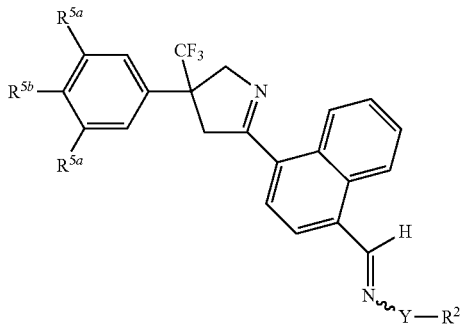
I.16
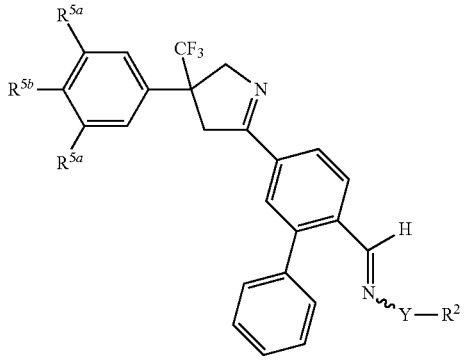
I.17
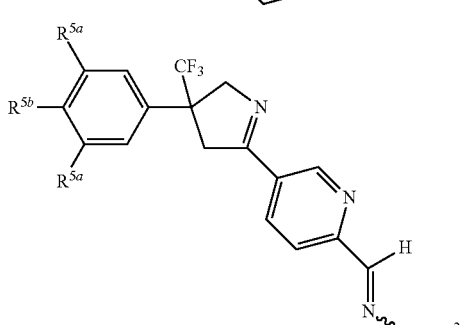
I.18
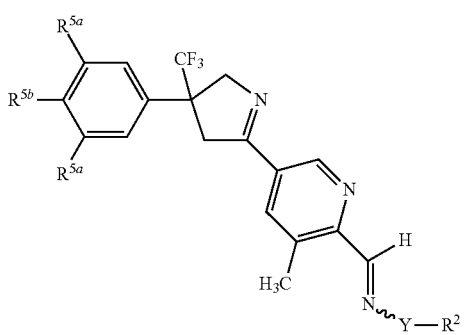
I.19
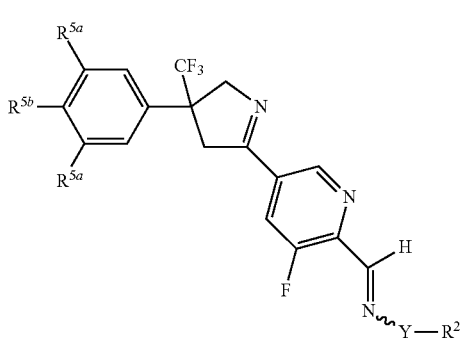
I.20

-continued
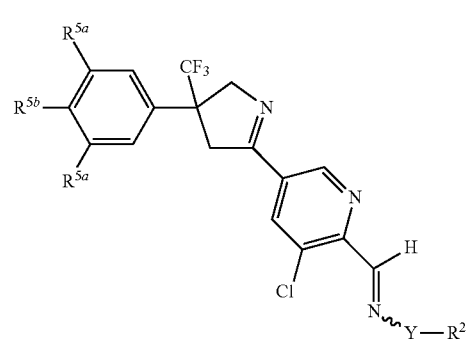
I.21
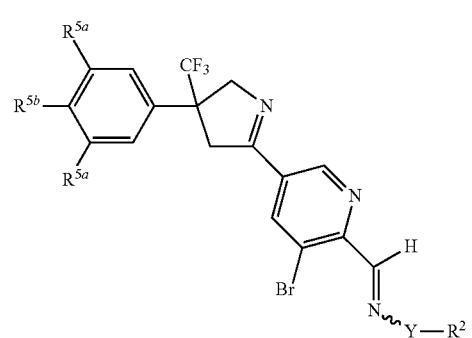
I.22
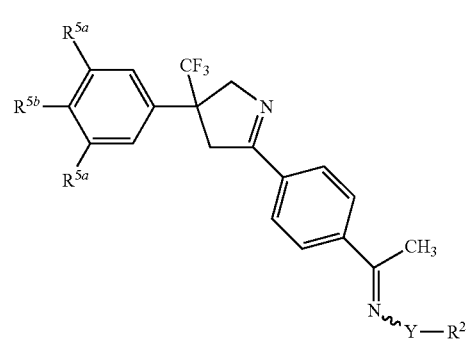
I.23
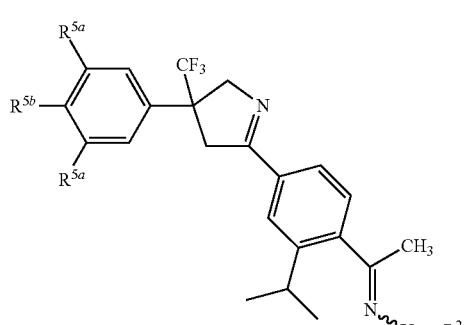
I.24
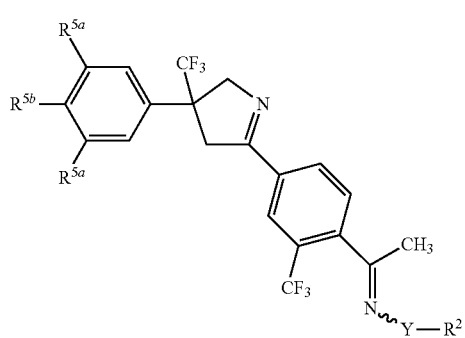
I.25
-continued
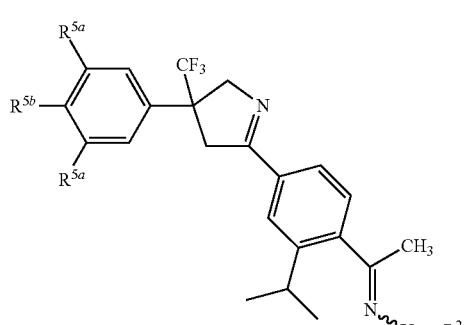
I.26
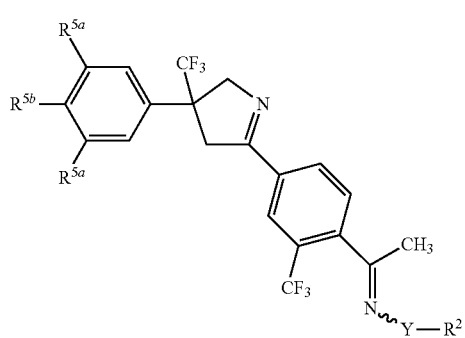
I.27
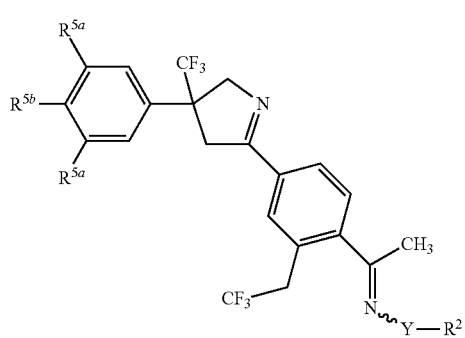
I.28
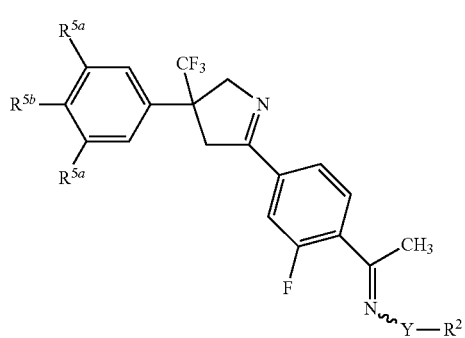
I.29
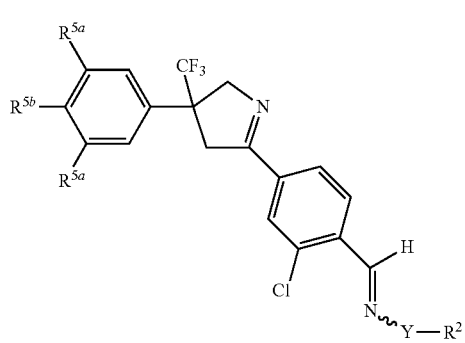
I.30

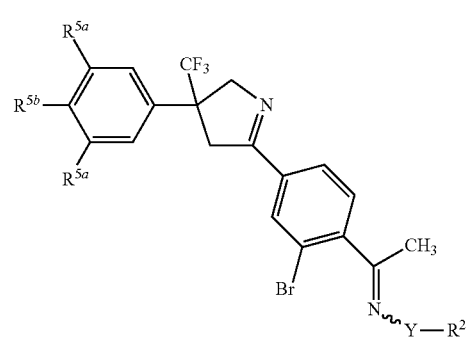
I.31
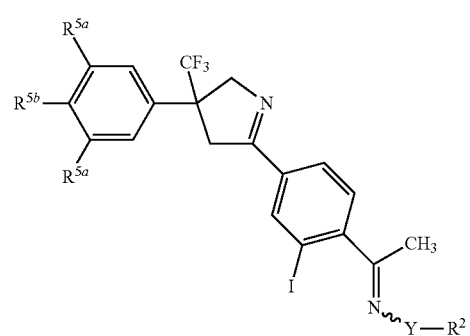
I.32
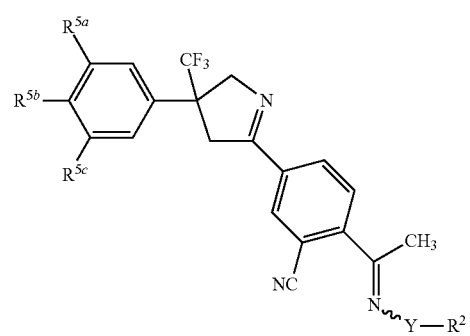
I.33
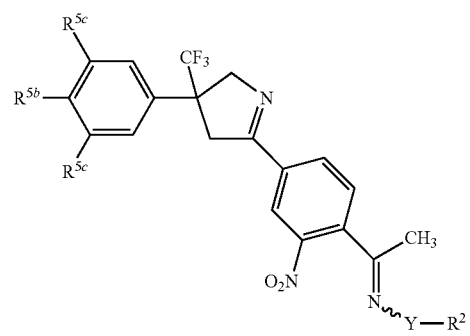
I.34
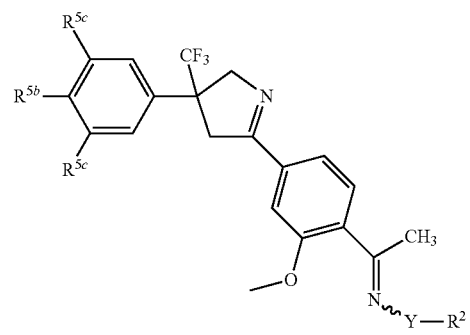
I.35
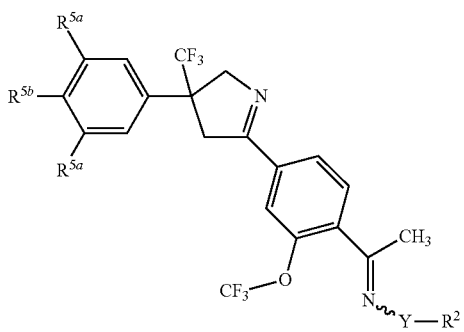
I.36
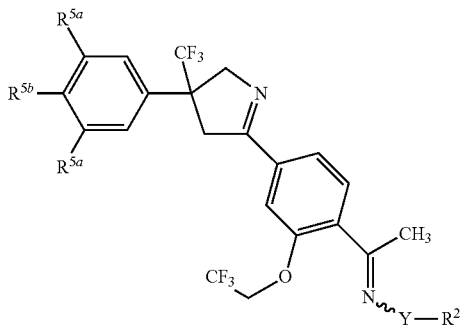
I.37
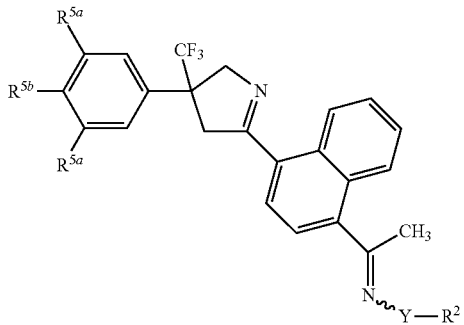
I.38
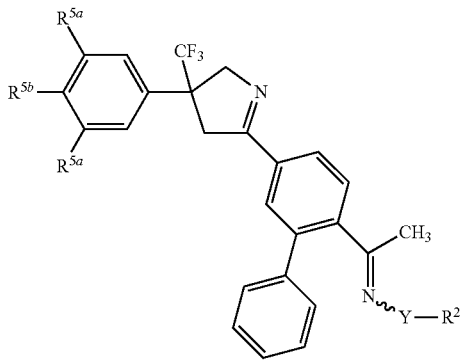
I.39
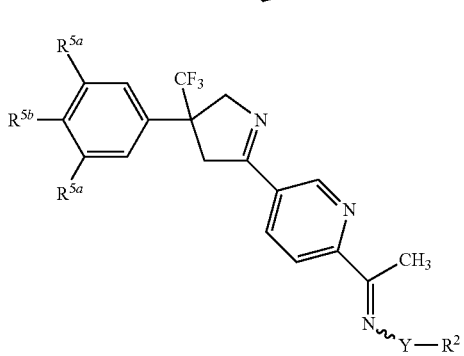
I.40

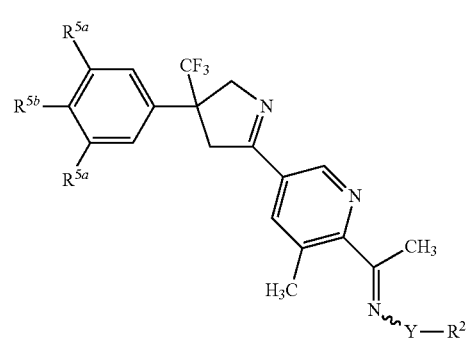 I.41
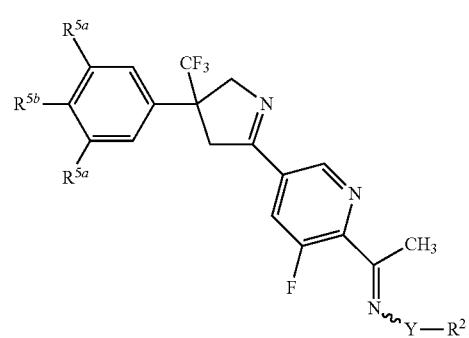 I.42
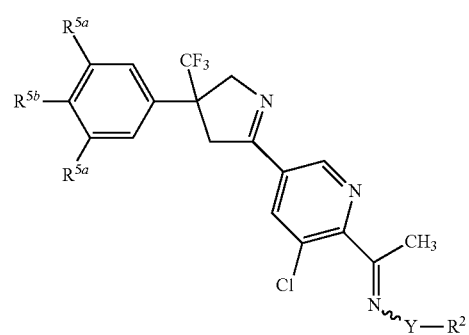 I.43
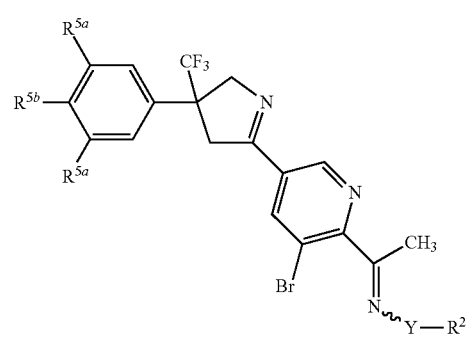 I.44
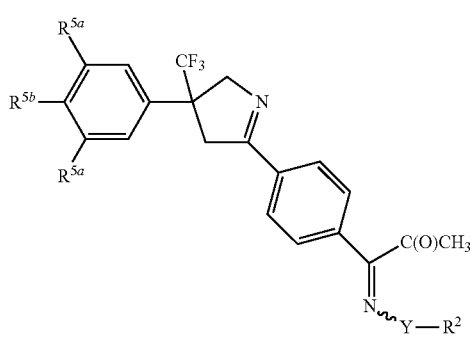 I.45
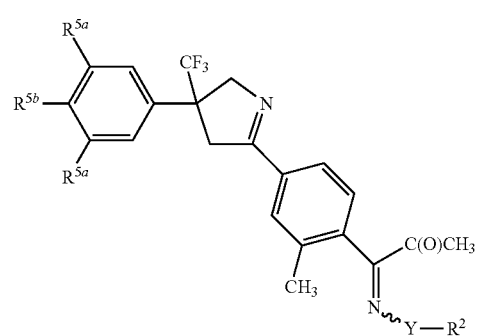 I.46
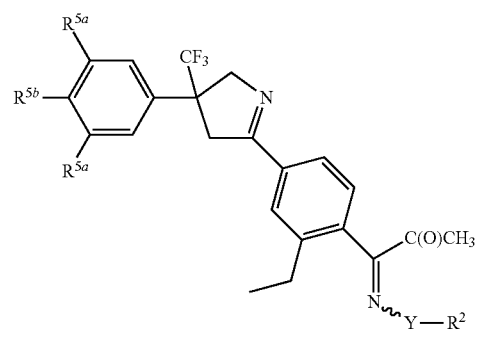 I.47
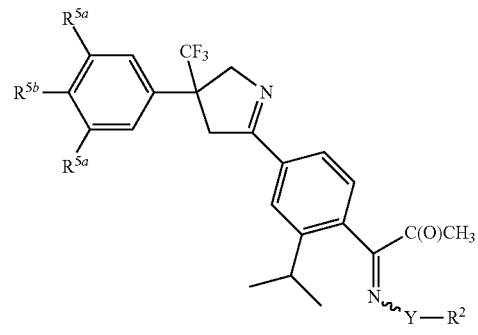 I.48
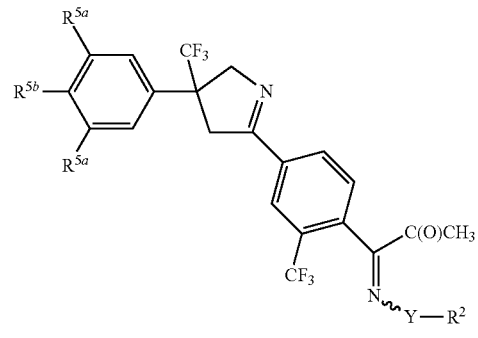 I.49
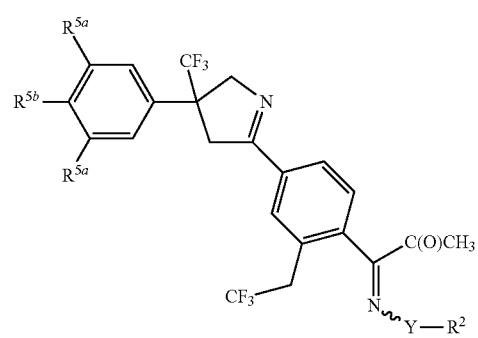 I.50

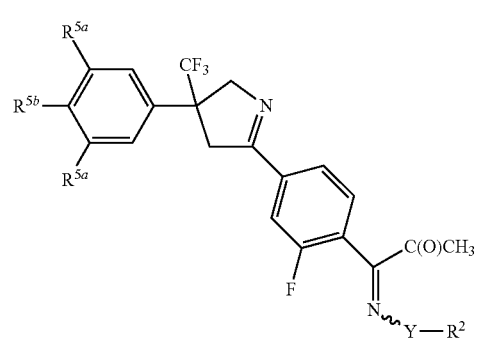 I.51
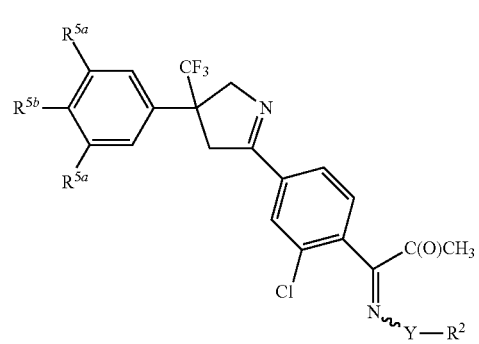 I.52
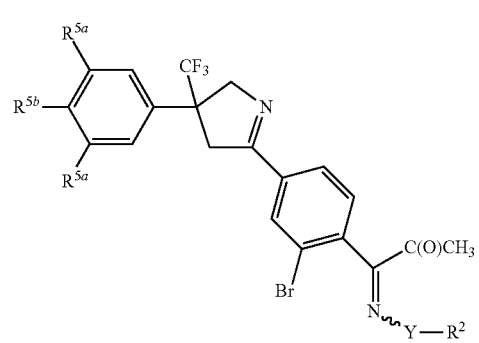 I.53
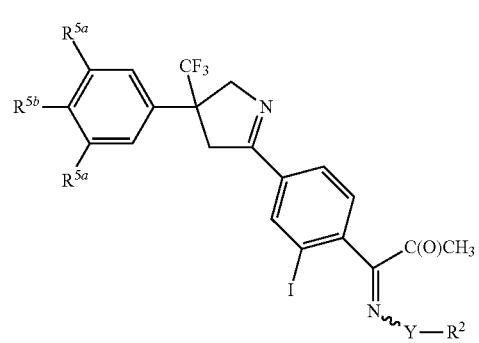 I.54
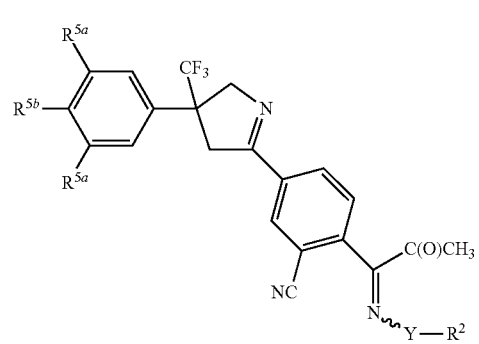 I.55
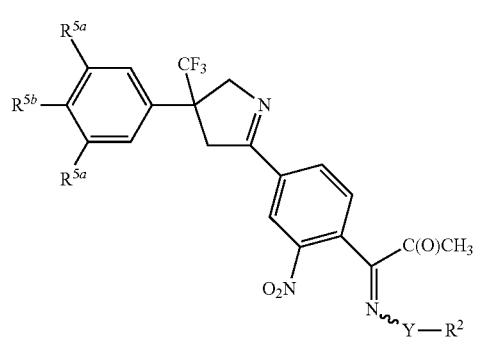 I.56
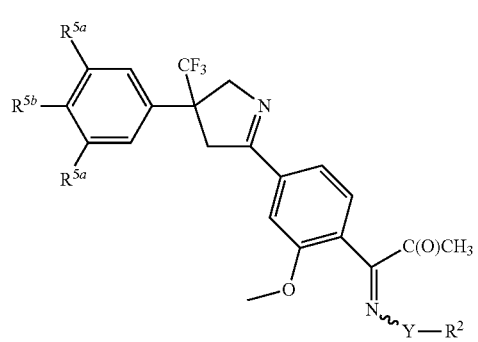 I.57
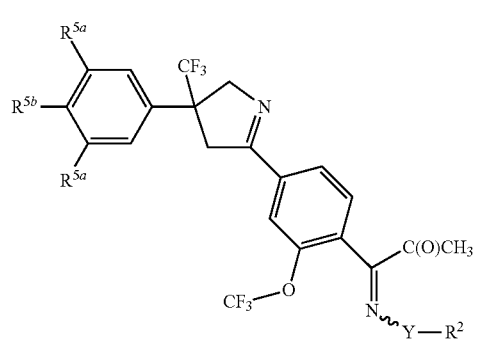 I.58
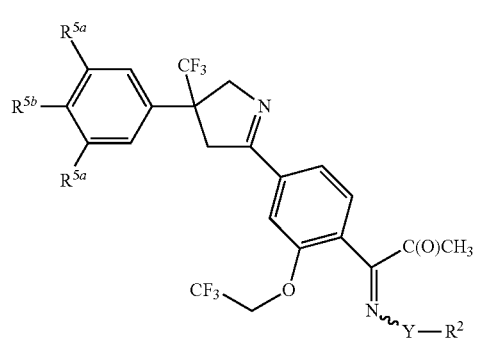 I.59
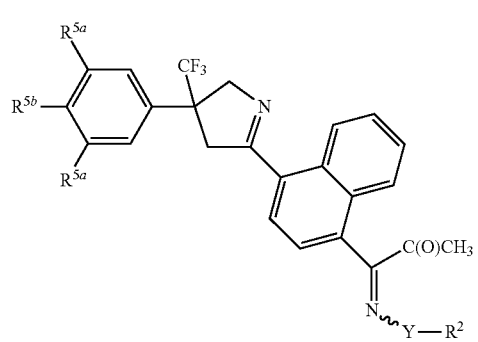 I.60

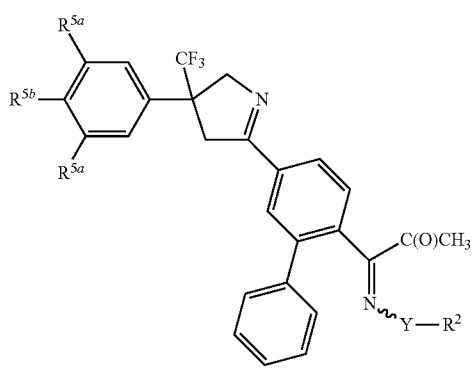
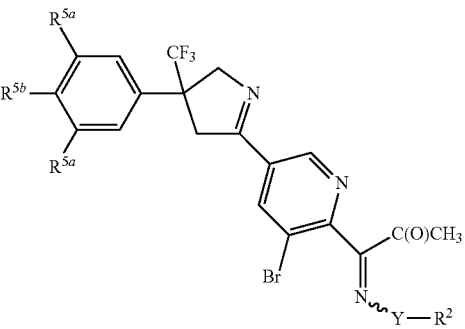

Table 1
Compounds of the formula I.1 in which $R^{5a}$ and $R^{5c}$ are chlorine, $R^{5b}$ is H and the combination of Y and $R^2$ for a compound corresponds in each case to one row of Table A.

Table 2
Compounds of the formula I.1 in which $R^{5a}$ and $R^{5c}$ are bromine, $R^{5b}$ is H and the combination of Y and $R^2$ for a compound corresponds in each case to one row of Table A.

Table 3
Compounds of the formula I.1 in which $R^{5a}$ and $R^{5c}$ are fluorine, $R^{5b}$ is H and the combination of Y and $R^2$ for a compound corresponds in each case to one row of Table A.

Table 4
Compounds of the formula I.1 in which $R^{5a}$ and $R^{5c}$ are methyl, $R^{5b}$ is H and the combination of Y and $R^2$ for a compound corresponds in each case to one row of Table A.

Table 5
Compounds of the formula I.1 in which $R^{5a}$ and $R^{5c}$ are $CF_3$, $R^{5b}$ is H and the combination of Y and $R^2$ for a compound corresponds in each case to one row of Table A.

Table 6
Compounds of the formula I.1 in which $R^{5a}$ is chlorine and $R^{5b}$ and $R^{5c}$ are H and the combination of Y and $R^2$ for a compound corresponds in each case to one row of Table A.

Table 7
Compounds of the formula I.1 in which $R^{5a}$ is $CF_3$ and $R^{5b}$ and $R^{5c}$ are H and the combination of Y and $R^2$ for a compound corresponds in each case to one row of Table A.

Table 8
Compounds of the formula I.1 in which $R^{5a}$, $R^{5b}$ and $R^{5c}$ are chlorine and the combination of Y and $R^2$ for a compound corresponds in each case to one row of Table A.

Table 9
Compounds of the formula I.1 in which $R^{5a}$, $R^{5b}$ and $R^{5c}$ are fluorine and the combination of Y and $R^2$ for a compound corresponds in each case to one row of Table A.

Table 10
Compounds of the formula I.1 in which $R^{5a}$ and $R^{5c}$ are chlorine and $R^{5b}$ is fluorine and the combination of Y and $R^2$ for a compound corresponds in each case to one row of Table A.

Tables 11 to 20
Compounds of the formula I.2 in which the combination of $R^{5a}$, $R^{5b}$ and $R^{5c}$ is as defined in Tables 1 to 10 and the combination of Y and $R^2$ for a compound corresponds in each case to one row of Table A.

Tables 21 to 30
Compounds of the formula I.3 in which the combination of $R^{5a}$, $R^{5b}$ and $R^{5c}$ is as defined in Tables 1 to 10 and the combination of Y and $R^2$ for a compound corresponds in each case to one row of Table A.

Tables 31 to 40
Compounds of the formula I.4 in which the combination of $R^{5a}$, $R^{5b}$ and $R^{5c}$ is as defined in Tables 1 to 10 and the combination of Y and $R^2$ for a compound corresponds in each case to one row of Table A.

Tables 41 to 50
Compounds of the formula I.5 in which the combination of $R^{5a}$, $R^{5b}$ and $R^{5c}$ is as defined in Tables 1 to 10 and the combination of Y and $R^2$ for a compound corresponds in each case to one row of Table A.

Tables 51 to 60
Compounds of the formula I.6 in which the combination of $R^{5a}$, $R^{5b}$ and $R^{5c}$ is as defined in Tables 1 to 10 and the combination of Y and $R^2$ for a compound corresponds in each case to one row of Table A.

Tables 61 to 70
Compounds of the formula I.7 in which the combination of $R^{5a}$, $R^{5b}$ and $R^{5c}$ is as defined in Tables 1 to 10 and the combination of Y and $R^2$ for a compound corresponds in each case to one row of Table A.

Tables 71 to 80
Compounds of the formula I.8 in which the combination of $R^{5a}$, $R^{5b}$ and $R^{5c}$ is as defined in Tables 1 to 10 and the combination of Y and $R^2$ for a compound corresponds in each case to one row of Table A.

Tables 81 to 90
Compounds of the formula I.9 in which the combination of $R^{5a}$, $R^{5b}$ and $R^{5c}$ is as defined in Tables 1 to 10 and the combination of Y and $R^2$ for a compound corresponds in each case to one row of Table A.

Tables 91 to 100
Compounds of the formula I.10 in which the combination of $R^{5a}$, $R^{5b}$ and $R^{5c}$ is as defined in Tables 1 to 10 and the combination of Y and $R^2$ for a compound corresponds in each case to one row of Table A.

Tables 101 to 110
Compounds of the formula I.11 in which the combination of $R^{5a}$, $R^{5b}$ and $R^{5c}$ is as defined in Tables 1 to 10 and the combination of Y and $R^2$ for a compound corresponds in each case to one row of Table A.

Tables 111 to 120
Compounds of the formula I.12 in which the combination of $R^{5a}$, $R^{5b}$ and $R^{5c}$ is as defined in Tables 1 to 10 and the combination of Y and $R^2$ for a compound corresponds in each case to one row of Table A.

Tables 121 to 130
Compounds of the formula I.13 in which the combination of $R^{5a}$, $R^{5b}$ and $R^{5c}$ is as defined in Tables 1 to 10 and the combination of Y and $R^2$ for a compound corresponds in each case to one row of Table A.

Tables 131 to 140
Compounds of the formula I.14 in which the combination of $R^{5a}$, $R^{5b}$ and $R^{5c}$ is as defined in Tables 1 to 10 and the combination of Y and $R^2$ for a compound corresponds in each case to one row of Table A.

Tables 141 to 150
Compounds of the formula I.15 in which the combination of $R^{5a}$, $R^{5b}$ and $R^{5c}$ is as defined in Tables 1 to 10 and the combination of Y and $R^2$ for a compound corresponds in each case to one row of Table A.

Tables 151 to 160
Compounds of the formula I.16 in which the combination of $R^{5a}$, $R^{5b}$ and $R^{5c}$ is as defined in Tables 1 to 10 and the combination of Y and $R^2$ for a compound corresponds in each case to one row of Table A.

Tables 161 to 170
Compounds of the formula I.17 in which the combination of $R^{5a}$, $R^{5b}$ and $R^{5c}$ is as defined in Tables 1 to 10 and the combination of Y and $R^2$ for a compound corresponds in each case to one row of Table A.

Tables 171 to 180
Compounds of the formula I.18 in which the combination of $R^{5a}$, $R^{5b}$ and $R^{5c}$ is as defined in Tables 1 to 10 and the combination of Y and $R^2$ for a compound corresponds in each case to one row of Table A.

Tables 181 to 190
Compounds of the formula I.19 in which the combination of $R^{5a}$, $R^{5b}$ and $R^{5c}$ is as defined in Tables 1 to 10 and the combination of Y and $R^2$ for a compound corresponds in each case to one row of Table A.

Tables 191 to 200
Compounds of the formula I.20 in which the combination of $R^{5a}$, $R^{5b}$ and $R^{5c}$ is as defined in Tables 1 to 10 and the combination of Y and $R^2$ for a compound corresponds in each case to one row of Table A.

Tables 201 to 210
Compounds of the formula I.21 in which the combination of $R^{5a}$, $R^{5b}$ and $R^{5c}$ is as defined in Tables 1 to 10 and the combination of Y and $R^2$ for a compound corresponds in each case to one row of Table A.

Tables 211 to 220
Compounds of the formula I.22 in which the combination of $R^{5a}$, $R^{5b}$ and $R^{5c}$ is as defined in Tables 1 to 10 and the combination of Y and $R^2$ for a compound corresponds in each case to one row of Table A.

Tables 221 to 230
Compounds of the formula I.23 in which the combination of $R^{5a}$, $R^{5b}$ and $R^{5c}$ is as defined in Tables 1 to 10 and the combination of Y and $R^2$ for a compound corresponds in each case to one row of Table A.

Tables 231 to 240
Compounds of the formula I.24 in which the combination of $R^{5a}$, $R^{5b}$ and $R^{5c}$ is as defined in Tables 1 to 10 and the combination of Y and $R^2$ for a compound corresponds in each case to one row of Table A.

Tables 241 to 250
Compounds of the formula I.25 in which the combination of $R^{5a}$, $R^{5b}$ and $R^{5c}$ is as defined in Tables 1 to 10 and the combination of Y and $R^2$ for a compound corresponds in each case to one row of Table A.

Tables 251 to 260
Compounds of the formula I.26 in which the combination of $R^{5a}$, $R^{5b}$ and $R^{5c}$ is as defined in Tables 1 to 10 and the combination of Y and $R^2$ for a compound corresponds in each case to one row of Table A.

Tables 261 to 270
Compounds of the formula I.27 in which the combination of $R^{5a}$, $R^{5b}$ and $R^{5c}$ is as defined in Tables 1 to 10 and the combination of Y and $R^2$ for a compound corresponds in each case to one row of Table A.

Tables 271 to 280
Compounds of the formula I.28 in which the combination of $R^{5a}$, $R^{5b}$ and $R^{5c}$ is as defined in Tables 1 to 10 and the combination of Y and $R^2$ for a compound corresponds in each case to one row of Table A.

Tables 281 to 290
Compounds of the formula I.29 in which the combination of $R^{5a}$, $R^{5b}$ and $R^{5c}$ is as defined in Tables 1 to 10 and the combination of Y and $R^2$ for a compound corresponds in each case to one row of Table A.

Tables 291 to 300
Compounds of the formula I.30 in which the combination of $R^{5a}$, $R^{5b}$ and $R^{5c}$ is as defined in Tables 1 to 10 and the combination of Y and $R^2$ for a compound corresponds in each case to one row of Table A.
Tables 301 to 310
Compounds of the formula I.31 in which the combination of $R^{5a}$, $R^{5b}$ and $R^{5c}$ is as defined in Tables 1 to 10 and the combination of Y and $R^2$ for a compound corresponds in each case to one row of Table A.
Tables 311 to 320
Compounds of the formula I.32 in which the combination of $R^{5a}$, $R^{5b}$ and $R^{5c}$ is as defined in Tables 1 to 10 and the combination of Y and $R^2$ for a compound corresponds in each case to one row of Table A.
Tables 321 to 330
Compounds of the formula I.33 in which the combination of $R^{5a}$, $R^{5b}$ and $R^{5c}$ is as defined in Tables 1 to 10 and the combination of Y and $R^2$ for a compound corresponds in each case to one row of Table A.
Tables 331 to 340
Compounds of the formula I.34 in which the combination of $R^{5a}$, $R^{5b}$ and $R^{5c}$ is as defined in Tables 1 to 10 and the combination of Y and $R^2$ for a compound corresponds in each case to one row of Table A.
Tables 341 to 350
Compounds of the formula I.35 in which the combination of $R^{5a}$, $R^{5b}$ and $R^{5c}$ is as defined in Tables 1 to 10 and the combination of Y and $R^2$ for a compound corresponds in each case to one row of Table A.
Tables 351 to 360
Compounds of the formula I.36 in which the combination of $R^{5a}$, $R^{5b}$ and $R^{5c}$ is as defined in Tables 1 to 10 and the combination of Y and $R^2$ for a compound corresponds in each case to one row of Table A.
Tables 361 to 370
Compounds of the formula I.37 in which the combination of $R^{5a}$, $R^{5b}$ and $R^{5c}$ is as defined in Tables 1 to 10 and the combination of Y and $R^2$ for a compound corresponds in each case to one row of Table A.
Tables 371 to 380
Compounds of the formula I.38 in which the combination of $R^{5a}$, $R^{5b}$ and $R^{5c}$ is as defined in Tables 1 to 10 and the combination of Y and $R^2$ for a compound corresponds in each case to one row of Table A.
Tables 381 to 390
Compounds of the formula I.39 in which the combination of $R^{5a}$, $R^{5b}$ and $R^{5c}$ is as defined in Tables 1 to 10 and the combination of Y and $R^2$ for a compound corresponds in each case to one row of Table A.
Tables 391 to 400
Compounds of the formula I.40 in which the combination of $R^{5a}$, $R^{5b}$ and $R^{5c}$ is as defined in Tables 1 to 10 and the combination of Y and $R^2$ for a compound corresponds in each case to one row of Table A.
Tables 401 to 410
Compounds of the formula I.41 in which the combination of $R^{5a}$, $R^{5b}$ and $R^{5c}$ is as defined in Tables 1 to 10 and the combination of Y and $R^2$ for a compound corresponds in each case to one row of Table A.
Tables 411 to 420
Compounds of the formula I.42 in which the combination of $R^{5a}$, $R^{5b}$ and $R^{5c}$ is as defined in Tables 1 to 10 and the combination of Y and $R^2$ for a compound corresponds in each case to one row of Table A.
Tables 421 to 430
Compounds of the formula I.43 in which the combination of $R^{5a}$, $R^{5b}$ and $R^{5c}$ is as defined in Tables 1 to 10 and the combination of Y and $R^2$ for a compound corresponds in each case to one row of Table A.
Tables 431 to 440
Compounds of the formula I.44 in which the combination of $R^{5a}$, $R^{5b}$ and $R^{5c}$ is as defined in Tables 1 to 10 and the combination of Y and $R^2$ for a compound corresponds in each case to one row of Table A.
Tables 441 to 450
Compounds of the formula I.45 in which the combination of $R^{5a}$, $R^{5b}$ and $R^{5c}$ is as defined in Tables 1 to 10 and the combination of Y and $R^2$ for a compound corresponds in each case to one row of Table A.
Tables 451 to 460
Compounds of the formula I.46 in which the combination of $R^{5a}$, $R^{5b}$ and $R^{5c}$ is as defined in Tables 1 to 10 and the combination of Y and $R^2$ for a compound corresponds in each case to one row of Table A.
Tables 461 to 470
Compounds of the formula I.47 in which the combination of $R^{5a}$, $R^{5b}$ and $R^{5c}$ is as defined in Tables 1 to 10 and the combination of Y and $R^2$ for a compound corresponds in each case to one row of Table A.
Tables 471 to 480
Compounds of the formula I.48 in which the combination of $R^{5a}$, $R^{5b}$ and $R^{5c}$ is as defined in Tables 1 to 10 and the combination of Y and $R^2$ for a compound corresponds in each case to one row of Table A.
Tables 481 to 490
Compounds of the formula I.49 in which the combination of $R^{5a}$, $R^{5b}$ and $R^{5c}$ is as defined in Tables 1 to 10 and the combination of Y and $R^2$ for a compound corresponds in each case to one row of Table A.
Tables 491 to 500
Compounds of the formula I.50 in which the combination of $R^{5a}$, $R^{5b}$ and $R^{5c}$ is as defined in Tables 1 to 10 and the combination of Y and $R^2$ for a compound corresponds in each case to one row of Table A.
Tables 501 to 510
Compounds of the formula I.51 in which the combination of $R^{5a}$, $R^{5b}$ and $R^{5c}$ is as defined in Tables 1 to 10 and the combination of Y and $R^2$ for a compound corresponds in each case to one row of Table A.
Tables 511 to 520
Compounds of the formula I.52 in which the combination of $R^{5a}$, $R^{5b}$ and $R^{5c}$ is as defined in Tables 1 to 10 and the combination of Y and $R^2$ for a compound corresponds in each case to one row of Table A.
Tables 521 to 530
Compounds of the formula I.53 in which the combination of $R^{5a}$, $R^{5b}$ and $R^{5c}$ is as defined in Tables 1 to 10 and the combination of Y and $R^2$ for a compound corresponds in each case to one row of Table A.
Tables 531 to 540
Compounds of the formula I.54 in which the combination of $R^{5a}$, $R^{5b}$ and $R^{5c}$ is as defined in Tables 1 to 10 and the combination of Y and $R^2$ for a compound corresponds in each case to one row of Table A.
Tables 541 to 550
Compounds of the formula I.55 in which the combination of $R^{5a}$, $R^{5b}$ and $R^{5c}$ is as defined in Tables 1 to 10 and the combination of Y and $R^2$ for a compound corresponds in each case to one row of Table A.

Tables 551 to 560

Compounds of the formula I.56 in which the combination of $R^{5a}$, $R^{5b}$ and $R^{5c}$ is as defined in Tables 1 to 10 and the combination of Y and $R^2$ for a compound corresponds in each case to one row of Table A.

Tables 561 to 570

Compounds of the formula I.57 in which the combination of $R^{5a}$, $R^{5b}$ and $R^{5c}$ is as defined in Tables 1 to 10 and the combination of Y and $R^2$ for a compound corresponds in each case to one row of Table A.

Tables 571 to 580

Compounds of the formula I.58 in which the combination of $R^{5a}$, $R^{5b}$ and $R^{5c}$ is as defined in Tables 1 to 10 and the combination of Y and $R^2$ for a compound corresponds in each case to one row of Table A.

Tables 581 to 590

Compounds of the formula I.59 in which the combination of $R^{5a}$, $R^{5b}$ and $R^{5c}$ is as defined in Tables 1 to 10 and the combination of Y and $R^2$ for a compound corresponds in each case to one row of Table A.

Tables 591 to 600

Compounds of the formula I.60 in which the combination of $R^{5a}$, $R^{5b}$ and $R^{5c}$ is as defined in Tables 1 to 10 and the combination of Y and $R^2$ for a compound corresponds in each case to one row of Table A.

Tables 601 to 610

Compounds of the formula I.61 in which the combination of $R^{5a}$, $R^{5b}$ and $R^{5c}$ is as defined in Tables 1 to 10 and the combination of Y and $R^2$ for a compound corresponds in each case to one row of Table A.

Tables 611 to 620

Compounds of the formula I.62 in which the combination of $R^{5a}$, $R^{5b}$ and $R^{5c}$ is as defined in Tables 1 to 10 and the combination of Y and $R^2$ for a compound corresponds in each case to one row of Table A.

Tables 621 to 630

Compounds of the formula I.63 in which the combination of $R^{5a}$, $R^{5b}$ and $R^{5c}$ is as defined in Tables 1 to 10 and the combination of Y and $R^2$ for a compound corresponds in each case to one row of Table A.

Tables 631 to 640

Compounds of the formula I.64 in which the combination of $R^{5a}$, $R^{5b}$ and $R^{5c}$ is as defined in Tables 1 to 10 and the combination of Y and $R^2$ for a compound corresponds in each case to one row of Table A.

Tables 641 to 650

Compounds of the formula I.65 in which the combination of $R^{5a}$, $R^{5b}$ and $R^{5c}$ is as defined in Tables 1 to 10 and the combination of Y and $R^2$ for a compound corresponds in each case to one row of Table A.

Tables 651 to 660

Compounds of the formula I.66 in which the combination of $R^{5a}$, $R^{5b}$ and $R^{5c}$ is as defined in Tables 1 to 10 and the combination of Y and $R^2$ for a compound corresponds in each case to one row of Table A.

TABLE A

| No. | Y | $R^2$ |
|---|---|---|
| 1. | O | H |
| 2. | O | $CH_3$ |
| 3. | O | $CF_3$ |
| 4. | O | $CH_2CH_3$ |
| 5. | O | $CH_2CF_3$ |
| 6. | O | $CH_2CH_2CH_3$ |
| 7. | O | $CH_2CH_2CF_3$ |
| 8. | O | $CH_2CF_2CF_3$ |
| 9. | O | $CH(CH_3)_2$ |
| 10. | O | $(CH_2)_3CH_3$ |
| 11. | O | $(CH_2)_3CF_3$ |
| 12. | O | $CH_2$-$^c$propyl |
| 13. | O | $CH(CH_3)$-$^c$propyl |
| 14. | O | $CH_2CN$ |
| 15. | O | $CH_2C(=O)OH$ |
| 16. | O | $CH_2C(=O)OCH_3$ |
| 17. | O | $CH_2C(=O)OCH_2CH_3$ |
| 18. | O | $CH_2C(=O)OCH_2CH_2CH_3$ |
| 19. | O | $CH_2C(=O)OCH(CH_3)_2$ |
| 20. | O | $CH_2C(=O)O(CH_2)_3CH_3$ |
| 21. | O | $CH_2C(=O)OCH_2CH(CH_3)_2$ |
| 22. | O | $CH_2C(=O)OC(CH_3)_3$ |
| 23. | O | $CH_2C(=O)NH_2$ |
| 24. | O | $CH_2C(=O)NHCH_3$ |
| 25. | O | $CH_2C(=O)N(CH_3)_2$ |
| 26. | O | $CH_2C(=O)NHCF_3$ |
| 27. | O | $CH_2C(=O)N(CF_3)_2$ |
| 28. | O | $CH_2C(=O)NHCH_2CH_3$ |
| 29. | O | $CH_2C(=O)N(CH_2CH_3)_2$ |
| 30. | O | $CH_2C(=O)NHCH_2CF_3$ |
| 31. | O | $CH_2C(=O)N(CH_2CF_3)_2$ |
| 32. | O | $CH_2C(=O)NHCH_2CH_2CH_3$ |
| 33. | O | $CH_2C(=O)NHCH(CH_3)_2$ |
| 34. | O | $CH_2C(=O)NH(CH_2)_3CH_3$ |
| 35. | O | $CH_2C(=O)NHCH_2$-$^c$propyl |
| 36. | O | $CH_2C(=O)NHCH_2$—$C_6H_5$ |
| 37. | O | $CH_2C(=O)NH$-propargyl |
| 38. | O | $CH_2C(=O)NHCH_2$-4-Cl—$C_6H_4$ |
| 39. | O | $CH_2C(=O)$-morpholin-4-yl |
| 40. | O | $C_6H_5$ |
| 41. | O | 2-F—$C_6H_4$ |
| 42. | O | 3-F—$C_6H_4$ |
| 43. | O | 4-F—$C_6H_4$ |
| 44. | O | 2-Cl—$C_6H_4$ |
| 45. | O | 3-Cl—$C_6H_4$ |
| 46. | O | 4-Cl—$C_6H_4$ |
| 47. | O | 2-Br—$C_6H_4$ |
| 48. | O | 3-Br—$C_6H_4$ |
| 49. | O | 4-Br—$C_6H_4$ |
| 50. | O | $C(=O)CH_3$ |
| 51. | O | $C(=O)CH_2CH_3$ |
| 52. | O | $C(=O)CH_2OCH_3$ |
| 53. | O | $C(=O)(CH_2)_2CH_3$ |
| 54. | O | $C(=O)CH(CH_3)_2$ |
| 55. | O | $C(=O)C_6H_5$ |
| 56. | O | $C(=O)$-2-F—$C_6H_4$ |
| 57. | O | $C(=O)$-3-F—$C_6H_4$ |
| 58. | O | $C(=O)$-4-F—$C_6H_4$ |
| 59. | O | $C(=O)$-2-Cl—$C_6H_4$ |
| 60. | O | $C(=O)$-3-Cl—$C_6H_4$ |
| 61. | O | $C(=O)$-4-Cl—$C_6H_4$ |
| 62. | O | $C(=O)$-2-Br—$C_6H_4$ |
| 63. | O | $C(=O)$-3-Br—$C_6H_4$ |
| 64. | O | $C(=O)$-4-Br—$C_6H_4$ |
| 65. | O | $C(=O)$-2-pyridyl |
| 66. | O | $C(=O)CF_3$ |
| 67. | O | $C(=O)CH_2CF_3$ |
| 68. | O | $C(=O)CH_2CCl_3$ |
| 69. | O | $C(=O)OCH_2Cl_3$ |
| 70. | O | $C(=O)OH$ |
| 71. | O | $C(=O)OCH_3$ |
| 72. | O | $C(=O)OCH_2CH_3$ |
| 73. | O | $C(=O)OCH_2CH_2CH_3$ |
| 74. | O | $C(=O)OCH(CH_3)_2$ |
| 75. | O | $C(=O)O(CH_2)_3CH_3$ |
| 76. | O | $C(=O)OCH_2CH(CH_3)_2$ |
| 77. | O | $C(=O)OC(CH_3)_3$ |
| 78. | O | $C(=O)NH_2$ |
| 79. | O | $C(=O)NHCH_3$ |
| 80. | O | $C(=O)N(CH_3)_2$ |
| 81. | O | $C(=O)NHCF_3$ |
| 82. | O | $C(=O)N(CF_3)_2$ |
| 83. | O | $C(=O)NHCH_2CH_3$ |
| 84. | O | $C(=O)N(CH_2CH_3)_2$ |
| 85. | O | $C(=O)N(CH_3)CH_2CH_3$ |
| 86. | O | $C(=O)NHCH_2CF_3$ |

TABLE A-continued

| No. | Y | R² |
|---|---|---|
| 87. | O | C(=O)N(CH₂CF₃)₂ |
| 88. | O | C(=O)N(CH₃)CH₂CF₃ |
| 89. | O | C(=O)NHCH₂CH₂CH₃ |
| 90. | O | C(=O)N(CH₃)CH₂CH₂CH₃ |
| 91. | O | C(=O)NHCH(CH₃)₂ |
| 92. | O | C(=O)NH(CH₂)₃CH₃ |
| 93. | O | C(=O)N(CH₃)—(CH₂)₃CH₃ |
| 94. | O | C(=O)N[(CH₂)₃CH₃]₂ |
| 95. | O | C(=O)N(CH₃)—CH₂—C₆H₅ |
| 96. | O | C(=O)NH-propargyl |
| 97. | O | C(=O)N(CH₃)-propargyl |
| 98. | O | C(=O)NH—CH₂-4-Cl—C₆H₄ |
| 99. | O | C(=O)N(CH₃)—CH₂-4-Cl—C₆H₄ |
| 100. | O | C(=O)morpholin-4-yl |
| 101. | O | C(=O)NH-3-thiolyl-1,1-dioxid |
| 102. | O | C(=O)N(CH₃)-3-thiolyl-1,1-dioxid |
| 103. | O | C(=O)-azirid-1-yl |
| 104. | O | C(=O)-pyrrolidin-1-yl |
| 105. | O | C(=O)-piperidin-1-yl |
| 106. | O | C(=O)-thiomorpholin-4-yl |
| 107. | O | C(=O)NH—CH₂CHF₂ |
| 108. | O | C(=O)NH—CH₂CH₂CHF₂ |
| 109. | O | C(=O)NH—CH₂CH₂CF₃ |
| 110. | O | C(=O)NH-cyclopropyl |
| 111. | O | C(=O)NH-cyclobutyl |
| 112. | O | C(=O)NH-cyclopentyl |
| 113. | O | C(=O)NH-cyclohexyl |
| 114. | O | C(=O)NH—CH₂-cyclopropyl |
| 115. | O | C(=O)NH—CH₂-cyclobutyl |
| 116. | O | C(=O)NH—CH₂-cyclopentyl |
| 117. | O | C(=O)NH—CH₂-cyclohexyl |
| 118. | O | C(=O)NH—CN |
| 119. | O | C(=O)NH—CH₂—CN |
| 120. | O | C(=O)NH—CH₂—CH=CH₂ |
| 121. | O | C(=O)NH—CH₂—CH=C(Cl)₂ |
| 122. | O | C(=O)NH—CH₂—CH=CH-phenyl |
| 123. | O | C(=O)NH—CH₂—CH=CH-(4-Cl-phenyl) |
| 124. | O | C(=O)NH—CH₂—SCH₃ |
| 125. | O | C(=O)NH—CH₂—SCF₃ |
| 126. | O | C(=O)NH—CH₂—CH₂—SCH₃ |
| 127. | O | C(=O)NH—CH₂—CH₂—SCF₃ |
| 128. | O | C(=O)NH—CH₂—SO₂—CH₃ |
| 129. | O | C(=O)NH—CH₂—SO₂—CF₃ |
| 130. | O | C(=O)NH—CH₂—CH₂—SO₂—CH₃ |
| 131. | O | C(=O)NH—CH₂—CH₂—SO₂—CF₃ |
| 132. | O | C(=O)NH—CH₂—CO—NH₂ |
| 133. | O | C(=O)NH—CH₂—CO—NHCH₃ |
| 134. | O | C(=O)NH—CH₂—CO—N(CH₃)₂ |
| 135. | O | C(=O)NH—CH₂—CO—NHCF₃ |
| 136. | O | C(=O)NH—CH₂—CO—N(CF₃)₂ |
| 137. | O | C(=O)NH—CH₂—CO—NHCH₂CH₃ |
| 138. | O | C(=O)NH—CH₂—CO—N(CH₂CH₃)₂ |
| 139. | O | C(=O)NH—CH₂—CO—NHCH₂CF₃ |
| 140. | O | C(=O)NH—CH₂—CO—N(CH₂CF₃)₂ |
| 141. | O | C(=O)NH—CH₂—CO—NHCH₂CH₂CH₃ |
| 142. | O | C(=O)NH—CH₂—CO—N(CH₂CH₂CH₃)₂ |
| 143. | O | C(=O)NH—CH₂—CO—NHCH₂CH₂CF₃ |
| 144. | O | C(=O)NH—CH₂—CO—N(CH₂CH₂CF₃)₂ |
| 145. | O | C(=O)NH—CH₂—CO—NHCH(CH₃)₂ |
| 146. | O | C(=O)NH—CH₂—CO—NHCH(CF₃)₂ |
| 147. | O | C(=O)NH—CH₂—CO—NH-cyclopropyl |
| 148. | O | C(=O)NH—CH₂—CO—NH—CH₂-cyclopropyl |
| 149. | O | C(=O)NH—CH₂—CO—OH |
| 150. | O | C(=O)NH—CH₂—CO—OCH₃ |
| 151. | O | C(=O)NH—CH₂—CO—OCF₃ |
| 152. | O | C(=O)NH—CH₂—CO—OCH₂CH₃ |
| 153. | O | C(=O)NH—CH₂—CO—OCH₂CF₃ |
| 154. | O | C(=O)NH—CH₂—CO—OCH₂CH₂CH₃ |
| 155. | O | C(=O)NH—CH₂—CO—OCH(CH₃)₂ |
| 156. | O | C(=O)NH—CH₂—CO—OCH₂CH₂CH₂CH₃ |
| 157. | O | C(=O)NH—CH₂—CO—OCH(CH₃)CH₂CH₃ |
| 158. | O | C(=O)NH—CH₂—CO—OCH₂CH(CH₃)₂ |
| 159. | O | C(=O)NH—CH₂—CO—OC(CH₃)₃ |
| 160. | O | C(=O)NH-A-1 |
| 161. | O | C(=O)NH-A-2 |
| 162. | O | C(=O)NH-A-3 |
| 163. | O | C(=O)NH-A-4 |
| 164. | O | C(=O)NH-A-5 |
| 165. | O | C(=O)NH-A-6 |
| 166. | O | C(=O)NH-A-7 |
| 167. | O | C(=O)NH-A-8 |
| 168. | O | C(=O)NH-A-9 |
| 169. | O | C(=O)NH-A-10 |
| 170. | O | C(=O)NH-A-11 |
| 171. | O | C(=O)NH-A-12 |
| 172. | O | C(=O)NH-A-13 |
| 173. | O | C(=O)NH-A-14 |
| 174. | O | C(=O)NH-A-15 |
| 175. | O | C(=O)NH-A-16 |
| 176. | O | C(=O)NH-A-17 |
| 177. | O | C(=O)NH-A-18 |
| 178. | O | C(=O)NH-A-19 |
| 179. | O | C(=O)NH-A-20 |
| 180. | O | C(=O)NH-A-21 |
| 181. | O | C(=O)NH-A-22 |
| 182. | O | C(=O)NH-A-23 |
| 183. | O | C(=O)NH-A-24 |
| 184. | O | C(=O)NH-A-25 |
| 185. | O | C(=O)NH-A-26 |
| 186. | O | C(=O)NH-A-27 |
| 187. | O | C(=O)NH-A-28 |
| 188. | O | C(=O)NH-A-29 |
| 189. | O | C(=O)NH-A-30 |
| 190. | O | C(=O)NH-A-31 |
| 191. | O | C(=O)NH-A-32 |
| 192. | O | C(=O)NH-A-33 |
| 193. | O | C(=O)NH—CH₂-A-1 |
| 194. | O | C(=O)NH—CH₂-A-2 |
| 195. | O | C(=O)NH—CH₂-A-3 |
| 196. | O | C(=O)NH—CH₂-A-4 |
| 197. | O | C(=O)NH—CH₂-A-5 |
| 198. | O | C(=O)NH—CH₂-A-6 |
| 199. | O | C(=O)NH—CH₂-A-7 |
| 200. | O | C(=O)NH—CH₂-A-8 |
| 201. | O | C(=O)NH—CH₂-A-9 |
| 202. | O | C(=O)NH—CH₂-A-10 |
| 203. | O | C(=O)NH—CH₂-A-11 |
| 204. | O | C(=O)NH—CH₂-A-12 |
| 205. | O | C(=O)NH—CH₂-A-13 |
| 206. | O | C(=O)NH—CH₂-A-14 |
| 207. | O | C(=O)NH—CH₂-A-15 |
| 208. | O | C(=O)NH—CH₂-A-16 |
| 209. | O | C(=O)NH—CH₂-A-17 |
| 210. | O | C(=O)NH—CH₂-A-18 |
| 211. | O | C(=O)NH—CH₂-A-19 |
| 212. | O | C(=O)NH—CH₂-A-20 |
| 213. | O | C(=O)NH—CH₂-A-21 |
| 214. | O | C(=O)NH—CH₂-A-22 |
| 215. | O | C(=O)NH—CH₂-A-23 |
| 216. | O | C(=O)NH—CH₂-A-24 |
| 217. | O | C(=O)NH—CH₂-A-25 |
| 218. | O | C(=O)NH—CH₂-A-26 |
| 219. | O | C(=O)NH—CH₂-A-27 |
| 220. | O | C(=O)NH—CH₂-A-28 |
| 221. | O | C(=O)NH—CH₂-A-29 |
| 222. | O | C(=O)NH—CH₂-A-30 |
| 223. | O | C(=O)NH—CH₂-A-31 |
| 224. | O | C(=O)NH—CH₂-A-32 |
| 225. | O | C(=O)NH—CH₂-A-33 |
| 226. | O | C(=O)NH—SO₂—CH₃ |
| 227. | O | C(=O)NH—SO₂—CF₃ |
| 228. | O | C(=O)NH—SO₂—CH₂CH₃ |
| 229. | O | C(=O)NH—SO₂—CH₂CF₃ |
| 230. | O | C(=O)NH—SO₂—CH₂CH₂CH₃ |
| 231. | O | C(=O)NH—SO₂—CH₂CH₂CF₃ |
| 232. | O | C(=O)NH—SO₂—CH₂CF₂CF₃ |
| 233. | O | C(=O)NH—SO₂—CH(CH₃)₂ |
| 234. | O | C(=O)NH—SO₂—CH(CF₃)₂ |
| 235. | O | C(=O)N(CH₃)—CH₂CHF₂ |
| 236. | O | C(=O)N(CH₃)—CH₂CH₂CHF₂ |
| 237. | O | C(=O)N(CH₃)—CH₂CH₂CF₃ |
| 238. | O | C(=O)N(CH₃)-cyclopropyl |
| 239. | O | C(=O)N(CH₃)-cyclobutyl |
| 240. | O | C(=O)N(CH₃)-cyclopentyl |
| 241. | O | C(=O)N(CH₃)-cyclohexyl |
| 242. | O | C(=O)N(CH₃)—CH₂-cyclopropyl |

TABLE A-continued

| No. | Y | R² |
|---|---|---|
| 243. | O | C(=O)N(CH₃)—CH₂-cyclobutyl |
| 244. | O | C(=O)N(CH₃)—CH₂-cyclopentyl |
| 245. | O | C(=O)N(CH₃)—CH₂-cyclohexyl |
| 246. | O | C(=O)N(CH₃)—CN |
| 247. | O | C(=O)N(CH₃)—CH₂—CN |
| 248. | O | C(=O)N(CH₃)—CH₂—CH=CH₂ |
| 249. | O | C(=O)N(CH₃)—CH₂—CH=C(Cl)₂ |
| 250. | O | C(=O)N(CH₃)—CH₂—CH=CH-phenyl |
| 251. | O | C(=O)N(CH₃)—CH₂—CH=CH-(4-Cl-phenyl) |
| 252. | O | C(=O)N(CH₃)—CH₂—SCH₃ |
| 253. | O | C(=O)N(CH₃)—CH₂—SCF₃ |
| 254. | O | C(=O)N(CH₃)—CH₂—CH₂—SCH₃ |
| 255. | O | C(=O)N(CH₃)—CH₂—CH₂—SCF₃ |
| 256. | O | C(=O)N(CH₃)—CH₂—SO₂—CH₃ |
| 257. | O | C(=O)N(CH₃)—CH₂—SO₂—CF₃ |
| 258. | O | C(=O)N(CH₃)—CH₂—CH₂—SO₂—CH₃ |
| 259. | O | C(=O)N(CH₃)—CH₂—CH₂—SO₂—CF₃ |
| 260. | O | C(=O)N(CH₃)—CH₂—CO—NH₂ |
| 261. | O | C(=O)N(CH₃)—CH₂—CO—NHCH₃ |
| 262. | O | C(=O)N(CH₃)—CH₂—CO—N(CH₃)₂ |
| 263. | O | C(=O)N(CH₃)—CH₂—CO—NHCF₃ |
| 264. | O | C(=O)N(CH₃)—CH₂—CO—N(CF₃)₂ |
| 265. | O | C(=O)N(CH₃)—CH₂—CO—NHCH₂CH₃ |
| 266. | O | C(=O)N(CH₃)—CH₂—CO—N(CH₂CH₃)₂ |
| 267. | O | C(=O)N(CH₃)—CH₂—CO—NHCH₂CF₃ |
| 268. | O | C(=O)N(CH₃)—CH₂—CO—N(CH₂CF₃)₂ |
| 269. | O | C(=O)N(CH₃)—CH₂—CO—NHCH₂CH₂CH₃ |
| 270. | O | C(=O)N(CH₃)—CH₂—CO—N(CH₂CH₂CH₃)₂ |
| 271. | O | C(=O)N(CH₃)—CH₂—CO—NHCH₂CH₂CF₃ |
| 272. | O | C(=O)N(CH₃)—CH₂—CO—N(CH₂CH₂CF₃)₂ |
| 273. | O | C(=O)N(CH₃)—CH₂—CO—NHCH(CH₃)₂ |
| 274. | O | C(=O)N(CH₃)—CH₂—CO—NHCH(CF₃)₂ |
| 275. | O | C(=O)N(CH₃)—CH₂—CO—NH-cyclopropyl |
| 276. | O | C(=O)N(CH₃)—CH₂—CO—NH—CH₂-cyclopropyl |
| 277. | O | C(=O)N(CH₃)—CH₂—CO—OH |
| 278. | O | C(=O)N(CH₃)—CH₂—CO—OCH₃ |
| 279. | O | C(=O)N(CH₃)—CH₂—CO—OCF₃ |
| 280. | O | C(=O)N(CH₃)—CH₂—CO—OCH₂CH₃ |
| 281. | O | C(=O)N(CH₃)—CH₂—CO—OCH₂CF₃ |
| 282. | O | C(=O)N(CH₃)—CH₂—CO—OCH₂CH₂CH₃ |
| 283. | O | C(=O)N(CH₃)—CH₂—CO—OCH(CH₃)₂ |
| 284. | O | C(=O)N(CH₃)—CH₂—CO—OCH₂CH₂CH₂CH₃ |
| 285. | O | C(=O)N(CH₃)—CH₂—CO—OCH(CH₃)CH₂CH₃ |
| 286. | O | C(=O)N(CH₃)—CH₂—CO—OCH₂CH(CH₃)₂ |
| 287. | O | C(=O)N(CH₃)—CH₂—CO—OC(CH₃)₃ |
| 288. | O | C(=O)N(CH₃)-A-1 |
| 289. | O | C(=O)N(CH₃)-A-2 |
| 290. | O | C(=O)N(CH₃)-A-3 |
| 291. | O | C(=O)N(CH₃)-A-4 |
| 292. | O | C(=O)N(CH₃)-A-5 |
| 293. | O | C(=O)N(CH₃)-A-6 |
| 294. | O | C(=O)N(CH₃)-A-7 |
| 295. | O | C(=O)N(CH₃)-A-8 |
| 296. | O | C(=O)N(CH₃)-A-9 |
| 297. | O | C(=O)N(CH₃)-A-10 |
| 298. | O | C(=O)N(CH₃)-A-11 |
| 299. | O | C(=O)N(CH₃)-A-12 |
| 300. | O | C(=O)N(CH₃)-A-13 |
| 301. | O | C(=O)N(CH₃)-A-14 |
| 302. | O | C(=O)N(CH₃)-A-15 |
| 303. | O | C(=O)N(CH₃)-A-16 |
| 304. | O | C(=O)N(CH₃)-A-17 |
| 305. | O | C(=O)N(CH₃)-A-18 |
| 306. | O | C(=O)N(CH₃)-A-19 |
| 307. | O | C(=O)N(CH₃)-A-20 |
| 308. | O | C(=O)N(CH₃)-A-21 |
| 309. | O | C(=O)N(CH₃)-A-22 |
| 310. | O | C(=O)N(CH₃)-A-23 |
| 311. | O | C(=O)N(CH₃)-A-24 |
| 312. | O | C(=O)N(CH₃)-A-25 |
| 313. | O | C(=O)N(CH₃)-A-26 |
| 314. | O | C(=O)N(CH₃)-A-27 |
| 315. | O | C(=O)N(CH₃)-A-28 |
| 316. | O | C(=O)N(CH₃)-A-29 |
| 317. | O | C(=O)N(CH₃)-A-30 |
| 318. | O | C(=O)N(CH₃)-A-31 |
| 319. | O | C(=O)N(CH₃)-A-32 |
| 320. | O | C(=O)N(CH₃)-A-33 |
| 321. | O | C(=O)N(CH₃)—CH₂-A-1 |
| 322. | O | C(=O)N(CH₃)—CH₂-A-2 |
| 323. | O | C(=O)N(CH₃)—CH₂-A-3 |
| 324. | O | C(=O)N(CH₃)—CH₂-A-4 |
| 325. | O | C(=O)N(CH₃)—CH₂-A-5 |
| 326. | O | C(=O)N(CH₃)—CH₂-A-6 |
| 327. | O | C(=O)N(CH₃)—CH₂-A-7 |
| 328. | O | C(=O)N(CH₃)—CH₂-A-8 |
| 329. | O | C(=O)N(CH₃)—CH₂-A-9 |
| 330. | O | C(=O)N(CH₃)—CH₂-A-10 |
| 331. | O | C(=O)N(CH₃)—CH₂-A-11 |
| 332. | O | C(=O)N(CH₃)—CH₂-A-12 |
| 333. | O | C(=O)N(CH₃)—CH₂-A-13 |
| 334. | O | C(=O)N(CH₃)—CH₂-A-14 |
| 335. | O | C(=O)N(CH₃)—CH₂-A-15 |
| 336. | O | C(=O)N(CH₃)—CH₂-A-16 |
| 337. | O | C(=O)N(CH₃)—CH₂-A-17 |
| 338. | O | C(=O)N(CH₃)—CH₂-A-18 |
| 339. | O | C(=O)N(CH₃)—CH₂-A-19 |
| 340. | O | C(=O)N(CH₃)—CH₂-A-20 |
| 341. | O | C(=O)N(CH₃)—CH₂-A-21 |
| 342. | O | C(=O)N(CH₃)—CH₂-A-22 |
| 343. | O | C(=O)N(CH₃)—CH₂-A-23 |
| 344. | O | C(=O)N(CH₃)—CH₂-A-24 |
| 345. | O | C(=O)N(CH₃)—CH₂-A-25 |
| 346. | O | C(=O)N(CH₃)—CH₂-A-26 |
| 347. | O | C(=O)N(CH₃)—CH₂-A-27 |
| 348. | O | C(=O)N(CH₃)—CH₂-A-28 |
| 349. | O | C(=O)N(CH₃)—CH₂-A-29 |
| 350. | O | C(=O)N(CH₃)—CH₂-A-30 |
| 351. | O | C(=O)N(CH₃)—CH₂-A-31 |
| 352. | O | C(=O)N(CH₃)—CH₂-A-32 |
| 353. | O | C(=O)N(CH₃)—CH₂-A-33 |
| 354. | O | C(=O)N(CH₃)—SO₂—CH₃ |
| 355. | O | C(=O)N(CH₃)—SO₂—CF₃ |
| 356. | O | C(=O)N(CH₃)—SO₂—CH₂CH₃ |
| 357. | O | C(=O)N(CH₃)—SO₂—CH₂CF₃ |
| 358. | O | C(=O)N(CH₃)—SO₂—CH₂CH₂CH₃ |
| 359. | O | C(=O)N(CH₃)—SO₂—CH₂CH₂CF₃ |
| 360. | O | C(=O)N(CH₃)—SO₂—CH₂CF₂CF₃ |
| 361. | O | C(=O)N(CH₃)—SO₂—CH(CH₃)₂ |
| 362. | O | C(=O)N(CH₃)—SO₂—CH(CF₃)₂ |
| 363. | O | C(=O)NH—SO₂—NH₂ |
| 364. | O | C(=O)NH—SO₂—NHCH₃ |
| 365. | O | C(=O)NH—SO₂—N(CH₃)₂ |
| 366. | O | C(=O)NH—SO₂—NHCF₃ |
| 367. | O | C(=O)NH—SO₂—N(CF₃)₂ |
| 368. | O | C(=O)NH—SO₂—NHCH₂CH₃ |
| 369. | O | C(=O)NH—SO₂—N(CH₂CH₃)₂ |
| 370. | O | C(=O)NH—SO₂—NHCH₂CF₃ |
| 371. | O | C(=O)NH—SO₂—N(CH₂CF₃)₂ |
| 372. | O | C(=O)NH—SO₂—N(CH₃)CH₂CH₃ |
| 373. | O | C(=O)NH—SO₂—N(CH₃)CH₂CF₃ |
| 374. | O | C(=O)NH—SO₂—N(CF₃)CH₂CH₃ |
| 375. | O | C(=O)NH—SO₂—NHCH₂CH₂CH₃ |
| 376. | O | C(=O)NH—SO₂—N(CH₂CH₂CH₃)₂ |
| 377. | O | C(=O)NH—SO₂—NHCH₂CH₂CF₃ |
| 378. | O | C(=O)NH—SO₂—N(CH₂CH₂CF₃)₂ |
| 379. | O | C(=O)NH—SO₂—N(CH₃)CH₂CH₂CH₃ |
| 380. | O | C(=O)NH—SO₂—N(CH₃)CH₂CH₂CF₃ |
| 381. | O | C(=O)NH—SO₂—N(CF₃)CH₂CH₂CH₃ |
| 382. | O | C(=O)NH—SO₂—NHCH(CH₃)₂ |
| 383. | O | C(=O)NH—SO₂—NHCH(CF₃)₂ |
| 384. | O | C(=O)NH—SO₂—N(CH₃)CH(CH₃)₂ |
| 385. | O | C(=O)NH—SO₂—N(CH₃)CH(CF₃)₂ |
| 386. | O | C(=O)NH—SO₂—N(CF₃)CH(CH₃)₂ |
| 387. | O | C(=O)NH—SO₂—NHCH₂CH₂CH₂CH₃ |
| 388. | O | C(=O)NH—SO₂—N(CH₂CH₂CH₂CH₃)₂ |
| 389. | O | C(=O)NH—SO₂—N(CH₃)CH₂CH₂CH₂CH₃ |
| 390. | O | C(=O)N(CH₃)—SO₂—NH₂ |
| 391. | O | C(=O)N(CH₃)—SO₂—NHCH₃ |
| 392. | O | C(=O)N(CH₃)—SO₂—N(CH₃)₂ |
| 393. | O | C(=O)N(CH₃)—SO₂—NHCF₃ |
| 394. | O | C(=O)N(CH₃)—SO₂—N(CF₃)₂ |
| 395. | O | C(=O)N(CH₃)—SO₂—NHCH₂CH₃ |
| 396. | O | C(=O)N(CH₃)—SO₂—N(CH₂CH₃)₂ |
| 397. | O | C(=O)N(CH₃)—SO₂—NHCH₂CF₃ |
| 398. | O | C(=O)N(CH₃)—SO₂—N(CH₂CF₃)₂ |

TABLE A-continued

| No. | Y | R² |
|---|---|---|
| 399. | O | C(=O)N(CH₃)—SO₂—N(CH₃)CH₂CH₃ |
| 400. | O | C(=O)N(CH₃)—SO₂—N(CH₃)CH₂CF₃ |
| 401. | O | C(=O)N(CH₃)—SO₂—N(CF₃)CH₂CH₃ |
| 402. | O | C(=O)N(CH₃)—SO₂—NHCH₂CH₃ |
| 403. | O | C(=O)N(CH₃)—SO₂—N(CH₂CH₂CH₃)₂ |
| 404. | O | C(=O)N(CH₃)—SO₂—NHCH₂CF₃ |
| 405. | O | C(=O)N(CH₃)—SO₂—N(CH₂CH₂CF₃)₂ |
| 406. | O | C(=O)N(CH₃)—SO₂—N(CH₃)CH₂CH₂CH₃ |
| 407. | O | C(=O)N(CH₃)—SO₂—N(CH₃)CH₂CH₂CF₃ |
| 408. | O | C(=O)N(CH₃)—SO₂—N(CF₃)CH₂CH₂CH₃ |
| 409. | O | C(=O)N(CH₃)—SO₂—NHCH(CH₃)₂ |
| 410. | O | C(=O)N(CH₃)—SO₂—NHCH(CF₃)₂ |
| 411. | O | C(=O)N(CH₃)—SO₂—N(CH₃)CH(CH₃)₂ |
| 412. | O | C(=O)N(CH₃)—SO₂—N(CH₃)CH(CF₃)₂ |
| 413. | O | C(=O)N(CH₃)—SO₂—N(CF₃)CH(CH₃)₂ |
| 414. | O | C(=O)N(CH₃)—SO₂—NHCH₂CH₂CH₂CH₃ |
| 415. | O | C(=O)N(CH₃)—SO₂—N(CH₂CH₂CH₃)₂ |
| 416. | O | C(=O)N(CH₃)—SO₂—N(CH₃)CH₂CH₂CH₂CH₃ |
| 417. | O | C(=O)—N=CHOCH₃ |
| 418. | O | C(=O)—N=CHOCH₂CH₃ |
| 419. | O | C(=O)—N=CHOCH₂CH₂CH₃ |
| 420. | O | C(=O)—N=CHOCH(CH₃)₂ |
| 421. | O | C(=O)—N=CHOCF₃ |
| 422. | O | C(=O)—N=CHOCH₂CF₃ |
| 423. | O | C(=O)—N=CHOCH₂CH₂CF₃ |
| 424. | O | C(=O)—N=CHOCH(CF₃)₂ |
| 425. | O | C(=O)—N=CH—CO—OCH₃ |
| 426. | O | C(=O)—N=CH—CO—OCH₂CH₃ |
| 427. | O | C(=O)—N=CH—CO—OCH₂CH₂CH₃ |
| 428. | O | C(=O)—N=CH—CO—OCH(CH₃)₂ |
| 429. | O | C(=O)—N=CH—CO—OCF₃ |
| 430. | O | C(=O)—N=CH—CO—OCH₂CF₃ |
| 431. | O | C(=O)—N=CH—CO—OCH₂CH₂CF₃ |
| 432. | O | C(=O)—N=CH—CO—OCH(CF₃)₂ |
| 433. | O | C(=O)—N=CH—CO—NHCH₃ |
| 434. | O | C(=O)—N=CH—CO—N(CH₃)₂ |
| 435. | O | C(=O)—N=CH—CO—NHCH₂CH₃ |
| 436. | O | C(=O)—N=CH—CO—N(CH₂CH₃)₂ |
| 437. | O | C(=O)—N=CH—CO—N(CH₃)CH₂CH₃ |
| 438. | O | C(=O)—N=CH—CO—NHCH₂CH₃ |
| 439. | O | C(=O)—N=CH—CO—N(CH₂CH₂CH₃)₂ |
| 440. | O | C(=O)—N=CH—CO—N(CH₃)CH₂CH₂CH₃ |
| 441. | O | C(=O)—N=CH—CO—NHCH(CH₃)₂ |
| 442. | O | C(=O)—N=CH—CO—N(CH₃)CH(CH₃)₂ |
| 443. | O | C(=O)—N=CH—CO—NHCF₃ |
| 444. | O | C(=O)—N=CH—CO—N(CF₃)₂ |
| 445. | O | C(=O)—N=CH—CO—NHCH₂CF₃ |
| 446. | O | C(=O)—N=CH—CO—N(CH₂CF₃)₂ |
| 447. | O | C(=O)—N=CH—CO—N(CH₃)CH₂CF₃ |
| 448. | O | C(=O)—N=CH—CO—N(CF₃)CH₂CF₃ |
| 449. | O | C(=O)—N=CH—CO—NHCH₂CH₂CF₃ |
| 450. | O | C(=O)—N=CH—CO—N(CH₂CF₃)₂ |
| 451. | O | C(=O)—N=CH—CO—N(CH₃)CH₂CH₂CF₃ |
| 452. | O | C(=O)—N=CH—CO—N(CF₃)CH₂CH₂CH₃ |
| 453. | O | C(=O)—N=CH—CO—NHCH(CF₃)₂ |
| 454. | O | C(=O)—N=CH—CO—N(CH₃)CH(CF₃)₂ |
| 455. | O | C(=O)—N=CH—CO—N(CF₃)CH(CH₃)₂ |
| 456. | O | C(=NH)NH₂ |
| 457. | O | C(=NH)NHCH₃ |
| 458. | O | C(=NH)N(CH₃)₂ |
| 459. | O | C(=NH)NHCF₃ |
| 460. | O | C(=NH)N(CF₃)₂ |
| 461. | O | C(=NH)NHCH₂CH₃ |
| 462. | O | C(=NH)N(CH₂CH₃)₂ |
| 463. | O | C(=NH)NHCH₂CF₃ |
| 464. | O | C(=NH)N(CH₂CF₃)₂ |
| 465. | O | C(=NH)NHCH₂CH₂CH₃ |
| 466. | O | C(=NH)NHCH(CH₃)₂ |
| 467. | O | C(=NH)NH(CH₂)₃CH₃ |
| 468. | O | C(=NH)NH(CH₂)₄CH₃ |
| 469. | O | C(=NH)NH(CH₂)₅CH₃ |
| 470. | O | C(=NH)NHCH₂-ᶜpropyl |
| 471. | O | C(=NH)NHCH₂—C₆H₅ |
| 472. | O | C(=NCH₃)NH₂ |
| 473. | O | C(=NCH₃)NHCH₃ |
| 474. | O | C(=NCH₃)N(CH₃)₂ |
| 475. | O | C(=NCH₃)NHCF₃ |
| 476. | O | C(=NCH₃)N(CF₃)₂ |
| 477. | O | C(=NCH₃)NHCH₂CH₃ |
| 478. | O | C(=NCH₃)N(CH₂CH₃)₂ |
| 479. | O | C(=NCH₃)NHCH₂CF₃ |
| 480. | O | C(=NCH₃)N(CH₂CF₃)₂ |
| 481. | O | C(=NCH₃)NHCH₂CH₂CH₃ |
| 482. | O | C(=NCH₃)NHCH(CH₃)₂ |
| 483. | O | C(=NCH₃)NH(CH₂)₃CH₃ |
| 484. | O | C(=NCH₃)NH(CH₂)₄CH₃ |
| 485. | O | C(=NCH₃)NH(CH₂)₅CH₃ |
| 486. | O | C(=NCH₃)NHCH₂-ᶜpropyl |
| 487. | O | C(=NCH₃)NHCH₂—C₆H₅ |
| 488. | O | CH₂C₆H₅ |
| 489. | O | CH₂CH₂C₆H₅ |
| 490. | O | CH₂-2-F—C₆H₄ |
| 491. | O | CH₂-3-F—C₆H₄ |
| 492. | O | CH₂-4-F—C₆H₄ |
| 493. | O | CH₂-2-Cl—C₆H₄ |
| 494. | O | CH₂-3-Cl—C₆H₄ |
| 495. | O | CH₂-4-Cl—C₆H₄ |
| 496. | O | CH₂-2-Br—C₆H₄ |
| 497. | O | CH₂-3-Br—C₆H₄ |
| 498. | O | CH₂-4-Br—C₆H₄ |
| 499. | O | CH₂-2-MeO—C₆H₄ |
| 500. | O | CH₂-3-MeO—C₆H₄ |
| 501. | O | CH₂-4-MeO—C₆H₄ |
| 502. | O | CH₂-2-F—C₆H₄ |
| 503. | O | CH₂-3-F—C₆H₄ |
| 504. | O | CH₂-4-F—C₆H₄ |
| 505. | O | A-1 |
| 506. | O | A-2 |
| 507. | O | A-3 |
| 508. | O | A-4 |
| 509. | O | A-5 |
| 510. | O | A-6 |
| 511. | O | A-7 |
| 512. | O | A-8 |
| 513. | O | A-9 |
| 514. | O | A-10 |
| 515. | O | A-11 |
| 516. | O | A-12 |
| 517. | O | A-13 |
| 518. | O | A-14 |
| 519. | O | A-15 |
| 520. | O | A-16 |
| 521. | O | A-17 |
| 522. | O | A-18 |
| 523. | O | A-19 |
| 524. | O | A-20 |
| 525. | O | A-21 |
| 526. | O | A-22 |
| 527. | O | A-23 |
| 528. | O | A-24 |
| 529. | O | A-25 |
| 530. | O | A-26 |
| 531. | O | A-27 |
| 532. | O | A-28 |
| 533. | O | A-29 |
| 534. | O | A-30 |
| 535. | O | A-31 |
| 536. | O | A-32 |
| 537. | O | A-33 |
| 538. | O | CH₂-A-1 |
| 539. | O | CH₂-A-2 |
| 540. | O | CH₂-A-3 |
| 541. | O | CH₂-A-4 |
| 542. | O | CH₂-A-5 |
| 543. | O | CH₂-A-6 |
| 544. | O | CH₂-A-7 |
| 545. | O | CH₂-A-8 |
| 546. | O | CH₂-A-9 |
| 547. | O | CH₂-A-10 |
| 548. | O | CH₂-A-11 |
| 549. | O | CH₂-A-12 |
| 550. | O | CH₂-A-13 |
| 551. | O | CH₂-A-14 |
| 552. | O | CH₂-A-15 |
| 553. | O | CH₂-A-16 |
| 554. | O | CH₂-A-17 |

TABLE A-continued

| No. | Y | R² |
|---|---|---|
| 555. | O | CH₂-A-18 |
| 556. | O | CH₂-A-19 |
| 557. | O | CH₂-A-20 |
| 558. | O | CH₂-A-21 |
| 559. | O | CH₂-A-22 |
| 560. | O | CH₂-A-23 |
| 561. | O | CH₂-A-24 |
| 562. | O | CH₂-A-25 |
| 563. | O | CH₂-A-26 |
| 564. | O | CH₂-A-27 |
| 565. | O | CH₂-A-28 |
| 566. | O | CH₂-A-29 |
| 567. | O | CH₂-A-30 |
| 568. | O | CH₂-A-31 |
| 569. | O | CH₂-A-32 |
| 570. | O | CH₂-A-33 |
| 571. | O | C(=O)-A-1 |
| 572. | O | C(=O)-A-2 |
| 573. | O | C(=O)-A-3 |
| 574. | O | C(=O)-A-4 |
| 575. | O | C(=O)-A-5 |
| 576. | O | C(=O)-A-6 |
| 577. | O | C(=O)-A-7 |
| 578. | O | C(=O)-A-8 |
| 579. | O | C(=O)-A-9 |
| 580. | O | C(=O)-A-10 |
| 581. | O | C(=O)-A-11 |
| 582. | O | C(=O)-A-12 |
| 583. | O | C(=O)-A-13 |
| 584. | O | C(=O)-A-14 |
| 585. | O | C(=O)-A-15 |
| 586. | O | C(=O)-A-16 |
| 587. | O | C(=O)-A-17 |
| 588. | O | C(=O)-A-18 |
| 589. | O | C(=O)-A-19 |
| 590. | O | C(=O)-A-20 |
| 591. | O | C(=O)-A-21 |
| 592. | O | C(=O)-A-22 |
| 593. | O | C(=O)-A-23 |
| 594. | O | C(=O)-A-24 |
| 595. | O | C(=O)-A-25 |
| 596. | O | C(=O)-A-26 |
| 597. | O | C(=O)-A-27 |
| 598. | O | C(=O)-A-28 |
| 599. | O | C(=O)-A-29 |
| 600. | O | C(=O)-A-30 |
| 601. | O | C(=O)-A-31 |
| 602. | O | C(=O)-A-32 |
| 603. | O | C(=O)-A-33 |
| 604. | NH | C(=O)NH₂ |
| 605. | NH | C(=O)NHCH₃ |
| 606. | NH | C(=O)N(CH₃)₂ |
| 607. | NH | C(=O)NHCF₃ |
| 608. | NH | C(=O)N(CF₃)₂ |
| 609. | NH | C(=O)NHCH₂CH₃ |
| 610. | NH | C(=O)N(CH₂CH₃)₂ |
| 611. | NH | C(=O)(CH₃)CH₂CH₃ |
| 612. | NH | C(=O)NHCH₂CF₃ |
| 613. | NH | C(=O)N(CH₂CF₃)₂ |
| 614. | NH | C(=O)N(CH₃)CH₂CF₃ |
| 615. | NH | C(=O)NHCH₂CH₂CH₃ |
| 616. | NH | C(=O)N(CH₃)CH₂CH₂CH₃ |
| 617. | NH | C(=O)NHCH(CH₃)₂ |
| 618. | NH | C(=O)NH(CH₂)₃CH₃ |
| 619. | NH | C(=O)N(CH₃)—(CH₂)₃CH₃ |
| 620. | NH | C(=O)N[(CH₂)₃CH₃]₂ |
| 621. | NH | C(=O)N(CH₃)—CH₂—C₆H₅ |
| 622. | NH | C(=O)NH-propargyl |
| 623. | NH | C(=O)N(CH₃)-propargyl |
| 624. | NH | C(=O)NH—CH₂-4-Cl—C₆H₄ |
| 625. | NH | C(=O)N(CH₃)—CH₂-4-Cl—C₆H₄ |
| 626. | NH | C(=O)morpholin-4-yl |
| 627. | NH | C(=O)NH-3-thiolyl-1,1-dioxid |
| 628. | NH | C(=O)N(CH₃)-3-thiolyl-1,1-dioxid |
| 629. | NH | C(=O)-azirid-1-yl |
| 630. | NH | C(=O)-pyrrolidin-1-yl |
| 631. | NH | C(=O)-piperidin-1-yl |
| 632. | NH | C(=O)-thiomorpholin-4-yl |
| 633. | NH | C(=O)NH—CH₂CHF₂ |
| 634. | NH | C(=O)NH—CH₂CH₂CHF₂ |
| 635. | NH | C(=O)NH—CH₂CH₂CF₃ |
| 636. | NH | C(=O)NH-cyclopropyl |
| 637. | NH | C(=O)NH-cyclobutyl |
| 638. | NH | C(=O)NH-cyclopentyl |
| 639. | NH | C(=O)NH-cyclohexyl |
| 640. | NH | C(=O)NH—CH₂-cyclopropyl |
| 641. | NH | C(=O)NH—CH₂-cyclobutyl |
| 642. | NH | C(=O)NH—CH₂-cyclopentyl |
| 643. | NH | C(=O)NH—CH₂-cyclohexyl |
| 644. | NH | C(=O)NH—CN |
| 645. | NH | C(=O)NH—CH₂—CN |
| 646. | NH | C(=O)NH—CH₂—CH=CH₂ |
| 647. | NH | C(=O)NH—CH₂—CH=C(Cl)₂ |
| 648. | NH | C(=O)NH—CH₂—CH=CH-phenyl |
| 649. | NH | C(=O)NH—CH₂—CH=CH-(4-Cl-phenyl) |
| 650. | NH | C(=O)NH—CH₂—SCH₃ |
| 651. | NH | C(=O)NH—CH₂—SCF₃ |
| 652. | NH | C(=O)NH—CH₂—CH₂—SCH₃ |
| 653. | NH | C(=O)NH—CH₂—CH₂—SCF₃ |
| 654. | NH | C(=O)NH—CH₂—SO₂—CH₃ |
| 655. | NH | C(=O)NH—CH₂—SO₂—CF₃ |
| 656. | NH | C(=O)NH—CH₂—CH₂—SO₂—CH₃ |
| 657. | NH | C(=O)NH—CH₂—CH₂—SO₂—CF₃ |
| 658. | NH | C(=O)NH—CH₂—CO—NH₂ |
| 659. | NH | C(=O)NH—CH₂—CO—NHCH₃ |
| 660. | NH | C(=O)NH—CH₂—CO—N(CH₃)₂ |
| 661. | NH | C(=O)NH—CH₂—CO—NHCF₃ |
| 662. | NH | C(=O)NH—CH₂—CO—N(CF₃)₂ |
| 663. | NH | C(=O)NH—CH₂—CO—NHCH₂CH₃ |
| 664. | NH | C(=O)NH—CH₂—CO—N(CH₂CH₃)₂ |
| 665. | NH | C(=O)NH—CH₂—CO—NHCH₂CF₃ |
| 666. | NH | C(=O)NH—CH₂—CO—N(CH₂CF₃)₂ |
| 667. | NH | C(=O)NH—CH₂—CO—NHCH₂CH₂CH₃ |
| 668. | NH | C(=O)NH—CH₂—CO—N(CH₂CH₂CH₃)₂ |
| 669. | NH | C(=O)NH—CH₂—CO—NHCH₂CH₂CF₃ |
| 670. | NH | C(=O)NH—CH₂—CO—N(CH₂CH₂CF₃)₂ |
| 671. | NH | C(=O)NH—CH₂—CO—NHCH(CH₃)₂ |
| 672. | NH | C(=O)NH—CH₂—CO—NHCH(CF₃)₂ |
| 673. | NH | C(=O)NH—CH₂—CO—NH-cyclopropyl |
| 674. | NH | C(=O)NH—CH₂—CO—NH—CH₂-cyclopropyl |
| 675. | NH | C(=O)NH—CH₂—CO—OH |
| 676. | NH | C(=O)NH—CH₂—CO—OCH₃ |
| 677. | NH | C(=O)NH—CH₂—CO—OCF₃ |
| 678. | NH | C(=O)NH—CH₂—CO—OCH₂CH₃ |
| 679. | NH | C(=O)NH—CH₂—CO—OCH₂CF₃ |
| 680. | NH | C(=O)NH—CH₂—CO—OCH₂CH₂CH₃ |
| 681. | NH | C(=O)NH—CH₂—CO—OCH(CH₃)₂ |
| 682. | NH | C(=O)NH—CH₂—CO—OCH₂CH₂CH₂CH₃ |
| 683. | NH | C(=O)NH—CH₂—CO—OCH(CH₃)CH₂CH₃ |
| 684. | NH | C(=O)NH—CH₂—CO—OCH₂CH(CH₃)₂ |
| 685. | NH | C(=O)NH—CH₂—CO—OC(CH₃)₃ |
| 686. | NH | C(=O)NH-A-1 |
| 687. | NH | C(=O)NH-A-2 |
| 688. | NH | C(=O)NH-A-3 |
| 689. | NH | C(=O)NH-A-4 |
| 690. | NH | C(=O)NH-A-5 |
| 691. | NH | C(=O)NH-A-6 |
| 692. | NH | C(=O)NH-A-7 |
| 693. | NH | C(=O)NH-A-8 |
| 694. | NH | C(=O)NH-A-9 |
| 695. | NH | C(=O)NH-A-10 |
| 696. | NH | C(=O)NH-A-11 |
| 697. | NH | C(=O)NH-A-12 |
| 698. | NH | C(=O)NH-A-13 |
| 699. | NH | C(=O)NH-A-14 |
| 700. | NH | C(=O)NH-A-15 |
| 701. | NH | C(=O)NH-A-16 |
| 702. | NH | C(=O)NH-A-17 |
| 703. | NH | C(=O)NH-A-18 |
| 704. | NH | C(=O)NH-A-19 |
| 705. | NH | C(=O)NH-A-20 |
| 706. | NH | C(=O)NH-A-21 |
| 707. | NH | C(=O)NH-A-22 |
| 708. | NH | C(=O)NH-A-23 |
| 709. | NH | C(=O)NH-A-24 |
| 710. | NH | C(=O)NH-A-25 |

TABLE A-continued

| No. | Y | R² |
|---|---|---|
| 711. | NH | C(=O)NH-A-26 |
| 712. | NH | C(=O)NH-A-27 |
| 713. | NH | C(=O)NH-A-28 |
| 714. | NH | C(=O)NH-A-29 |
| 715. | NH | C(=O)NH-A-30 |
| 716. | NH | C(=O)NH-A-31 |
| 717. | NH | C(=O)NH-A-32 |
| 718. | NH | C(=O)NH-A-33 |
| 719. | NH | C(=O)NH—CH$_2$-A-1 |
| 720. | NH | C(=O)NH—CH$_2$-A-2 |
| 721. | NH | C(=O)NH—CH$_2$-A-3 |
| 722. | NH | C(=O)NH—CH$_2$-A-4 |
| 723. | NH | C(=O)NH—CH$_2$-A-5 |
| 724. | NH | C(=O)NH—CH$_2$-A-6 |
| 725. | NH | C(=O)NH—CH$_2$-A-7 |
| 726. | NH | C(=O)NH—CH$_2$-A-8 |
| 727. | NH | C(=O)NH—CH$_2$-A-9 |
| 728. | NH | C(=O)NH—CH$_2$-A-10 |
| 729. | NH | C(=O)NH—CH$_2$-A-11 |
| 730. | NH | C(=O)NH—CH$_2$-A-12 |
| 731. | NH | C(=O)NH—CH$_2$-A-13 |
| 732. | NH | C(=O)NH—CH$_2$-A-14 |
| 733. | NH | C(=O)NH—CH$_2$-A-15 |
| 734. | NH | C(=O)NH—CH$_2$-A-16 |
| 735. | NH | C(=O)NH—CH$_2$-A-17 |
| 736. | NH | C(=O)NH—CH$_2$-A-18 |
| 737. | NH | C(=O)NH—CH$_2$-A-19 |
| 738. | NH | C(=O)NH—CH$_2$-A-20 |
| 739. | NH | C(=O)NH—CH$_2$-A-21 |
| 740. | NH | C(=O)NH—CH$_2$-A-22 |
| 741. | NH | C(=O)NH—CH$_2$-A-23 |
| 742. | NH | C(=O)NH—CH$_2$-A-24 |
| 743. | NH | C(=O)NH—CH$_2$-A-25 |
| 744. | NH | C(=O)NH—CH$_2$-A-26 |
| 745. | NH | C(=O)NH—CH$_2$-A-27 |
| 746. | NH | C(=O)NH—CH$_2$-A-28 |
| 747. | NH | C(=O)NH—CH$_2$-A-29 |
| 748. | NH | C(=O)NH—CH$_2$-A-30 |
| 749. | NH | C(=O)NH—CH$_2$-A-31 |
| 750. | NH | C(=O)NH—CH$_2$-A-32 |
| 751. | NH | C(=O)NH—CH$_2$-A-33 |
| 752. | NH | C(=O)NH—SO$_2$—CH$_3$ |
| 753. | NH | C(=O)NH—SO$_2$—CF$_3$ |
| 754. | NH | C(=O)NH—SO$_2$—CH$_2$CH$_3$ |
| 755. | NH | C(=O)NH—SO$_2$—CH$_2$CF$_3$ |
| 756. | NH | C(=O)NH—SO$_2$—CH$_2$CH$_2$CH$_3$ |
| 757. | NH | C(=O)NH—SO$_2$—CH$_2$CH$_2$CF$_3$ |
| 758. | NH | C(=O)NH—SO$_2$—CH$_2$CF$_2$CF$_3$ |
| 759. | NH | C(=O)NH—SO$_2$—CH(CH$_3$)$_2$ |
| 760. | NH | C(=O)NH—SO$_2$—CH(CF$_3$)$_2$ |
| 761. | NH | C(=O)N(CH$_3$)—CH$_2$CHF$_2$ |
| 762. | NH | C(=O)N(CH$_3$)—CH$_2$CH$_2$CHF$_2$ |
| 763. | NH | C(=O)N(CH$_3$)—CH$_2$CH$_2$CF$_3$ |
| 764. | NH | C(=O)N(CH$_3$)-cyclopropyl |
| 765. | NH | C(=O)N(CH$_3$)-cyclobutyl |
| 766. | NH | C(=O)N(CH$_3$)-cyclopentyl |
| 767. | NH | C(=O)N(CH$_3$)-cyclohexyl |
| 768. | NH | C(=O)N(CH$_3$)—CH$_2$-cyclopropyl |
| 769. | NH | C(=O)N(CH$_3$)—CH$_2$-cyclobutyl |
| 770. | NH | C(=O)N(CH$_3$)—CH$_2$-cyclopentyl |
| 771. | NH | C(=O)N(CH$_3$)—CH$_2$-cyclohexyl |
| 772. | NH | C(=O)N(CH$_3$)—CN |
| 773. | NH | C(=O)N(CH$_3$)—CH$_2$—CN |
| 774. | NH | C(=O)N(CH$_3$)—CH$_2$—CH=CH$_2$ |
| 775. | NH | C(=O)N(CH$_3$)—CH$_2$—CH=C(Cl)$_2$ |
| 776. | NH | C(=O)N(CH$_3$)—CH$_2$—CH=CH-phenyl |
| 777. | NH | C(=O)N(CH$_3$)—CH$_2$—CH=CH-(4-Cl-phenyl) |
| 778. | NH | C(=O)N(CH$_3$)—CH$_2$—SCH$_3$ |
| 779. | NH | C(=O)N(CH$_3$)—CH$_2$—SCF$_3$ |
| 780. | NH | C(=O)N(CH$_3$)—CH$_2$—CH$_2$—SCH$_3$ |
| 781. | NH | C(=O)N(CH$_3$)—CH$_2$—CH$_2$—SCF$_3$ |
| 782. | NH | C(=O)N(CH$_3$)—CH$_2$—SO$_2$—CH$_3$ |
| 783. | NH | C(=O)N(CH$_3$)—CH$_2$—SO$_2$—CF$_3$ |
| 784. | NH | C(=O)N(CH$_3$)—CH$_2$—CH$_2$—SO$_2$—CH$_3$ |
| 785. | NH | C(=O)N(CH$_3$)—CH$_2$—CH$_2$—SO$_2$—CF$_3$ |
| 786. | NH | C(=O)N(CH$_3$)—CH$_2$—CO—NH$_2$ |
| 787. | NH | C(=O)N(CH$_3$)—CH$_2$—CO—NHCH$_3$ |
| 788. | NH | C(=O)N(CH$_3$)—CH$_2$—CO—N(CH$_3$)$_2$ |
| 789. | NH | C(=O)N(CH$_3$)—CH$_2$—CO—NHCF$_3$ |
| 790. | NH | C(=O)N(CH$_3$)—CH$_2$—CO—N(CF$_3$)$_2$ |
| 791. | NH | C(=O)N(CH$_3$)—CH$_2$—CO—NHCH$_2$CH$_3$ |
| 792. | NH | C(=O)N(CH$_3$)—CH$_2$—CO—N(CH$_2$CH$_3$)$_2$ |
| 793. | NH | C(=O)N(CH$_3$)—CH$_2$—CO—NHCH$_2$CF$_3$ |
| 794. | NH | C(=O)N(CH$_3$)—CH$_2$—CO—N(CH$_2$CF$_3$)$_2$ |
| 795. | NH | C(=O)N(CH$_3$)—CH$_2$—CO—NHCH$_2$CH$_2$CH$_3$ |
| 796. | NH | C(=O)N(CH$_3$)—CH$_2$—CO—N(CH$_2$CH$_2$CH$_3$)$_2$ |
| 797. | NH | C(=O)N(CH$_3$)—CH$_2$—CO—NHCH$_2$CH$_2$CF$_3$ |
| 798. | NH | C(=O)N(CH$_3$)—CH$_2$—CO—N(CH$_2$CH$_2$CF$_3$)$_2$ |
| 799. | NH | C(=O)N(CH$_3$)—CH$_2$—CO—NHCH(CH$_3$)$_2$ |
| 800. | NH | C(=O)N(CH$_3$)—CH$_2$—CO—NHCH(CF$_3$)$_2$ |
| 801. | NH | C(=O)N(CH$_3$)—CH$_2$—CO—NH-cyclopropyl |
| 802. | NH | C(=O)N(CH$_3$)—CH$_2$—CO—NH—CH$_2$-cyclopropyl |
| 803. | NH | C(=O)N(CH$_3$)—CH$_2$—CO—OH |
| 804. | NH | C(=O)N(CH$_3$)—CH$_2$—CO—OCH$_3$ |
| 805. | NH | C(=O)N(CH$_3$)—CH$_2$—CO—OCF$_3$ |
| 806. | NH | C(=O)N(CH$_3$)—CH$_2$—CO—OCH$_2$CH$_3$ |
| 807. | NH | C(=O)N(CH$_3$)—CH$_2$—CO—OCH$_2$CF$_3$ |
| 808. | NH | C(=O)N(CH$_3$)—CH$_2$—CO—OCH$_2$CH$_2$CH$_3$ |
| 809. | NH | C(=O)N(CH$_3$)—CH$_2$—CO—OCH(CH$_3$)$_2$ |
| 810. | NH | C(=O)N(CH$_3$)—CH$_2$—CO—OCH$_2$CH$_2$CH$_2$CH$_3$ |
| 811. | NH | C(=O)N(CH$_3$)—CH$_2$—CO—OCH(CH$_3$)CH$_2$CH$_3$ |
| 812. | NH | C(=O)N(CH$_3$)—CH$_2$—CO—OCH$_2$CH(CH$_3$)$_2$ |
| 813. | NH | C(=O)N(CH$_3$)—CH$_2$—CO—OC(CH$_3$)$_3$ |
| 814. | NH | C(=O)N(CH$_3$)-A-1 |
| 815. | NH | C(=O)N(CH$_3$)-A-2 |
| 816. | NH | C(=O)N(CH$_3$)-A-3 |
| 817. | NH | C(=O)N(CH$_3$)-A-4 |
| 818. | NH | C(=O)N(CH$_3$)-A-5 |
| 819. | NH | C(=O)N(CH$_3$)-A-6 |
| 820. | NH | C(=O)N(CH$_3$)-A-7 |
| 821. | NH | C(=O)N(CH$_3$)-A-8 |
| 822. | NH | C(=O)N(CH$_3$)-A-9 |
| 823. | NH | C(=O)N(CH$_3$)-A-10 |
| 824. | NH | C(=O)N(CH$_3$)-A-11 |
| 825. | NH | C(=O)N(CH$_3$)-A-12 |
| 826. | NH | C(=O)N(CH$_3$)-A-13 |
| 827. | NH | C(=O)N(CH$_3$)-A-14 |
| 828. | NH | C(=O)N(CH$_3$)-A-15 |
| 829. | NH | C(=O)N(CH$_3$)-A-16 |
| 830. | NH | C(=O)N(CH$_3$)-A-17 |
| 831. | NH | C(=O)N(CH$_3$)-A-18 |
| 832. | NH | C(=O)N(CH$_3$)-A-19 |
| 833. | NH | C(=O)N(CH$_3$)-A-20 |
| 834. | NH | C(=O)N(CH$_3$)-A-21 |
| 835. | NH | C(=O)N(CH$_3$)-A-22 |
| 836. | NH | C(=O)N(CH$_3$)-A-23 |
| 837. | NH | C(=O)N(CH$_3$)-A-24 |
| 838. | NH | C(=O)N(CH$_3$)-A-25 |
| 839. | NH | C(=O)N(CH$_3$)-A-26 |
| 840. | NH | C(=O)N(CH$_3$)-A-27 |
| 841. | NH | C(=O)N(CH$_3$)-A-28 |
| 842. | NH | C(=O)N(CH$_3$)-A-29 |
| 843. | NH | C(=O)N(CH$_3$)-A-30 |
| 844. | NH | C(=O)N(CH$_3$)-A-31 |
| 845. | NH | C(=O)N(CH$_3$)-A-32 |
| 846. | NH | C(=O)N(CH$_3$)-A-33 |
| 847. | NH | C(=O)N(CH$_3$)—CH$_2$-A-1 |
| 848. | NH | C(=O)N(CH$_3$)—CH$_2$-A-2 |
| 849. | NH | C(=O)N(CH$_3$)—CH$_2$-A-3 |
| 850. | NH | C(=O)N(CH$_3$)—CH$_2$-A-4 |
| 851. | NH | C(=O)N(CH$_3$)—CH$_2$-A-5 |
| 852. | NH | C(=O)N(CH$_3$)—CH$_2$-A-6 |
| 853. | NH | C(=O)N(CH$_3$)—CH$_2$-A-7 |
| 854. | NH | C(=O)N(CH$_3$)—CH$_2$-A-8 |
| 855. | NH | C(=O)N(CH$_3$)—CH$_2$-A-9 |
| 856. | NH | C(=O)N(CH$_3$)—CH$_2$-A-10 |
| 857. | NH | C(=O)N(CH$_3$)—CH$_2$-A-11 |
| 858. | NH | C(=O)N(CH$_3$)—CH$_2$-A-12 |
| 859. | NH | C(=O)N(CH$_3$)—CH$_2$-A-13 |
| 860. | NH | C(=O)N(CH$_3$)—CH$_2$-A-14 |
| 861. | NH | C(=O)N(CH$_3$)—CH$_2$-A-15 |
| 862. | NH | C(=O)N(CH$_3$)—CH$_2$-A-16 |
| 863. | NH | C(=O)N(CH$_3$)—CH$_2$-A-17 |
| 864. | NH | C(=O)N(CH$_3$)—CH$_2$-A-18 |
| 865. | NH | C(=O)N(CH$_3$)—CH$_2$-A-19 |
| 866. | NH | C(=O)N(CH$_3$)—CH$_2$-A-20 |

TABLE A-continued

| No. | Y | R² |
|---|---|---|
| 867. | NH | C(=O)N(CH₃)—CH₂-A-21 |
| 868. | NH | C(=O)N(CH₃)—CH₂-A-22 |
| 869. | NH | C(=O)N(CH₃)—CH₂-A-23 |
| 870. | NH | C(=O)N(CH₃)—CH₂-A-24 |
| 871. | NH | C(=O)N(CH₃)—CH₂-A-25 |
| 872. | NH | C(=O)N(CH₃)—CH₂-A-26 |
| 873. | NH | C(=O)N(CH₃)—CH₂-A-27 |
| 874. | NH | C(=O)N(CH₃)—CH₂-A-28 |
| 875. | NH | C(=O)N(CH₃)—CH₂-A-29 |
| 876. | NH | C(=O)N(CH₃)—CH₂-A-30 |
| 877. | NH | C(=O)N(CH₃)—CH₂-A-31 |
| 878. | NH | C(=O)N(CH₃)—CH₂-A-32 |
| 879. | NH | C(=O)N(CH₃)—CH₂-A-33 |
| 880. | NH | C(=O)N(CH₃)—SO₂—CH₃ |
| 881. | NH | C(=O)N(CH₃)—SO₂—CF₃ |
| 882. | NH | C(=O)N(CH₃)—SO₂—CH₂CH₃ |
| 883. | NH | C(=O)N(CH₃)—SO₂—CH₂CF₃ |
| 884. | NH | C(=O)N(CH₃)—SO₂—CH₂CH₂CH₃ |
| 885. | NH | C(=O)N(CH₃)—SO₂—CH₂CH₂CF₃ |
| 886. | NH | C(=O)N(CH₃)—SO₂—CH₂CF₂CF₃ |
| 887. | NH | C(=O)N(CH₃)—SO₂—CH(CH₃)₂ |
| 888. | NH | C(=O)N(CH₃)—SO₂—CH(CF₃)₂ |
| 889. | NH | C(=O)NH—SO₂—NH₂ |
| 890. | NH | C(=O)NH—SO₂—NHCH₃ |
| 891. | NH | C(=O)NH—SO₂—N(CH₃)₂ |
| 892. | NH | C(=O)NH—SO₂—NHCF₃ |
| 893. | NH | C(=O)NH—SO₂—N(CF₃)₂ |
| 894. | NH | C(=O)NH—SO₂—NHCH₂CH₃ |
| 895. | NH | C(=O)NH—SO₂—N(CH₂CH₃)₂ |
| 896. | NH | C(=O)NH—SO₂—NHCH₂CF₃ |
| 897. | NH | C(=O)NH—SO₂—N(CH₂CF₃)₂ |
| 898. | NH | C(=O)NH—SO₂—N(CH₃)CH₂CH₃ |
| 899. | NH | C(=O)NH—SO₂—N(CH₃)CH₂CF₃ |
| 900. | NH | C(=O)NH—SO₂—N(CF₃)CH₂CH₃ |
| 901. | NH | C(=O)NH—SO₂—NHCH₂CH₂CH₃ |
| 902. | NH | C(=O)NH—SO₂—N(CH₂CH₂CH₃)₂ |
| 903. | NH | C(=O)NH—SO₂—NHCH₂CH₂CF₃ |
| 904. | NH | C(=O)NH—SO₂—N(CH₂CH₂CF₃)₂ |
| 905. | NH | C(=O)NH—SO₂—N(CH₃)CH₂CH₂CH₃ |
| 906. | NH | C(=O)NH—SO₂—N(CH₃)CH₂CH₂CF₃ |
| 907. | NH | C(=O)NH—SO₂—N(CF₃)CH₂CH₂CH₃ |
| 908. | NH | C(=O)NH—SO₂—NHCH(CH₃)₂ |
| 909. | NH | C(=O)NH—SO₂—NHCH(CF₃)₂ |
| 910. | NH | C(=O)NH—SO₂—N(CH₃)CH(CH₃)₂ |
| 911. | NH | C(=O)NH—SO₂—N(CH₃)CH(CF₃)₂ |
| 912. | NH | C(=O)NH—SO₂—N(CF₃)CH(CH₃)₂ |
| 913. | NH | C(=O)NH—SO₂—NHCH₂CH₂CH₂CH₃ |
| 914. | NH | C(=O)NH—SO₂—N(CH₂CH₂CH₂CH₃)₂ |
| 915. | NH | C(=O)NH—SO₂—N(CH₃)CH₂CH₂CH₂CH₃ |
| 916. | NH | C(=O)N(CH₃)—SO₂—NH₂ |
| 917. | NH | C(=O)N(CH₃)—SO₂—NHCH₃ |
| 918. | NH | C(=O)N(CH₃)—SO₂—N(CH₃)₂ |
| 919. | NH | C(=O)N(CH₃)—SO₂—NHCF₃ |
| 920. | NH | C(=O)N(CH₃)—SO₂—N(CF₃)₂ |
| 921. | NH | C(=O)N(CH₃)—SO₂—NHCH₂CH₃ |
| 922. | NH | C(=O)N(CH₃)—SO₂—N(CH₂CH₃)₂ |
| 923. | NH | C(=O)N(CH₃)—SO₂—NHCH₂CF₃ |
| 924. | NH | C(=O)N(CH₃)—SO₂—N(CH₂CF₃)₂ |
| 925. | NH | C(=O)N(CH₃)—SO₂—N(CH₃)CH₂CH₃ |
| 926. | NH | C(=O)N(CH₃)—SO₂—N(CH₃)CH₂CF₃ |
| 927. | NH | C(=O)N(CH₃)—SO₂—N(CF₃)CH₂CH₃ |
| 928. | NH | C(=O)N(CH₃)—SO₂—NHCH₂CH₂CH₃ |
| 929. | NH | C(=O)N(CH₃)—SO₂—N(CH₂CH₂CH₃)₂ |
| 930. | NH | C(=O)N(CH₃)—SO₂—NHCH₂CH₂CF₃ |
| 931. | NH | C(=O)N(CH₃)—SO₂—N(CH₂CH₂CF₃)₂ |
| 932. | NH | C(=O)N(CH₃)—SO₂—N(CH₃)CH₂CH₂CH₃ |
| 933. | NH | C(=O)N(CH₃)—SO₂—N(CH₃)CH₂CH₂CF₃ |
| 934. | NH | C(=O)N(CH₃)—SO₂—N(CF₃)CH₂CH₂CH₃ |
| 935. | NH | C(=O)N(CH₃)—SO₂—NHCH(CH₃)₂ |
| 936. | NH | C(=O)N(CH₃)—SO₂—NHCH(CF₃)₂ |
| 937. | NH | C(=O)N(CH₃)—SO₂—N(CH₃)CH(CH₃)₂ |
| 938. | NH | C(=O)N(CH₃)—SO₂—N(CH₃)CH(CF₃)₂ |
| 939. | NH | C(=O)N(CH₃)—SO₂—N(CF₃)CH(CH₃)₂ |
| 940. | NH | C(=O)N(CH₃)—SO₂—NHCH₂CH₂CH₂CH₃ |
| 941. | NH | C(=O)N(CH₃)—SO₂—N(CH₂CH₂CH₂CH₃)₂ |
| 942. | NH | C(=O)N(CH₃)—SO₂—N(CH₃)CH₂CH₂CH₂CH₃ |
| 943. | NH | C(=O)—N=CHOCH₃ |
| 944. | NH | C(=O)—N=CHOCH₂CH₃ |
| 945. | NH | C(=O)—N=CHOCH₂CH₂CH₃ |
| 946. | NH | C(=O)—N=CHOCH(CH₃)₂ |
| 947. | NH | C(=O)—N=CHOCF₃ |
| 948. | NH | C(=O)—N=CHOCH₂CF₃ |
| 949. | NH | C(=O)—N=CHOCH₂CH₂CF₃ |
| 950. | NH | C(=O)—N=CHOCH(CF₃)₂ |
| 951. | NH | C(=O)—N=CH—CO—OCH₃ |
| 952. | NH | C(=O)—N=CH—CO—OCH₂CH₃ |
| 953. | NH | C(=O)—N=CH—CO—OCH₂CH₂CH₃ |
| 954. | NH | C(=O)—N=CH—CO—OCH(CH₃)₂ |
| 955. | NH | C(=O)—N=CH—CO—OCF₃ |
| 956. | NH | C(=O)—N=CH—CO—OCH₂CF₃ |
| 957. | NH | C(=O)—N=CH—CO—OCH₂CH₂CF₃ |
| 958. | NH | C(=O)—N=CH—CO—OCH(CF₃)₂ |
| 959. | NH | C(=O)—N=CH—CO—NHCH₃ |
| 960. | NH | C(=O)—N=CH—CO—N(CH₃)₂ |
| 961. | NH | C(=O)—N=CH—CO—NHCH₂CH₃ |
| 962. | NH | C(=O)—N=CH—CO—N(CH₂CH₃)₂ |
| 963. | NH | C(=O)—N=CH—CO—N(CH₃)CH₂CH₃ |
| 964. | NH | C(=O)—N=CH—CO—NHCH₂CH₂CH₃ |
| 965. | NH | C(=O)—N=CH—CO—N(CH₂CH₃)₂ |
| 966. | NH | C(=O)—N=CH—CO—N(CH₃)CH₂CH₂CH₃ |
| 967. | NH | C(=O)—N=CH—CO—NHCH(CH₃)₂ |
| 968. | NH | C(=O)—N=CH—CO—N(CH₃)CH(CH₃)₂ |
| 969. | NH | C(=O)—N=CH—CO—NHCF₃ |
| 970. | NH | C(=O)—N=CH—CO—N(CF₃)₂ |
| 971. | NH | C(=O)—N=CH—CO—NHCH₂CF₃ |
| 972. | NH | C(=O)—N=CH—CO—N(CH₂CF₃)₂ |
| 973. | NH | C(=O)—N=CH—CO—N(CH₃)CH₂CF₃ |
| 974. | NH | C(=O)—N=CH—CO—N(CF₃)CH₂CF₃ |
| 975. | NH | C(=O)—N=CH—CO—NHCH₂CH₂CF₃ |
| 976. | NH | C(=O)—N=CH—CO—N(CH₂CH₂CF₃)₂ |
| 977. | NH | C(=O)—N=CH—CO—N(CH₃)CH₂CH₂CF₃ |
| 978. | NH | C(=O)—N=CH—CO—N(CF₃)CH₂CH₂CH₃ |
| 979. | NH | C(=O)—N=CH—CO—NHCH(CF₃)₂ |
| 980. | NH | C(=O)—N=CH—CO—N(CH₃)CH(CF₃)₂ |
| 981. | NH | C(=O)—N=CH—CO—N(CF₃)CH(CH₃)₂ |
| 982. | NH | C(=S)NH₂ |
| 983. | NH | C(=S)NHCH₃ |
| 984. | NH | C(=S)N(CH₃)₂ |
| 985. | NH | C(=S)NHCF₃ |
| 986. | NH | C(=S)N(CF₃)₂ |
| 987. | NH | C(=S)NHCH₂CH₃ |
| 988. | NH | C(=S)N(CH₂CH₃)₂ |
| 989. | NH | C(=S)(CH₃)CH₂CH₃ |
| 990. | NH | C(=S)NHCH₂CF₃ |
| 991. | NH | C(=S)N(CH₂CF₃)₂ |
| 992. | NH | C(=S)N(CH₃)CH₂CF₃ |
| 993. | NH | C(=S)NHCH₂CH₃ |
| 994. | NH | C(=S)N(CH₃)CH₂CH₂CH₃ |
| 995. | NH | C(=S)NHCH(CH₃)₂ |
| 996. | NH | C(=S)NH(CH₂)₃CH₃ |
| 997. | NH | C(=S)N(CH₃)—(CH₂)₃CH₃ |
| 998. | NH | C(=S)N[(CH₂)₃CH₃]₂ |
| 999. | NH | C(=S)N(CH₃)—CH₂—C₆H₅ |
| 1000. | NH | C(=S)NH-propargyl |
| 1001. | NH | C(=S)N(CH₃)-propargyl |
| 1002. | NH | C(=S)NH—CH₂-4-Cl—C₆H₄ |
| 1003. | NH | C(=S)N(CH₃)—CH₂-4-Cl—C₆H₄ |
| 1004. | NH | C(=S)morpholin-4-yl |
| 1005. | NH | C(=S)NH-3-thiolyl-1,1-dioxid |
| 1006. | NH | C(=S)N(CH₃)-3-thiolyl-1,1-dioxid |
| 1007. | NH | C(=S)-azirid-1-yl |
| 1008. | NH | C(=S)-pyrrolidin-1-yl |
| 1009. | NH | C(=S)-piperidin-1-yl |
| 1010. | NH | C(=S)-thiomorpholin-4-yl |
| 1011. | NH | C(=S)NH—CH₂CHF₂ |
| 1012. | NH | C(=S)NH—CH₂CH₂CHF₂ |
| 1013. | NH | C(=S)NH—CH₂CH₂CF₃ |
| 1014. | NH | C(=S)NH-cyclopropyl |
| 1015. | NH | C(=S)NH-cyclobutyl |
| 1016. | NH | C(=S)NH-cyclopentyl |
| 1017. | NH | C(=S)NH-cyclohexyl |
| 1018. | NH | C(=S)NH—CH₂-cyclopropyl |
| 1019. | NH | C(=S)NH—CH₂-cyclobutyl |
| 1020. | NH | C(=S)NH—CH₂-cyclopentyl |
| 1021. | NH | C(=S)NH—CH₂-cyclohexyl |
| 1022. | NH | C(=S)NH—CN |

TABLE A-continued

| No. | Y | R² |
|---|---|---|
| 1023. | NH | C(=S)NH—CH₂—CN |
| 1024. | NH | C(=S)NH—CH₂—CH=CH₂ |
| 1025. | NH | C(=S)NH—CH₂—CH=C(Cl)₂ |
| 1026. | NH | C(=S)NH—CH₂—CH=CH-phenyl |
| 1027. | NH | C(=S)NH—CH₂—CH=CH-(4-Cl-phenyl) |
| 1028. | NH | C(=S)NH—CH₂—SCH₃ |
| 1029. | NH | C(=S)NH—CH₂—SCF₃ |
| 1030. | NH | C(=S)NH—CH₂—CH₂—SCH₃ |
| 1031. | NH | C(=S)NH—CH₂—CH₂—SCF₃ |
| 1032. | NH | C(=S)NH—CH₂—SO₂—CH₃ |
| 1033. | NH | C(=S)NH—CH₂—SO₂—CF₃ |
| 1034. | NH | C(=S)NH—CH₂—CH₂—SO₂—CH₃ |
| 1035. | NH | C(=S)NH—CH₂—CH₂—SO₂—CF₃ |
| 1036. | NH | C(=S)NH—CH₂—CO—NH₂ |
| 1037. | NH | C(=S)NH—CH₂—CO—NHCH₃ |
| 1038. | NH | C(=S)NH—CH₂—CO—N(CH₃)₂ |
| 1039. | NH | C(=S)NH—CH₂—CO—NHCF₃ |
| 1040. | NH | C(=S)NH—CH₂—CO—N(CF₃)₂ |
| 1041. | NH | C(=S)NH—CH₂—CO—NHCH₂CH₃ |
| 1042. | NH | C(=S)NH—CH₂—CO—N(CH₂CH₃)₂ |
| 1043. | NH | C(=S)NH—CH₂—CO—NHCH₂CF₃ |
| 1044. | NH | C(=S)NH—CH₂—CO—N(CH₂CF₃)₂ |
| 1045. | NH | C(=S)NH—CH₂—CO—NHCH₂CH₂CH₃ |
| 1046. | NH | C(=S)NH—CH₂—CO—N(CH₂CH₂CH₃)₂ |
| 1047. | NH | C(=S)NH—CH₂—CO—NHCH₂CH₂CF₃ |
| 1048. | NH | C(=S)NH—CH₂—CO—N(CH₂CH₂CF₃)₂ |
| 1049. | NH | C(=S)NH—CH₂—CO—NHCH(CH₃)₂ |
| 1050. | NH | C(=S)NH—CH₂—CO—NHCH(CF₃)₂ |
| 1051. | NH | C(=S)NH—CH₂—CO—NH-cyclopropyl |
| 1052. | NH | C(=S)NH—CH₂—CO—NH—CH₂-cyclopropyl |
| 1053. | NH | C(=S)NH—CH₂—CO—OH |
| 1054. | NH | C(=S)NH—CH₂—CO—OCH₃ |
| 1055. | NH | C(=S)NH—CH₂—CO—OCF₃ |
| 1056. | NH | C(=S)NH—CH₂—CO—OCH₂CH₃ |
| 1057. | NH | C(=S)NH—CH₂—CO—OCH₂CF₃ |
| 1058. | NH | C(=S)NH—CH₂—CO—OCH₂CH₂CH₃ |
| 1059. | NH | C(=S)NH—CH₂—CO—OCH(CH₃)₂ |
| 1060. | NH | C(=S)NH—CH₂—CO—OCH₂CH₂CH₂CH₃ |
| 1061. | NH | C(=S)NH—CH₂—CO—OCH(CH₃)CH₂CH₃ |
| 1062. | NH | C(=S)NH—CH₂—CO—OCH(CH₃)₂ |
| 1063. | NH | C(=S)NH—CH₂—CO—OC(CH₃)₃ |
| 1064. | NH | C(=S)NH-A-1 |
| 1065. | NH | C(=S)NH-A-2 |
| 1066. | NH | C(=S)NH-A-3 |
| 1067. | NH | C(=S)NH-A-4 |
| 1068. | NH | C(=S)NH-A-5 |
| 1069. | NH | C(=S)NH-A-6 |
| 1070. | NH | C(=S)NH-A-7 |
| 1071. | NH | C(=S)NH-A-8 |
| 1072. | NH | C(=S)NH-A-9 |
| 1073. | NH | C(=S)NH-A-10 |
| 1074. | NH | C(=S)NH-A-11 |
| 1075. | NH | C(=S)NH-A-12 |
| 1076. | NH | C(=S)NH-A-13 |
| 1077. | NH | C(=S)NH-A-14 |
| 1078. | NH | C(=S)NH-A-15 |
| 1079. | NH | C(=S)NH-A-16 |
| 1080. | NH | C(=S)NH-A-17 |
| 1081. | NH | C(=S)NH-A-18 |
| 1082. | NH | C(=S)NH-A-19 |
| 1083. | NH | C(=S)NH-A-20 |
| 1084. | NH | C(=S)NH-A-21 |
| 1085. | NH | C(=S)NH-A-22 |
| 1086. | NH | C(=S)NH-A-23 |
| 1087. | NH | C(=S)NH-A-24 |
| 1088. | NH | C(=S)NH-A-25 |
| 1089. | NH | C(=S)NH-A-26 |
| 1090. | NH | C(=S)NH-A-27 |
| 1091. | NH | C(=S)NH-A-28 |
| 1092. | NH | C(=S)NH-A-29 |
| 1093. | NH | C(=S)NH-A-30 |
| 1094. | NH | C(=S)NH-A-31 |
| 1095. | NH | C(=S)NH-A-32 |
| 1096. | NH | C(=S)NH-A-33 |
| 1097. | NH | C(=S)NH—CH₂-A-1 |
| 1098. | NH | C(=S)NH—CH₂-A-2 |
| 1099. | NH | C(=S)NH—CH₂-A-3 |
| 1100. | NH | C(=S)NH—CH₂-A-4 |
| 1101. | NH | C(=S)NH—CH₂-A-5 |
| 1102. | NH | C(=S)NH—CH₂-A-6 |
| 1103. | NH | C(=S)NH—CH₂-A-7 |
| 1104. | NH | C(=S)NH—CH₂-A-8 |
| 1105. | NH | C(=S)NH—CH₂-A-9 |
| 1106. | NH | C(=S)NH—CH₂-A-10 |
| 1107. | NH | C(=S)NH—CH₂-A-11 |
| 1108. | NH | C(=S)NH—CH₂-A-12 |
| 1109. | NH | C(=S)NH—CH₂-A-13 |
| 1110. | NH | C(=S)NH—CH₂-A-14 |
| 1111. | NH | C(=S)NH—CH₂-A-15 |
| 1112. | NH | C(=S)NH—CH₂-A-16 |
| 1113. | NH | C(=S)NH—CH₂-A-17 |
| 1114. | NH | C(=S)NH—CH₂-A-18 |
| 1115. | NH | C(=S)NH—CH₂-A-19 |
| 1116. | NH | C(=S)NH—CH₂-A-20 |
| 1117. | NH | C(=S)NH—CH₂-A-21 |
| 1118. | NH | C(=S)NH—CH₂-A-22 |
| 1119. | NH | C(=S)NH—CH₂-A-23 |
| 1120. | NH | C(=S)NH—CH₂-A-24 |
| 1121. | NH | C(=S)NH—CH₂-A-25 |
| 1122. | NH | C(=S)NH—CH₂-A-26 |
| 1123. | NH | C(=S)NH—CH₂-A-27 |
| 1124. | NH | C(=S)NH—CH₂-A-28 |
| 1125. | NH | C(=S)NH—CH₂-A-29 |
| 1126. | NH | C(=S)NH—CH₂-A-30 |
| 1127. | NH | C(=S)NH—CH₂-A-31 |
| 1128. | NH | C(=S)NH—CH₂-A-32 |
| 1129. | NH | C(=S)NH—CH₂-A-33 |
| 1130. | NH | C(=S)NH—SO₂—CH₃ |
| 1131. | NH | C(=S)NH—SO₂—CF₃ |
| 1132. | NH | C(=S)NH—SO₂—CH₂CH₃ |
| 1133. | NH | C(=S)NH—SO₂—CH₂CF₃ |
| 1134. | NH | C(=S)NH—SO₂—CH₂CH₂CH₃ |
| 1135. | NH | C(=S)NH—SO₂—CH₂CH₂CF₃ |
| 1136. | NH | C(=S)NH—SO₂—CH₂CF₂CF₃ |
| 1137. | NH | C(=S)NH—SO₂—CH(CH₃)₂ |
| 1138. | NH | C(=S)NH—SO₂—CH(CF₃)₂ |
| 1139. | NH | C(=S)N(CH₃)—CH₂CHF₂ |
| 1140. | NH | C(=S)N(CH₃)—CH₂CH₂CHF₂ |
| 1141. | NH | C(=S)N(CH₃)—CH₂CH₂CF₃ |
| 1142. | NH | C(=S)N(CH₃)-cyclopropyl |
| 1143. | NH | C(=S)N(CH₃)-cyclobutyl |
| 1144. | NH | C(=S)N(CH₃)-cyclopentyl |
| 1145. | NH | C(=S)N(CH₃)-cyclohexyl |
| 1146. | NH | C(=S)N(CH₃)—CH₂-cyclopropyl |
| 1147. | NH | C(=S)N(CH₃)—CH₂-cyclobutyl |
| 1148. | NH | C(=S)N(CH₃)—CH₂-cyclopentyl |
| 1149. | NH | C(=S)N(CH₃)—CH₂-cyclohexyl |
| 1150. | NH | C(=S)N(CH₃)—CN |
| 1151. | NH | C(=S)N(CH₃)—CH₂—CN |
| 1152. | NH | C(=S)N(CH₃)—CH₂—CH=CH₂ |
| 1153. | NH | C(=S)N(CH₃)—CH₂—CH=C(Cl)₂ |
| 1154. | NH | C(=S)N(CH₃)—CH₂—CH=CH-phenyl |
| 1155. | NH | C(=S)N(CH₃)—CH₂—CH=CH-(4-Cl-phenyl) |
| 1156. | NH | C(=S)N(CH₃)—CH₂—SCH₃ |
| 1157. | NH | C(=S)N(CH₃)—CH₂—SCF₃ |
| 1158. | NH | C(=S)N(CH₃)—CH₂—CH₂—SCH₃ |
| 1159. | NH | C(=S)N(CH₃)—CH₂—CH₂—SCF₃ |
| 1160. | NH | C(=S)N(CH₃)—CH₂—SO₂—CH₃ |
| 1161. | NH | C(=S)N(CH₃)—CH₂—SO₂—CF₃ |
| 1162. | NH | C(=S)N(CH₃)—CH₂—CH₂—SO₂—CH₃ |
| 1163. | NH | C(=S)N(CH₃)—CH₂—CH₂—SO₂—CF₃ |
| 1164. | NH | C(=S)N(CH₃)—CH₂—CO—NH₂ |
| 1165. | NH | C(=S)N(CH₃)—CH₂—CO—NHCH₃ |
| 1166. | NH | C(=S)N(CH₃)—CH₂—CO—N(CH₃)₂ |
| 1167. | NH | C(=S)N(CH₃)—CH₂—CO—NHCF₃ |
| 1168. | NH | C(=S)N(CH₃)—CH₂—CO—N(CF₃)₂ |
| 1169. | NH | C(=S)N(CH₃)—CH₂—CO—NHCH₂CH₃ |
| 1170. | NH | C(=S)N(CH₃)—CH₂—CO—N(CH₂CH₃)₂ |
| 1171. | NH | C(=S)N(CH₃)—CH₂—CO—NHCH₂CF₃ |
| 1172. | NH | C(=S)N(CH₃)—CH₂—CO—N(CH₂CF₃)₂ |
| 1173. | NH | C(=S)N(CH₃)—CH₂—CO—NHCH₂CH₂CH₃ |
| 1174. | NH | C(=S)N(CH₃)—CH₂—CO—N(CH₂CH₂CH₃)₂ |
| 1175. | NH | C(=S)N(CH₃)—CH₂—CO—NHCH₂CH₂CF₃ |
| 1176. | NH | C(=S)N(CH₃)—CH₂—CO—N(CH₂CH₂CF₃)₂ |
| 1177. | NH | C(=S)N(CH₃)—CH₂—CO—NHCH(CH₃)₂ |
| 1178. | NH | C(=S)N(CH₃)—CH₂—CO—NHCH(CF₃)₂ |

TABLE A-continued

| No. | Y | R² |
|---|---|---|
| 1179. | NH | C(=S)N(CH₃)—CH₂—CO—NH-cyclopropyl |
| 1180. | NH | C(=S)N(CH₃)—CH₂—CO—NH—CH₂-cyclopropyl |
| 1181. | NH | C(=S)N(CH₃)—CH₂—CO—OH |
| 1182. | NH | C(=S)N(CH₃)—CH₂—CO—OCH₃ |
| 1183. | NH | C(=S)N(CH₃)—CH₂—CO—OCF₃ |
| 1184. | NH | C(=S)N(CH₃)—CH₂—CO—OCH₂CH₃ |
| 1185. | NH | C(=S)N(CH₃)—CH₂—CO—OCH₂CF₃ |
| 1186. | NH | C(=S)N(CH₃)—CH₂—CO—OCH₂CH₂CH₃ |
| 1187. | NH | C(=S)N(CH₃)—CH₂—CO—OCH(CH₃)₂ |
| 1188. | NH | C(=S)N(CH₃)—CH₂—CO—OCH₂CH₂CH₂CH₃ |
| 1189. | NH | C(=S)N(CH₃)—CH₂—CO—OCH(CH₃)CH₂CH₃ |
| 1190. | NH | C(=S)N(CH₃)—CH₂—CO—OCH₂CH(CH₃)₂ |
| 1191. | NH | C(=S)N(CH₃)—CH₂—CO—OC(CH₃)₃ |
| 1192. | NH | C(=S)N(CH₃)-A-1 |
| 1193. | NH | C(=S)N(CH₃)-A-2 |
| 1194. | NH | C(=S)N(CH₃)-A-3 |
| 1195. | NH | C(=S)N(CH₃)-A-4 |
| 1196. | NH | C(=S)N(CH₃)-A-5 |
| 1197. | NH | C(=S)N(CH₃)-A-6 |
| 1198. | NH | C(=S)N(CH₃)-A-7 |
| 1199. | NH | C(=S)N(CH₃)-A-8 |
| 1200. | NH | C(=S)N(CH₃)-A-9 |
| 1201. | NH | C(=S)N(CH₃)-A-10 |
| 1202. | NH | C(=S)N(CH₃)-A-11 |
| 1203. | NH | C(=S)N(CH₃)-A-12 |
| 1204. | NH | C(=S)N(CH₃)-A-13 |
| 1205. | NH | C(=S)N(CH₃)-A-14 |
| 1206. | NH | C(=S)N(CH₃)-A-15 |
| 1207. | NH | C(=S)N(CH₃)-A-16 |
| 1208. | NH | C(=S)N(CH₃)-A-17 |
| 1209. | NH | C(=S)N(CH₃)-A-18 |
| 1210. | NH | C(=S)N(CH₃)-A-19 |
| 1211. | NH | C(=S)N(CH₃)-A-20 |
| 1212. | NH | C(=S)N(CH₃)-A-21 |
| 1213. | NH | C(=S)N(CH₃)-A-22 |
| 1214. | NH | C(=S)N(CH₃)-A-23 |
| 1215. | NH | C(=S)N(CH₃)-A-24 |
| 1216. | NH | C(=S)N(CH₃)-A-25 |
| 1217. | NH | C(=S)N(CH₃)-A-26 |
| 1218. | NH | C(=S)N(CH₃)-A-27 |
| 1219. | NH | C(=S)N(CH₃)-A-28 |
| 1220. | NH | C(=S)N(CH₃)-A-29 |
| 1221. | NH | C(=S)N(CH₃)-A-30 |
| 1222. | NH | C(=S)N(CH₃)-A-31 |
| 1223. | NH | C(=S)N(CH₃)-A-32 |
| 1224. | NH | C(=S)N(CH₃)-A-33 |
| 1225. | NH | C(=S)N(CH₃)—CH₂-A-1 |
| 1226. | NH | C(=S)N(CH₃)—CH₂-A-2 |
| 1227. | NH | C(=S)N(CH₃)—CH₂-A-3 |
| 1228. | NH | C(=S)N(CH₃)—CH₂-A-4 |
| 1229. | NH | C(=S)N(CH₃)—CH₂-A-5 |
| 1230. | NH | C(=S)N(CH₃)—CH₂-A-6 |
| 1231. | NH | C(=S)N(CH₃)—CH₂-A-7 |
| 1232. | NH | C(=S)N(CH₃)—CH₂-A-8 |
| 1233. | NH | C(=S)N(CH₃)—CH₂-A-9 |
| 1234. | NH | C(=S)N(CH₃)—CH₂-A-10 |
| 1235. | NH | C(=S)N(CH₃)—CH₂-A-11 |
| 1236. | NH | C(=S)N(CH₃)—CH₂-A-12 |
| 1237. | NH | C(=S)N(CH₃)—CH₂-A-13 |
| 1238. | NH | C(=S)N(CH₃)—CH₂-A-14 |
| 1239. | NH | C(=S)N(CH₃)—CH₂-A-15 |
| 1240. | NH | C(=S)N(CH₃)—CH₂-A-16 |
| 1241. | NH | C(=S)N(CH₃)—CH₂-A-17 |
| 1242. | NH | C(=S)N(CH₃)—CH₂-A-18 |
| 1243. | NH | C(=S)N(CH₃)—CH₂-A-19 |
| 1244. | NH | C(=S)N(CH₃)—CH₂-A-20 |
| 1245. | NH | C(=S)N(CH₃)—CH₂-A-21 |
| 1246. | NH | C(=S)N(CH₃)—CH₂-A-22 |
| 1247. | NH | C(=S)N(CH₃)—CH₂-A-23 |
| 1248. | NH | C(=S)N(CH₃)—CH₂-A-24 |
| 1249. | NH | C(=S)N(CH₃)—CH₂-A-25 |
| 1250. | NH | C(=S)N(CH₃)—CH₂-A-26 |
| 1251. | NH | C(=S)N(CH₃)—CH₂-A-27 |
| 1252. | NH | C(=S)N(CH₃)—CH₂-A-28 |
| 1253. | NH | C(=S)N(CH₃)—CH₂-A-29 |
| 1254. | NH | C(=S)N(CH₃)—CH₂-A-30 |
| 1255. | NH | C(=S)N(CH₃)—CH₂-A-31 |
| 1256. | NH | C(=S)N(CH₃)—CH₂-A-32 |
| 1257. | NH | C(=S)N(CH₃)—CH₂-A-33 |
| 1258. | NH | C(=S)N(CH₃)—SO₂—CH₃ |
| 1259. | NH | C(=S)N(CH₃)—SO₂—CF₃ |
| 1260. | NH | C(=S)N(CH₃)—SO₂—CH₂CH₃ |
| 1261. | NH | C(=S)N(CH₃)—SO₂—CH₂CF₃ |
| 1262. | NH | C(=S)N(CH₃)—SO₂—CH₂CH₂CH₃ |
| 1263. | NH | C(=S)N(CH₃)—SO₂—CH₂CH₂CF₃ |
| 1264. | NH | C(=S)N(CH₃)—SO₂—CH₂CF₂CF₃ |
| 1265. | NH | C(=S)N(CH₃)—SO₂—CH(CH₃)₂ |
| 1266. | NH | C(=S)N(CH₃)—SO₂—CH(CF₃)₂ |
| 1267. | NH | C(=S)NH—SO₂—NH₂ |
| 1268. | NH | C(=S)NH—SO₂—NHCH₃ |
| 1269. | NH | C(=S)NH—SO₂—N(CH₃)₂ |
| 1270. | NH | C(=S)NH—SO₂—NHCF₃ |
| 1271. | NH | C(=S)NH—SO₂—N(CF₃)₂ |
| 1272. | NH | C(=S)NH—SO₂—NHCH₂CH₃ |
| 1273. | NH | C(=S)NH—SO₂—N(CH₂CH₃)₂ |
| 1274. | NH | C(=S)NH—SO₂—NHCH₂CF₃ |
| 1275. | NH | C(=S)NH—SO₂—N(CH₂CF₃)₂ |
| 1276. | NH | C(=S)NH—SO₂—N(CH₃)CH₂CH₃ |
| 1277. | NH | C(=S)NH—SO₂—N(CH₃)CH₂CF₃ |
| 1278. | NH | C(=S)NH—SO₂—N(CF₃)CH₂CH₃ |
| 1279. | NH | C(=S)NH—SO₂—NHCH₂CH₂CH₃ |
| 1280. | NH | C(=S)NH—SO₂—N(CH₂CH₂CH₃)₂ |
| 1281. | NH | C(=S)NH—SO₂—NHCH₂CH₂CF₃ |
| 1282. | NH | C(=S)NH—SO₂—N(CH₂CH₂CF₃)₂ |
| 1283. | NH | C(=S)NH—SO₂—N(CH₃)CH₂CH₂CH₃ |
| 1284. | NH | C(=S)NH—SO₂—N(CH₃)CH₂CH₂CF₃ |
| 1285. | NH | C(=S)NH—SO₂—N(CF₃)CH₂CH₂CH₃ |
| 1286. | NH | C(=S)NH—SO₂—NHCH(CH₃)₂ |
| 1287. | NH | C(=S)NH—SO₂—NHCH(CF₃)₂ |
| 1288. | NH | C(=S)NH—SO₂—N(CH₃)CH(CH₃)₂ |
| 1289. | NH | C(=S)NH—SO₂—N(CH₃)CH(CF₃)₂ |
| 1290. | NH | C(=S)NH—SO₂—N(CF₃)CH(CH₃)₂ |
| 1291. | NH | C(=S)NH—SO₂—NHCH₂CH₂CH₂CH₃ |
| 1292. | NH | C(=S)NH—SO₂—N(CH₂CH₂CH₃)₂ |
| 1293. | NH | C(=S)NH—SO₂—N(CH₃)CH₂CH₂CH₂CH₃ |
| 1294. | NH | C(=S)N(CH₃)—SO₂—NH₂ |
| 1295. | NH | C(=S)N(CH₃)—SO₂—NHCH₃ |
| 1296. | NH | C(=S)N(CH₃)—SO₂—N(CH₃)₂ |
| 1297. | NH | C(=S)N(CH₃)—SO₂—NHCF₃ |
| 1298. | NH | C(=S)N(CH₃)—SO₂—N(CF₃)₂ |
| 1299. | NH | C(=S)N(CH₃)—SO₂—NHCH₂CH₃ |
| 1300. | NH | C(=S)N(CH₃)—SO₂—N(CH₂CH₃)₂ |
| 1301. | NH | C(=S)N(CH₃)—SO₂—NHCH₂CF₃ |
| 1302. | NH | C(=S)N(CH₃)—SO₂—N(CH₂CF₃)₂ |
| 1303. | NH | C(=S)N(CH₃)—SO₂—N(CH₃)CH₂CH₃ |
| 1304. | NH | C(=S)N(CH₃)—SO₂—N(CH₃)CH₂CF₃ |
| 1305. | NH | C(=S)N(CH₃)—SO₂—N(CF₃)CH₂CH₃ |
| 1306. | NH | C(=S)N(CH₃)—SO₂—NHCH₂CH₂CH₃ |
| 1307. | NH | C(=S)N(CH₃)—SO₂—N(CH₂CH₂CH₃)₂ |
| 1308. | NH | C(=S)N(CH₃)—SO₂—NHCH₂CH₂CF₃ |
| 1309. | NH | C(=S)N(CH₃)—SO₂—N(CH₂CH₂CF₃)₂ |
| 1310. | NH | C(=S)N(CH₃)—SO₂—N(CH₃)CH₂CH₂CH₃ |
| 1311. | NH | C(=S)N(CH₃)—SO₂—N(CH₃)CH₂CH₂CF₃ |
| 1312. | NH | C(=S)N(CH₃)—SO₂—N(CF₃)CH₂CH₂CH₃ |
| 1313. | NH | C(=S)N(CH₃)—SO₂—NHCH(CH₃)₂ |
| 1314. | NH | C(=S)N(CH₃)—SO₂—NHCH(CF₃)₂ |
| 1315. | NH | C(=S)N(CH₃)—SO₂—N(CH₃)CH(CH₃)₂ |
| 1316. | NH | C(=S)N(CH₃)—SO₂—N(CH₃)CH(CF₃)₂ |
| 1317. | NH | C(=S)N(CH₃)—SO₂—N(CF₃)CH(CH₃)₂ |
| 1318. | NH | C(=S)N(CH₃)—SO₂—NHCH₂CH₂CH₂CH₃ |
| 1319. | NH | C(=S)N(CH₃)—SO₂—N(CH₂CH₂CH₃)₂ |
| 1320. | NH | C(=S)N(CH₃)—SO₂—N(CH₃)CH₂CH₂CH₂CH₃ |
| 1321. | NH | C(=S)—N=CHOCH₃ |
| 1322. | NH | C(=S)—N=CHOCH₂CH₃ |
| 1323. | NH | C(=S)—N=CHOCH₂CH₂CH₃ |
| 1324. | NH | C(=S)—N=CHOCH(CH₃)₂ |
| 1325. | NH | C(=S)—N=CHOCF₃ |
| 1326. | NH | C(=S)—N=CHOCH₂CF₃ |
| 1327. | NH | C(=S)—N=CHOCH₂CH₂CF₃ |
| 1328. | NH | C(=S)—N=CHOCH(CF₃)₂ |
| 1329. | NH | C(=S)—N=CH—CO—OCH₃ |
| 1330. | NH | C(=S)—N=CH—CO—OCH₂CH₃ |
| 1331. | NH | C(=S)—N=CH—CO—OCH₂CH₂CH₃ |
| 1332. | NH | C(=S)—N=CH—CO—OCH(CH₃)₂ |
| 1333. | NH | C(=S)—N=CH—CO—OCF₃ |
| 1334. | NH | C(=S)—N=CH—CO—OCH₂CF₃ |

TABLE A-continued

| No. | Y | R² |
|---|---|---|
| 1335. | NH | C(=S)—N=CH—CO—OCH₂CH₂CF₃ |
| 1336. | NH | C(=S)—N=CH—CO—OCH(CF₃)₂ |
| 1337. | NH | C(=S)—N=CH—CO—NHCH₃ |
| 1338. | NH | C(=S)—N=CH—CO—N(CH₃)₂ |
| 1339. | NH | C(=S)—N=CH—CO—NHCH₂CH₃ |
| 1340. | NH | C(=S)—N=CH—CO—N(CH₂CH₃)₂ |
| 1341. | NH | C(=S)—N=CH—CO—N(CH₃)CH₂CH₃ |
| 1342. | NH | C(=S)—N=CH—CO—NHCH₂CH₃ |
| 1343. | NH | C(=S)—N=CH—CO—N(CH₂CH₂CH₃)₂ |
| 1344. | NH | C(=S)—N=CH—CO—N(CH₃)CH₂CH₂CH₃ |
| 1345. | NH | C(=S)—N=CH—CO—NHCH(CH₃)₂ |
| 1346. | NH | C(=S)—N=CH—CO—N(CH₃)CH(CH₃)₂ |
| 1347. | NH | C(=S)—N=CH—CO—NHCF₃ |
| 1348. | NH | C(=S)—N=CH—CO—N(CF₃)₂ |
| 1349. | NH | C(=S)—N=CH—CO—NHCH₂CF₃ |
| 1350. | NH | C(=S)—N=CH—CO—N(CH₂CF₃)₂ |
| 1351. | NH | C(=S)—N=CH—CO—N(CH₃)CH₂CF₃ |
| 1352. | NH | C(=S)—N=CH—CO—N(CF₃)CH₂CF₃ |
| 1353. | NH | C(=S)—N=CH—CO—NHCH₂CH₂CF₃ |
| 1354. | NH | C(=S)—N=CH—CO—N(CH₂CH₂CF₃)₂ |
| 1355. | NH | C(=S)—N=CH—CO—N(CH₃)CH₂CH₂CF₃ |
| 1356. | NH | C(=S)—N=CH—CO—N(CF₃)CH₂CH₂CH₃ |
| 1357. | NH | C(=S)—N=CH—CO—NHCH(CF₃)₂ |
| 1358. | NH | C(=S)—N=CH—CO—N(CH₃)CH(CF₃)₂ |
| 1359. | NH | C(=S)—N=CH—CO—N(CF₃)CH(CH₃)₂ |
| 1360. | NCH₃ | C(=O)NH₂ |
| 1361. | NCH₃ | C(=O)NHCH₃ |
| 1362. | NCH₃ | C(=O)N(CH₃)₂ |
| 1363. | NCH₃ | C(=O)NHCF₃ |
| 1364. | NCH₃ | C(=O)N(CF₃)₂ |
| 1365. | NCH₃ | C(=O)NHCH₂CH₃ |
| 1366. | NCH₃ | C(=O)N(CH₂CH₃)₂ |
| 1367. | NCH₃ | C(=O)(CH₃)CH₂CH₃ |
| 1368. | NCH₃ | C(=O)NHCH₂CF₃ |
| 1369. | NCH₃ | C(=O)N(CH₂CF₃)₂ |
| 1370. | NCH₃ | C(=O)N(CH₃)CH₂CF₃ |
| 1371. | NCH₃ | C(=O)NHCH₂CH₃ |
| 1372. | NCH₃ | C(=O)N(CH₃)CH₂CH₂CH₃ |
| 1373. | NCH₃ | C(=O)NHCH(CH₃)₂ |
| 1374. | NCH₃ | C(=O)NH(CH₂)₃CH₃ |
| 1375. | NCH₃ | C(=O)N(CH₃)—(CH₂)₃CH₃ |
| 1376. | NCH₃ | C(=O)N[(CH₂)₃CH₃]₂ |
| 1377. | NCH₃ | C(=O)N(CH₃)—CH₂—C₆H₅ |
| 1378. | NCH₃ | C(=O)NH-propargyl |
| 1379. | NCH₃ | C(=O)N(CH₃)-propargyl |
| 1380. | NCH₃ | C(=O)NH—CH₂-4-Cl—C₆H₄ |
| 1381. | NCH₃ | C(=O)N(CH₃)—CH₂-4-Cl—C₆H₄ |
| 1382. | NCH₃ | C(=O)morpholin-4-yl |
| 1383. | NCH₃ | C(=O)NH-3-thiolyl-1,1-dioxid |
| 1384. | NCH₃ | C(=O)N(CH₃)-3-thiolyl-1,1-dioxid |
| 1385. | NCH₃ | C(=O)-azirid-1-yl |
| 1386. | NCH₃ | C(=O)-pyrrolidin-1-yl |
| 1387. | NCH₃ | C(=O)-piperidin-1-yl |
| 1388. | NCH₃ | C(=O)-thiomorpholin-4-yl |
| 1389. | NCH₃ | C(=O)NH—CH₂CHF₂ |
| 1390. | NCH₃ | C(=O)NH—CH₂CH₂CHF₂ |
| 1391. | NCH₃ | C(=O)NH—CH₂CH₂CF₃ |
| 1392. | NCH₃ | C(=O)NH-cyclopropyl |
| 1393. | NCH₃ | C(=O)NH-cyclobutyl |
| 1394. | NCH₃ | C(=O)NH-cyclopentyl |
| 1395. | NCH₃ | C(=O)NH-cyclohexyl |
| 1396. | NCH₃ | C(=O)NH—CH₂-cyclopropyl |
| 1397. | NCH₃ | C(=O)NH—CH₂-cyclobutyl |
| 1398. | NCH₃ | C(=O)NH—CH₂-cyclopentyl |
| 1399. | NCH₃ | C(=O)NH—CH₂-cyclohexyl |
| 1400. | NCH₃ | C(=O)NH—CN |
| 1401. | NCH₃ | C(=O)NH—CH₂—CN |
| 1402. | NCH₃ | C(=O)NH—CH₂—CH=CH₂ |
| 1403. | NCH₃ | C(=O)NH—CH₂—CH=C(Cl)₂ |
| 1404. | NCH₃ | C(=O)NH—CH₂—CH=CH-phenyl |
| 1405. | NCH₃ | C(=O)NH—CH₂—CH=CH-(4-Cl-phenyl) |
| 1406. | NCH₃ | C(=O)NH—CH₂—SCH₃ |
| 1407. | NCH₃ | C(=O)NH—CH₂—SCF₃ |
| 1408. | NCH₃ | C(=O)NH—CH₂—CH₂—SCH₃ |
| 1409. | NCH₃ | C(=O)NH—CH₂—CH₂—SCF₃ |
| 1410. | NCH₃ | C(=O)NH—CH₂—SO₂—CH₃ |
| 1411. | NCH₃ | C(=O)NH—CH₂—SO₂—CF₃ |
| 1412. | NCH₃ | C(=O)NH—CH₂—CH₂—SO₂—CH₃ |
| 1413. | NCH₃ | C(=O)NH—CH₂—CH₂—SO₂—CF₃ |
| 1414. | NCH₃ | C(=O)NH—CH₂—CO—NH₂ |
| 1415. | NCH₃ | C(=O)NH—CH₂—CO—NHCH₃ |
| 1416. | NCH₃ | C(=O)NH—CH₂—CO—N(CH₃)₂ |
| 1417. | NCH₃ | C(=O)NH—CH₂—CO—NHCF₃ |
| 1418. | NCH₃ | C(=O)NH—CH₂—CO—N(CF₃)₂ |
| 1419. | NCH₃ | C(=O)NH—CH₂—CO—NHCH₂CH₃ |
| 1420. | NCH₃ | C(=O)NH—CH₂—CO—N(CH₂CH₃)₂ |
| 1421. | NCH₃ | C(=O)NH—CH₂—CO—NHCH₂CF₃ |
| 1422. | NCH₃ | C(=O)NH—CH₂—CO—N(CH₂CF₃)₂ |
| 1423. | NCH₃ | C(=O)NH—CH₂—CO—NHCH₂CH₂CH₃ |
| 1424. | NCH₃ | C(=O)NH—CH₂—CO—N(CH₂CH₂CH₃)₂ |
| 1425. | NCH₃ | C(=O)NH—CH₂—CO—NHCH₂CH₂CF₃ |
| 1426. | NCH₃ | C(=O)NH—CH₂—CO—N(CH₂CH₂CF₃)₂ |
| 1427. | NCH₃ | C(=O)NH—CH₂—CO—NHCH(CH₃)₂ |
| 1428. | NCH₃ | C(=O)NH—CH₂—CO—NHCH(CF₃)₂ |
| 1429. | NCH₃ | C(=O)NH—CH₂—CO—NH-cyclopropyl |
| 1430. | NCH₃ | C(=O)NH—CH₂—CO—NH—CH₂-cyclopropyl |
| 1431. | NCH₃ | C(=O)NH—CH₂—CO—OH |
| 1432. | NCH₃ | C(=O)NH—CH₂—CO—OCH₃ |
| 1433. | NCH₃ | C(=O)NH—CH₂—CO—OCF₃ |
| 1434. | NCH₃ | C(=O)NH—CH₂—CO—OCH₂CH₃ |
| 1435. | NCH₃ | C(=O)NH—CH₂—CO—OCH₂CF₃ |
| 1436. | NCH₃ | C(=O)NH—CH₂—CO—OCH₂CH₂CH₃ |
| 1437. | NCH₃ | C(=O)NH—CH₂—CO—OCH(CH₃)₂ |
| 1438. | NCH₃ | C(=O)NH—CH₂—CO—OCH₂CH₂CH₂CH₃ |
| 1439. | NCH₃ | C(=O)NH—CH₂—CO—OCH(CH₃)CH₂CH₃ |
| 1440. | NCH₃ | C(=O)NH—CH₂—CO—OCH₂CH(CH₃)₂ |
| 1441. | NCH₃ | C(=O)NH—CH₂—CO—OC(CH₃)₃ |
| 1442. | NCH₃ | C(=O)NH-A-1 |
| 1443. | NCH₃ | C(=O)NH-A-2 |
| 1444. | NCH₃ | C(=O)NH-A-3 |
| 1445. | NCH₃ | C(=O)NH-A-4 |
| 1446. | NCH₃ | C(=O)NH-A-5 |
| 1447. | NCH₃ | C(=O)NH-A-6 |
| 1448. | NCH₃ | C(=O)NH-A-7 |
| 1449. | NCH₃ | C(=O)NH-A-8 |
| 1450. | NCH₃ | C(=O)NH-A-9 |
| 1451. | NCH₃ | C(=O)NH-A-10 |
| 1452. | NCH₃ | C(=O)NH-A-11 |
| 1453. | NCH₃ | C(=O)NH-A-12 |
| 1454. | NCH₃ | C(=O)NH-A-13 |
| 1455. | NCH₃ | C(=O)NH-A-14 |
| 1456. | NCH₃ | C(=O)NH-A-15 |
| 1457. | NCH₃ | C(=O)NH-A-16 |
| 1458. | NCH₃ | C(=O)NH-A-17 |
| 1459. | NCH₃ | C(=O)NH-A-18 |
| 1460. | NCH₃ | C(=O)NH-A-19 |
| 1461. | NCH₃ | C(=O)NH-A-20 |
| 1462. | NCH₃ | C(=O)NH-A-21 |
| 1463. | NCH₃ | C(=O)NH-A-22 |
| 1464. | NCH₃ | C(=O)NH-A-23 |
| 1465. | NCH₃ | C(=O)NH-A-24 |
| 1466. | NCH₃ | C(=O)NH-A-25 |
| 1467. | NCH₃ | C(=O)NH-A-26 |
| 1468. | NCH₃ | C(=O)NH-A-27 |
| 1469. | NCH₃ | C(=O)NH-A-28 |
| 1470. | NCH₃ | C(=O)NH-A-29 |
| 1471. | NCH₃ | C(=O)NH-A-30 |
| 1472. | NCH₃ | C(=O)NH-A-31 |
| 1473. | NCH₃ | C(=O)NH-A-32 |
| 1474. | NCH₃ | C(=O)NH-A-33 |
| 1475. | NCH₃ | C(=O)NH—CH₂-A-1 |
| 1476. | NCH₃ | C(=O)NH—CH₂-A-2 |
| 1477. | NCH₃ | C(=O)NH—CH₂-A-3 |
| 1478. | NCH₃ | C(=O)NH—CH₂-A-4 |
| 1479. | NCH₃ | C(=O)NH—CH₂-A-5 |
| 1480. | NCH₃ | C(=O)NH—CH₂-A-6 |
| 1481. | NCH₃ | C(=O)NH—CH₂-A-7 |
| 1482. | NCH₃ | C(=O)NH—CH₂-A-8 |
| 1483. | NCH₃ | C(=O)NH—CH₂-A-9 |
| 1484. | NCH₃ | C(=O)NH—CH₂-A-10 |
| 1485. | NCH₃ | C(=O)NH—CH₂-A-11 |
| 1486. | NCH₃ | C(=O)NH—CH₂-A-12 |
| 1487. | NCH₃ | C(=O)NH—CH₂-A-13 |
| 1488. | NCH₃ | C(=O)NH—CH₂-A-14 |
| 1489. | NCH₃ | C(=O)NH—CH₂-A-15 |
| 1490. | NCH₃ | C(=O)NH—CH₂-A-16 |

TABLE A-continued

| No. | Y | R² |
|---|---|---|
| 1491. | NCH₃ | C(=O)NH—CH₂-A-17 |
| 1492. | NCH₃ | C(=O)NH—CH₂-A-18 |
| 1493. | NCH₃ | C(=O)NH—CH₂-A-19 |
| 1494. | NCH₃ | C(=O)NH—CH₂-A-20 |
| 1495. | NCH₃ | C(=O)NH—CH₂-A-21 |
| 1496. | NCH₃ | C(=O)NH—CH₂-A-22 |
| 1497. | NCH₃ | C(=O)NH—CH₂-A-23 |
| 1498. | NCH₃ | C(=O)NH—CH₂-A-24 |
| 1499. | NCH₃ | C(=O)NH—CH₂-A-25 |
| 1500. | NCH₃ | C(=O)NH—CH₂-A-26 |
| 1501. | NCH₃ | C(=O)NH—CH₂-A-27 |
| 1502. | NCH₃ | C(=O)NH—CH₂-A-28 |
| 1503. | NCH₃ | C(=O)NH—CH₂-A-29 |
| 1504. | NCH₃ | C(=O)NH—CH₂-A-30 |
| 1505. | NCH₃ | C(=O)NH—CH₂-A-31 |
| 1506. | NCH₃ | C(=O)NH—CH₂-A-32 |
| 1507. | NCH₃ | C(=O)NH—CH₂-A-33 |
| 1508. | NCH₃ | C(=O)NH—SO₂—CH₃ |
| 1509. | NCH₃ | C(=O)NH—SO₂—CF₃ |
| 1510. | NCH₃ | C(=O)NH—SO₂—CH₂CH₃ |
| 1511. | NCH₃ | C(=O)NH—SO₂—CH₂CF₃ |
| 1512. | NCH₃ | C(=O)NH—SO₂—CH₂CH₂CH₃ |
| 1513. | NCH₃ | C(=O)NH—SO₂—CH₂CH₂CF₃ |
| 1514. | NCH₃ | C(=O)NH—SO₂—CH₂CF₂CF₃ |
| 1515. | NCH₃ | C(=O)NH—SO₂—CH(CH₃)₂ |
| 1516. | NCH₃ | C(=O)NH—SO₂—CH(CF₃)₂ |
| 1517. | NCH₃ | C(=O)N(CH₃)—CH₂CHF₂ |
| 1518. | NCH₃ | C(=O)N(CH₃)—CH₂CH₂CHF₂ |
| 1519. | NCH₃ | C(=O)N(CH₃)—CH₂CH₂CF₃ |
| 1520. | NCH₃ | C(=O)N(CH₃)-cyclopropyl |
| 1521. | NCH₃ | C(=O)N(CH₃)-cyclobutyl |
| 1522. | NCH₃ | C(=O)N(CH₃)-cyclopentyl |
| 1523. | NCH₃ | C(=O)N(CH₃)-cyclohexyl |
| 1524. | NCH₃ | C(=O)N(CH₃)—CH₂-cyclopropyl |
| 1525. | NCH₃ | C(=O)N(CH₃)—CH₂-cyclobutyl |
| 1526. | NCH₃ | C(=O)N(CH₃)—CH₂-cyclopentyl |
| 1527. | NCH₃ | C(=O)N(CH₃)—CH₂-cyclohexyl |
| 1528. | NCH₃ | C(=O)N(CH₃)—CN |
| 1529. | NCH₃ | C(=O)N(CH₃)—CH₂—CN |
| 1530. | NCH₃ | C(=O)N(CH₃)—CH₂—CH=CH₂ |
| 1531. | NCH₃ | C(=O)N(CH₃)—CH₂—CH=C(Cl)₂ |
| 1532. | NCH₃ | C(=O)N(CH₃)—CH₂—CH=CH-phenyl |
| 1533. | NCH₃ | C(=O)N(CH₃)—CH₂—CH=CH-(4-Cl-phenyl) |
| 1534. | NCH₃ | C(=O)N(CH₃)—CH₂—SCH₃ |
| 1535. | NCH₃ | C(=O)N(CH₃)—CH₂—SCF₃ |
| 1536. | NCH₃ | C(=O)N(CH₃)—CH₂—CH₂—SCH₃ |
| 1537. | NCH₃ | C(=O)N(CH₃)—CH₂—CH₂—SCF₃ |
| 1538. | NCH₃ | C(=O)N(CH₃)—CH₂—SO₂—CH₃ |
| 1539. | NCH₃ | C(=O)N(CH₃)—CH₂—SO₂—CF₃ |
| 1540. | NCH₃ | C(=O)N(CH₃)—CH₂—CH₂—SO₂—CH₃ |
| 1541. | NCH₃ | C(=O)N(CH₃)—CH₂—CH₂—SO₂—CF₃ |
| 1542. | NCH₃ | C(=O)N(CH₃)—CH₂—CO—NH₂ |
| 1543. | NCH₃ | C(=O)N(CH₃)—CH₂—CO—NHCH₃ |
| 1544. | NCH₃ | C(=O)N(CH₃)—CH₂—CO—N(CH₃)₂ |
| 1545. | NCH₃ | C(=O)N(CH₃)—CH₂—CO—NHCF₃ |
| 1546. | NCH₃ | C(=O)N(CH₃)—CH₂—CO—N(CF₃)₂ |
| 1547. | NCH₃ | C(=O)N(CH₃)—CH₂—CO—NHCH₂CH₃ |
| 1548. | NCH₃ | C(=O)N(CH₃)—CH₂—CO—N(CH₂CH₃)₂ |
| 1549. | NCH₃ | C(=O)N(CH₃)—CH₂—CO—NHCH₂CF₃ |
| 1550. | NCH₃ | C(=O)N(CH₃)—CH₂—CO—N(CH₂CF₃)₂ |
| 1551. | NCH₃ | C(=O)N(CH₃)—CH₂—CO—NHCH₂CH₂CH₃ |
| 1552. | NCH₃ | C(=O)N(CH₃)—CH₂—CO—N(CH₂CH₂CH₃)₂ |
| 1553. | NCH₃ | C(=O)N(CH₃)—CH₂—CO—NHCH₂CH₂CF₃ |
| 1554. | NCH₃ | C(=O)N(CH₃)—CH₂—CO—N(CH₂CH₂CF₃)₂ |
| 1555. | NCH₃ | C(=O)N(CH₃)—CH₂—CO—NHCH(CH₃)₂ |
| 1556. | NCH₃ | C(=O)N(CH₃)—CH₂—CO—NHCH(CF₃)₂ |
| 1557. | NCH₃ | C(=O)N(CH₃)—CH₂—CO—NH-cyclopropyl |
| 1558. | NCH₃ | C(=O)N(CH₃)—CH₂—CO—NH—CH₂-cyclopropyl |
| 1559. | NCH₃ | C(=O)N(CH₃)—CH₂—CO—OH |
| 1560. | NCH₃ | C(=O)N(CH₃)—CH₂—CO—OCH₃ |
| 1561. | NCH₃ | C(=O)N(CH₃)—CH₂—CO—OCF₃ |
| 1562. | NCH₃ | C(=O)N(CH₃)—CH₂—CO—OCH₂CH₃ |
| 1563. | NCH₃ | C(=O)N(CH₃)—CH₂—CO—OCH₂CF₃ |
| 1564. | NCH₃ | C(=O)N(CH₃)—CH₂—CO—OCH₂CH₂CH₃ |
| 1565. | NCH₃ | C(=O)N(CH₃)—CH₂—CO—OCH(CH₃)₂ |
| 1566. | NCH₃ | C(=O)N(CH₃)—CH₂—CO—OCH₂CH₂CH₂CH₃ |
| 1567. | NCH₃ | C(=O)N(CH₃)—CH₂—CO—OCH(CH₃)CH₂CH₃ |
| 1568. | NCH₃ | C(=O)N(CH₃)—CH₂—CO—OCH₂CH(CH₃)₂ |
| 1569. | NCH₃ | C(=O)N(CH₃)—CH₂—CO—OC(CH₃)₃ |
| 1570. | NCH₃ | C(=O)N(CH₃)-A-1 |
| 1571. | NCH₃ | C(=O)N(CH₃)-A-2 |
| 1572. | NCH₃ | C(=O)N(CH₃)-A-3 |
| 1573. | NCH₃ | C(=O)N(CH₃)-A-4 |
| 1574. | NCH₃ | C(=O)N(CH₃)-A-5 |
| 1575. | NCH₃ | C(=O)N(CH₃)-A-6 |
| 1576. | NCH₃ | C(=O)N(CH₃)-A-7 |
| 1577. | NCH₃ | C(=O)N(CH₃)-A-8 |
| 1578. | NCH₃ | C(=O)N(CH₃)-A-9 |
| 1579. | NCH₃ | C(=O)N(CH₃)-A-10 |
| 1580. | NCH₃ | C(=O)N(CH₃)-A-11 |
| 1581. | NCH₃ | C(=O)N(CH₃)-A-12 |
| 1582. | NCH₃ | C(=O)N(CH₃)-A-13 |
| 1583. | NCH₃ | C(=O)N(CH₃)-A-14 |
| 1584. | NCH₃ | C(=O)N(CH₃)-A-15 |
| 1585. | NCH₃ | C(=O)N(CH₃)-A-16 |
| 1586. | NCH₃ | C(=O)N(CH₃)-A-17 |
| 1587. | NCH₃ | C(=O)N(CH₃)-A-18 |
| 1588. | NCH₃ | C(=O)N(CH₃)-A-19 |
| 1589. | NCH₃ | C(=O)N(CH₃)-A-20 |
| 1590. | NCH₃ | C(=O)N(CH₃)-A-21 |
| 1591. | NCH₃ | C(=O)N(CH₃)-A-22 |
| 1592. | NCH₃ | C(=O)N(CH₃)-A-23 |
| 1593. | NCH₃ | C(=O)N(CH₃)-A-24 |
| 1594. | NCH₃ | C(=O)N(CH₃)-A-25 |
| 1595. | NCH₃ | C(=O)N(CH₃)-A-26 |
| 1596. | NCH₃ | C(=O)N(CH₃)-A-27 |
| 1597. | NCH₃ | C(=O)N(CH₃)-A-28 |
| 1598. | NCH₃ | C(=O)N(CH₃)-A-29 |
| 1599. | NCH₃ | C(=O)N(CH₃)-A-30 |
| 1600. | NCH₃ | C(=O)N(CH₃)-A-31 |
| 1601. | NCH₃ | C(=O)N(CH₃)-A-32 |
| 1602. | NCH₃ | C(=O)N(CH₃)-A-33 |
| 1603. | NCH₃ | C(=O)N(CH₃)—CH₂-A-1 |
| 1604. | NCH₃ | C(=O)N(CH₃)—CH₂-A-2 |
| 1605. | NCH₃ | C(=O)N(CH₃)—CH₂-A-3 |
| 1606. | NCH₃ | C(=O)N(CH₃)—CH₂-A-4 |
| 1607. | NCH₃ | C(=O)N(CH₃)—CH₂-A-5 |
| 1608. | NCH₃ | C(=O)N(CH₃)—CH₂-A-6 |
| 1609. | NCH₃ | C(=O)N(CH₃)—CH₂-A-7 |
| 1610. | NCH₃ | C(=O)N(CH₃)—CH₂-A-8 |
| 1611. | NCH₃ | C(=O)N(CH₃)—CH₂-A-9 |
| 1612. | NCH₃ | C(=O)N(CH₃)—CH₂-A-10 |
| 1613. | NCH₃ | C(=O)N(CH₃)—CH₂-A-11 |
| 1614. | NCH₃ | C(=O)N(CH₃)—CH₂-A-12 |
| 1615. | NCH₃ | C(=O)N(CH₃)—CH₂-A-13 |
| 1616. | NCH₃ | C(=O)N(CH₃)—CH₂-A-14 |
| 1617. | NCH₃ | C(=O)N(CH₃)—CH₂-A-15 |
| 1618. | NCH₃ | C(=O)N(CH₃)—CH₂-A-16 |
| 1619. | NCH₃ | C(=O)N(CH₃)—CH₂-A-17 |
| 1620. | NCH₃ | C(=O)N(CH₃)—CH₂-A-18 |
| 1621. | NCH₃ | C(=O)N(CH₃)—CH₂-A-19 |
| 1622. | NCH₃ | C(=O)N(CH₃)—CH₂-A-20 |
| 1623. | NCH₃ | C(=O)N(CH₃)—CH₂-A-21 |
| 1624. | NCH₃ | C(=O)N(CH₃)—CH₂-A-22 |
| 1625. | NCH₃ | C(=O)N(CH₃)—CH₂-A-23 |
| 1626. | NCH₃ | C(=O)N(CH₃)—CH₂-A-24 |
| 1627. | NCH₃ | C(=O)N(CH₃)—CH₂-A-25 |
| 1628. | NCH₃ | C(=O)N(CH₃)—CH₂-A-26 |
| 1629. | NCH₃ | C(=O)N(CH₃)—CH₂-A-27 |
| 1630. | NCH₃ | C(=O)N(CH₃)—CH₂-A-28 |
| 1631. | NCH₃ | C(=O)N(CH₃)—CH₂-A-29 |
| 1632. | NCH₃ | C(=O)N(CH₃)—CH₂-A-30 |
| 1633. | NCH₃ | C(=O)N(CH₃)—CH₂-A-31 |
| 1634. | NCH₃ | C(=O)N(CH₃)—CH₂-A-32 |
| 1635. | NCH₃ | C(=O)N(CH₃)—CH₂-A-33 |
| 1636. | NCH₃ | C(=O)N(CH₃)—SO₂—CH₃ |
| 1637. | NCH₃ | C(=O)N(CH₃)—SO₂—CF₃ |
| 1638. | NCH₃ | C(=O)N(CH₃)—SO₂—CH₂CH₃ |
| 1639. | NCH₃ | C(=O)N(CH₃)—SO₂—CH₂CF₃ |
| 1640. | NCH₃ | C(=O)N(CH₃)—SO₂—CH₂CH₂CH₃ |
| 1641. | NCH₃ | C(=O)N(CH₃)—SO₂—CH₂CH₂CF₃ |
| 1642. | NCH₃ | C(=O)N(CH₃)—SO₂—CH₂CF₂CF₃ |
| 1643. | NCH₃ | C(=O)N(CH₃)—SO₂—CH(CH₃)₂ |
| 1644. | NCH₃ | C(=O)N(CH₃)—SO₂—CH(CF₃)₂ |
| 1645. | NCH₃ | C(=O)NH—SO₂—NH₂ |
| 1646. | NCH₃ | C(=O)NH—SO₂—NHCH₃ |

TABLE A-continued

| No. | Y | R² |
|---|---|---|
| 1647. | NCH₃ | C(=O)NH—SO₂—N(CH₃)₂ |
| 1648. | NCH₃ | C(=O)NH—SO₂—NHCF₃ |
| 1649. | NCH₃ | C(=O)NH—SO₂—N(CF₃)₂ |
| 1650. | NCH₃ | C(=O)NH—SO₂—NHCH₂CH₃ |
| 1651. | NCH₃ | C(=O)NH—SO₂—N(CH₂CH₃)₂ |
| 1652. | NCH₃ | C(=O)NH—SO₂—NHCH₂CF₃ |
| 1653. | NCH₃ | C(=O)NH—SO₂—N(CH₂CF₃)₂ |
| 1654. | NCH₃ | C(=O)NH—SO₂—N(CH₃)CH₂CH₃ |
| 1655. | NCH₃ | C(=O)NH—SO₂—N(CH₃)CH₂CF₃ |
| 1656. | NCH₃ | C(=O)NH—SO₂—N(CF₃)CH₂CH₃ |
| 1657. | NCH₃ | C(=O)NH—SO₂—NHCH₂CH₂CH₃ |
| 1658. | NCH₃ | C(=O)NH—SO₂—N(CH₂CH₂CH₃)₂ |
| 1659. | NCH₃ | C(=O)NH—SO₂—NHCH₂CH₂CF₃ |
| 1660. | NCH₃ | C(=O)NH—SO₂—N(CH₂CH₂CF₃)₂ |
| 1661. | NCH₃ | C(=O)NH—SO₂—N(CH₃)CH₂CH₂CH₃ |
| 1662. | NCH₃ | C(=O)NH—SO₂—N(CH₃)CH₂CH₂CF₃ |
| 1663. | NCH₃ | C(=O)NH—SO₂—N(CF₃)CH₂CH₂CH₃ |
| 1664. | NCH₃ | C(=O)NH—SO₂—NHCH(CH₃)₂ |
| 1665. | NCH₃ | C(=O)NH—SO₂—NHCH(CF₃)₂ |
| 1666. | NCH₃ | C(=O)NH—SO₂—N(CH₃)CH(CH₃)₂ |
| 1667. | NCH₃ | C(=O)NH—SO₂—N(CH₃)CH(CF₃)₂ |
| 1668. | NCH₃ | C(=O)NH—SO₂—N(CF₃)CH(CH₃)₂ |
| 1669. | NCH₃ | C(=O)NH—SO₂—NHCH₂CH₂CH₂CH₃ |
| 1670. | NCH₃ | C(=O)NH—SO₂—N(CH₂CH₂CH₂CH₃)₂ |
| 1671. | NCH₃ | C(=O)NH—SO₂—N(CH₃)CH₂CH₂CH₂CH₃ |
| 1672. | NCH₃ | C(=O)N(CH₃)—SO₂—NH₂ |
| 1673. | NCH₃ | C(=O)N(CH₃)—SO₂—NHCH₃ |
| 1674. | NCH₃ | C(=O)N(CH₃)—SO₂—N(CH₃)₂ |
| 1675. | NCH₃ | C(=O)N(CH₃)—SO₂—NHCF₃ |
| 1676. | NCH₃ | C(=O)N(CH₃)—SO₂—N(CF₃)₂ |
| 1677. | NCH₃ | C(=O)N(CH₃)—SO₂—NHCH₂CH₃ |
| 1678. | NCH₃ | C(=O)N(CH₃)—SO₂—N(CH₂CH₃)₂ |
| 1679. | NCH₃ | C(=O)N(CH₃)—SO₂—NHCH₂CF₃ |
| 1680. | NCH₃ | C(=O)N(CH₃)—SO₂—N(CH₂CF₃)₂ |
| 1681. | NCH₃ | C(=O)N(CH₃)—SO₂—N(CH₃)CH₂CH₃ |
| 1682. | NCH₃ | C(=O)N(CH₃)—SO₂—N(CH₃)CH₂CF₃ |
| 1683. | NCH₃ | C(=O)N(CH₃)—SO₂—N(CF₃)CH₂CH₃ |
| 1684. | NCH₃ | C(=O)N(CH₃)—SO₂—NHCH₂CH₂CH₃ |
| 1685. | NCH₃ | C(=O)N(CH₃)—SO₂—N(CH₂CH₂CH₃)₂ |
| 1686. | NCH₃ | C(=O)N(CH₃)—SO₂—NHCH₂CH₂CF₃ |
| 1687. | NCH₃ | C(=O)N(CH₃)—SO₂—N(CH₂CH₂CF₃)₂ |
| 1688. | NCH₃ | C(=O)N(CH₃)—SO₂—N(CH₃)CH₂CH₂CH₃ |
| 1689. | NCH₃ | C(=O)N(CH₃)—SO₂—N(CH₃)CH₂CH₂CF₃ |
| 1690. | NCH₃ | C(=O)N(CH₃)—SO₂—N(CF₃)CH₂CH₂CH₃ |
| 1691. | NCH₃ | C(=O)N(CH₃)—SO₂—NHCH(CH₃)₂ |
| 1692. | NCH₃ | C(=O)N(CH₃)—SO₂—NHCH(CF₃)₂ |
| 1693. | NCH₃ | C(=O)N(CH₃)—SO₂—N(CH₃)CH(CH₃)₂ |
| 1694. | NCH₃ | C(=O)N(CH₃)—SO₂—N(CH₃)CH(CF₃)₂ |
| 1695. | NCH₃ | C(=O)N(CH₃)—SO₂—N(CF₃)CH(CH₃)₂ |
| 1696. | NCH₃ | C(=O)N(CH₃)—SO₂—NHCH₂CH₂CH₂CH₃ |
| 1697. | NCH₃ | C(=O)N(CH₃)—SO₂—N(CH₂CH₂CH₂CH₃)₂ |
| 1698. | NCH₃ | C(=O)N(CH₃)—SO₂—N(CH₃)CH₂CH₂CH₂CH₃ |
| 1699. | NCH₃ | C(=O)—N=CHOCH₃ |
| 1700. | NCH₃ | C(=O)—N=CHOCH₂CH₃ |
| 1701. | NCH₃ | C(=O)—N=CHOCH₂CH₂CH₃ |
| 1702. | NCH₃ | C(=O)—N=CHOCH(CH₃)₂ |
| 1703. | NCH₃ | C(=O)—N=CHOCF₃ |
| 1704. | NCH₃ | C(=O)—N=CHOCH₂CF₃ |
| 1705. | NCH₃ | C(=O)—N=CHOCH₂CH₂CF₃ |
| 1706. | NCH₃ | C(=O)—N=CHOCH(CF₃)₂ |
| 1707. | NCH₃ | C(=O)—N=CH—CO—OCH₃ |
| 1708. | NCH₃ | C(=O)—N=CH—CO—OCH₂CH₃ |
| 1709. | NCH₃ | C(=O)—N=CH—CO—OCH₂CH₂CH₃ |
| 1710. | NCH₃ | C(=O)—N=CH—CO—OCH(CH₃)₂ |
| 1711. | NCH₃ | C(=O)—N=CH—CO—OCF₃ |
| 1712. | NCH₃ | C(=O)—N=CH—CO—OCH₂CF₃ |
| 1713. | NCH₃ | C(=O)—N=CH—CO—OCH₂CH₂CF₃ |
| 1714. | NCH₃ | C(=O)—N=CH—CO—OCH(CF₃)₂ |
| 1715. | NCH₃ | C(=O)—N=CH—CO—NHCH₃ |
| 1716. | NCH₃ | C(=O)—N=CH—CO—N(CH₃)₂ |
| 1717. | NCH₃ | C(=O)—N=CH—CO—NHCH₂CH₃ |
| 1718. | NCH₃ | C(=O)—N=CH—CO—N(CH₂CH₃)₂ |
| 1719. | NCH₃ | C(=O)—N=CH—CO—NHCH₂CH₂CH₃ |
| 1720. | NCH₃ | C(=O)—N=CH—CO—NHCH₂CH₂CH₃ |
| 1721. | NCH₃ | C(=O)—N=CH—CO—N(CH₂CH₂CH₃)₂ |
| 1722. | NCH₃ | C(=O)—N=CH—CO—N(CH₃)CH₂CH₂CH₃ |
| 1723. | NCH₃ | C(=O)—N=CH—CO—NHCH(CH₃)₂ |
| 1724. | NCH₃ | C(=O)—N=CH—CO—N(CH₃)CH(CH₃)₂ |
| 1725. | NCH₃ | C(=O)—N=CH—CO—NHCF₃ |
| 1726. | NCH₃ | C(=O)—N=CH—CO—N(CF₃)₂ |
| 1727. | NCH₃ | C(=O)—N=CH—CO—NHCH₂CF₃ |
| 1728. | NCH₃ | C(=O)—N=CH—CO—N(CH₂CF₃)₂ |
| 1729. | NCH₃ | C(=O)—N=CH—CO—N(CH₃)CH₂CF₃ |
| 1730. | NCH₃ | C(=O)—N=CH—CO—N(CF₃)CH₂CF₃ |
| 1731. | NCH₃ | C(=O)—N=CH—CO—NHCH₂CH₂CF₃ |
| 1732. | NCH₃ | C(=O)—N=CH—CO—N(CH₂CH₂CF₃)₂ |
| 1733. | NCH₃ | C(=O)—N=CH—CO—N(CH₃)CH₂CH₂CF₃ |
| 1734. | NCH₃ | C(=O)—N=CH—CO—N(CF₃)CH₂CH₂CH₃ |
| 1735. | NCH₃ | C(=O)—N=CH—CO—NHCH(CF₃)₂ |
| 1736. | NCH₃ | C(=O)—N=CH—CO—N(CH₃)CH(CF₃)₂ |
| 1737. | NCH₃ | C(=O)—N=CH—CO—N(CF₃)CH(CH₃)₂ |
| 1738. | NCH₃ | C(=S)NH₂ |
| 1739. | NCH₃ | C(=S)NHCH₃ |
| 1740. | NCH₃ | C(=S)N(CH₃)₂ |
| 1741. | NCH₃ | C(=S)NHCF₃ |
| 1742. | NCH₃ | C(=S)N(CF₃)₂ |
| 1743. | NCH₃ | C(=S)NHCH₂CH₃ |
| 1744. | NCH₃ | C(=S)N(CH₂CH₃)₂ |
| 1745. | NCH₃ | C(=S)(CH₃)CH₂CH₃ |
| 1746. | NCH₃ | C(=S)NHCH₂CF₃ |
| 1747. | NCH₃ | C(=S)N(CF₃)₂ |
| 1748. | NCH₃ | C(=S)N(CH₃)CH₂CF₃ |
| 1749. | NCH₃ | C(=S)NHCH₂CH₂CH₃ |
| 1750. | NCH₃ | C(=S)N(CH₃)CH₂CH₂CH₃ |
| 1751. | NCH₃ | C(=S)NHCH(CH₃)₂ |
| 1752. | NCH₃ | C(=S)NH(CH₂)₃CH₃ |
| 1753. | NCH₃ | C(=S)N(CH₃)—(CH₂)₃CH₃ |
| 1754. | NCH₃ | C(=S)N[(CH₂)₃CH₃]₂ |
| 1755. | NCH₃ | C(=S)N(CH₃)—CH₂—C₆H₅ |
| 1756. | NCH₃ | C(=S)NH-propargyl |
| 1757. | NCH₃ | C(=S)N(CH₃)-propargyl |
| 1758. | NCH₃ | C(=S)NH—CH₂-4-Cl—C₆H₄ |
| 1759. | NCH₃ | C(=S)N(CH₃)—CH₂-4-Cl—C₆H₄ |
| 1760. | NCH₃ | C(=S)morpholin-4-yl |
| 1761. | NCH₃ | C(=S)NH-3-thiolyl-1,1-dioxid |
| 1762. | NCH₃ | C(=S)N(CH₃)-3-thiolyl-1,1-dioxid |
| 1763. | NCH₃ | C(=S)-azirid-1-yl |
| 1764. | NCH₃ | C(=S)-pyrrolidin-1-yl |
| 1765. | NCH₃ | C(=S)-piperidin-1-yl |
| 1766. | NCH₃ | C(=S)-thiomorpholin-4-yl |
| 1767. | NCH₃ | C(=S)NH—CH₂CHF₂ |
| 1768. | NCH₃ | C(=S)NH—CH₂CH₂CHF₂ |
| 1769. | NCH₃ | C(=S)NH—CH₂CH₂CF₃ |
| 1770. | NCH₃ | C(=S)NH-cyclopropyl |
| 1771. | NCH₃ | C(=S)NH-cyclobutyl |
| 1772. | NCH₃ | C(=S)NH-cyclopentyl |
| 1773. | NCH₃ | C(=S)NH-cyclohexyl |
| 1774. | NCH₃ | C(=S)NH—CH₂-cyclopropyl |
| 1775. | NCH₃ | C(=S)NH—CH₂-cyclobutyl |
| 1776. | NCH₃ | C(=S)NH—CH₂-cyclopentyl |
| 1777. | NCH₃ | C(=S)NH—CH₂-cyclohexyl |
| 1778. | NCH₃ | C(=S)NH—CN |
| 1779. | NCH₃ | C(=S)NH—CH₂—CN |
| 1780. | NCH₃ | C(=S)NH—CH₂—CH=CH₂ |
| 1781. | NCH₃ | C(=S)NH—CH₂—CH=C(Cl)₂ |
| 1782. | NCH₃ | C(=S)NH—CH₂—CH=CH-phenyl |
| 1783. | NCH₃ | C(=S)NH—CH₂—CH=CH-(4-Cl-phenyl) |
| 1784. | NCH₃ | C(=S)NH—CH₂—SCH₃ |
| 1785. | NCH₃ | C(=S)NH—CH₂—SCF₃ |
| 1786. | NCH₃ | C(=S)NH—CH₂—CH₂—SCH₃ |
| 1787. | NCH₃ | C(=S)NH—CH₂—CH₂—SCF₃ |
| 1788. | NCH₃ | C(=S)NH—CH₂—SO₂—CH₃ |
| 1789. | NCH₃ | C(=S)NH—CH₂—SO₂—CF₃ |
| 1790. | NCH₃ | C(=S)NH—CH₂—CH₂—SO₂—CH₃ |
| 1791. | NCH₃ | C(=S)NH—CH₂—CH₂—SO₂—CF₃ |
| 1792. | NCH₃ | C(=S)NH—CH₂—CO—NH₂ |
| 1793. | NCH₃ | C(=S)NH—CH₂—CO—NHCH₃ |
| 1794. | NCH₃ | C(=S)NH—CH₂—CO—N(CH₃)₂ |
| 1795. | NCH₃ | C(=S)NH—CH₂—CO—NHCF₃ |
| 1796. | NCH₃ | C(=S)NH—CH₂—CO—N(CF₃)₂ |
| 1797. | NCH₃ | C(=S)NH—CH₂—CO—N(CH₂CH₃)₂ |
| 1798. | NCH₃ | C(=S)NH—CH₂—CO—NHCH₂CH₃ |
| 1799. | NCH₃ | C(=S)NH—CH₂—CO—NHCH₂CF₃ |
| 1800. | NCH₃ | C(=S)NH—CH₂—CO—N(CH₂CF₃)₂ |
| 1801. | NCH₃ | C(=S)NH—CH₂—CO—NHCH₂CH₂CH₃ |
| 1802. | NCH₃ | C(=S)NH—CH₂—CO—N(CH₂CH₂CH₃)₂ |

TABLE A-continued

| No. | Y | R² |
|---|---|---|
| 1803. | NCH₃ | C(=S)NH—CH₂—CO—NHCH₂CH₂CF₃ |
| 1804. | NCH₃ | C(=S)NH—CH₂—CO—N(CH₂CH₂CF₃)₂ |
| 1805. | NCH₃ | C(=S)NH—CH₂—CO—NHCH(CH₃)₂ |
| 1806. | NCH₃ | C(=S)NH—CH₂—CO—NHCH(CF₃)₂ |
| 1807. | NCH₃ | C(=S)NH—CH₂—CO—NH-cyclopropyl |
| 1808. | NCH₃ | C(=S)NH—CH₂—CO—NH—CH₂-cyclopropyl |
| 1809. | NCH₃ | C(=S)NH—CH₂—CO—OH |
| 1810. | NCH₃ | C(=S)NH—CH₂—CO—OCH₃ |
| 1811. | NCH₃ | C(=S)NH—CH₂—CO—OCF₃ |
| 1812. | NCH₃ | C(=S)NH—CH₂—CO—OCH₂CH₃ |
| 1813. | NCH₃ | C(=S)NH—CH₂—CO—OCH₂CF₃ |
| 1814. | NCH₃ | C(=S)NH—CH₂—CO—OCH₂CH₂CH₃ |
| 1815. | NCH₃ | C(=S)NH—CH₂—CO—OCH(CH₃)₂ |
| 1816. | NCH₃ | C(=S)NH—CH₂—CO—OCH₂CH₂CH₂CH₃ |
| 1817. | NCH₃ | C(=S)NH—CH₂—CO—OCH(CH₃)CH₂CH₃ |
| 1818. | NCH₃ | C(=S)NH—CH₂—CO—OCH₂CH(CH₃)₂ |
| 1819. | NCH₃ | C(=S)NH—CH₂—CO—OC(CH₃)₃ |
| 1820. | NCH₃ | C(=S)NH-A-1 |
| 1821. | NCH₃ | C(=S)NH-A-2 |
| 1822. | NCH₃ | C(=S)NH-A-3 |
| 1823. | NCH₃ | C(=S)NH-A-4 |
| 1824. | NCH₃ | C(=S)NH-A-5 |
| 1825. | NCH₃ | C(=S)NH-A-6 |
| 1826. | NCH₃ | C(=S)NH-A-7 |
| 1827. | NCH₃ | C(=S)NH-A-8 |
| 1828. | NCH₃ | C(=S)NH-A-9 |
| 1829. | NCH₃ | C(=S)NH-A-10 |
| 1830. | NCH₃ | C(=S)NH-A-11 |
| 1831. | NCH₃ | C(=S)NH-A-12 |
| 1832. | NCH₃ | C(=S)NH-A-13 |
| 1833. | NCH₃ | C(=S)NH-A-14 |
| 1834. | NCH₃ | C(=S)NH-A-15 |
| 1835. | NCH₃ | C(=S)NH-A-16 |
| 1836. | NCH₃ | C(=S)NH-A-17 |
| 1837. | NCH₃ | C(=S)NH-A-18 |
| 1838. | NCH₃ | C(=S)NH-A-19 |
| 1839. | NCH₃ | C(=S)NH-A-20 |
| 1840. | NCH₃ | C(=S)NH-A-21 |
| 1841. | NCH₃ | C(=S)NH-A-22 |
| 1842. | NCH₃ | C(=S)NH-A-23 |
| 1843. | NCH₃ | C(=S)NH-A-24 |
| 1844. | NCH₃ | C(=S)NH-A-25 |
| 1845. | NCH₃ | C(=S)NH-A-26 |
| 1846. | NCH₃ | C(=S)NH-A-27 |
| 1847. | NCH₃ | C(=S)NH-A-28 |
| 1848. | NCH₃ | C(=S)NH-A-29 |
| 1849. | NCH₃ | C(=S)NH-A-30 |
| 1850. | NCH₃ | C(=S)NH-A-31 |
| 1851. | NCH₃ | C(=S)NH-A-32 |
| 1852. | NCH₃ | C(=S)NH-A-33 |
| 1853. | NCH₃ | C(=S)NH—CH₂-A-1 |
| 1854. | NCH₃ | C(=S)NH—CH₂-A-2 |
| 1855. | NCH₃ | C(=S)NH—CH₂-A-3 |
| 1856. | NCH₃ | C(=S)NH—CH₂-A-4 |
| 1857. | NCH₃ | C(=S)NH—CH₂-A-5 |
| 1858. | NCH₃ | C(=S)NH—CH₂-A-6 |
| 1859. | NCH₃ | C(=S)NH—CH₂-A-7 |
| 1860. | NCH₃ | C(=S)NH—CH₂-A-8 |
| 1861. | NCH₃ | C(=S)NH—CH₂-A-9 |
| 1862. | NCH₃ | C(=S)NH—CH₂-A-10 |
| 1863. | NCH₃ | C(=S)NH—CH₂-A-11 |
| 1864. | NCH₃ | C(=S)NH—CH₂-A-12 |
| 1865. | NCH₃ | C(=S)NH—CH₂-A-13 |
| 1866. | NCH₃ | C(=S)NH—CH₂-A-14 |
| 1867. | NCH₃ | C(=S)NH—CH₂-A-15 |
| 1868. | NCH₃ | C(=S)NH—CH₂-A-16 |
| 1869. | NCH₃ | C(=S)NH—CH₂-A-17 |
| 1870. | NCH₃ | C(=S)NH—CH₂-A-18 |
| 1871. | NCH₃ | C(=S)NH—CH₂-A-19 |
| 1872. | NCH₃ | C(=S)NH—CH₂-A-20 |
| 1873. | NCH₃ | C(=S)NH—CH₂-A-21 |
| 1874. | NCH₃ | C(=S)NH—CH₂-A-22 |
| 1875. | NCH₃ | C(=S)NH—CH₂-A-23 |
| 1876. | NCH₃ | C(=S)NH—CH₂-A-24 |
| 1877. | NCH₃ | C(=S)NH—CH₂-A-25 |
| 1878. | NCH₃ | C(=S)NH—CH₂-A-26 |
| 1879. | NCH₃ | C(=S)NH—CH₂-A-27 |
| 1880. | NCH₃ | C(=S)NH—CH₂-A-28 |
| 1881. | NCH₃ | C(=S)NH—CH₂-A-29 |
| 1882. | NCH₃ | C(=S)NH—CH₂-A-30 |
| 1883. | NCH₃ | C(=S)NH—CH₂-A-31 |
| 1884. | NCH₃ | C(=S)NH—CH₂-A-32 |
| 1885. | NCH₃ | C(=S)NH—CH₂-A-33 |
| 1886. | NCH₃ | C(=S)NH—SO₂—CH₃ |
| 1887. | NCH₃ | C(=S)NH—SO₂—CF₃ |
| 1888. | NCH₃ | C(=S)NH—SO₂—CH₂CH₃ |
| 1889. | NCH₃ | C(=S)NH—SO₂—CH₂CF₃ |
| 1890. | NCH₃ | C(=S)NH—SO₂—CH₂CH₂CH₃ |
| 1891. | NCH₃ | C(=S)NH—SO₂—CH₂CH₂CF₃ |
| 1892. | NCH₃ | C(=S)NH—SO₂—CH₂CF₂CF₃ |
| 1893. | NCH₃ | C(=S)NH—SO₂—CH(CH₃)₂ |
| 1894. | NCH₃ | C(=S)NH—SO₂—CH(CF₃)₂ |
| 1895. | NCH₃ | C(=S)N(CH₃)—CH₂CHF₂ |
| 1896. | NCH₃ | C(=S)N(CH₃)—CH₂CH₂CHF₂ |
| 1897. | NCH₃ | C(=S)N(CH₃)—CH₂CH₂CF₃ |
| 1898. | NCH₃ | C(=S)N(CH₃)-cyclopropyl |
| 1899. | NCH₃ | C(=S)N(CH₃)-cyclobutyl |
| 1900. | NCH₃ | C(=S)N(CH₃)-cyclopentyl |
| 1901. | NCH₃ | C(=S)N(CH₃)-cyclohexyl |
| 1902. | NCH₃ | C(=S)N(CH₃)—CH₂-cyclopropyl |
| 1903. | NCH₃ | C(=S)N(CH₃)—CH₂-cyclobutyl |
| 1904. | NCH₃ | C(=S)N(CH₃)—CH₂-cyclopentyl |
| 1905. | NCH₃ | C(=S)N(CH₃)—CH₂-cyclohexyl |
| 1906. | NCH₃ | C(=S)N(CH₃)—CN |
| 1907. | NCH₃ | C(=S)N(CH₃)—CH₂—CN |
| 1908. | NCH₃ | C(=S)N(CH₃)—CH₂—CH=CH₂ |
| 1909. | NCH₃ | C(=S)N(CH₃)—CH₂—CH=C(Cl)₂ |
| 1910. | NCH₃ | C(=S)N(CH₃)—CH₂—CH=CH-phenyl |
| 1911. | NCH₃ | C(=S)N(CH₃)—CH₂—CH=CH-(4-Cl-phenyl) |
| 1912. | NCH₃ | C(=S)N(CH₃)—CH₂—SCH₃ |
| 1913. | NCH₃ | C(=S)N(CH₃)—CH₂—SCF₃ |
| 1914. | NCH₃ | C(=S)N(CH₃)—CH₂—CH₂—SCH₃ |
| 1915. | NCH₃ | C(=S)N(CH₃)—CH₂—CH₂—SCF₃ |
| 1916. | NCH₃ | C(=S)N(CH₃)—CH₂—SO₂—CH₃ |
| 1917. | NCH₃ | C(=S)N(CH₃)—CH₂—SO₂—CF₃ |
| 1918. | NCH₃ | C(=S)N(CH₃)—CH₂—CH₂—SO₂—CH₃ |
| 1919. | NCH₃ | C(=S)N(CH₃)—CH₂—CH₂—SO₂—CF₃ |
| 1920. | NCH₃ | C(=S)N(CH₃)—CH₂—CO—NH₂ |
| 1921. | NCH₃ | C(=S)N(CH₃)—CH₂—CO—NHCH₃ |
| 1922. | NCH₃ | C(=S)N(CH₃)—CH₂—CO—N(CH₃)₂ |
| 1923. | NCH₃ | C(=S)N(CH₃)—CH₂—CO—NHCF₃ |
| 1924. | NCH₃ | C(=S)N(CH₃)—CH₂—CO—N(CF₃)₂ |
| 1925. | NCH₃ | C(=S)N(CH₃)—CH₂—CO—NHCH₂CH₃ |
| 1926. | NCH₃ | C(=S)N(CH₃)—CH₂—CO—N(CH₂CH₃)₂ |
| 1927. | NCH₃ | C(=S)N(CH₃)—CH₂—CO—NHCH₂CF₃ |
| 1928. | NCH₃ | C(=S)N(CH₃)—CH₂—CO—N(CH₂CF₃)₂ |
| 1929. | NCH₃ | C(=S)N(CH₃)—CH₂—CO—NHCH₂CH₂CH₃ |
| 1930. | NCH₃ | C(=S)N(CH₃)—CH₂—CO—N(CH₂CH₂CH₃)₂ |
| 1931. | NCH₃ | C(=S)N(CH₃)—CH₂—CO—NHCH₂CH₂CF₃ |
| 1932. | NCH₃ | C(=S)N(CH₃)—CH₂—CO—N(CH₂CH₂CF₃)₂ |
| 1933. | NCH₃ | C(=S)N(CH₃)—CH₂—CO—NHCH(CH₃)₂ |
| 1934. | NCH₃ | C(=S)N(CH₃)—CH₂—CO—NHCH(CF₃)₂ |
| 1935. | NCH₃ | C(=S)N(CH₃)—CH₂—CO—NH-cyclopropyl |
| 1936. | NCH₃ | C(=S)N(CH₃)—CH₂—CO—NH—CH₂-cyclopropyl |
| 1937. | NCH₃ | C(=S)N(CH₃)—CH₂—CO—OH |
| 1938. | NCH₃ | C(=S)N(CH₃)—CH₂—CO—OCH₃ |
| 1939. | NCH₃ | C(=S)N(CH₃)—CH₂—CO—OCF₃ |
| 1940. | NCH₃ | C(=S)N(CH₃)—CH₂—CO—OCH₂CH₃ |
| 1941. | NCH₃ | C(=S)N(CH₃)—CH₂—CO—OCH₂CF₃ |
| 1942. | NCH₃ | C(=S)N(CH₃)—CH₂—CO—OCH₂CH₂CH₃ |
| 1943. | NCH₃ | C(=S)N(CH₃)—CH₂—CO—OCH(CH₃)₂ |
| 1944. | NCH₃ | C(=S)N(CH₃)—CH₂—CO—OCH₂CH₂CH₂CH₃ |
| 1945. | NCH₃ | C(=S)N(CH₃)—CH₂—CO—OCH(CH₃)CH₂CH₃ |
| 1946. | NCH₃ | C(=S)N(CH₃)—CH₂—CO—OCH₂CH(CH₃)₂ |
| 1947. | NCH₃ | C(=S)N(CH₃)—CH₂—CO—OC(CH₃)₃ |
| 1948. | NCH₃ | C(=S)N(CH₃)-A-1 |
| 1949. | NCH₃ | C(=S)N(CH₃)-A-2 |
| 1950. | NCH₃ | C(=S)N(CH₃)-A-3 |
| 1951. | NCH₃ | C(=S)N(CH₃)-A-4 |
| 1952. | NCH₃ | C(=S)N(CH₃)-A-5 |
| 1953. | NCH₃ | C(=S)N(CH₃)-A-6 |
| 1954. | NCH₃ | C(=S)N(CH₃)-A-7 |
| 1955. | NCH₃ | C(=S)N(CH₃)-A-8 |
| 1956. | NCH₃ | C(=S)N(CH₃)-A-9 |
| 1957. | NCH₃ | C(=S)N(CH₃)-A-10 |
| 1958. | NCH₃ | C(=S)N(CH₃)-A-11 |

TABLE A-continued

| No. | Y | R² |
|---|---|---|
| 1959. | NCH₃ | C(=S)N(CH₃)-A-12 |
| 1960. | NCH₃ | C(=S)N(CH₃)-A-13 |
| 1961. | NCH₃ | C(=S)N(CH₃)-A-14 |
| 1962. | NCH₃ | C(=S)N(CH₃)-A-15 |
| 1963. | NCH₃ | C(=S)N(CH₃)-A-16 |
| 1964. | NCH₃ | C(=S)N(CH₃)-A-17 |
| 1965. | NCH₃ | C(=S)N(CH₃)-A-18 |
| 1966. | NCH₃ | C(=S)N(CH₃)-A-19 |
| 1967. | NCH₃ | C(=S)N(CH₃)-A-20 |
| 1968. | NCH₃ | C(=S)N(CH₃)-A-21 |
| 1969. | NCH₃ | C(=S)N(CH₃)-A-22 |
| 1970. | NCH₃ | C(=S)N(CH₃)-A-23 |
| 1971. | NCH₃ | C(=S)N(CH₃)-A-24 |
| 1972. | NCH₃ | C(=S)N(CH₃)-A-25 |
| 1973. | NCH₃ | C(=S)N(CH₃)-A-26 |
| 1974. | NCH₃ | C(=S)N(CH₃)-A-27 |
| 1975. | NCH₃ | C(=S)N(CH₃)-A-28 |
| 1976. | NCH₃ | C(=S)N(CH₃)-A-29 |
| 1977. | NCH₃ | C(=S)N(CH₃)-A-30 |
| 1978. | NCH₃ | C(=S)N(CH₃)-A-31 |
| 1979. | NCH₃ | C(=S)N(CH₃)-A-32 |
| 1980. | NCH₃ | C(=S)N(CH₃)-A-33 |
| 1981. | NCH₃ | C(=S)N(CH₃)—CH₂-A-1 |
| 1982. | NCH₃ | C(=S)N(CH₃)—CH₂-A-2 |
| 1983. | NCH₃ | C(=S)N(CH₃)—CH₂-A-3 |
| 1984. | NCH₃ | C(=S)N(CH₃)—CH₂-A-4 |
| 1985. | NCH₃ | C(=S)N(CH₃)—CH₂-A-5 |
| 1986. | NCH₃ | C(=S)N(CH₃)—CH₂-A-6 |
| 1987. | NCH₃ | C(=S)N(CH₃)—CH₂-A-7 |
| 1988. | NCH₃ | C(=S)N(CH₃)—CH₂-A-8 |
| 1989. | NCH₃ | C(=S)N(CH₃)—CH₂-A-9 |
| 1990. | NCH₃ | C(=S)N(CH₃)—CH₂-A-10 |
| 1991. | NCH₃ | C(=S)N(CH₃)—CH₂-A-11 |
| 1992. | NCH₃ | C(=S)N(CH₃)—CH₂-A-12 |
| 1993. | NCH₃ | C(=S)N(CH₃)—CH₂-A-13 |
| 1994. | NCH₃ | C(=S)N(CH₃)—CH₂-A-14 |
| 1995. | NCH₃ | C(=S)N(CH₃)—CH₂-A-15 |
| 1996. | NCH₃ | C(=S)N(CH₃)—CH₂-A-16 |
| 1997. | NCH₃ | C(=S)N(CH₃)—CH₂-A-17 |
| 1998. | NCH₃ | C(=S)N(CH₃)—CH₂-A-18 |
| 1999. | NCH₃ | C(=S)N(CH₃)—CH₂-A-19 |
| 2000. | NCH₃ | C(=S)N(CH₃)—CH₂-A-20 |
| 2001. | NCH₃ | C(=S)N(CH₃)—CH₂-A-21 |
| 2002. | NCH₃ | C(=S)N(CH₃)—CH₂-A-22 |
| 2003. | NCH₃ | C(=S)N(CH₃)—CH₂-A-23 |
| 2004. | NCH₃ | C(=S)N(CH₃)—CH₂-A-24 |
| 2005. | NCH₃ | C(=S)N(CH₃)—CH₂-A-25 |
| 2006. | NCH₃ | C(=S)N(CH₃)—CH₂-A-26 |
| 2007. | NCH₃ | C(=S)N(CH₃)—CH₂-A-27 |
| 2008. | NCH₃ | C(=S)N(CH₃)—CH₂-A-28 |
| 2009. | NCH₃ | C(=S)N(CH₃)—CH₂-A-29 |
| 2010. | NCH₃ | C(=S)N(CH₃)—CH₂-A-30 |
| 2011. | NCH₃ | C(=S)N(CH₃)—CH₂-A-31 |
| 2012. | NCH₃ | C(=S)N(CH₃)—CH₂-A-32 |
| 2013. | NCH₃ | C(=S)N(CH₃)—CH₂-A-33 |
| 2014. | NCH₃ | C(=S)N(CH₃)—SO₂—CH₃ |
| 2015. | NCH₃ | C(=S)N(CH₃)—SO₂—CF₃ |
| 2016. | NCH₃ | C(=S)N(CH₃)—SO₂—CH₂CH₃ |
| 2017. | NCH₃ | C(=S)N(CH₃)—SO₂—CH₂CF₃ |
| 2018. | NCH₃ | C(=S)N(CH₃)—SO₂—CH₂CH₂CH₃ |
| 2019. | NCH₃ | C(=S)N(CH₃)—SO₂—CH₂CH₂CF₃ |
| 2020. | NCH₃ | C(=S)N(CH₃)—SO₂—CH₂CF₂CF₃ |
| 2021. | NCH₃ | C(=S)N(CH₃)—SO₂—CH(CH₃)₂ |
| 2022. | NCH₃ | C(=S)N(CH₃)—SO₂—CH(CF₃)₂ |
| 2023. | NCH₃ | C(=S)NH—SO₂—NH₂ |
| 2024. | NCH₃ | C(=S)NH—SO₂—NHCH₃ |
| 2025. | NCH₃ | C(=S)NH—SO₂—N(CH₃)₂ |
| 2026. | NCH₃ | C(=S)NH—SO₂—NHCF₃ |
| 2027. | NCH₃ | C(=S)NH—SO₂—N(CF₃)₂ |
| 2028. | NCH₃ | C(=S)NH—SO₂—NHCH₂CH₃ |
| 2029. | NCH₃ | C(=S)NH—SO₂—N(CH₂CH₃)₂ |
| 2030. | NCH₃ | C(=S)NH—SO₂—NHCH₂CF₃ |
| 2031. | NCH₃ | C(=S)NH—SO₂—N(CH₂CF₃)₂ |
| 2032. | NCH₃ | C(=S)NH—SO₂—N(CH₃)CH₂CH₃ |
| 2033. | NCH₃ | C(=S)NH—SO₂—N(CH₃)CH₂CF₃ |
| 2034. | NCH₃ | C(=S)NH—SO₂—N(CF₃)CH₂CH₃ |
| 2035. | NCH₃ | C(=S)NH—SO₂—NHCH₂CH₂CH₃ |
| 2036. | NCH₃ | C(=S)NH—SO₂—N(CH₂CH₂CH₃)₂ |
| 2037. | NCH₃ | C(=S)NH—SO₂—NHCH₂CH₂CF₃ |
| 2038. | NCH₃ | C(=S)NH—SO₂—N(CH₂CH₂CF₃)₂ |
| 2039. | NCH₃ | C(=S)NH—SO₂—N(CH₃)CH₂CH₂CH₃ |
| 2040. | NCH₃ | C(=S)NH—SO₂—N(CH₃)CH₂CH₂CF₃ |
| 2041. | NCH₃ | C(=S)NH—SO₂—N(CF₃)CH₂CH₂CH₃ |
| 2042. | NCH₃ | C(=S)NH—SO₂—NHCH(CH₃)₂ |
| 2043. | NCH₃ | C(=S)NH—SO₂—NHCH(CF₃)₂ |
| 2044. | NCH₃ | C(=S)NH—SO₂—N(CH₃)CH(CH₃)₂ |
| 2045. | NCH₃ | C(=S)NH—SO₂—N(CH₃)CH(CF₃)₂ |
| 2046. | NCH₃ | C(=S)NH—SO₂—N(CF₃)CH(CH₃)₂ |
| 2047. | NCH₃ | C(=S)NH—SO₂—NHCH₂CH₂CH₂CH₃ |
| 2048. | NCH₃ | C(=S)NH—SO₂—N(CH₂CH₂CH₂CH₃)₂ |
| 2049. | NCH₃ | C(=S)NH—SO₂—N(CH₃)CH₂CH₂CH₂CH₃ |
| 2050. | NCH₃ | C(=S)N(CH₃)—SO₂—NH₂ |
| 2051. | NCH₃ | C(=S)N(CH₃)—SO₂—NHCH₃ |
| 2052. | NCH₃ | C(=S)N(CH₃)—SO₂—N(CH₃)₂ |
| 2053. | NCH₃ | C(=S)N(CH₃)—SO₂—NHCF₃ |
| 2054. | NCH₃ | C(=S)N(CH₃)—SO₂—N(CF₃)₂ |
| 2055. | NCH₃ | C(=S)N(CH₃)—SO₂—NHCH₂CH₃ |
| 2056. | NCH₃ | C(=S)N(CH₃)—SO₂—N(CH₂CH₃)₂ |
| 2057. | NCH₃ | C(=S)N(CH₃)—SO₂—NHCH₂CF₃ |
| 2058. | NCH₃ | C(=S)N(CH₃)—SO₂—N(CH₂CF₃)₂ |
| 2059. | NCH₃ | C(=S)N(CH₃)—SO₂—N(CH₃)CH₂CH₃ |
| 2060. | NCH₃ | C(=S)N(CH₃)—SO₂—N(CH₃)CH₂CF₃ |
| 2061. | NCH₃ | C(=S)N(CH₃)—SO₂—N(CF₃)CH₂CH₃ |
| 2062. | NCH₃ | C(=S)N(CH₃)—SO₂—NHCH₂CH₂CH₃ |
| 2063. | NCH₃ | C(=S)N(CH₃)—SO₂—N(CH₃)CH₂CH₂CH₃ |
| 2064. | NCH₃ | C(=S)N(CH₃)—SO₂—NHCH₂CH₂CF₃ |
| 2065. | NCH₃ | C(=S)N(CH₃)—SO₂—N(CH₂CH₂CF₃)₂ |
| 2066. | NCH₃ | C(=S)N(CH₃)—SO₂—N(CH₃)CH₂CH₂CH₃ |
| 2067. | NCH₃ | C(=S)N(CH₃)—SO₂—N(CH₃)CH₂CH₂CF₃ |
| 2068. | NCH₃ | C(=S)N(CH₃)—SO₂—N(CF₃)CH₂CH₂CH₃ |
| 2069. | NCH₃ | C(=S)N(CH₃)—SO₂—NHCH(CH₃)₂ |
| 2070. | NCH₃ | C(=S)N(CH₃)—SO₂—NHCH(CF₃)₂ |
| 2071. | NCH₃ | C(=S)N(CH₃)—SO₂—N(CH₃)CH(CH₃)₂ |
| 2072. | NCH₃ | C(=S)N(CH₃)—SO₂—N(CH₃)CH(CF₃)₂ |
| 2073. | NCH₃ | C(=S)N(CH₃)—SO₂—N(CF₃)CH(CH₃)₂ |
| 2074. | NCH₃ | C(=S)N(CH₃)—SO₂—NHCH₂CH₂CH₂CH₃ |
| 2075. | NCH₃ | C(=S)N(CH₃)—SO₂—N(CH₂CH₂CH₂CH₃)₂ |
| 2076. | NCH₃ | C(=S)N(CH₃)—SO₂—N(CH₃)CH₂CH₂CH₂CH₃ |
| 2077. | NCH₃ | C(=S)—N=CHOCH₃ |
| 2078. | NCH₃ | C(=S)—N=CHOCH₂CH₃ |
| 2079. | NCH₃ | C(=S)—N=CHOCH₂CH₂CH₃ |
| 2080. | NCH₃ | C(=S)—N=CHOCH(CH₃)₂ |
| 2081. | NCH₃ | C(=S)—N=CHOCF₃ |
| 2082. | NCH₃ | C(=S)—N=CHOCH₂CF₃ |
| 2083. | NCH₃ | C(=S)—N=CHOCH₂CH₂CF₃ |
| 2084. | NCH₃ | C(=S)—N=CHOCH(CF₃)₂ |
| 2085. | NCH₃ | C(=S)—N=CH—CO—OCH₃ |
| 2086. | NCH₃ | C(=S)—N=CH—CO—OCH₂CH₃ |
| 2087. | NCH₃ | C(=S)—N=CH—CO—OCH₂CH₂CH₃ |
| 2088. | NCH₃ | C(=S)—N=CH—CO—OCH(CH₃)₂ |
| 2089. | NCH₃ | C(=S)—N=CH—CO—OCF₃ |
| 2090. | NCH₃ | C(=S)—N=CH—CO—OCH₂CF₃ |
| 2091. | NCH₃ | C(=S)—N=CH—CO—OCH₂CH₂CF₃ |
| 2092. | NCH₃ | C(=S)—N=CH—CO—OCH(CF₃)₂ |
| 2093. | NCH₃ | C(=S)—N=CH—CO—NHCH₃ |
| 2094. | NCH₃ | C(=S)—N=CH—CO—N(CH₃)₂ |
| 2095. | NCH₃ | C(=S)—N=CH—CO—NHCH₂CH₃ |
| 2096. | NCH₃ | C(=S)—N=CH—CO—N(CH₂CH₃)₂ |
| 2097. | NCH₃ | C(=S)—N=CH—CO—N(CH₃)CH₂CH₃ |
| 2098. | NCH₃ | C(=S)—N=CH—CO—NHCH₂CH₂CH₃ |
| 2099. | NCH₃ | C(=S)—N=CH—CO—N(CH₂CH₂CH₃)₂ |
| 2100. | NCH₃ | C(=S)—N=CH—CO—N(CH₃)CH₂CH₂CH₃ |
| 2101. | NCH₃ | C(=S)—N=CH—CO—NHCH(CH₃)₂ |
| 2102. | NCH₃ | C(=S)—N=CH—CO—N(CH₃)CH(CH₃)₂ |
| 2103. | NCH₃ | C(=S)—N=CH—CO—NHCF₃ |
| 2104. | NCH₃ | C(=S)—N=CH—CO—N(CF₃)₂ |
| 2105. | NCH₃ | C(=S)—N=CH—CO—NHCH₂CF₃ |
| 2106. | NCH₃ | C(=S)—N=CH—CO—N(CH₂CF₃)₂ |
| 2107. | NCH₃ | C(=S)—N=CH—CO—N(CH₃)CH₂CF₃ |
| 2108. | NCH₃ | C(=S)—N=CH—CO—N(CF₃)CH₂CF₃ |
| 2109. | NCH₃ | C(=S)—N=CH—CO—NHCH₂CH₂CF₃ |
| 2110. | NCH₃ | C(=S)—N=CH—CO—N(CH₂CH₂CF₃)₂ |
| 2111. | NCH₃ | C(=S)—N=CH—CO—N(CH₃)CH₂CH₂CF₃ |
| 2112. | NCH₃ | C(=S)—N=CH—CO—N(CF₃)CH₂CH₂CH₃ |
| 2113. | NCH₃ | C(=S)—N=CH—CO—NHCH(CF₃)₂ |
| 2114. | NCH₃ | C(=S)—N=CH—CO—N(CH₃)CH(CF₃)₂ |

TABLE A-continued

| No. | Y | R² |
|---|---|---|
| 2115. | NCH₃ | C(=S)—N=CH—CO—N(CF₃)CH(CH₃)₂ |
| 2116. | NC(O)CH₃ | C(=O)NH₂ |
| 2117. | NC(O)CH₃ | C(=O)NHCH₃ |
| 2118. | NC(O)CH₃ | C(=O)N(CH₃)₂ |
| 2119. | NC(O)CH₃ | C(=O)NHCF₃ |
| 2120. | NC(O)CH₃ | C(=O)N(CF₃)₂ |
| 2121. | NC(O)CH₃ | C(=O)NHCH₂CH₃ |
| 2122. | NC(O)CH₃ | C(=O)N(CH₂CH₃)₂ |
| 2123. | NC(O)CH₃ | C(=O)(CH₃)CH₂CH₃ |
| 2124. | NC(O)CH₃ | C(=O)NHCH₂CF₃ |
| 2125. | NC(O)CH₃ | C(=O)N(CH₂CF₃)₂ |
| 2126. | NC(O)CH₃ | C(=O)N(CH₃)CH₂CF₃ |
| 2127. | NC(O)CH₃ | C(=O)NHCH₂CH₂CH₃ |
| 2128. | NC(O)CH₃ | C(=O)N(CH₃)CH₂CH₂CH₃ |
| 2129. | NC(O)CH₃ | C(=O)NHCH(CH₃)₂ |
| 2130. | NC(O)CH₃ | C(=O)NH(CH₂)₃CH₃ |
| 2131. | NC(O)CH₃ | C(=O)N(CH₃)—(CH₂)₃CH₃ |
| 2132. | NC(O)CH₃ | C(=O)N[(CH₂)₃CH₃]₂ |
| 2133. | NC(O)CH₃ | C(=O)N(CH₃)—CH₂—C₆H₅ |
| 2134. | NC(O)CH₃ | C(=O)NH-propargyl |
| 2135. | NC(O)CH₃ | C(=O)N(CH₃)-propargyl |
| 2136. | NC(O)CH₃ | C(=O)NH—CH₂-4-Cl—C₆H₄ |
| 2137. | NC(O)CH₃ | C(=O)N(CH₃)—CH₂-4-Cl—C₆H₄ |
| 2138. | NC(O)CH₃ | C(=O)morpholin-4-yl |
| 2139. | NC(O)CH₃ | C(=O)NH-3-thiolyl-1,1-dioxid |
| 2140. | NC(O)CH₃ | C(=O)N(CH₃)-3-thiolyl-1,1-dioxid |
| 2141. | NC(O)CH₃ | C(=O)-azirid-1-yl |
| 2142. | NC(O)CH₃ | C(=O)-pyrrolidin-1-yl |
| 2143. | NC(O)CH₃ | C(=O)-piperidin-1-yl |
| 2144. | NC(O)CH₃ | C(=O)-thiomorpholin-4-yl |
| 2145. | NC(O)CH₃ | C(=O)NH—CH₂CHF₂ |
| 2146. | NC(O)CH₃ | C(=O)NH—CH₂CH₂CHF₂ |
| 2147. | NC(O)CH₃ | C(=O)NH—CH₂CH₂CF₃ |
| 2148. | NC(O)CH₃ | C(=O)NH-cyclopropyl |
| 2149. | NC(O)CH₃ | C(=O)NH-cyclobutyl |
| 2150. | NC(O)CH₃ | C(=O)NH-cyclopentyl |
| 2151. | NC(O)CH₃ | C(=O)NH-cyclohexyl |
| 2152. | NC(O)CH₃ | C(=O)NH—CH₂-cyclopropyl |
| 2153. | NC(O)CH₃ | C(=O)NH—CH₂-cyclobutyl |
| 2154. | NC(O)CH₃ | C(=O)NH—CH₂-cyclopentyl |
| 2155. | NC(O)CH₃ | C(=O)NH—CH₂-cyclohexyl |
| 2156. | NC(O)CH₃ | C(=O)NH—CN |
| 2157. | NC(O)CH₃ | C(=O)NH—CH₂—CN |
| 2158. | NC(O)CH₃ | C(=O)NH—CH₂—CH=CH₂ |
| 2159. | NC(O)CH₃ | C(=O)NH—CH₂—CH=C(Cl)₂ |
| 2160. | NC(O)CH₃ | C(=O)NH—CH₂—CH=CH-phenyl |
| 2161. | NC(O)CH₃ | C(=O)NH—CH₂—CH=CH-(4-Cl-phenyl) |
| 2162. | NC(O)CH₃ | C(=O)NH—CH₂—SCH₃ |
| 2163. | NC(O)CH₃ | C(=O)NH—CH₂—SCF₃ |
| 2164. | NC(O)CH₃ | C(=O)NH—CH₂—CH₂—SCH₃ |
| 2165. | NC(O)CH₃ | C(=O)NH—CH₂—CH₂—SCF₃ |
| 2166. | NC(O)CH₃ | C(=O)NH—CH₂—SO₂—CH₃ |
| 2167. | NC(O)CH₃ | C(=O)NH—CH₂—SO₂—CF₃ |
| 2168. | NC(O)CH₃ | C(=O)NH—CH₂—CH₂—SO₂—CH₃ |
| 2169. | NC(O)CH₃ | C(=O)NH—CH₂—CH₂—SO₂—CF₃ |
| 2170. | NC(O)CH₃ | C(=O)NH—CH₂—CO—NH₂ |
| 2171. | NC(O)CH₃ | C(=O)NH—CH₂—CO—NHCH₃ |
| 2172. | NC(O)CH₃ | C(=O)NH—CH₂—CO—N(CH₃)₂ |
| 2173. | NC(O)CH₃ | C(=O)NH—CH₂—CO—NHCF₃ |
| 2174. | NC(O)CH₃ | C(=O)NH—CH₂—CO—N(CF₃)₂ |
| 2175. | NC(O)CH₃ | C(=O)NH—CH₂—CO—NHCH₂CH₃ |
| 2176. | NC(O)CH₃ | C(=O)NH—CH₂—CO—N(CH₂CH₃)₂ |
| 2177. | NC(O)CH₃ | C(=O)NH—CH₂—CO—NHCH₂CF₃ |
| 2178. | NC(O)CH₃ | C(=O)NH—CH₂—CO—N(CH₂CF₃)₂ |
| 2179. | NC(O)CH₃ | C(=O)NH—CH₂—CO—NHCH₂CH₂CH₃ |
| 2180. | NC(O)CH₃ | C(=O)NH—CH₂—CO—N(CH₂CH₂CH₃)₂ |
| 2181. | NC(O)CH₃ | C(=O)NH—CH₂—CO—NHCH₂CH₂CF₃ |
| 2182. | NC(O)CH₃ | C(=O)NH—CH₂—CO—N(CH₂CH₂CF₃)₂ |
| 2183. | NC(O)CH₃ | C(=O)NH—CH₂—CO—NHCH(CH₃)₂ |
| 2184. | NC(O)CH₃ | C(=O)NH—CH₂—CO—NHCH(CF₃)₂ |
| 2185. | NC(O)CH₃ | C(=O)NH—CH₂—CO—NH-cyclopropyl |
| 2186. | NC(O)CH₃ | C(=O)NH—CH₂—CO—NH—CH₂-cyclopropyl |
| 2187. | NC(O)CH₃ | C(=O)NH—CH₂—CO—OH |
| 2188. | NC(O)CH₃ | C(=O)NH—CH₂—CO—OCH₃ |
| 2189. | NC(O)CH₃ | C(=O)NH—CH₂—CO—OCF₃ |
| 2190. | NC(O)CH₃ | C(=O)NH—CH₂—CO—OCH₂CH₃ |
| 2191. | NC(O)CH₃ | C(=O)NH—CH₂—CO—OCH₂CF₃ |
| 2192. | NC(O)CH₃ | C(=O)NH—CH₂—CO—OCH₂CH₂CH₃ |
| 2193. | NC(O)CH₃ | C(=O)NH—CH₂—CO—OCH(CH₃)₂ |
| 2194. | NC(O)CH₃ | C(=O)NH—CH₂—CO—OCH₂CH₂CH₃ |
| 2195. | NC(O)CH₃ | C(=O)NH—CH₂—CO—OCH(CH₃)CH₂CH₃ |
| 2196. | NC(O)CH₃ | C(=O)NH—CH₂—CO—OCH₂CH(CH₃)₂ |
| 2197. | NC(O)CH₃ | C(=O)NH—CH₂—CO—OC(CH₃)₃ |
| 2198. | NC(O)CH₃ | C(=O)NH-A-1 |
| 2199. | NC(O)CH₃ | C(=O)NH-A-2 |
| 2200. | NC(O)CH₃ | C(=O)NH-A-3 |
| 2201. | NC(O)CH₃ | C(=O)NH-A-4 |
| 2202. | NC(O)CH₃ | C(=O)NH-A-5 |
| 2203. | NC(O)CH₃ | C(=O)NH-A-6 |
| 2204. | NC(O)CH₃ | C(=O)NH-A-7 |
| 2205. | NC(O)CH₃ | C(=O)NH-A-8 |
| 2206. | NC(O)CH₃ | C(=O)NH-A-9 |
| 2207. | NC(O)CH₃ | C(=O)NH-A-10 |
| 2208. | NC(O)CH₃ | C(=O)NH-A-11 |
| 2209. | NC(O)CH₃ | C(=O)NH-A-12 |
| 2210. | NC(O)CH₃ | C(=O)NH-A-13 |
| 2211. | NC(O)CH₃ | C(=O)NH-A-14 |
| 2212. | NC(O)CH₃ | C(=O)NH-A-15 |
| 2213. | NC(O)CH₃ | C(=O)NH-A-16 |
| 2214. | NC(O)CH₃ | C(=O)NH-A-17 |
| 2215. | NC(O)CH₃ | C(=O)NH-A-18 |
| 2216. | NC(O)CH₃ | C(=O)NH-A-19 |
| 2217. | NC(O)CH₃ | C(=O)NH-A-20 |
| 2218. | NC(O)CH₃ | C(=O)NH-A-21 |
| 2219. | NC(O)CH₃ | C(=O)NH-A-22 |
| 2220. | NC(O)CH₃ | C(=O)NH-A-23 |
| 2221. | NC(O)CH₃ | C(=O)NH-A-24 |
| 2222. | NC(O)CH₃ | C(=O)NH-A-25 |
| 2223. | NC(O)CH₃ | C(=O)NH-A-26 |
| 2224. | NC(O)CH₃ | C(=O)NH-A-27 |
| 2225. | NC(O)CH₃ | C(=O)NH-A-28 |
| 2226. | NC(O)CH₃ | C(=O)NH-A-29 |
| 2227. | NC(O)CH₃ | C(=O)NH-A-30 |
| 2228. | NC(O)CH₃ | C(=O)NH-A-31 |
| 2229. | NC(O)CH₃ | C(=O)NH-A-32 |
| 2230. | NC(O)CH₃ | C(=O)NH-A-33 |
| 2231. | NC(O)CH₃ | C(=O)NH—CH₂-A-1 |
| 2232. | NC(O)CH₃ | C(=O)NH—CH₂-A-2 |
| 2233. | NC(O)CH₃ | C(=O)NH—CH₂-A-3 |
| 2234. | NC(O)CH₃ | C(=O)NH—CH₂-A-4 |
| 2235. | NC(O)CH₃ | C(=O)NH—CH₂-A-5 |
| 2236. | NC(O)CH₃ | C(=O)NH—CH₂-A-6 |
| 2237. | NC(O)CH₃ | C(=O)NH—CH₂-A-7 |
| 2238. | NC(O)CH₃ | C(=O)NH—CH₂-A-8 |
| 2239. | NC(O)CH₃ | C(=O)NH—CH₂-A-9 |
| 2240. | NC(O)CH₃ | C(=O)NH—CH₂-A-10 |
| 2241. | NC(O)CH₃ | C(=O)NH—CH₂-A-11 |
| 2242. | NC(O)CH₃ | C(=O)NH—CH₂-A-12 |
| 2243. | NC(O)CH₃ | C(=O)NH—CH₂-A-13 |
| 2244. | NC(O)CH₃ | C(=O)NH—CH₂-A-14 |
| 2245. | NC(O)CH₃ | C(=O)NH—CH₂-A-15 |
| 2246. | NC(O)CH₃ | C(=O)NH—CH₂-A-16 |
| 2247. | NC(O)CH₃ | C(=O)NH—CH₂-A-17 |
| 2248. | NC(O)CH₃ | C(=O)NH—CH₂-A-18 |
| 2249. | NC(O)CH₃ | C(=O)NH—CH₂-A-19 |
| 2250. | NC(O)CH₃ | C(=O)NH—CH₂-A-20 |
| 2251. | NC(O)CH₃ | C(=O)NH—CH₂-A-21 |
| 2252. | NC(O)CH₃ | C(=O)NH—CH₂-A-22 |
| 2253. | NC(O)CH₃ | C(=O)NH—CH₂-A-23 |
| 2254. | NC(O)CH₃ | C(=O)NH—CH₂-A-24 |
| 2255. | NC(O)CH₃ | C(=O)NH—CH₂-A-25 |
| 2256. | NC(O)CH₃ | C(=O)NH—CH₂-A-26 |
| 2257. | NC(O)CH₃ | C(=O)NH—CH₂-A-27 |
| 2258. | NC(O)CH₃ | C(=O)NH—CH₂-A-28 |
| 2259. | NC(O)CH₃ | C(=O)NH—CH₂-A-29 |
| 2260. | NC(O)CH₃ | C(=O)NH—CH₂-A-30 |
| 2261. | NC(O)CH₃ | C(=O)NH—CH₂-A-31 |
| 2262. | NC(O)CH₃ | C(=O)NH—CH₂-A-32 |
| 2263. | NC(O)CH₃ | C(=O)NH—CH₂-A-33 |
| 2264. | NC(O)CH₃ | C(=O)NH—SO₂—CH₃ |
| 2265. | NC(O)CH₃ | C(=O)NH—SO₂—CF₃ |
| 2266. | NC(O)CH₃ | C(=O)NH—SO₂—CH₂CH₃ |
| 2267. | NC(O)CH₃ | C(=O)NH—SO₂—CH₂CF₃ |
| 2268. | NC(O)CH₃ | C(=O)NH—SO₂—CH₂CH₂CH₃ |
| 2269. | NC(O)CH₃ | C(=O)NH—SO₂—CH₂CH₂CF₃ |
| 2270. | NC(O)CH₃ | C(=O)NH—SO₂—CH₂CF₂CF₃ |

TABLE A-continued

| No. | Y | R² |
|---|---|---|
| 2271. | NC(O)CH₃ | C(=O)NH—SO₂—CH(CH₃)₂ |
| 2272. | NC(O)CH₃ | C(=O)NH—SO₂—CH(CF₃)₂ |
| 2273. | NC(O)CH₃ | C(=O)N(CH₃)—CH₂CHF₂ |
| 2274. | NC(O)CH₃ | C(=O)N(CH₃)—CH₂CH₂CHF₂ |
| 2275. | NC(O)CH₃ | C(=O)N(CH₃)—CH₂CH₂CF₃ |
| 2276. | NC(O)CH₃ | C(=O)N(CH₃)-cyclopropyl |
| 2277. | NC(O)CH₃ | C(=O)N(CH₃)-cyclobutyl |
| 2278. | NC(O)CH₃ | C(=O)N(CH₃)-cyclopentyl |
| 2279. | NC(O)CH₃ | C(=O)N(CH₃)-cyclohexyl |
| 2280. | NC(O)CH₃ | C(=O)N(CH₃)—CH₂-cyclopropyl |
| 2281. | NC(O)CH₃ | C(=O)N(CH₃)—CH₂-cyclobutyl |
| 2282. | NC(O)CH₃ | C(=O)N(CH₃)—CH₂-cyclopentyl |
| 2283. | NC(O)CH₃ | C(=O)N(CH₃)—CH₂-cyclohexyl |
| 2284. | NC(O)CH₃ | C(=O)N(CH₃)—CN |
| 2285. | NC(O)CH₃ | C(=O)N(CH₃)—CH₂—CN |
| 2286. | NC(O)CH₃ | C(=O)N(CH₃)—CH₂—CH=CH₂ |
| 2287. | NC(O)CH₃ | C(=O)N(CH₃)—CH₂—CH=C(Cl)₂ |
| 2288. | NC(O)CH₃ | C(=O)N(CH₃)—CH₂—CH=CH-phenyl |
| 2289. | NC(O)CH₃ | C(=O)N(CH₃)—CH₂—CH=CH-(4-Cl-phenyl) |
| 2290. | NC(O)CH₃ | C(=O)N(CH₃)—CH₂—SCH₃ |
| 2291. | NC(O)CH₃ | C(=O)N(CH₃)—CH₂—SCF₃ |
| 2292. | NC(O)CH₃ | C(=O)N(CH₃)—CH₂—CH₂—SCH₃ |
| 2293. | NC(O)CH₃ | C(=O)N(CH₃)—CH₂—CH₂—SCF₃ |
| 2294. | NC(O)CH₃ | C(=O)N(CH₃)—CH₂—SO₂—CH₃ |
| 2295. | NC(O)CH₃ | C(=O)N(CH₃)—CH₂—SO₂—CF₃ |
| 2296. | NC(O)CH₃ | C(=O)N(CH₃)—CH₂—CH₂—SO₂—CH₃ |
| 2297. | NC(O)CH₃ | C(=O)N(CH₃)—CH₂—CH₂—SO₂—CF₃ |
| 2298. | NC(O)CH₃ | C(=O)N(CH₃)—CH₂—CO—NH₂ |
| 2299. | NC(O)CH₃ | C(=O)N(CH₃)—CH₂—CO—NHCH₃ |
| 2300. | NC(O)CH₃ | C(=O)N(CH₃)—CH₂—CO—N(CH₃)₂ |
| 2301. | NC(O)CH₃ | C(=O)N(CH₃)—CH₂—CO—NHCF₃ |
| 2302. | NC(O)CH₃ | C(=O)N(CH₃)—CH₂—CO—N(CF₃)₂ |
| 2303. | NC(O)CH₃ | C(=O)N(CH₃)—CH₂—CO—NHCH₂CH₃ |
| 2304. | NC(O)CH₃ | C(=O)N(CH₃)—CH₂—CO—N(CH₂CH₃)₂ |
| 2305. | NC(O)CH₃ | C(=O)N(CH₃)—CH₂—CO—NHCH₂CF₃ |
| 2306. | NC(O)CH₃ | C(=O)N(CH₃)—CH₂—CO—N(CH₂CF₃)₂ |
| 2307. | NC(O)CH₃ | C(=O)N(CH₃)—CH₂—CO—NHCH₂CH₂CH₃ |
| 2308. | NC(O)CH₃ | C(=O)N(CH₃)—CH₂—CO—N(CH₂CH₂CH₃)₂ |
| 2309. | NC(O)CH₃ | C(=O)N(CH₃)—CH₂—CO—NHCH₂CH₂CF₃ |
| 2310. | NC(O)CH₃ | C(=O)N(CH₃)—CH₂—CO—N(CH₂CH₂CF₃)₂ |
| 2311. | NC(O)CH₃ | C(=O)N(CH₃)—CH₂—CO—NHCH(CH₃)₂ |
| 2312. | NC(O)CH₃ | C(=O)N(CH₃)—CH₂—CO—NHCH(CF₃)₂ |
| 2313. | NC(O)CH₃ | C(=O)N(CH₃)—CH₂—CO—NH-cyclopropyl |
| 2314. | NC(O)CH₃ | C(=O)N(CH₃)—CH₂—CO—NH—CH₂-cyclopropyl |
| 2315. | NC(O)CH₃ | C(=O)N(CH₃)—CH₂—CO—OH |
| 2316. | NC(O)CH₃ | C(=O)N(CH₃)—CH₂—CO—OCH₃ |
| 2317. | NC(O)CH₃ | C(=O)N(CH₃)—CH₂—CO—OCF₃ |
| 2318. | NC(O)CH₃ | C(=O)N(CH₃)—CH₂—CO—OCH₂CH₃ |
| 2319. | NC(O)CH₃ | C(=O)N(CH₃)—CH₂—CO—OCH₂CF₃ |
| 2320. | NC(O)CH₃ | C(=O)N(CH₃)—CH₂—CO—OCH₂CH₂CH₃ |
| 2321. | NC(O)CH₃ | C(=O)N(CH₃)—CH₂—CO—OCH(CH₃)₂ |
| 2322. | NC(O)CH₃ | C(=O)N(CH₃)—CH₂—CO—OCH₂CH₂CH₂CH₃ |
| 2323. | NC(O)CH₃ | C(=O)N(CH₃)—CH₂—CO—OCH(CH₃)CH₂CH₃ |
| 2324. | NC(O)CH₃ | C(=O)N(CH₃)—CH₂—CO—OCH₂CH(CH₃)₂ |
| 2325. | NC(O)CH₃ | C(=O)N(CH₃)—CH₂—CO—OC(CH₃)₃ |
| 2326. | NC(O)CH₃ | C(=O)N(CH₃)-A-1 |
| 2327. | NC(O)CH₃ | C(=O)N(CH₃)-A-2 |
| 2328. | NC(O)CH₃ | C(=O)N(CH₃)-A-3 |
| 2329. | NC(O)CH₃ | C(=O)N(CH₃)-A-4 |
| 2330. | NC(O)CH₃ | C(=O)N(CH₃)-A-5 |
| 2331. | NC(O)CH₃ | C(=O)N(CH₃)-A-6 |
| 2332. | NC(O)CH₃ | C(=O)N(CH₃)-A-7 |
| 2333. | NC(O)CH₃ | C(=O)N(CH₃)-A-8 |
| 2334. | NC(O)CH₃ | C(=O)N(CH₃)-A-9 |
| 2335. | NC(O)CH₃ | C(=O)N(CH₃)-A-10 |
| 2336. | NC(O)CH₃ | C(=O)N(CH₃)-A-11 |
| 2337. | NC(O)CH₃ | C(=O)N(CH₃)-A-12 |
| 2338. | NC(O)CH₃ | C(=O)N(CH₃)-A-13 |
| 2339. | NC(O)CH₃ | C(=O)N(CH₃)-A-14 |
| 2340. | NC(O)CH₃ | C(=O)N(CH₃)-A-15 |
| 2341. | NC(O)CH₃ | C(=O)N(CH₃)-A-16 |
| 2342. | NC(O)CH₃ | C(=O)N(CH₃)-A-17 |
| 2343. | NC(O)CH₃ | C(=O)N(CH₃)-A-18 |
| 2344. | NC(O)CH₃ | C(=O)N(CH₃)-A-19 |
| 2345. | NC(O)CH₃ | C(=O)N(CH₃)-A-20 |
| 2346. | NC(O)CH₃ | C(=O)N(CH₃)-A-21 |
| 2347. | NC(O)CH₃ | C(=O)N(CH₃)-A-22 |
| 2348. | NC(O)CH₃ | C(=O)N(CH₃)-A-23 |
| 2349. | NC(O)CH₃ | C(=O)N(CH₃)-A-24 |
| 2350. | NC(O)CH₃ | C(=O)N(CH₃)-A-25 |
| 2351. | NC(O)CH₃ | C(=O)N(CH₃)-A-26 |
| 2352. | NC(O)CH₃ | C(=O)N(CH₃)-A-27 |
| 2353. | NC(O)CH₃ | C(=O)N(CH₃)-A-28 |
| 2354. | NC(O)CH₃ | C(=O)N(CH₃)-A-29 |
| 2355. | NC(O)CH₃ | C(=O)N(CH₃)-A-30 |
| 2356. | NC(O)CH₃ | C(=O)N(CH₃)-A-31 |
| 2357. | NC(O)CH₃ | C(=O)N(CH₃)-A-32 |
| 2358. | NC(O)CH₃ | C(=O)N(CH₃)-A-33 |
| 2359. | NC(O)CH₃ | C(=O)N(CH₃)—CH₂-A-1 |
| 2360. | NC(O)CH₃ | C(=O)N(CH₃)—CH₂-A-2 |
| 2361. | NC(O)CH₃ | C(=O)N(CH₃)—CH₂-A-3 |
| 2362. | NC(O)CH₃ | C(=O)N(CH₃)—CH₂-A-4 |
| 2363. | NC(O)CH₃ | C(=O)N(CH₃)—CH₂-A-5 |
| 2364. | NC(O)CH₃ | C(=O)N(CH₃)—CH₂-A-6 |
| 2365. | NC(O)CH₃ | C(=O)N(CH₃)—CH₂-A-7 |
| 2366. | NC(O)CH₃ | C(=O)N(CH₃)—CH₂-A-8 |
| 2367. | NC(O)CH₃ | C(=O)N(CH₃)—CH₂-A-9 |
| 2368. | NC(O)CH₃ | C(=O)N(CH₃)—CH₂-A-10 |
| 2369. | NC(O)CH₃ | C(=O)N(CH₃)—CH₂-A-11 |
| 2370. | NC(O)CH₃ | C(=O)N(CH₃)—CH₂-A-12 |
| 2371. | NC(O)CH₃ | C(=O)N(CH₃)—CH₂-A-13 |
| 2372. | NC(O)CH₃ | C(=O)N(CH₃)—CH₂-A-14 |
| 2373. | NC(O)CH₃ | C(=O)N(CH₃)—CH₂-A-15 |
| 2374. | NC(O)CH₃ | C(=O)N(CH₃)—CH₂-A-16 |
| 2375. | NC(O)CH₃ | C(=O)N(CH₃)—CH₂-A-17 |
| 2376. | NC(O)CH₃ | C(=O)N(CH₃)—CH₂-A-18 |
| 2377. | NC(O)CH₃ | C(=O)N(CH₃)—CH₂-A-19 |
| 2378. | NC(O)CH₃ | C(=O)N(CH₃)—CH₂-A-20 |
| 2379. | NC(O)CH₃ | C(=O)N(CH₃)—CH₂-A-21 |
| 2380. | NC(O)CH₃ | C(=O)N(CH₃)—CH₂-A-22 |
| 2381. | NC(O)CH₃ | C(=O)N(CH₃)—CH₂-A-23 |
| 2382. | NC(O)CH₃ | C(=O)N(CH₃)—CH₂-A-24 |
| 2383. | NC(O)CH₃ | C(=O)N(CH₃)—CH₂-A-25 |
| 2384. | NC(O)CH₃ | C(=O)N(CH₃)—CH₂-A-26 |
| 2385. | NC(O)CH₃ | C(=O)N(CH₃)—CH₂-A-27 |
| 2386. | NC(O)CH₃ | C(=O)N(CH₃)—CH₂-A-28 |
| 2387. | NC(O)CH₃ | C(=O)N(CH₃)—CH₂-A-29 |
| 2388. | NC(O)CH₃ | C(=O)N(CH₃)—CH₂-A-30 |
| 2389. | NC(O)CH₃ | C(=O)N(CH₃)—CH₂-A-31 |
| 2390. | NC(O)CH₃ | C(=O)N(CH₃)—CH₂-A-32 |
| 2391. | NC(O)CH₃ | C(=O)N(CH₃)—CH₂-A-33 |
| 2392. | NC(O)CH₃ | C(=O)N(CH₃)—SO₂—CH₃ |
| 2393. | NC(O)CH₃ | C(=O)N(CH₃)—SO₂—CF₃ |
| 2394. | NC(O)CH₃ | C(=O)N(CH₃)—SO₂—CH₂CH₃ |
| 2395. | NC(O)CH₃ | C(=O)N(CH₃)—SO₂—CH₂CF₃ |
| 2396. | NC(O)CH₃ | C(=O)N(CH₃)—SO₂—CH₂CH₂CH₃ |
| 2397. | NC(O)CH₃ | C(=O)N(CH₃)—SO₂—CH₂CH₂CF₃ |
| 2398. | NC(O)CH₃ | C(=O)N(CH₃)—SO₂—CH₂CF₂CF₃ |
| 2399. | NC(O)CH₃ | C(=O)N(CH₃)—SO₂—CH(CH₃)₂ |
| 2400. | NC(O)CH₃ | C(=O)N(CH₃)—SO₂—CH(CF₃)₂ |
| 2401. | NC(O)CH₃ | C(=O)NH—SO₂—NH₂ |
| 2402. | NC(O)CH₃ | C(=O)NH—SO₂—NHCH₃ |
| 2403. | NC(O)CH₃ | C(=O)NH—SO₂—N(CH₃)₂ |
| 2404. | NC(O)CH₃ | C(=O)NH—SO₂—NHCF₃ |
| 2405. | NC(O)CH₃ | C(=O)NH—SO₂—N(CF₃)₂ |
| 2406. | NC(O)CH₃ | C(=O)NH—SO₂—NHCH₂CH₃ |
| 2407. | NC(O)CH₃ | C(=O)NH—SO₂—N(CH₂CH₃)₂ |
| 2408. | NC(O)CH₃ | C(=O)NH—SO₂—NHCH₂CF₃ |
| 2409. | NC(O)CH₃ | C(=O)NH—SO₂—N(CH₂CF₃)₂ |
| 2410. | NC(O)CH₃ | C(=O)NH—SO₂—N(CH₃)CH₂CH₃ |
| 2411. | NC(O)CH₃ | C(=O)NH—SO₂—N(CH₃)CH₂CF₃ |
| 2412. | NC(O)CH₃ | C(=O)NH—SO₂—N(CF₃)CH₂CH₃ |
| 2413. | NC(O)CH₃ | C(=O)NH—SO₂—NHCH₂CH₂CH₃ |
| 2414. | NC(O)CH₃ | C(=O)NH—SO₂—N(CH₂CH₂CH₃)₂ |
| 2415. | NC(O)CH₃ | C(=O)NH—SO₂—NHCH₂CH₂CF₃ |
| 2416. | NC(O)CH₃ | C(=O)NH—SO₂—N(CH₂CH₂CF₃)₂ |
| 2417. | NC(O)CH₃ | C(=O)NH—SO₂—N(CH₃)CH₂CH₂CH₃ |
| 2418. | NC(O)CH₃ | C(=O)NH—SO₂—N(CH₃)CH₂CH₂CF₃ |
| 2419. | NC(O)CH₃ | C(=O)NH—SO₂—N(CF₃)CH₂CH₂CH₃ |
| 2420. | NC(O)CH₃ | C(=O)NH—SO₂—NHCH(CH₃)₂ |
| 2421. | NC(O)CH₃ | C(=O)NH—SO₂—NHCH(CF₃)₂ |
| 2422. | NC(O)CH₃ | C(=O)NH—SO₂—N(CH₃)CH(CH₃)₂ |
| 2423. | NC(O)CH₃ | C(=O)NH—SO₂—N(CH₃)CH(CF₃)₂ |
| 2424. | NC(O)CH₃ | C(=O)NH—SO₂—N(CF₃)CH(CH₃)₂ |
| 2425. | NC(O)CH₃ | C(=O)NH—SO₂—NHCH₂CH₂CH₂CH₃ |
| 2426. | NC(O)CH₃ | C(=O)NH—SO₂—N(CH₂CH₂CH₂CH₃)₂ |

TABLE A-continued

| No. | Y | R² |
|---|---|---|
| 2427. | NC(O)CH₃ | C(=O)NH—SO₂—N(CH₃)CH₂CH₂CH₂CH₃ |
| 2428. | NC(O)CH₃ | C(=O)N(CH₃)—SO₂—NH₂ |
| 2429. | NC(O)CH₃ | C(=O)N(CH₃)—SO₂—NHCH₃ |
| 2430. | NC(O)CH₃ | C(=O)N(CH₃)—SO₂—N(CH₃)₂ |
| 2431. | NC(O)CH₃ | C(=O)N(CH₃)—SO₂—NHCF₃ |
| 2432. | NC(O)CH₃ | C(=O)N(CH₃)—SO₂—N(CF₃)₂ |
| 2433. | NC(O)CH₃ | C(=O)N(CH₃)—SO₂—NHCH₂CH₃ |
| 2434. | NC(O)CH₃ | C(=O)N(CH₃)—SO₂—N(CH₂CH₃)₂ |
| 2435. | NC(O)CH₃ | C(=O)N(CH₃)—SO₂—NHCH₂CF₃ |
| 2436. | NC(O)CH₃ | C(=O)N(CH₃)—SO₂—N(CH₂CF₃)₂ |
| 2437. | NC(O)CH₃ | C(=O)N(CH₃)—SO₂—NHCH₂CH₂CH₃ |
| 2438. | NC(O)CH₃ | C(=O)N(CH₃)—SO₂—N(CH₃)CH₂CF₃ |
| 2439. | NC(O)CH₃ | C(=O)N(CH₃)—SO₂—N(CF₃)CH₂CH₃ |
| 2440. | NC(O)CH₃ | C(=O)N(CH₃)—SO₂—NHCH₂CH₂CH₃ |
| 2441. | NC(O)CH₃ | C(=O)N(CH₃)—SO₂—N(CH₂CH₃)₂ |
| 2442. | NC(O)CH₃ | C(=O)N(CH₃)—SO₂—NHCH₂CH₂CF₃ |
| 2443. | NC(O)CH₃ | C(=O)N(CH₃)—SO₂—N(CH₂CH₂CF₃)₂ |
| 2444. | NC(O)CH₃ | C(=O)N(CH₃)—SO₂—N(CH₃CH₂CH₂CH₃ |
| 2445. | NC(O)CH₃ | C(=O)N(CH₃)—SO₂—N(CH₃)CH₂CH₂CF₃ |
| 2446. | NC(O)CH₃ | C(=O)N(CH₃)—SO₂—N(CF₃)CH₂CH₂CH₃ |
| 2447. | NC(O)CH₃ | C(=O)N(CH₃)—SO₂—NHCH(CH₃)₂ |
| 2448. | NC(O)CH₃ | C(=O)N(CH₃)—SO₂—NHCH(CF₃)₂ |
| 2449. | NC(O)CH₃ | C(=O)N(CH₃)—SO₂—N(CH₃)CH(CH₃)₂ |
| 2450. | NC(O)CH₃ | C(=O)N(CH₃)—SO₂—N(CH₃)CH(CF₃)₂ |
| 2451. | NC(O)CH₃ | C(=O)N(CH₃)—SO₂—N(CF₃)CH(CH₃)₂ |
| 2452. | NC(O)CH₃ | C(=O)N(CH₃)—SO₂—NHCH₂CH₂CH₂CH₃ |
| 2453. | NC(O)CH₃ | C(=O)N(CH₃)—SO₂—N(CH₂CH₂CH₃)₂ |
| 2454. | NC(O)CH₃ | C(=O)N(CH₃)—SO₂—N(CH₃)CH₂CH₂CH₂CH₃ |
| 2455. | NC(O)CH₃ | C(=O)—N=CHOCH₃ |
| 2456. | NC(O)CH₃ | C(=O)—N=CHOCH₂CH₃ |
| 2457. | NC(O)CH₃ | C(=O)—N=CHOCH₂CH₂CH₃ |
| 2458. | NC(O)CH₃ | C(=O)—N=CHOCH(CH₃)₂ |
| 2459. | NC(O)CH₃ | C(=O)—N=CHOCF₃ |
| 2460. | NC(O)CH₃ | C(=O)—N=CHOCH₂CF₃ |
| 2461. | NC(O)CH₃ | C(=O)—N=CHOCH₂CH₂CF₃ |
| 2462. | NC(O)CH₃ | C(=O)—N=CHOCH(CF₃)₂ |
| 2463. | NC(O)CH₃ | C(=O)—N=CH—CO—OCH₃ |
| 2464. | NC(O)CH₃ | C(=O)—N=CH—CO—OCH₂CH₃ |
| 2465. | NC(O)CH₃ | C(=O)—N=CH—CO—OCH₂CH₂CH₃ |
| 2466. | NC(O)CH₃ | C(=O)—N=CH—CO—OCH(CH₃)₂ |
| 2467. | NC(O)CH₃ | C(=O)—N=CH—CO—OCF₃ |
| 2468. | NC(O)CH₃ | C(=O)—N=CH—CO—OCH₂CF₃ |
| 2469. | NC(O)CH₃ | C(=O)—N=CH—CO—OCH₂CH₂CF₃ |
| 2470. | NC(O)CH₃ | C(=O)—N=CH—CO—OCH(CF₃)₂ |
| 2471. | NC(O)CH₃ | C(=O)—N=CH—CO—NHCH₃ |
| 2472. | NC(O)CH₃ | C(=O)—N=CH—CO—N(CH₃)₂ |
| 2473. | NC(O)CH₃ | C(=O)—N=CH—CO—NHCH₂CH₃ |
| 2474. | NC(O)CH₃ | C(=O)—N=CH—CO—N(CH₂CH₃)₂ |
| 2475. | NC(O)CH₃ | C(=O)—N=CH—CO—N(CH₃)CH₂CH₃ |
| 2476. | NC(O)CH₃ | C(=O)—N=CH—CO—NHCH₂CH₂CH₃ |
| 2477. | NC(O)CH₃ | C(=O)—N=CH—CO—N(CH₂CH₂CH₃)₂ |
| 2478. | NC(O)CH₃ | C(=O)—N=CH—CO—N(CH₃)CH₂CH₂CH₃ |
| 2479. | NC(O)CH₃ | C(=O)—N=CH—CO—NHCH(CH₃)₂ |
| 2480. | NC(O)CH₃ | C(=O)—N=CH—CO—N(CH₃)CH(CH₃)₂ |
| 2481. | NC(O)CH₃ | C(=O)—N=CH—CO—NHCF₃ |
| 2482. | NC(O)CH₃ | C(=O)—N=CH—CO—N(CF₃)₂ |
| 2483. | NC(O)CH₃ | C(=O)—N=CH—CO—NHCH₂CF₃ |
| 2484. | NC(O)CH₃ | C(=O)—N=CH—CO—N(CH₂CF₃)₂ |
| 2485. | NC(O)CH₃ | C(=O)—N=CH—CO—N(CH₃)CH₂CF₃ |
| 2486. | NC(O)CH₃ | C(=O)—N=CH—CO—N(CF₃)CH₂CF₃ |
| 2487. | NC(O)CH₃ | C(=O)—N=CH—CO—NHCH₂CH₂CF₃ |
| 2488. | NC(O)CH₃ | C(=O)—N=CH—CO—N(CH₂CH₂CF₃)₂ |
| 2489. | NC(O)CH₃ | C(=O)—N=CH—CO—N(CH₃)CH₂CH₂CF₃ |
| 2490. | NC(O)CH₃ | C(=O)—N=CH—CO—N(CF₃)CH₂CH₂CH₃ |
| 2491. | NC(O)CH₃ | C(=O)—N=CH—CO—NHCH(CF₃)₂ |
| 2492. | NC(O)CH₃ | C(=O)—N=CH—CO—N(CH₃)CH(CF₃)₂ |
| 2493. | NC(O)CH₃ | C(=O)—N=CH—CO—N(CF₃)CH(CH₃)₂ |
| 2494. | NC(O)CH₃ | C(=S)NH₂ |
| 2495. | NC(O)CH₃ | C(=S)NHCH₃ |
| 2496. | NC(O)CH₃ | C(=S)N(CH₃)₂ |
| 2497. | NC(O)CH₃ | C(=S)NHCF₃ |
| 2498. | NC(O)CH₃ | C(=S)N(CF₃)₂ |
| 2499. | NC(O)CH₃ | C(=S)NHCH₂CH₃ |
| 2500. | NC(O)CH₃ | C(=S)N(CH₂CH₃)₂ |
| 2501. | NC(O)CH₃ | C(=S)(CH₃)CH₂CH₃ |
| 2502. | NC(O)CH₃ | C(=S)NHCH₂CF₃ |
| 2503. | NC(O)CH₃ | C(=S)N(CH₂CF₃)₂ |
| 2504. | NC(O)CH₃ | C(=S)N(CH₃)CH₂CF₃ |
| 2505. | NC(O)CH₃ | C(=S)NHCH₂CH₂CH₃ |
| 2506. | NC(O)CH₃ | C(=S)N(CH₃)CH₂CH₂CH₃ |
| 2507. | NC(O)CH₃ | C(=S)NHCH(CH₃)₂ |
| 2508. | NC(O)CH₃ | C(=S)NH(CH₂)₃CH₃ |
| 2509. | NC(O)CH₃ | C(=S)N(CH₃)—(CH₂)₃CH₃ |
| 2510. | NC(O)CH₃ | C(=S)N[(CH₂)₃CH₃]₂ |
| 2511. | NC(O)CH₃ | C(=S)N(CH₃)—CH₂—C₆H₅ |
| 2512. | NC(O)CH₃ | C(=S)NH-propargyl |
| 2513. | NC(O)CH₃ | C(=S)N(CH₃)-propargyl |
| 2514. | NC(O)CH₃ | C(=S)NH—CH₂-4-Cl—C₆H₄ |
| 2515. | NC(O)CH₃ | C(=S)N(CH₃)—CH₂-4-Cl—C₆H₄ |
| 2516. | NC(O)CH₃ | C(=S)morpholin-4-yl |
| 2517. | NC(O)CH₃ | C(=S)NH-3-thiolyl-1,1-dioxid |
| 2518. | NC(O)CH₃ | C(=S)N(CH₃)-3-thiolyl-1,1-dioxid |
| 2519. | NC(O)CH₃ | C(=S)-azirid-1-yl |
| 2520. | NC(O)CH₃ | C(=S)-pyrrolidin-1-yl |
| 2521. | NC(O)CH₃ | C(=S)-piperidin-1-yl |
| 2522. | NC(O)CH₃ | C(=S)-thiomorpholin-4-yl |
| 2523. | NC(O)CH₃ | C(=S)NH—CH₂CHF₂ |
| 2524. | NC(O)CH₃ | C(=S)NH—CH₂CH₂CHF₂ |
| 2525. | NC(O)CH₃ | C(=S)NH—CH₂CH₂CF₃ |
| 2526. | NC(O)CH₃ | C(=S)NH-cyclopropyl |
| 2527. | NC(O)CH₃ | C(=S)NH-cyclobutyl |
| 2528. | NC(O)CH₃ | C(=S)NH-cyclopentyl |
| 2529. | NC(O)CH₃ | C(=S)NH-cyclohexyl |
| 2530. | NC(O)CH₃ | C(=S)NH—CH₂-cyclopropyl |
| 2531. | NC(O)CH₃ | C(=S)NH—CH₂-cyclobutyl |
| 2532. | NC(O)CH₃ | C(=S)NH—CH₂-cyclopentyl |
| 2533. | NC(O)CH₃ | C(=S)NH—CH₂-cyclohexyl |
| 2534. | NC(O)CH₃ | C(=S)NH—CN |
| 2535. | NC(O)CH₃ | C(=S)NH—CH₂—CN |
| 2536. | NC(O)CH₃ | C(=S)NH—CH₂—CH=CH₂ |
| 2537. | NC(O)CH₃ | C(=S)NH—CH₂—CH=C(Cl)₂ |
| 2538. | NC(O)CH₃ | C(=S)NH—CH₂—CH=CH-phenyl |
| 2539. | NC(O)CH₃ | C(=S)NH—CH₂—CH=CH-(4-Cl-phenyl) |
| 2540. | NC(O)CH₃ | C(=S)NH—CH₂—SCH₃ |
| 2541. | NC(O)CH₃ | C(=S)NH—CH₂—SCF₃ |
| 2542. | NC(O)CH₃ | C(=S)NH—CH₂—CH₂—SCH₃ |
| 2543. | NC(O)CH₃ | C(=S)NH—CH₂—CH₂—SCF₃ |
| 2544. | NC(O)CH₃ | C(=S)NH—CH₂—SO₂—CH₃ |
| 2545. | NC(O)CH₃ | C(=S)NH—CH₂—SO₂—CF₃ |
| 2546. | NC(O)CH₃ | C(=S)NH—CH₂—CH₂—SO₂—CH₃ |
| 2547. | NC(O)CH₃ | C(=S)NH—CH₂—CH₂—SO₂—CF₃ |
| 2548. | NC(O)CH₃ | C(=S)NH—CH₂—CO—NH₂ |
| 2549. | NC(O)CH₃ | C(=S)NH—CH₂—CO—NHCH₃ |
| 2550. | NC(O)CH₃ | C(=S)NH—CH₂—CO—N(CH₃)₂ |
| 2551. | NC(O)CH₃ | C(=S)NH—CH₂—CO—NHCF₃ |
| 2552. | NC(O)CH₃ | C(=S)NH—CH₂—CO—N(CF₃)₂ |
| 2553. | NC(O)CH₃ | C(=S)NH—CH₂—CO—NHCH₂CH₃ |
| 2554. | NC(O)CH₃ | C(=S)NH—CH₂—CO—N(CH₂CH₃)₂ |
| 2555. | NC(O)CH₃ | C(=S)NH—CH₂—CO—NHCH₂CF₃ |
| 2556. | NC(O)CH₃ | C(=S)NH—CH₂—CO—N(CH₂CF₃)₂ |
| 2557. | NC(O)CH₃ | C(=S)NH—CH₂—CO—NHCH₂CH₂CH₃ |
| 2558. | NC(O)CH₃ | C(=S)NH—CH₂—CO—N(CH₂CH₂CH₃)₂ |
| 2559. | NC(O)CH₃ | C(=S)NH—CH₂—CO—NHCH₂CH₂CF₃ |
| 2560. | NC(O)CH₃ | C(=S)NH—CH₂—CO—N(CH₂CH₂CF₃)₂ |
| 2561. | NC(O)CH₃ | C(=S)NH—CH₂—CO—NHCH(CH₃)₂ |
| 2562. | NC(O)CH₃ | C(=S)NH—CH₂—CO—NHCH(CF₃)₂ |
| 2563. | NC(O)CH₃ | C(=S)NH—CH₂—CO—NH-cyclopropyl |
| 2564. | NC(O)CH₃ | C(=S)NH—CH₂—CO—NH—CH₂-cyclopropyl |
| 2565. | NC(O)CH₃ | C(=S)NH—CH₂—CO—OH |
| 2566. | NC(O)CH₃ | C(=S)NH—CH₂—CO—OCH₃ |
| 2567. | NC(O)CH₃ | C(=S)NH—CH₂—CO—OCF₃ |
| 2568. | NC(O)CH₃ | C(=S)NH—CH₂—CO—OCH₂CH₃ |
| 2569. | NC(O)CH₃ | C(=S)NH—CH₂—CO—OCH₂CF₃ |
| 2570. | NC(O)CH₃ | C(=S)NH—CH₂—CO—OCH₂CH₂CH₃ |
| 2571. | NC(O)CH₃ | C(=S)NH—CH₂—CO—OCH(CH₃)₂ |
| 2572. | NC(O)CH₃ | C(=S)NH—CH₂—CO—OCH₂CH₂CH₂CH₃ |
| 2573. | NC(O)CH₃ | C(=S)NH—CH₂—CO—OCH(CH₃)CH₂CH₃ |
| 2574. | NC(O)CH₃ | C(=S)NH—CH₂—CO—OCH₂CH(CH₃)₂ |
| 2575. | NC(O)CH₃ | C(=S)NH—CH₂—CO—OC(CH₃)₃ |
| 2576. | NC(O)CH₃ | C(=S)NH-A-1 |
| 2577. | NC(O)CH₃ | C(=S)NH-A-2 |
| 2578. | NC(O)CH₃ | C(=S)NH-A-3 |
| 2579. | NC(O)CH₃ | C(=S)NH-A-4 |
| 2580. | NC(O)CH₃ | C(=S)NH-A-5 |
| 2581. | NC(O)CH₃ | C(=S)NH-A-6 |
| 2582. | NC(O)CH₃ | C(=S)NH-A-7 |

TABLE A-continued

| No. | Y | R² |
|---|---|---|
| 2583. | NC(O)CH₃ | C(=S)NH-A-8 |
| 2584. | NC(O)CH₃ | C(=S)NH-A-9 |
| 2585. | NC(O)CH₃ | C(=S)NH-A-10 |
| 2586. | NC(O)CH₃ | C(=S)NH-A-11 |
| 2587. | NC(O)CH₃ | C(=S)NH-A-12 |
| 2588. | NC(O)CH₃ | C(=S)NH-A-13 |
| 2589. | NC(O)CH₃ | C(=S)NH-A-14 |
| 2590. | NC(O)CH₃ | C(=S)NH-A-15 |
| 2591. | NC(O)CH₃ | C(=S)NH-A-16 |
| 2592. | NC(O)CH₃ | C(=S)NH-A-17 |
| 2593. | NC(O)CH₃ | C(=S)NH-A-18 |
| 2594. | NC(O)CH₃ | C(=S)NH-A-19 |
| 2595. | NC(O)CH₃ | C(=S)NH-A-20 |
| 2596. | NC(O)CH₃ | C(=S)NH-A-21 |
| 2597. | NC(O)CH₃ | C(=S)NH-A-22 |
| 2598. | NC(O)CH₃ | C(=S)NH-A-23 |
| 2599. | NC(O)CH₃ | C(=S)NH-A-24 |
| 2600. | NC(O)CH₃ | C(=S)NH-A-25 |
| 2601. | NC(O)CH₃ | C(=S)NH-A-26 |
| 2602. | NC(O)CH₃ | C(=S)NH-A-27 |
| 2603. | NC(O)CH₃ | C(=S)NH-A-28 |
| 2604. | NC(O)CH₃ | C(=S)NH-A-29 |
| 2605. | NC(O)CH₃ | C(=S)NH-A-30 |
| 2606. | NC(O)CH₃ | C(=S)NH-A-31 |
| 2607. | NC(O)CH₃ | C(=S)NH-A-32 |
| 2608. | NC(O)CH₃ | C(=S)NH-A-33 |
| 2609. | NC(O)CH₃ | C(=S)NH—CH₂-A-1 |
| 2610. | NC(O)CH₃ | C(=S)NH—CH₂-A-2 |
| 2611. | NC(O)CH₃ | C(=S)NH—CH₂-A-3 |
| 2612. | NC(O)CH₃ | C(=S)NH—CH₂-A-4 |
| 2613. | NC(O)CH₃ | C(=S)NH—CH₂-A-5 |
| 2614. | NC(O)CH₃ | C(=S)NH—CH₂-A-6 |
| 2615. | NC(O)CH₃ | C(=S)NH—CH₂-A-7 |
| 2616. | NC(O)CH₃ | C(=S)NH—CH₂-A-8 |
| 2617. | NC(O)CH₃ | C(=S)NH—CH₂-A-9 |
| 2618. | NC(O)CH₃ | C(=S)NH—CH₂-A-10 |
| 2619. | NC(O)CH₃ | C(=S)NH—CH₂-A-11 |
| 2620. | NC(O)CH₃ | C(=S)NH—CH₂-A-12 |
| 2621. | NC(O)CH₃ | C(=S)NH—CH₂-A-13 |
| 2622. | NC(O)CH₃ | C(=S)NH—CH₂-A-14 |
| 2623. | NC(O)CH₃ | C(=S)NH—CH₂-A-15 |
| 2624. | NC(O)CH₃ | C(=S)NH—CH₂-A-16 |
| 2625. | NC(O)CH₃ | C(=S)NH—CH₂-A-17 |
| 2626. | NC(O)CH₃ | C(=S)NH—CH₂-A-18 |
| 2627. | NC(O)CH₃ | C(=S)NH—CH₂-A-19 |
| 2628. | NC(O)CH₃ | C(=S)NH—CH₂-A-20 |
| 2629. | NC(O)CH₃ | C(=S)NH—CH₂-A-21 |
| 2630. | NC(O)CH₃ | C(=S)NH—CH₂-A-22 |
| 2631. | NC(O)CH₃ | C(=S)NH—CH₂-A-23 |
| 2632. | NC(O)CH₃ | C(=S)NH—CH₂-A-24 |
| 2633. | NC(O)CH₃ | C(=S)NH—CH₂-A-25 |
| 2634. | NC(O)CH₃ | C(=S)NH—CH₂-A-26 |
| 2635. | NC(O)CH₃ | C(=S)NH—CH₂-A-27 |
| 2636. | NC(O)CH₃ | C(=S)NH—CH₂-A-28 |
| 2637. | NC(O)CH₃ | C(=S)NH—CH₂-A-29 |
| 2638. | NC(O)CH₃ | C(=S)NH—CH₂-A-30 |
| 2639. | NC(O)CH₃ | C(=S)NH—CH₂-A-31 |
| 2640. | NC(O)CH₃ | C(=S)NH—CH₂-A-32 |
| 2641. | NC(O)CH₃ | C(=S)NH—CH₂-A-33 |
| 2642. | NC(O)CH₃ | C(=S)NH—SO₂—CH₃ |
| 2643. | NC(O)CH₃ | C(=S)NH—SO₂—CF₃ |
| 2644. | NC(O)CH₃ | C(=S)NH—SO₂—CH₂CH₃ |
| 2645. | NC(O)CH₃ | C(=S)NH—SO₂—CH₂CF₃ |
| 2646. | NC(O)CH₃ | C(=S)NH—SO₂—CH₂CH₂CH₃ |
| 2647. | NC(O)CH₃ | C(=S)NH—SO₂—CH₂CH₂CF₃ |
| 2648. | NC(O)CH₃ | C(=S)NH—SO₂—CH₂CF₂CF₃ |
| 2649. | NC(O)CH₃ | C(=S)NH—SO₂—CH(CH₃)₂ |
| 2650. | NC(O)CH₃ | C(=S)NH—SO₂—CH(CF₃)₂ |
| 2651. | NC(O)CH₃ | C(=S)N(CH₃)—CH₂CHF₂ |
| 2652. | NC(O)CH₃ | C(=S)N(CH₃)—CH₂CH₂CHF₂ |
| 2653. | NC(O)CH₃ | C(=S)N(CH₃)—CH₂CH₂CF₃ |
| 2654. | NC(O)CH₃ | C(=S)N(CH₃)-cyclopropyl |
| 2655. | NC(O)CH₃ | C(=S)N(CH₃)-cyclobutyl |
| 2656. | NC(O)CH₃ | C(=S)N(CH₃)-cyclopentyl |
| 2657. | NC(O)CH₃ | C(=S)N(CH₃)-cyclohexyl |
| 2658. | NC(O)CH₃ | C(=S)N(CH₃)—CH₂-cyclopropyl |
| 2659. | NC(O)CH₃ | C(=S)N(CH₃)—CH₂-cyclobutyl |
| 2660. | NC(O)CH₃ | C(=S)N(CH₃)—CH₂-cyclopentyl |
| 2661. | NC(O)CH₃ | C(=S)N(CH₃)—CH₂-cyclohexyl |
| 2662. | NC(O)CH₃ | C(=S)N(CH₃)—CN |
| 2663. | NC(O)CH₃ | C(=S)N(CH₃)—CH₂—CN |
| 2664. | NC(O)CH₃ | C(=S)N(CH₃)—CH₂—CH=CH₂ |
| 2665. | NC(O)CH₃ | C(=S)N(CH₃)—CH₂—CH=C(Cl)₂ |
| 2666. | NC(O)CH₃ | C(=S)N(CH₃)—CH₂—CH=CH-phenyl |
| 2667. | NC(O)CH₃ | C(=S)N(CH₃)—CH₂—CH=CH-(4-Cl-phenyl) |
| 2668. | NC(O)CH₃ | C(=S)N(CH₃)—CH₂—SCH₃ |
| 2669. | NC(O)CH₃ | C(=S)N(CH₃)—CH₂—SCF₃ |
| 2670. | NC(O)CH₃ | C(=S)N(CH₃)—CH₂—CH₂—SCH₃ |
| 2671. | NC(O)CH₃ | C(=S)N(CH₃)—CH₂—CH₂—SCF₃ |
| 2672. | NC(O)CH₃ | C(=S)N(CH₃)—CH₂—SO₂—CH₃ |
| 2673. | NC(O)CH₃ | C(=S)N(CH₃)—CH₂—SO₂—CF₃ |
| 2674. | NC(O)CH₃ | C(=S)N(CH₃)—CH₂—CH₂—SO₂—CH₃ |
| 2675. | NC(O)CH₃ | C(=S)N(CH₃)—CH₂—CH₂—SO₂—CF₃ |
| 2676. | NC(O)CH₃ | C(=S)N(CH₃)—CH₂—CO—NH₂ |
| 2677. | NC(O)CH₃ | C(=S)N(CH₃)—CH₂—CO—NHCH₃ |
| 2678. | NC(O)CH₃ | C(=S)N(CH₃)—CH₂—CO—N(CH₃)₂ |
| 2679. | NC(O)CH₃ | C(=S)N(CH₃)—CH₂—CO—NHCF₃ |
| 2680. | NC(O)CH₃ | C(=S)N(CH₃)—CH₂—CO—N(CF₃)₂ |
| 2681. | NC(O)CH₃ | C(=S)N(CH₃)—CH₂—CO—NHCH₂CH₃ |
| 2682. | NC(O)CH₃ | C(=S)N(CH₃)—CH₂—CO—N(CH₂CH₃)₂ |
| 2683. | NC(O)CH₃ | C(=S)N(CH₃)—CH₂—CO—NHCH₂CF₃ |
| 2684. | NC(O)CH₃ | C(=S)N(CH₃)—CH₂—CO—N(CH₂CF₃)₂ |
| 2685. | NC(O)CH₃ | C(=S)N(CH₃)—CH₂—CO—NHCH₂CH₂CH₃ |
| 2686. | NC(O)CH₃ | C(=S)N(CH₃)—CH₂—CO—N(CH₂CH₂CH₃)₂ |
| 2687. | NC(O)CH₃ | C(=S)N(CH₃)—CH₂—CO—NHCH₂CH₂CF₃ |
| 2688. | NC(O)CH₃ | C(=S)N(CH₃)—CH₂—CO—N(CH₂CH₂CF₃)₂ |
| 2689. | NC(O)CH₃ | C(=S)N(CH₃)—CH₂—CO—NHCH(CH₃)₂ |
| 2690. | NC(O)CH₃ | C(=S)N(CH₃)—CH₂—CO—NHCH(CF₃)₂ |
| 2691. | NC(O)CH₃ | C(=S)N(CH₃)—CH₂—CO—NH-cyclopropyl |
| 2692. | NC(O)CH₃ | C(=S)N(CH₃)—CH₂—CO—NH—CH₂-cyclopropyl |
| 2693. | NC(O)CH₃ | C(=S)N(CH₃)—CH₂—CO—OH |
| 2694. | NC(O)CH₃ | C(=S)N(CH₃)—CH₂—CO—OCH₃ |
| 2695. | NC(O)CH₃ | C(=S)N(CH₃)—CH₂—CO—OCF₃ |
| 2696. | NC(O)CH₃ | C(=S)N(CH₃)—CH₂—CO—OCH₂CH₃ |
| 2697. | NC(O)CH₃ | C(=S)N(CH₃)—CH₂—CO—OCH₂CF₃ |
| 2698. | NC(O)CH₃ | C(=S)N(CH₃)—CH₂—CO—OCH₂CH₂CH₃ |
| 2699. | NC(O)CH₃ | C(=S)N(CH₃)—CH₂—CO—OCH(CH₃)₂ |
| 2700. | NC(O)CH₃ | C(=S)N(CH₃)—CH₂—CO—OCH₂CH₂CH₂CH₃ |
| 2701. | NC(O)CH₃ | C(=S)N(CH₃)—CH₂—CO—OCH(CH₃)CH₂CH₃ |
| 2702. | NC(O)CH₃ | C(=S)N(CH₃)—CH₂—CO—OCH₂CH(CH₃)₂ |
| 2703. | NC(O)CH₃ | C(=S)N(CH₃)—CH₂—CO—OC(CH₃)₃ |
| 2704. | NC(O)CH₃ | C(=S)N(CH₃)-A-1 |
| 2705. | NC(O)CH₃ | C(=S)N(CH₃)-A-2 |
| 2706. | NC(O)CH₃ | C(=S)N(CH₃)-A-3 |
| 2707. | NC(O)CH₃ | C(=S)N(CH₃)-A-4 |
| 2708. | NC(O)CH₃ | C(=S)N(CH₃)-A-5 |
| 2709. | NC(O)CH₃ | C(=S)N(CH₃)-A-6 |
| 2710. | NC(O)CH₃ | C(=S)N(CH₃)-A-7 |
| 2711. | NC(O)CH₃ | C(=S)N(CH₃)-A-8 |
| 2712. | NC(O)CH₃ | C(=S)N(CH₃)-A-9 |
| 2713. | NC(O)CH₃ | C(=S)N(CH₃)-A-10 |
| 2714. | NC(O)CH₃ | C(=S)N(CH₃)-A-11 |
| 2715. | NC(O)CH₃ | C(=S)N(CH₃)-A-12 |
| 2716. | NC(O)CH₃ | C(=S)N(CH₃)-A-13 |
| 2717. | NC(O)CH₃ | C(=S)N(CH₃)-A-14 |
| 2718. | NC(O)CH₃ | C(=S)N(CH₃)-A-15 |
| 2719. | NC(O)CH₃ | C(=S)N(CH₃)-A-16 |
| 2720. | NC(O)CH₃ | C(=S)N(CH₃)-A-17 |
| 2721. | NC(O)CH₃ | C(=S)N(CH₃)-A-18 |
| 2722. | NC(O)CH₃ | C(=S)N(CH₃)-A-19 |
| 2723. | NC(O)CH₃ | C(=S)N(CH₃)-A-20 |
| 2724. | NC(O)CH₃ | C(=S)N(CH₃)-A-21 |
| 2725. | NC(O)CH₃ | C(=S)N(CH₃)-A-22 |
| 2726. | NC(O)CH₃ | C(=S)N(CH₃)-A-23 |
| 2727. | NC(O)CH₃ | C(=S)N(CH₃)-A-24 |
| 2728. | NC(O)CH₃ | C(=S)N(CH₃)-A-25 |
| 2729. | NC(O)CH₃ | C(=S)N(CH₃)-A-26 |
| 2730. | NC(O)CH₃ | C(=S)N(CH₃)-A-27 |
| 2731. | NC(O)CH₃ | C(=S)N(CH₃)-A-28 |
| 2732. | NC(O)CH₃ | C(=S)N(CH₃)-A-29 |
| 2733. | NC(O)CH₃ | C(=S)N(CH₃)-A-30 |
| 2734. | NC(O)CH₃ | C(=S)N(CH₃)-A-31 |
| 2735. | NC(O)CH₃ | C(=S)N(CH₃)-A-32 |
| 2736. | NC(O)CH₃ | C(=S)N(CH₃)-A-33 |
| 2737. | NC(O)CH₃ | C(=S)N(CH₃)—CH₂-A-1 |
| 2738. | NC(O)CH₃ | C(=S)N(CH₃)—CH₂-A-2 |

TABLE A-continued

| No. | Y | R² |
|---|---|---|
| 2739. | NC(O)CH₃ | C(=S)N(CH₃)—CH₂-A-3 |
| 2740. | NC(O)CH₃ | C(=S)N(CH₃)—CH₂-A-4 |
| 2741. | NC(O)CH₃ | C(=S)N(CH₃)—CH₂-A-5 |
| 2742. | NC(O)CH₃ | C(=S)N(CH₃)—CH₂-A-6 |
| 2743. | NC(O)CH₃ | C(=S)N(CH₃)—CH₂-A-7 |
| 2744. | NC(O)CH₃ | C(=S)N(CH₃)—CH₂-A-8 |
| 2745. | NC(O)CH₃ | C(=S)N(CH₃)—CH₂-A-9 |
| 2746. | NC(O)CH₃ | C(=S)N(CH₃)—CH₂-A-10 |
| 2747. | NC(O)CH₃ | C(=S)N(CH₃)—CH₂-A-11 |
| 2748. | NC(O)CH₃ | C(=S)N(CH₃)—CH₂-A-12 |
| 2749. | NC(O)CH₃ | C(=S)N(CH₃)—CH₂-A-13 |
| 2750. | NC(O)CH₃ | C(=S)N(CH₃)—CH₂-A-14 |
| 2751. | NC(O)CH₃ | C(=S)N(CH₃)—CH₂-A-15 |
| 2752. | NC(O)CH₃ | C(=S)N(CH₃)—CH₂-A-16 |
| 2753. | NC(O)CH₃ | C(=S)N(CH₃)—CH₂-A-17 |
| 2754. | NC(O)CH₃ | C(=S)N(CH₃)—CH₂-A-18 |
| 2755. | NC(O)CH₃ | C(=S)N(CH₃)—CH₂-A-19 |
| 2756. | NC(O)CH₃ | C(=S)N(CH₃)—CH₂-A-20 |
| 2757. | NC(O)CH₃ | C(=S)N(CH₃)—CH₂-A-21 |
| 2758. | NC(O)CH₃ | C(=S)N(CH₃)—CH₂-A-22 |
| 2759. | NC(O)CH₃ | C(=S)N(CH₃)—CH₂-A-23 |
| 2760. | NC(O)CH₃ | C(=S)N(CH₃)—CH₂-A-24 |
| 2761. | NC(O)CH₃ | C(=S)N(CH₃)—CH₂-A-25 |
| 2762. | NC(O)CH₃ | C(=S)N(CH₃)—CH₂-A-26 |
| 2763. | NC(O)CH₃ | C(=S)N(CH₃)—CH₂-A-27 |
| 2764. | NC(O)CH₃ | C(=S)N(CH₃)—CH₂-A-28 |
| 2765. | NC(O)CH₃ | C(=S)N(CH₃)—CH₂-A-29 |
| 2766. | NC(O)CH₃ | C(=S)N(CH₃)—CH₂-A-30 |
| 2767. | NC(O)CH₃ | C(=S)N(CH₃)—CH₂-A-31 |
| 2768. | NC(O)CH₃ | C(=S)N(CH₃)—CH₂-A-32 |
| 2769. | NC(O)CH₃ | C(=S)N(CH₃)—CH₂-A-33 |
| 2770. | NC(O)CH₃ | C(=S)N(CH₃)—SO₂—CH₃ |
| 2771. | NC(O)CH₃ | C(=S)N(CH₃)—SO₂—CF₃ |
| 2772. | NC(O)CH₃ | C(=S)N(CH₃)—SO₂—CH₂CH₃ |
| 2773. | NC(O)CH₃ | C(=S)N(CH₃)—SO₂—CH₂CF₃ |
| 2774. | NC(O)CH₃ | C(=S)N(CH₃)—SO₂—CH₂CH₂CH₃ |
| 2775. | NC(O)CH₃ | C(=S)N(CH₃)—SO₂—CH₂CH₂CF₃ |
| 2776. | NC(O)CH₃ | C(=S)N(CH₃)—SO₂—CH₂CF₂CF₃ |
| 2777. | NC(O)CH₃ | C(=S)N(CH₃)—SO₂—CH(CH₃)₂ |
| 2778. | NC(O)CH₃ | C(=S)N(CH₃)—SO₂—CH(CF₃)₂ |
| 2779. | NC(O)CH₃ | C(=S)NH—SO₂—NH₂ |
| 2780. | NC(O)CH₃ | C(=S)NH—SO₂—NHCH₃ |
| 2781. | NC(O)CH₃ | C(=S)NH—SO₂—N(CH₃)₂ |
| 2782. | NC(O)CH₃ | C(=S)NH—SO₂—NHCF₃ |
| 2783. | NC(O)CH₃ | C(=S)NH—SO₂—N(CF₃)₂ |
| 2784. | NC(O)CH₃ | C(=S)NH—SO₂—NHCH₂CH₃ |
| 2785. | NC(O)CH₃ | C(=S)NH—SO₂—N(CH₂CH₃)₂ |
| 2786. | NC(O)CH₃ | C(=S)NH—SO₂—NHCH₂CF₃ |
| 2787. | NC(O)CH₃ | C(=S)NH—SO₂—N(CH₂CF₃)₂ |
| 2788. | NC(O)CH₃ | C(=S)NH—SO₂—N(CH₃)CH₂CH₃ |
| 2789. | NC(O)CH₃ | C(=S)NH—SO₂—N(CH₃)CH₂CF₃ |
| 2790. | NC(O)CH₃ | C(=S)NH—SO₂—N(CF₃)CH₂CH₃ |
| 2791. | NC(O)CH₃ | C(=S)NH—SO₂—NHCH₂CH₂CH₃ |
| 2792. | NC(O)CH₃ | C(=S)NH—SO₂—N(CH₂CH₂CH₃)₂ |
| 2793. | NC(O)CH₃ | C(=S)NH—SO₂—NHCH₂CH₂CF₃ |
| 2794. | NC(O)CH₃ | C(=S)NH—SO₂—N(CH₂CH₂CF₃)₂ |
| 2795. | NC(O)CH₃ | C(=S)NH—SO₂—N(CH₃)CH₂CH₂CH₃ |
| 2796. | NC(O)CH₃ | C(=S)NH—SO₂—N(CH₃)CH₂CH₂CF₃ |
| 2797. | NC(O)CH₃ | C(=S)NH—SO₂—N(CF₃)CH₂CH₂CH₃ |
| 2798. | NC(O)CH₃ | C(=S)NH—SO₂—NHCH(CH₃)₂ |
| 2799. | NC(O)CH₃ | C(=S)NH—SO₂—NHCH(CF₃)₂ |
| 2800. | NC(O)CH₃ | C(=S)NH—SO₂—N(CH₃)CH(CH₃)₂ |
| 2801. | NC(O)CH₃ | C(=S)NH—SO₂—N(CH₃)CH(CF₃)₂ |
| 2802. | NC(O)CH₃ | C(=S)NH—SO₂—N(CF₃)CH(CH₃)₂ |
| 2803. | NC(O)CH₃ | C(=S)NH—SO₂—NHCH₂CH₂CH₂CH₃ |
| 2804. | NC(O)CH₃ | C(=S)NH—SO₂—N(CH₂CH₂CH₂CH₃)₂ |
| 2805. | NC(O)CH₃ | C(=S)NH—SO₂—N(CH₃)CH₂CH₂CH₂CH₃ |
| 2806. | NC(O)CH₃ | C(=S)N(CH₃)—SO₂—NH₂ |
| 2807. | NC(O)CH₃ | C(=S)N(CH₃)—SO₂—NHCH₃ |
| 2808. | NC(O)CH₃ | C(=S)N(CH₃)—SO₂—N(CH₃)₂ |
| 2809. | NC(O)CH₃ | C(=S)N(CH₃)—SO₂—NHCF₃ |
| 2810. | NC(O)CH₃ | C(=S)N(CH₃)—SO₂—N(CF₃)₂ |
| 2811. | NC(O)CH₃ | C(=S)N(CH₃)—SO₂—NHCH₂CH₃ |
| 2812. | NC(O)CH₃ | C(=S)N(CH₃)—SO₂—N(CH₂CH₃)₂ |
| 2813. | NC(O)CH₃ | C(=S)N(CH₃)—SO₂—NHCH₂CF₃ |
| 2814. | NC(O)CH₃ | C(=S)N(CH₃)—SO₂—N(CH₂CF₃)₂ |
| 2815. | NC(O)CH₃ | C(=S)N(CH₃)—SO₂—N(CH₃)CH₂CH₃ |
| 2816. | NC(O)CH₃ | C(=S)N(CH₃)—SO₂—N(CH₃)CH₂CF₃ |
| 2817. | NC(O)CH₃ | C(=S)N(CH₃)—SO₂—N(CF₃)CH₂CH₃ |
| 2818. | NC(O)CH₃ | C(=S)N(CH₃)—SO₂—NHCH₂CH₂CH₃ |
| 2819. | NC(O)CH₃ | C(=S)N(CH₃)—SO₂—N(CH₂CH₂CH₃)₂ |
| 2820. | NC(O)CH₃ | C(=S)N(CH₃)—SO₂—NHCH₂CH₂CF₃ |
| 2821. | NC(O)CH₃ | C(=S)N(CH₃)—SO₂—N(CH₂CH₂CF₃)₂ |
| 2822. | NC(O)CH₃ | C(=S)N(CH₃)—SO₂—N(CH₃)CH₂CH₂CH₃ |
| 2823. | NC(O)CH₃ | C(=S)N(CH₃)—SO₂—N(CH₃)CH₂CH₂CF₃ |
| 2824. | NC(O)CH₃ | C(=S)N(CH₃)—SO₂—N(CF₃)CH₂CH₂CH₃ |
| 2825. | NC(O)CH₃ | C(=S)N(CH₃)—SO₂—NHCH(CH₃)₂ |
| 2826. | NC(O)CH₃ | C(=S)N(CH₃)—SO₂—NHCH(CF₃)₂ |
| 2827. | NC(O)CH₃ | C(=S)N(CH₃)—SO₂—N(CH₃)CH(CH₃)₂ |
| 2828. | NC(O)CH₃ | C(=S)N(CH₃)—SO₂—N(CH₃)CH(CF₃)₂ |
| 2829. | NC(O)CH₃ | C(=S)N(CH₃)—SO₂—N(CF₃)CH(CH₃)₂ |
| 2830. | NC(O)CH₃ | C(=S)N(CH₃)—SO₂—NHCH₂CH₂CH₂CH₃ |
| 2831. | NC(O)CH₃ | C(=S)N(CH₃)—SO₂—N(CH₂CH₂CH₂CH₃)₂ |
| 2832. | NC(O)CH₃ | C(=S)N(CH₃)—SO₂—N(CH₃)CH₂CH₂CH₂CH₃ |
| 2833. | NC(O)CH₃ | C(=S)—N=CHOCH₃ |
| 2834. | NC(O)CH₃ | C(=S)—N=CHOCH₂CH₃ |
| 2835. | NC(O)CH₃ | C(=S)—N=CHOCH₂CH₂CH₃ |
| 2836. | NC(O)CH₃ | C(=S)—N=CHOCH(CH₃)₂ |
| 2837. | NC(O)CH₃ | C(=S)—N=CHOCF₃ |
| 2838. | NC(O)CH₃ | C(=S)—N=CHOCH₂CF₃ |
| 2839. | NC(O)CH₃ | C(=S)—N=CHOCH₂CH₂CF₃ |
| 2840. | NC(O)CH₃ | C(=S)—N=CHOCH(CF₃)₂ |
| 2841. | NC(O)CH₃ | C(=S)—N=CH—CO—OCH₃ |
| 2842. | NC(O)CH₃ | C(=S)—N=CH—CO—OCH₂CH₃ |
| 2843. | NC(O)CH₃ | C(=S)—N=CH—CO—OCH₂CH₂CH₃ |
| 2844. | NC(O)CH₃ | C(=S)—N=CH—CO—OCH(CH₃)₂ |
| 2845. | NC(O)CH₃ | C(=S)—N=CH—CO—OCF₃ |
| 2846. | NC(O)CH₃ | C(=S)—N=CH—CO—OCH₂CF₃ |
| 2847. | NC(O)CH₃ | C(=S)—N=CH—CO—OCH₂CH₂CF₃ |
| 2848. | NC(O)CH₃ | C(=S)—N=CH—CO—OCH(CF₃)₂ |
| 2849. | NC(O)CH₃ | C(=S)—N=CH—CO—NHCH₃ |
| 2850. | NC(O)CH₃ | C(=S)—N=CH—CO—N(CH₃)₂ |
| 2851. | NC(O)CH₃ | C(=S)—N=CH—CO—NHCH₂CH₃ |
| 2852. | NC(O)CH₃ | C(=S)—N=CH—CO—N(CH₂CH₃)₂ |
| 2853. | NC(O)CH₃ | C(=S)—N=CH—CO—N(CH₃)CH₂CH₃ |
| 2854. | NC(O)CH₃ | C(=S)—N=CH—CO—NHCH₂CH₂CH₃ |
| 2855. | NC(O)CH₃ | C(=S)—N=CH—CO—N(CH₂CH₂CH₃)₂ |
| 2856. | NC(O)CH₃ | C(=S)—N=CH—CO—N(CH₃)CH₂CH₂CH₃ |
| 2857. | NC(O)CH₃ | C(=S)—N=CH—CO—NHCH(CH₃)₂ |
| 2858. | NC(O)CH₃ | C(=S)—N=CH—CO—N(CH₃)CH(CH₃)₂ |
| 2859. | NC(O)CH₃ | C(=S)—N=CH—CO—NHCF₃ |
| 2860. | NC(O)CH₃ | C(=S)—N=CH—CO—N(CF₃)₂ |
| 2861. | NC(O)CH₃ | C(=S)—N=CH—CO—NHCH₂CF₃ |
| 2862. | NC(O)CH₃ | C(=S)—N=CH—CO—N(CH₂CF₃)₂ |
| 2863. | NC(O)CH₃ | C(=S)—N=CH—CO—N(CH₃)CH₂CF₃ |
| 2864. | NC(O)CH₃ | C(=S)—N=CH—CO—N(CF₃)CH₂CF₃ |
| 2865. | NC(O)CH₃ | C(=S)—N=CH—CO—NHCH₂CH₂CF₃ |
| 2866. | NC(O)CH₃ | C(=S)—N=CH—CO—N(CH₂CH₂CF₃)₂ |
| 2867. | NC(O)CH₃ | C(=S)—N=CH—CO—N(CH₃)CH₂CH₂CF₃ |
| 2868. | NC(O)CH₃ | C(=S)—N=CH—CO—N(CF₃)CH₂CH₂CH₃ |
| 2869. | NC(O)CH₃ | C(=S)—N=CH—CO—NHCH(CF₃)₂ |
| 2870. | NC(O)CH₃ | C(=S)—N=CH—CO—N(CH₃)CH(CF₃)₂ |
| 2871. | NC(O)CH₃ | C(=S)—N=CH—CO—N(CF₃)CH(CH₃)₂ |

ᶜpropyl = cyclopropyl

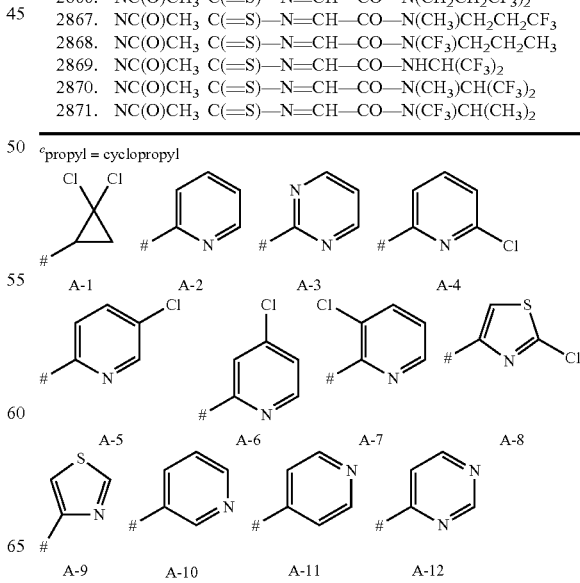

TABLE A-continued

| No. | Y | R² |
|---|---|---|

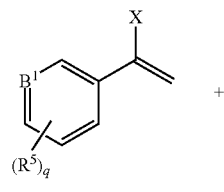

Among the above compounds of formulae I.1 to I.66, preference is given to compounds of formulae I.2 and I.8.

Compounds of formula I can be prepared by one or more of the following methods and variations as described in schemes 1 to 9. The variables $A^1$, $B^1$, X, Y, $R^1$, $R^2$, $R^4$, $R^5$, p and q are as defined above for formula I.

Compounds of formula I can be prepared by reaction of a styrene compound of formula 2 with a compound of formula II ($R^a$, $R^b$ and $R^c$ each independently represent optionally substituted alkyl, preferably $C_1$-$C_{12}$-alkyl, or optionally substituted phenyl and $R^d$ represents hydrogen or is selected from optionally substituted alkyl, preferably $C_1$-$C_{12}$-alkyl, optionally substituted alkenyl, preferably $C_2$-$C_{12}$-alkenyl, optinally substituted alkynyl, preferably $C_2$-$C_{12}$-alkynyl or optionally substituted benzyl) as outlined in scheme 1. Such a procedure has been described, for example, in WO 2009/097992.

Scheme 1:

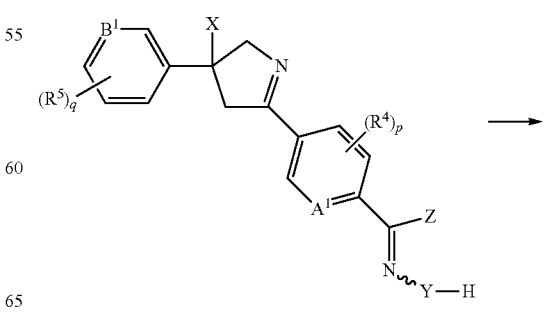

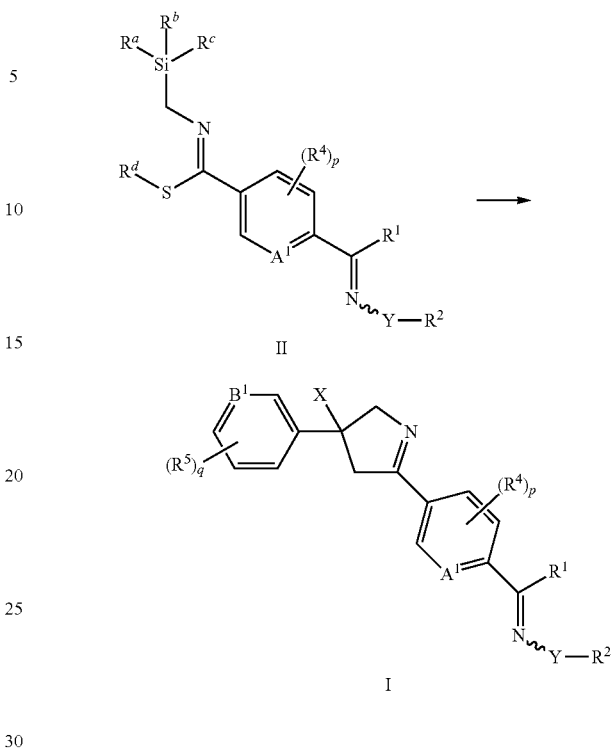

The corresponding styrene compounds can be prepared as described in unpublished PCT/EP2010/055773.

Alternative preparation methods for compounds of formula I can be found in the aforementioned reference WO 2009/097992.

Compounds of formula I can also be prepared as outlined in scheme 2 by condensation of an hydroxamic acid derivative 3 with a Grignard reagent or an organolithium compound as for example described by Reutrakul et al, e-EROS Encyclopedia of Reagents for Organic Synthesis, 2001, Wiley, Chichester, UK for the oximes and by Danko et al, Pest Management Science, 2006, 62, 229-236 for the hydrazones (Z is a leaving group like halogen, OR" or SR"). The obtained ketoxime 4 is then converted into compounds of formula I by reaction with an alkylating agent as for example described by Huang et al, J. Org. Chem. 2008, 73, 4017-4026.

Scheme 2

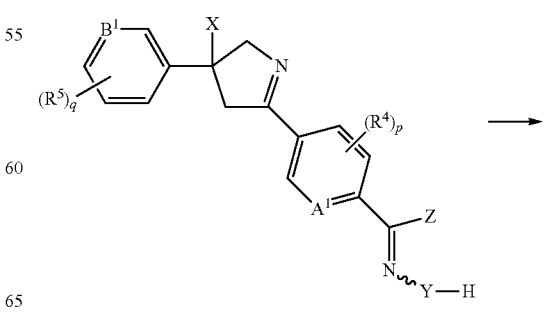

-continued

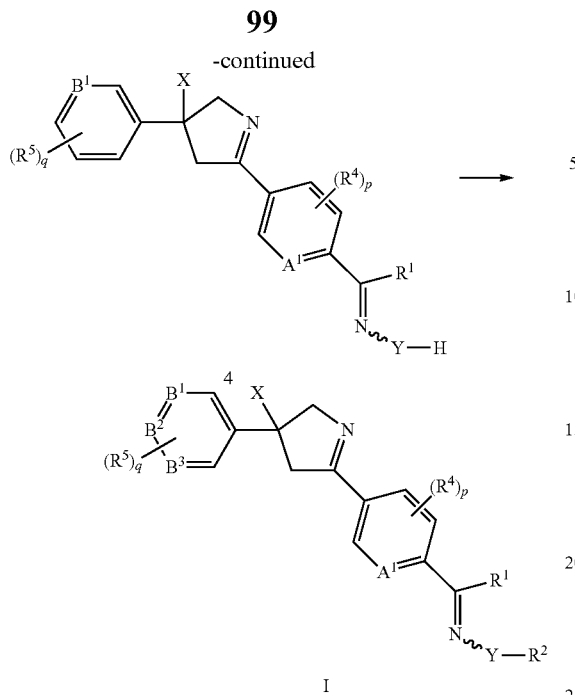

Compounds of formula I can also be prepared as outlined in scheme 3 by reaction of an hydrazone 5 with a formylating agent to yield hydrazone 6 as for example described by Brehme et al, Zeitschrift f. Chemie, 1968, 8, 226-227.

Scheme 3

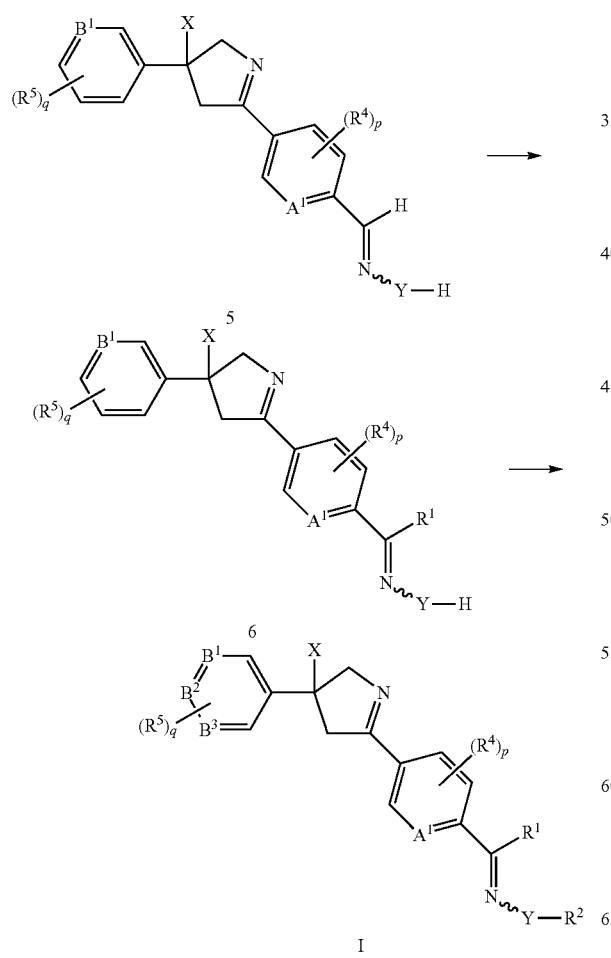

Compounds of formula I can also be prepared as outlined in scheme 4 by reaction of an aldehyde or ketone 7 with a hydroxylamine derivative as for example described by Stivers et al, WO 2006135763. Alternatively, compounds of formula I can also be prepared by reaction of an aldehyde or ketone 7 with a hydrazine derivative as for example described by Fattorusso et al, J. Med. Chem. 2008, 51, 1333-1343. Compounds of formula 7 can be prepared as described for example by Mihara et al, WO 2008/122375.

Scheme 4

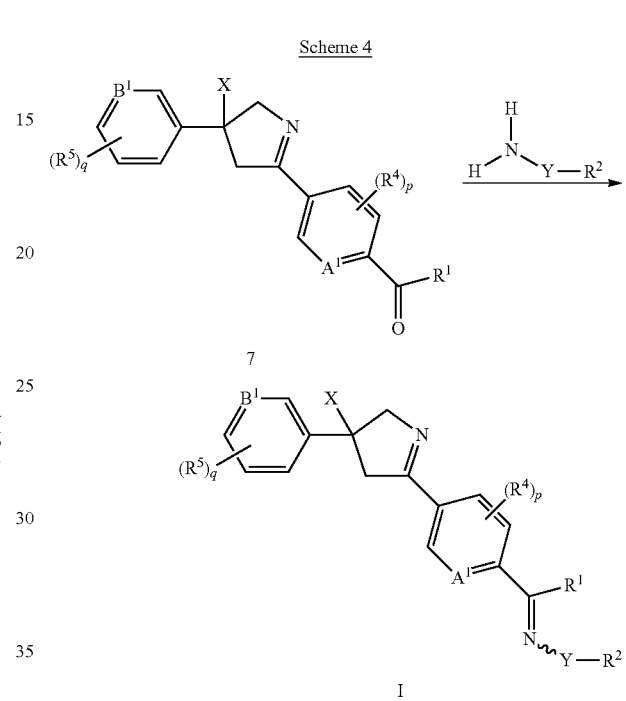

Compounds of formula I can also be prepared as outlined in scheme 5 by reaction of an organo lithium reagent or a Grignard reagent 8 with an electrophile as for example described by Fujisawa et al, Chem. Lett. 1983, 51, 1537-1540 for nitro compounds as electrophile or by Ziegler et al, WO 95/20569 for hydroxamic acid derivatives. Hydrazone compounds of formula I can also be prepared as for example described by Benomar et al, J. Fluorine Chem. 1990, 50, 207-215 (J may be a metal, as for example Li, Na, K or MgX, SnX$_3$; Z may be a leaving group like halogen, OR" or SR")

Scheme 5

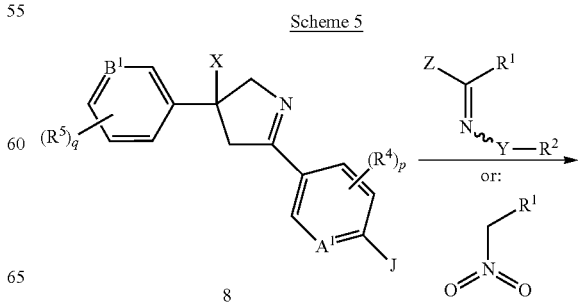

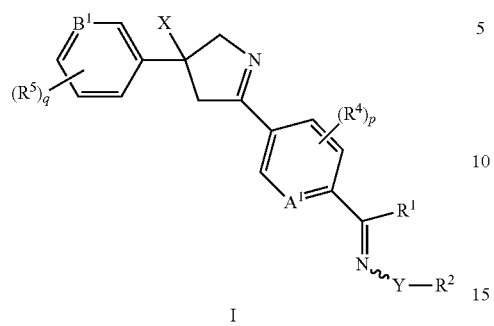

I

Compounds of formula I can also be prepared as outlined in scheme 6 by reaction of a boronic acid 9 with an electrophile (e.g. a hydroxamic acid chloride) as for example described by Dolliver et al, Can. J. Chem. 2007, 85, 913-922. (M is a boronic acid derivative; Z may be a leaving group like halogen, OR" or SR"). Compounds of formula 9 can be prepared as described for example in WO 2005/085216.

Scheme 6

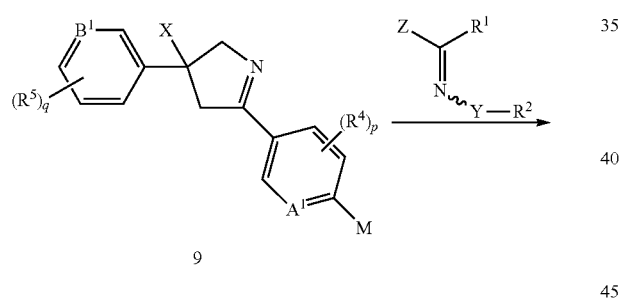

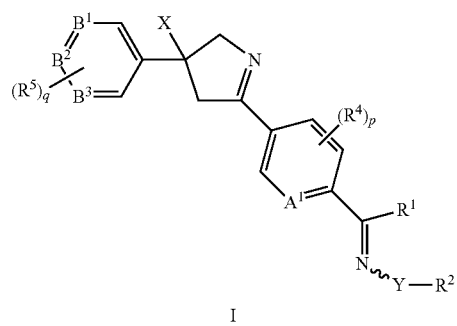

I

Compounds of formula I can also be prepared as outlined in scheme 7 by reaction of an olefin of formula 10 with a nitrite as for example described by Sugamoto et al, Synlett, 1998, 1270-1272.

Scheme 7

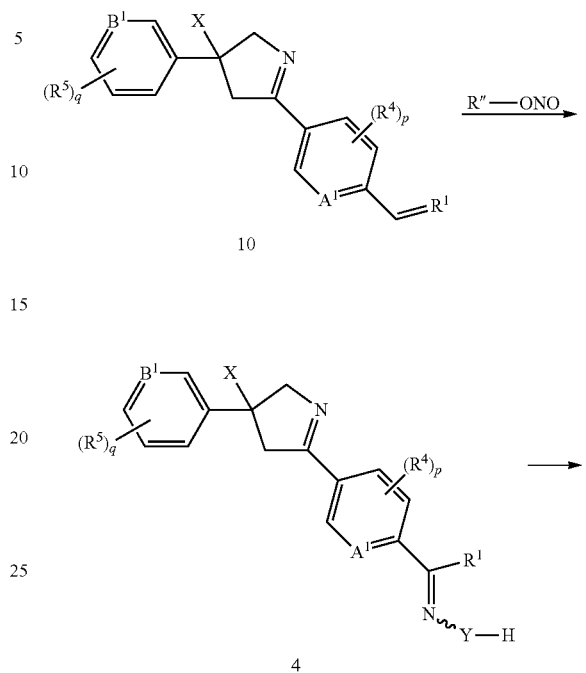

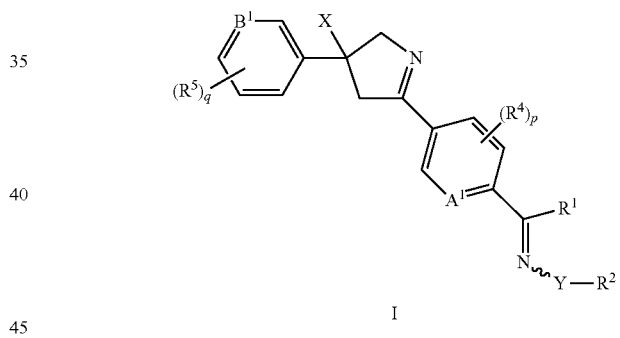

I

Compounds of formula 7 can also be prepared as outlined in scheme 8 by reaction of an organometallic coumpound of formula 11 with a carboxylic acid derivative (Q may be a metal as for example ZnE, MgE, Li, Na, K, SnE$_3$ with E being a leaving group such as halogen, or OR$^{16}$ or S(O)$_n$R$^{16}$ and wherein n is 0-2); as described e.g. in WO 2008/156721 or by Dieter et al, Tetrahedron (2003), 59(7), 1083-1094. Compounds of formula 7 can also be prepared from secondary alcohols of formula 13 by oxidation, as for example described in US 2007265321. Compounds of formula 13 can be prepared by reaction of compounds of formula 11 with an aldehyde, as for example described by Yamagishi et al, Journal of Organic Chemistry (2009), 74(16), 6350-6353.

Scheme 8:

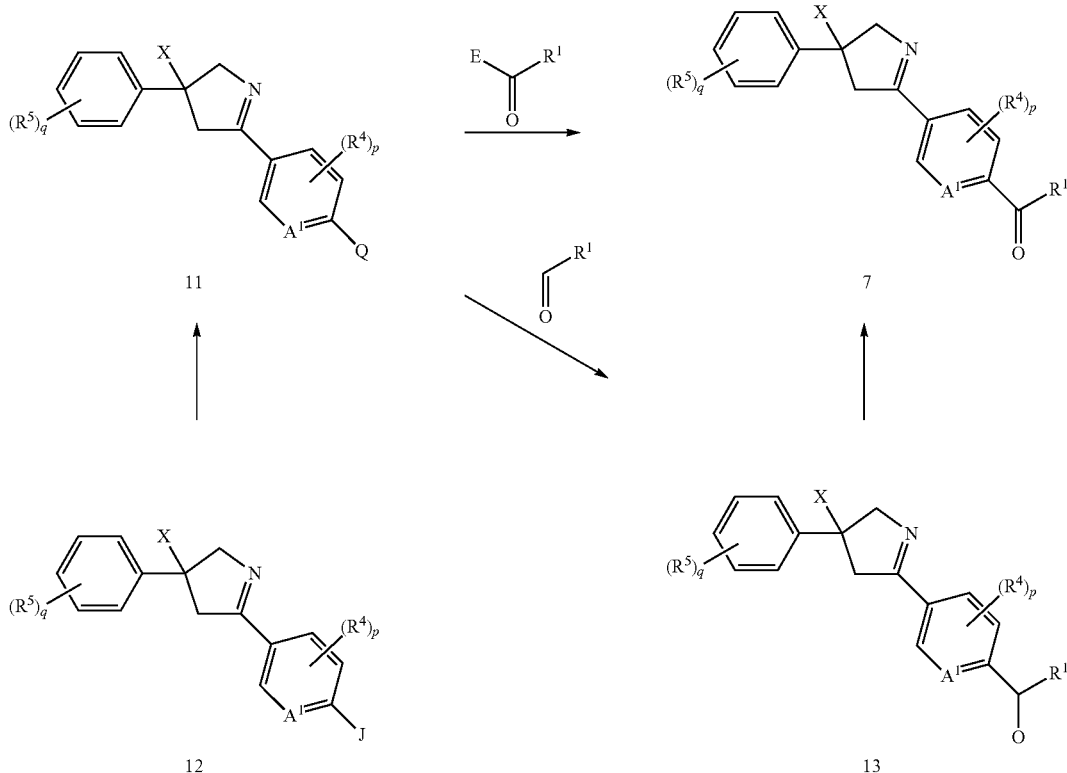

The corresponding metal organyls of formula 11 can be prepared by a halogen-metal exchange reaction of halides of formula 12. The corresponding halides of formula 12 can be prepared as for example described in US 2007066617 or in unpublished PCT/EP2010/055773 (J may be a halogen as for example Cl, Br, I):

Compounds of formula 7 can also be prepared as outlined in scheme 9 by acidic hydrolysis of compounds of formula 14 [Z in this case equals $R^1$], as for example described by Singh et al, European Journal of Organic Chemistry (2008), (32), 5446-5460.

Scheme 9:

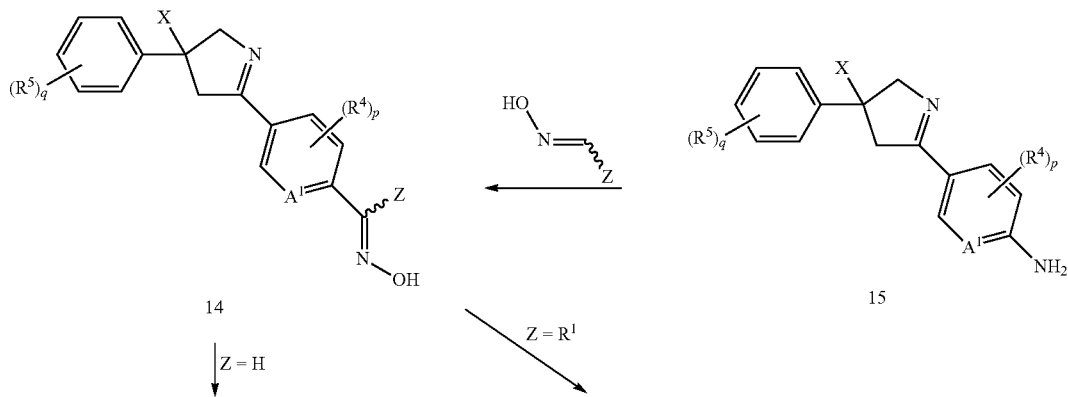

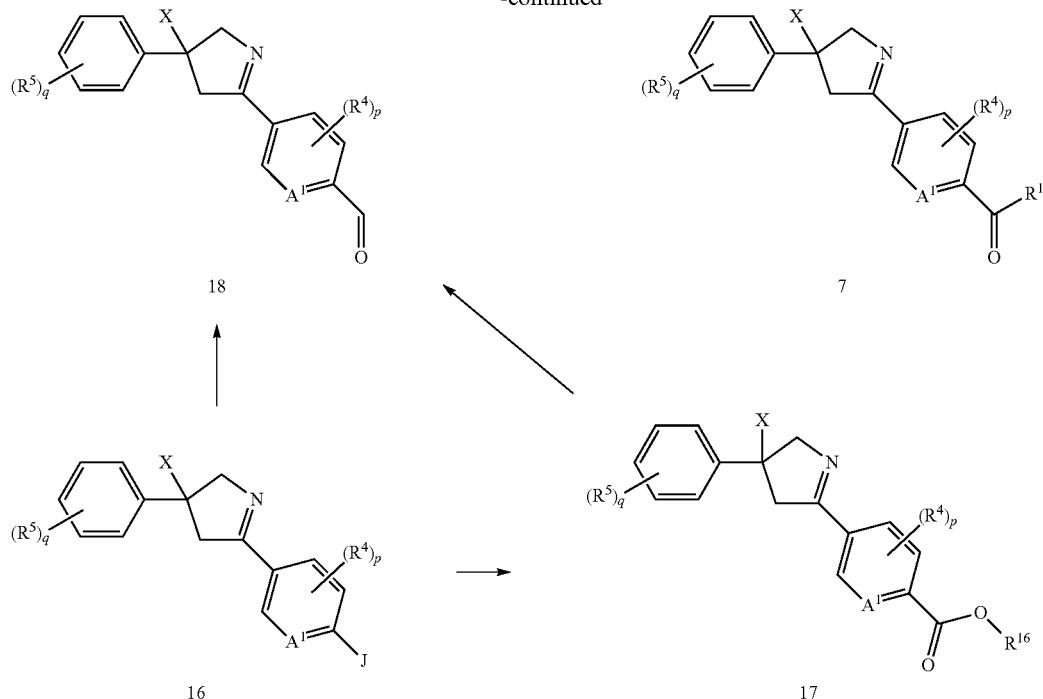

The corresponding aldehydes of formula 18 can be prepared from oximes of formula 14 by acidic hydrolysis (Z in this case equals H), as for example described by Lin et al, Chemistry—A European Journal (2009), 15(10), 2305-2309. Compounds of formula 14 can be prepared by diazotation of an amine of formula 15 and copper catalyzed reaction with a formoxime or a higher substituted oxime, as for example described by Philipp et al, Justus Liebigs Annalen der Chemie (1936), 523, 285-289 or by Woodward et al, Tetrahedron (1958), 2, 1-57 or in WO 2010/072781 or in WO 2010/072602. The corresponding compounds of formula 15 can be prepared according to WO 2007/125984.

Compounds of formula 18 can also be prepared by palladium catalyzed carbonylation of compounds of formula 16, as for example described by Banard et al, Organic Process Research & Development (2008), 12(4), 566-574. Compounds of formula 16 can also be prepared by reduction or a reduction/oxidation sequence of esters of formula 17, as for example described in WO 2007/017468 (reduction) or in WO 2006/128803 (reduction/oxidation sequence). Compounds of formula 17 can be prepared by carbonylation of compounds of formula 16, as for example described in WO 2005/085216.

If individual compounds cannot be prepared via the above-described routes, they can be prepared by derivatization of other compounds I or by customary modifications of the synthesis routes described.

The reaction mixtures are worked up in the customary manner, for example by mixing with water, separating the phases, and, if appropriate, purifying the crude products by chromatography, for example on alumina or silica gel. Some of the intermediates and end products may be obtained in the form of colorless or pale brown viscous oils, which are freed or purified from volatile components under reduced pressure and at moderately elevated temperature. If the intermediates and end products are obtained as solids, they may be purified by recrystallization or digestion.

Compound II is a valuable intermediate in the synthesis of compounds I. Thus the invention also relates to compounds of formula II

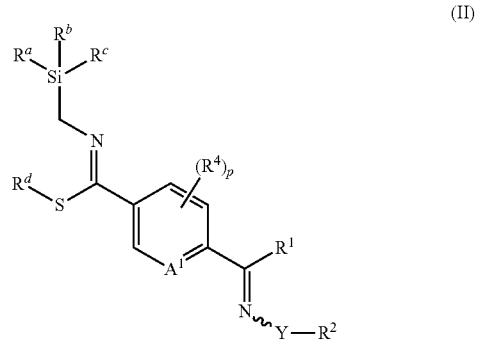

(II)

wherein
$R^a$, $R^b$ and $R^c$, independently of each other, are selected from $C_1$-$C_{12}$-alkyl which may be partially or fully halogenated and/or may be substituted by one or more radicals $R^6$, and phenyl which may be substituted by 1, 2, 3, 4 or 5 radicals $R^{10}$; and
$R^d$ is selected from hydrogen, $C_1$-$C_{12}$-alkyl which may be partially or fully halogenated and/or may be substituted by one or more radicals $R^6$, $C_2$-$C_{12}$-alkenyl which may be partially or fully halogenated and/or may be substituted by one or more radicals $R^6$, $C_2$-$C_{12}$-alkynyl which may be partially or fully halogenated and/or may be substituted by one or more radicals $R^6$, and benzyl where the phenyl moiety may be substituted by 1, 2, 3, 4 or 5 radicals $R^{10}$;
and $A^1$, Y, $R^1$, $R^2$, $R^4$ and p have one of the above-given general or, in particular, one of the above-given preferred meanings;
and the tautomers, stereoisomers and agriculturally or veterinarily acceptable salts thereof.

Tautomers of compounds II can for example occur if $R^d$ is hydrogen. Such a tautomer, which is also a specific embodiment of compound II, can be represented by formula II':

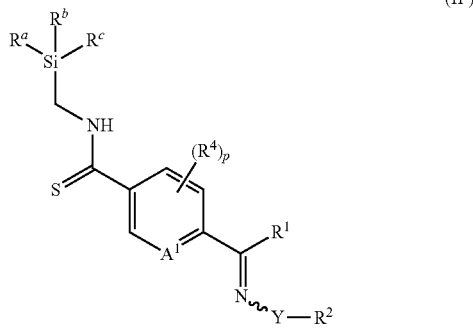

Preferably, in compounds II and II' $R^a$, $R^b$ and $R^c$, independently of each other, are selected from $C_1$-$C_4$-alkyl and are specifically methyl.

Preferably, in compounds II $R^d$ is selected from hydrogen, $C_1$-$C_4$-alkyl and $C_1$-$C_4$-haloalkyl.

Due to their excellent activity, the compounds of formula I may be used for controlling invertebrate pests.

Accordingly, the present invention also provides an agricultural composition comprising at least one compound of the formula I, as defined above, a stereoisomer thereof and/or at least one agriculturally acceptable salt thereof, and at least one inert liquid and/or solid agriculturally acceptable carrier.

The present invention also provides a veterinary composition comprising at least one compound of the formula I, as defined above, a stereoisomer thereof and/or at least one veterinarily acceptable salt thereof, and at least one inert liquid and/or solid veterinarily acceptable carrier.

Such compositions may contain a single active compound of formula I or a salt thereof or a mixture of several active compounds of formula I or their salts according to the present invention. The composition according to the present invention may comprise an individual isomer or mixtures of isomers as well as individual tautomers or mixtures of tautomers.

The present invention further relates to the use of a compound as defined above, of a stereoisomer and/or of an agriculturally or veterinarily acceptable salt thereof for combating invertebrate pests.

The present invention further relates to the use of a compound as defined above, of a stereoisomer and/or of a veterinarily acceptable salt thereof, for treating or protecting an animal from infestation or infection by invertebrate pests.

Moreover the present invention also provides a method for controlling invertebrate pests which method comprises treating the pests, their food supply, their habitat or their breeding ground or a plant, plant propagation material, soil, area, material or environment in which the pests are growing or may grow, or the materials, plants, plant propagation material, soils, surfaces or spaces to be protected from invertebrate pest attack or infestation with a pesticidally effective amount of at least one imine compound of the formula I as defined above, a stereoisomer thereof and/or at least one agriculturally acceptable salt thereof.

Preferably, the method of the invention serves for protecting plants or plant propagation material (such as seed) and the plant which grows therefrom from animal pest attack or infestation and comprises treating the plants or the plant propagation material (such as seed) with a pesticidally effective amount of a compound of the formula I or an agriculturally acceptable salt thereof as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

The invention furthermore relates to plant propagation material (such as seeds), comprising at least one compound of the formula I as defined above, a stereoisomer thereof and/or at least one agriculturally acceptable salt thereof.

The invention also provides a method for treating or protecting an animal from infestation or infection by invertebrate pests which comprises bringing the animal in contact with a pesticidally effective amount of at least one compound of the formula I as defined above, a stereoisomer thereof and/or at least one veterinarily acceptable salt thereof.

The compounds of the formula I and the pesticidical compositions comprising them are effective agents for controlling arthropod pests and nematodes. Invertebrate pests controlled by the compounds of formula I include for example:

insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocol-letis blancardella, Lobesia botrana, Loxostege sticticalis, Lymantria dispar, Lymantria monacha, Lyonetia clerkella, Malacosoma neustria, Mamestra brassicae, Orgyia pseu-dotsugata, Ostrinia nubilalis, Panolis flammea, Pectinophora gossypiella, Peridroma saucia, Phalera bucephala, Phthorimaea operculella, Phyllocnistis citrella, Pieris bras-sicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12 punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus* oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus and Sitophilus granaria;

dipterans (Diptera), for example Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea and Tipula paludosa;

thrips (Thysanoptera), e.g. Dichromothrips corbetti, Frankliniella fusca, Frankliniella occidentalis, Frankliniella tritici, Scirtothrips citri, Thrips oryzae, Thrips palmi and Thrips tabaci;

hymenopterans (Hymenoptera), e.g. Athalia rosae, Atta cephalotes, Atta sexdens, Atta texana, Hoplocampa minuta, Hoplocampa testudinea, Monomorium pharaonis, Solenopsis geminata and Solenopsis invicta;

heteropterans (Heteroptera), e.g. Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis and Thyanta perditor;

homopterans (Homoptera), e.g. Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiiand, and Viteus vitifolii;

termites (Isoptera), e.g. Calotermes flavicollis, Leucotermes flavipes, Reticulitermes flavipes, Reticulitermes lucifugus und Termes natalensis;

orthopterans (Orthoptera), e.g. Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus and Tachycines asynamorus;

Arachnoidea, such as arachnids (Acarina), e.g. of the families Argasidae, Ixodidae and Sarcoptidae, such as Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei, and Eriophyidae spp. such as Aculus schlechtendali, Phyllocoptruta oleivora and Eriophyes sheldoni; Tarsonemidae spp. such as Phytonemus pallidus and Polyphagotarsonemus latus; Tenuipalpidae spp. such as Brevipalpus phoenicis; Tetranychidae spp. such as Tetranychus cinnabarinus, Tetranychus kanzawai, Tetranychus pacificus, Tetranychus telarius and Tetranychus urticae, Panonychus ulmi, Panonychus citri, and oligonychus pratensis;

Siphonatera, e.g. Xenopsylla cheopsis, Ceratophyllus spp;

The compositions and compounds of formula I are useful for the control of nematodes, especially plant parasitic nematodes such as root knot nematodes, Meloidogyne hapla, Meloidogyne incognita, Meloidogyne javanica, and other Meloidogyne species;

cyst-forming nematodes, Globodera rostochiensis and other Globodera species; Heterodera avenae, Heterodera glycines, Heterodera schachtii, Heterodera trifolii, and other Heterodera species; Seed gall nematodes, Anguina species; Stem and foliar nematodes, Aphelenchoides species; Sting nematodes, Belonolaimus longicaudatus and other Belonolaimus species; Pine nematodes, Bursaphelenchus xylophilus and other Bursaphelenchus species; Ring nematodes, Criconema species, Criconemella species, Criconemoides species, Mesocriconema species; Stem and bulb nematodes, Ditylenchus destructor, Ditylenchus dipsaci and other Ditylenchus species; Awl nematodes, Dolichodorus species; Spiral nematodes, Heliocotylenchus multicinctus and other Helicotylenchus species; Sheath and sheathoid nematodes, Hemicycliophora species and Hemicriconemoides species; Hirshmanniella species; Lance nematodes, Hoploaimus species; false rootknot nematodes, Nacobbus species; Needle nematodes, Longidorus elongatus and other Longidorus species; Pin nematodes, Paratylen-chus species; Lesion nematodes, Pratylenchus neglectus, Pratylenchus penetrans, Pratylenchus curvitatus, Pratylenchus goodeyi and other Pratylenchus species; Burrowing nematodes, Radopholus similis and other Radopholus species; Reniform nematodes, Rotylenchus robustus and other Rotylenchus species; Scutellonema species; Stubby root nematodes, Trichodorus primitivus and other Trichodorus species, Paratrichodorus species; Stunt nematodes, Tylenchorhynchus claytoni, Tylenchorhynchus dubius and other Tylenchorhynchus species; Citrus nematodes, Tylenchulus species; Dagger nematodes, Xiphinema species; and other plant parasitic nematode species.

In a preferred embodiment of the invention the compounds of formula I are used for controlling insects or arachnids, in particular insects of the orders Lepidoptera, Coleoptera, Thysanoptera and Homoptera and arachnids of the order Acarina. The compounds of the formula I according to the present invention are particularly useful for controlling insects of the order Thysanoptera and Homoptera.

The compounds of formula I or the pesticidal compositions comprising them may be used to protect growing plants and crops from attack or infestation by invertebrate pests, especially insects, acaridae or arachnids by contacting the plant/crop with a pesticidally effective amount of compounds of formula I. The term "crop" refers both to growing and harvested crops.

The compounds of formula I can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (N-methylpyrrolidone [NMP], N-octylpyrrolidone [NOP]), acetates (glycol diacetate), glycols, fatty acid dimethylamides, fatty acids and fatty acid esters. In principle, solvent mixtures may also be used.

Suitable emulsifiers are non-ionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

A suitable preservative is e.g. dichlorophen.

Seed treatment formulations may additionally comprise binders and optionally colorants.

Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybute-nes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®).

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound(s). In this case, the active compound(s) are employed in a purity of from 90% to 100% by weight, preferably 95% to 100% by weight (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compounds of formula I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compound(s) according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier.

However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The active compound(s) may also be used successfully in the ultra-low-volume process (ULV), it being possible to apply formulations comprising over 95% by weight of active compound, or even to apply the active compound without additives.

The following are examples of formulations:
1. Products for dilution with water for foliar applications. For seed treatment purposes, such products may be applied to the seed diluted or undiluted.

A) Water-soluble Concentrates (SL, LS)

10 parts by weight of the active compound(s) are dissolved in 90 parts by weight of water or a water-soluble solvent. As an alternative, wetters or other auxiliaries are added. The active compound(s) dissolves upon dilution with water, whereby a formulation with 10% (w/w) of active compound(s) is obtained.

B) Dispersible Concentrates (DC)

20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable Concentrates (EC)

15 parts by weight of the active compound(s) are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetters and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-dispersible Granules and Water-soluble Granules (WG, SG)

50 parts by weight of the active compound(s) are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-dispersible Powders and Water-soluble Powders (WP, SP, SS, WS)

75 parts by weight of the active compound(s) are ground in a rotor-stator mill with addition of 25 parts by weight of dispersants, wetters and silica gel. Dilution with water gives a stable dispersion or solution of the active compound(s), whereby a formulation with 75% (w/w) of active compound(s) is obtained.

H) Gel-Formulation (GF)

In an agitated ball mill, 20 parts by weight of the active compound(s) are comminuted with addition of 10 parts by weight of dispersants, 1 part by weight of a gelling agent wetters and 70 parts by weight of water or of an organic solvent to give a fine active compound(s) suspension. Dilution with water gives a stable suspension of the active compound(s), whereby a formulation with 20% (w/w) of active compound(s) is obtained.

2. Products to be applied undiluted for foliar applications. For seed treatment purposes, such products may be applied to the seed diluted or undiluted.

I) Dustable Powders (DP, DS)

5 parts by weight of the active compound(s) are ground finely and mixed intimately with 95 parts by weight of finely divided kaolin. This gives a dustable product having 5% (w/w) of active compound(s)

J) Granules (GR, FG, GG, MG)

0.5 parts by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

K) ULV Solutions (UL)

10 parts by weight of the active compound(s) are dissolved in 90 parts by weight of an organic solvent, for example xylene. This gives a product having 10% (w/w) of active compound(s), which is applied undiluted for foliar use.

The compounds of formula I are also suitable for the treatment of plant propagation materials (such as seed). Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having preger-minated the latter In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Other preferred FS formulations of compounds of formula I for seed treatment comprise from 0.5 to 80 wt % of the active ingredient, from 0.05 to 5 wt % of a wetter, from 0.5 to 15 wt % of a dispersing agent, from 0.1 to 5 wt % of a thickener, from 5 to 20 wt % of an anti-freeze agent, from 0.1 to 2 wt % of an anti-foam agent, from 1 to 20 wt % of a pigment and/or a dye, from 0 to 15 wt % of a sticker/adhesion agent, from 0 to 75 wt % of a filler/vehicle, and from 0.01 to 1 wt % of a preservative.

Various types of oils, wetters, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds of formula I are effective through both contact (via soil, glass, wall, bed net, carpet, plant parts or animal parts), and ingestion (bait, or plant part).

For use against ants, termites, wasps, flies, mosquitos, crickets, or cockroaches, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formula I as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylfomaamide, N methylpyrrolidone, dimethyl sulphoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

The compounds of formula I and their respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and their respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for exam-pie are N,N-diethyl-meta-toluamide (DEET), N,N-diethylphenylacetamide (DEPA), 1-(3-cyclohexan-1-yl-carbonyl)-2-methylpiperine, (2-hydroxymethyl-cyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like Eucalyptus maculata, Vitex rotundifolia, Cymbopogan martinii, Cymbopogan citratus (lemon grass), Cymopogan nartdus (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and diethylenically unsaturated hydrocarbons, such as styrene, and aliphatic diens, such as butadiene.

The impregnation of curtains and bednets is done in general by dipping the textile material into emulsions or dispersions of the active compounds of formula I or spraying them onto the nets.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of formula I into contact with each other, and "seed dressing" to methods of seed treatment which provide the seeds with an amount of the compounds of formula I, i.e. which generate a seed comprising the compound of formula I. In principle, the treatment can be applied to the seed at any time from the harvest of the seed to the sowing of the seed. The seed can be treated immediately before, or during, the planting of the seed, for example using the "planter's box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previous dilution with water, until the composition is distributed uniformly on the seed. If appropriate, this is followed by a drying step.

The compounds of formula I or veterinarily acceptable salts thereof are in particular also suitable for being used for combating parasites in and on animals.

A further object of the present invention is therefore to provide new methods for controlling parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formula I or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formula I or veterinarily ac-ceptable salts thereof or a composition comprising it.

The present invention also provides a non-therapeutic method for treating, controlling, preventing and protecting animals against infestation and infection by parasites, which comprises applying to a locus a parasiticidally effective amount of a compound of formula I or the enantiomers or veterinarily acceptable salts thereof or a composition comprising it.

The invention also provides a process for the preparation of a composition for treating, controlling, preventing or protecting animals against infestation or infection by parasites which comprises including a parasiticidally effective amount of a compound of formula I or the veterinarily acceptable salts thereof or a composition comprising it.

The invention relates further to the use of compounds of formula I for treating, controlling, preventing or protecting animals against infestation or infection by parasites.

The invention relates also to the use of a compound of formula I, or a composition comprising it, for the manufacture of a medicament for the therapeutic treatment of animals against infections or infestations by parasites.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly, it has been found that compounds of formula I are suitable for com-bating endo- and ectoparasites in and on animals.

Compounds of formula I or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I or veterinarily acceptable salts thereof and compositions comprising them are suitable for systemic and/or non-systemic control of ecto- and/or endoparasites. They are active against all or some stages of development.

The compounds of formula I are especially useful for combating ectoparasites.

The compounds of formula I are especially useful for combating endoparasites.

The compounds of formula I are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus,* cockroaches (Blattaria—Blattodea), e.g. *Blattella germanica, Blattella asahinae, Periplaneta americana, Periplaneta japonica, Periplaneta brunnea, Periplaneta fulligginosa, Periplaneta australasiae*, and *Blatta orientalis,* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola*, and *Tabanus similis,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.* ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae,* actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, bugs (Heteropterida): *Cimex lectularius, Cimex hemipterus, Reduvius senilis, Triatoma* spp., *Rhodnius* ssp., *Panstrongylus* ssp. and *Arilus critatus,*
Anoplurida, e.g. *Haematopinus* spp., *Linognathus* spp., *Pediculus* spp., *Phtirus* spp., and *Solenopotes* spp,
Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp,
Roundworms Nematoda:
Wipeworms and Trichinosis (Trichosyringida), e.g. Trichinellidae (*Trichinella* spp.), (Trichuridae) *Trichuris* spp., *Capillaria* spp,
Rhabditida, e.g. *Rhabditis* spp, *Strongyloides* spp., *Helicephalobus* spp,
Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stepha-nurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus,* and *Dioctophyma renale,*
Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*
Camallanida, e.g. *Dracunculus medinensis* (guinea worm)
Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi,* and *Habronema* spp.,
Thorny headed worms (Acanthocephala), e.g. *Acanthocephalus* spp., *Macracanthorhynchus hirudinaceus* and *Oncicola* spp,
Planarians (Plathelminthes):
Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp,
Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula I and compositions containing them are particularly useful for the control of pests from the orders Diptera, Siphonaptera and Ixodida.

Moreover, the use of compounds of formula I and compositions containing them for combating mosquitoes is especially preferred.

The use of the compounds of formula I and compositions containing them for combating flies is a further preferred embodiment of the present invention.

Furthermore, the use of the compounds of formula I and compositions containing them for combating fleas is especially preferred.

The use of the compounds of formula I and of the compositions containing them for combating ticks is a further preferred embodiment of the present invention.

The compounds of formula I also are especially useful for combating endoparasites (roundworms nematoda, thorny headed worms and planarians).

The compounds of formula I can be effective through both contact (via soil, glass, wall, bed net, carpet, blankets or animal parts) and ingestion (e.g. baits).

The present invention relates to the therapeutic and the non-therapeutic use of compounds of formula I for controlling and/or combating parasites in and/or on animals.

The compounds of formula I may be used to protect the animals from attack or infestation by parasites by contacting them with a parasitically effective amount of compounds of formula I. As such, "contacting" includes both direct contact (applying the compounds/compositions directly on the parasite, e.g. also at it's locus, and optionally also administrating the compounds/composition directly on the animal) and indirect contact (applying the compounds/compositions to the locus of the parasite).

The contact of the parasite through application to its locus is an example of a non-therapeutic use of compounds of formula I.

"Locus" as defined above means the habitat, food supply, breeding ground, area, material or environment in which a parasite is growing or may grow outside of the animal. The compounds of the invention can also be applied preventively to places at which occurrence of the pests or parasites is expected.

Administration to the animal can be carried out both prophylactically and therapeutically.

Administration of the active compounds is carried out directly or in the form of suitable preparations, orally, topically/dermally or parenterally.

For oral administration to warm-blooded animals, the compounds of formula I may be formulated as animal feeds, animal feed premixes, animal feed concentrates, pills, solutions, pastes, suspensions, drenches, gels, tablets, boluses and capsules. In addition, the compounds of formulae I may be administered to the animals in their drinking water. For oral administration, the dosage form chosen should provide the animal with 0.01 mg/kg to 100 mg/kg of animal body weight per day of the compounds of formula I, preferably with 0.5 mg/kg to 100 mg/kg of animal body weight per day.

Alternatively, the compounds of formula I may be administered to animals parenterally, for example, by intraluminal, intramuscular, intravenous or subcutaneous injection. The compounds of formula I may be dispersed or dissolved in a physiologically acceptable carrier for subcutaneous injection. Alternatively, the compounds of formula I may be formulated into an implant for subcutaneous administration. In addition the compounds of formula I may be transdermally administered to animals. For parenteral administration, the dosage form chosen should provide the animal with 0.01 mg/kg to 100 mg/kg of animal body weight per day of the compounds of formula I.

The compounds of formula I may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the compounds of formula I. In addition, the compounds of formula I may be formulated as ear tags for animals, particularly quadrupeds such as cattle and sheep.

Suitable Preparations are:
Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methylpyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointmentlike consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents are water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N methylpyrrolidone, 2-pyrrolidone, 2,2-dimethyl-4-oxy-methylene-1,3-diox-olane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable Hydrophobic Phases (Oils) are:

liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable Emulsifiers are:

non-ionic surfactants, e.g. polyethoxylated castor oil, polyethoxylated sorbitan monooleate, sorbitan monostearate, glycerol monostearate, polyoxyethyl stearate, alkylphenol polyglycol ether;

ampholytic surfactants such as di-sodium N-lauryl-p-iminodipropionate or lecithin; anionic surfactants, such as sodium lauryl sulfate, fatty alcohol ether sulfates, mono/ dialkyl polyglycol ether orthophosphoric acid ester monoethanolamine salt; cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compounds of formula I.

Generally, it is favorable to apply the compounds of formula I in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formula I are applied dermally/topically.

In a further preferred embodiment, the topical application is conducted in the form of compound-containing shaped articles such as collars, medallions, ear tags, bands for fixing at body parts, and adhesive strips and foils.

Generally, it is favorable to apply solid formulations which release compounds of formula I in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

Compositions to be used according to this invention may also contain other active ingredients, for example other pesticides, insecticides, herbicides, fungicides, other pesticides, or bactericides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

These agents can be admixed with the agents used according to the invention in a weight ratio of 1:10 to 10:1. Mixing the compounds of formula I or the compositions comprising them in the use form as pesticides with other pesticides frequently results in a broader pesticidal spectrum of action.

The following list M of pesticides together with which the compounds according to the invention can be used and with which potential synergistic effects might be produced, is intended to illustrate the possible combinations, but not to impose any limitation:

M.1. Organo(thio)phosphate compounds: acephate, azamethiphos, azinphos-ethyl, azinphos-methyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamate compounds: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroid compounds: acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zetacypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, trans-fluthrin;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022.

M.6. GABA gated chloride channel antagonist compounds: chlordane, endosulfan, gamma-HCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonsits: amitraz;

M.21. Ryanodine receptor modulators: flubendiamide and the phtalamid compound (R)- , (S)-3-Chlor-N-1-{2-methyl-4-[1,2,2,2-tetrafluor-1-(trifluormethyl)ethyl]phenyl}-N2-(1-methyl-2-methylsulfonylethyl)phthalamid (M21.1)

M.22. Isoxazoline compounds: 4-[5-(3,5-Dichloro-phenyl)-5-trifluoromethyl-4,5-dihydroisoxazol-3-yl]-2-methyl-N-pyridin-2-ylmethyl-benzamide (M22.1), 4-[5-(3,5-Dichloro-phenyl)-5-trifluoromethyl-4,5-dihydro-isoxazol-3-yl]-2-methyl-N-(2,2,2-trifluoro-ethyl)-benzamide (M22.2), 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide (M22.3), 4-[5-(3,5-Dichloro-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.4) 4-[5-(3,5-Dichlorophenyl)-5-trifluoromethyl-4,5-dihydro-isoxazol-3-yl]-N-[(methoxyimino)methyl]-2-methyl-benzamide (M22.5), 4-[5-(3-Chloro-5-trifluoromethylphenyl)-5-trifluoromethyl-4,5-dihydro-isoxazol-3-yl]-2-methyl-N-[(2,2,2-trifluoroethylcarbamoyl)-methyl]-benzamide (M22.6), 4-[5-(3-Chloro-5-trifluoromethyl-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.7) and 5-[5-(3,5-Dichloro-4-fluorophenyl)-5-trifluoromethyl-4,5-dihydro-isoxazol-3-yl]-2-[1,2,4]triazol-1-yl-benzonitrile (M22.8);

M.23. Anthranilamide compounds: chloranthraniliprole, cyantraniliprole, 5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M23.1), 5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M23.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide (M23.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M23.4), 5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M23.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M23.6), N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester (M23.7), N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester (M23.8), N'-(2-{[5-Bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (M23.9), N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester (M23.10), N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester (M23.11) and N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M23.12);

M.24. Malononitrile compounds: 2-(2,2,3,3,4,4,5,5-octafluoropentyl)-2-(3,3,3-trifluoropropyl)malononitrile ($CF_2H-CF_2-CF_2-CF_2-CH_2-C(CN)_2-CH_2-CH_2-CF_3$) (M24.1) and 2-(2,2,3,3,4,4,5,5-octafluoropentyl)-2-(3,3,4,4,4-pentafluorobutyl)-malonodinitrile (CF$_2$H—CF$_2$—CF$_2$—CF$_2$—CH$_2$—C(CN)$_2$—CH$_2$—CH$_2$—CF$_2$—CF$_3$) (M24.2);

M.25. Microbial disruptors: *Bacillus thuringiensis* subsp. *Israelensis*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

M.26. Aminofuranone compounds: 4-{[(6-Bromopyrid-3-yl)methyl](2-fluoroethyl)amino}furan-2(5H)-on (M26.1), 4-{[(6-Fluoropyrid-3-yl)methyl](2,2-difluoroethyl)amino}furan-2(5H)-on (M26.2), 4-{[(2-Chloro-1,3-thiazolo-5-yl)methyl](2-fluoroethyl)amino}furan-2(5H)-on (M26.3), 4-{[(6-Chloropyrid-3-yl)methyl](2-fluoroethyl)amino}furan-2(5H)-on (M26.4), 4-{[(6-Chloropyrid-3-yl)methyl](2,2-difluoroethyl)amino}furan-2(5H)-on (M26.5), 4-{[(6-Chloro-5-fluoropyrid-3-yl)methyl](methyl)amino}furan-2(5H)-on (M26.6), 4-{[(5,6-Dichloropyrid-3-yl)methyl](2-fluoroethyl)amino}furan-2(5H)-on (M26.7), 4-{[(6-Chloro-5-fluoropyrid-3-yl)methyl](cyclopropyl)amino}furan-2(5H)-on (M26.8), 4-{[(6-Chloropyrid-3-yl)methyl](cyclopropyl)amino}furan-2(5H)-on (M26.9) and 4-{[(6-Chloropyrid-3-yl)methyl](methyl)amino}furan-2(5H)-on (M26.10);

M.27. Various compounds: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, N—R'-2,2-dihalo-1-R"cyclopropanecarboxamide-2-(2,6-dichloro-α,α,α-trifluoro-p-tolyl) hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, 4-But-2-ynyloxy-6-(3,5-dimethyl-piperidin-1-yl)-2-fluoro-pyrimidine (M27.1), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-[2-hydroxy-4,6a,12b-trimethyl-11-oxo-9-(3-pyridinyl)-2H,11H-naphtho[2,1-b]pyrano[3,4-e]pyran-3,6-diyl]ester (M27.2) and 8-(2-Cyclopropylmethoxy-4-trifluoromethyl-phenoxy)-3-(6-trifluoromethyl-pyridazin-3-yl)-3-aza-bicyclo[3.2.1]octane (M27.3).

The commercially available compounds of the group M may be found in The Pesticide Manual, 13th Edition, British Crop Protection Council (2003) among other publications.

Paraoxon and their preparation have been described in Farm Chemicals Handbook, Volume 88, Meister Publishing Company, 2001. Flupyrazofos has been described in Pesticide Science 54, 1988, p. 237-243 and in U.S. Pat. No. 4,822,779. AKD 1022 and its preparation have been described in U.S. Pat. No. 6,300,348. The anthranilamides M23.1 to M23.6 have been described in WO 2008/72743 and WO 200872783, those M23.7 to M23.12 in WO2007/043677. The phthalamide M 21.1 is known from WO 2007/101540. The alkynylether compound M27.1 is described e.g. in JP 2006131529. Organic sulfur compounds have been described in WO 2007060839. The isoxazoline compounds M 22.1 to M 22.8 have been described in e.g. WO2005/085216, WO 2007/079162, WO 2007/026965, WO 2009/126668 and WO2009/051956. The aminofuranone compounds M 26.1 to M 26.10 have been described eg. in WO 2007/115644. The pyripyropene derivative M 27.2 has been described in WO 2008/66153 and WO 2008/108491. The pyridazin compound M 27.3 has been described in JP 2008/115155. Malononitrile compounds as those (M24.1) and (M24.2) have been described in WO 02/089579, WO 02/090320, WO 02/090321, WO 04/006677, WO 05/068423, WO 05/068432 and WO 05/063694.

The following list F of fungicides together with which the compounds according to the invention can be used and with which potential synergistic effects might be produced, is intended to illustrate the possible combinations, but not to impose any limitation:

F.I) Respiration Inhibitors

F.I-1) Inhibitors of complex III at Qo site (e.g. strobilurins) strobilurins: azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, 2-[2-(2,5-dimethylphenoxymethyl)-phenyl]-3-methoxy-acrylic acid methyl ester and 2 (2-(3-(2,6-dichlorophenyl)-1-methyl-allylideneaminooxymethyl)-phenyl)-2-methoxyimino-N methylacetamide; oxazolidinediones and imidazolinones: famoxadone, fenamidone;

F.I-2) Inhibitors of complex II (e.g. carboxamides): carboxanilides: benodanil, bixafen, boscalid, carboxin, fenfuram, fenhexamid, fluopyram, flutolanil, furametpyr, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3',4',5' trifluorobiphenyl-2-yl)-3-difluoromethyl-1-methyl-1H-pyrazole-4-carboxamide, N-(4'-trifluoromethylthiobiphenyl-2-yl)-3 difluoromethyl-1-methyl-1H pyrazole-4-carboxamide and N-(2-(1,3,3-trimethyl-butyl)-phenyl)-1,3-dimethyl-5 fluoro-1H-pyrazole-4 carboxamide;

F.I-3) Inhibitors of Complex III at Qi Site: Cyazofamid, Amisulbrom;

F.I-4) Other respiration inhibitors (complex I, uncouplers) diflumetorim; tecnazen; ferimzone; ametoctradin; silthiofam; nitrophenyl derivates: binapacryl, dinobuton, dinocap, fluazinam, nitrthal-isopropyl, organometal compounds: fentin salts, such as fentin-acetate, fentin chloride or fentin hydroxide;

F.II) Sterol Biosynthesis Inhibitors (SBI Fungicides)

F.II-1) C14 demethylase inhibitors (DMI fungicides, e.g. triazoles, imidazoles) triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole; imidazoles: imazalil, pefurazoate, oxpoconazole, prochloraz, triflumizole; pyrimidines, pyridines and piperazines: fenarimol, nuarimol, pyrifenox, triforine;

F.II-2) Delta14-reductase inhitors (Amines, e.g. morpholines, piperidines) morpholines: aldimorph, dodemorph, dodemorph-acetate, fenpropimorph, tridemorph; piperidines: fenpropidin, piperalin; spiroketalamines: spiroxamine;

F.II-3) Inhibitors of 3-keto reductase: hydroxyanilides: fenhexamid;

F.III) Nucleic Acid Synthesis Inhibitors

F.III-1) RNA, DNA synthesis phenylamides or acyl amino acid fungicides: benalaxyl, benalaxyl-M, kiralaxyl, metalaxyl, metalaxyl-M (mefenoxam), ofurace, oxadixyl; isoxazoles and isoothiazolones: hymexazole, octhilinone;

F.III-2) DNA topisomerase inhibitors: oxolinic acid;

F.III-3) Nucleotide metabolism (e.g. adenosin-deaminase) hydroxy(2-amino)-pyrimidines: bupirimate;

F.IV) Inhibitors of Cell Division and or Cytoskeleton

F.IV-1) Tubulin inhibitors: benzimidazoles and thiophanates: benomyl, carbendazim, fuberidazole, thiabendazole, thiophanate-methyl; triazolopyrimidines: 5-chloro-7 (4-methylpiperidin-1-yl)-6-(2,4,6-trifluorophenyl)-[1,2,4]triazolo[1,5a]pyrimidine F.IV-2) other cell division inhibitors benzamides and phenyl acetamides: diethofencarb, ethaboxam, pencycuron, fluopicolide, zoxamide;

F.IV-3) Actin inhibitors: benzophenones: metrafenone;

F.V) Inhibitors of Amino Acid and Protein Synthesis

F.V-1) Mmethionine synthesis inhibitors (anilino-pyrimidines)

anilino-pyrimidines: cyprodinil, mepanipyrim, nitrapyrin, pyrimethanil;

F.V-2) Protein Synthesis Inhibitors (Anilino-Pyrimidines) antibiotics: blasticidin-S, kasugamycin, kasugamycin hydrochloride-hydrate, mildiomycin, streptomycin, oxytetracyclin, polyoxine, validamycin A;

F.VI) Signal Transduction Inhibitors

F.VI-1) MAP/Histidine kinase inhibitors (e.g. anilino-pyrimidines) dicarboximides: fluoroimid, iprodione, procymidone, vinclozolin; phenylpyrroles: fenpiclonil, fludioxonil;

F.VI-2) G protein inhibitors: quinolines: quinoxyfen;

F.VII) Lipid and Membrane Synthesis Inhibitors

F.VII-1) Phospholipid biosynthesis inhibitors organophosphorus compounds: edifenphos, iprobenfos, pyrazophos; dithiolanes: isoprothiolane;

F.VII-2) Lipid peroxidation aromatic hydrocarbons: dicloran, quintozene, tecnazene, tolclofos-methyl, biphenyl, chloroneb, etridiazole;

F.VII-3) Carboxyl acid amides (CAA fungicides) cinnamic or mandelic acid amides: dimethomorph, flumorph, mandiproamid, pyrimorph; valinamide carbamates: benthiavalicarb, iprovalicarb, pyribencarb, valifenalate and N-(1-(1-(4-cyano-phenyl)ethanesulfonyl)-but-2-yl) carbamic acid-(4-fluorophenyl)ester;

F.VII-4) Compounds affecting cell membrane permeability and fatty acides carbamates: propamocarb, propamocarb-hydrochlorid F.VIII) Inhibitors with Multi Site Action F.VIII-1) Inorganic active substances: Bordeaux mixture, copper acetate, copper hydroxide, copper oxychloride, basic copper sulfate, sulfur;

F.VIII-2) Thio- and dithiocarbamates: ferbam, mancozeb, maneb, metam, methasulphocarb, metiram, propineb, thiram, zineb, ziram;

F.VIII-3) Organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;

F.VIII-4) Guanidines: guanidine, dodine, dodine free base, guazatine, guazatineacetate, iminoctadine, iminoctadine-triacetate, iminoctadine-tris(albesilate);

F.VIII-5) Ahtraquinones: dithianon;

F.IX) Cell Wall Synthesis Inhibitors

F.IX-1) Inhibitors of glucan synthesis: validamycin, polyoxin B;

F.IX-2) Melanin synthesis inhibitors: pyroquilon, tricyclazole, carpropamide, dicyclomet, fenoxanil;

F.X) Plant Defence Inducers

F.X-1) Salicylic acid pathway: acibenzolar-5-methyl;

F.X-2) Others: probenazole, isotianil, tiadinil, prohexadione-calcium; phosphonates: fosetyl, fosetyl-aluminum, phosphorous acid and its salts;

F.XI) Unknown Mode of Action:

bronopol, chinomethionat, cyflufenamid, cymoxanil, dazomet, debacarb, diclomezine, difenzoquat, difenzoquat-methylsulfate, diphenylamin, flumetover, flusulfamide, flutianil, methasulfocarb, oxin-copper, proquinazid, tebufloquin, tecloftalam, triazoxide, 2-butoxy-6-iodo-3-propylchromen-4-one, N-(cyclopropylmethoxyimino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N' (4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2 methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-chloro-phenyl)-2,3-dimethylisoxazolidin-3-yl]-pyridine (pyrisoxazole), 3-[5-(4-methyl-phenyl)-2,3-dimethylisoxazolidin-3-yl]-pyridine, 5-amino-2-isopropyl-3-oxo-4-ortho-tolyl-2,3-dihydropyrazole-1 carbothioic acid S-allyl ester, N-(6-methoxy-pyridin-3-yl)cyclopropanecarboxylic acid amide, 5-chloro-1 (4,6-dimethoxy-pyrimidin-2-yl)-2-methyl-1Hbenzoimidazole, 2-(4-chloro-phenyl)-N-[4-(3,4-dimethoxy-phenyl)-isoxazol-5-yl]-2-prop-2-ynyloxy-acetamide;

F.XII) Growth Regulators:

abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6 benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole;

F.XIII) Biological Control Agents antifungal biocontrol agents: *Bacillus* substilis strain with NRRL No. B-21661 (e.g. RHAPSODY®, SERENADE® MAX and SERENADE® ASO from AgraQuest, Inc., USA), *Bacillus pumilus* strain with NRRL No. B-30087 (e.g. SONATA® and BALLAD® Plus from AgraQuest, Inc., USA), Ulocladium oudemansii (e.g. the product BOTRYZEN from BotriZen Ltd., New Zealand), Chitosan (e.g. ARMOUR-ZEN from BotriZen Ltd., New Zealand).

The invertebrate pest, i.e. arthropodes and nematodes, the plant, soil or water in which the plant is growing can be contacted with the present compound(s) of formula I or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

Moreover, invertebrate pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

"Locus" means a habitat, breeding ground, cultivated plants, plant propagation material (such as seed), soil, area, material or environ-ment in which a pest or parasite is growing or may grow.

In general "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formula I and their compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of are applied not only to the surrounding soil surface or into the under-floor soil in order to protect wooden materials but it can also be applied to lumbered articles such as surfaces of the under-floor concrete, alcove posts, beams, plywood, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of formula I can also be applied preventively to places at which occurrence of the pests is expected.

The compounds of formula I may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95% by weight, preferably from 0.1 to 45% by weight, and more preferably from 1 to 25% by weight of at least one repellent and/or insecticide.

For use in bait compositions, the typical content of active ingredient is from 0.001% by weight to 15% by weight, desirably from 0.001% by weight to 5% by weight of active compound.

For use in spray compositions, the content of active ingredient is from 0.001 to 80% by weight, preferably from 0.01 to 50% by weight and most preferably from 0.01 to 15% by weight.

For use in treating crop plants, the rate of application of the active ingredients of this invention may be in the range of 0.1 g to 4000 g per hectare, desirably from 25 g to 600 g per hectare, more desirably from 50 g to 500 g per hectare.

In the treatment of seed, the application rates of the active ingredients are generally from 0.1 g to 10 kg per 100 kg of seed, preferably from 1 g to 5 kg per 100 kg of seed, in particular from 1 g to 200 g per 100 kg of seed.

The present invention is now illustrated in further detail by the following examples.

I. PREPARATION EXAMPLES

Compounds were characterized e.g. by coupled High Performance Liquid Chromatography/mass spectrometry (HPLC/MS), by $^1$H-NMR and/or by their melting points.

Analytical HPLC column: RP-18 column Chromolith Speed ROD from Merck KgaA, Germany). Elution: acetonitrile+0.1% trifluoroacetic acid (TFA)/water+0.1% trifluoroacetic acid (TFA) in a ratio of from 5:95 to 95:5 in 5 minutes at 40° C.

$^1$H-NMR, respectively $^{13}$C-NMR: The signals are characterized by chemical shift (ppm) vs. tetramethylsilane, respectively CDCl$_3$ for $^{13}$C-NMR, by their multiplicity and by their integral (relative number of hydrogen atoms given). The following abbreviations are used to characterize the multiplicity of the signals: m=multiplett, q=quartett, t=triplett, d=doublet and s=singulett.

S. Syntheses

S.1 Synthesis of 4-[4-(3,5-dichloro-phenyl)-4-trifluoromethyl-4,5-dihydro-3H-pyrrol-2-yl]-2-methyl-benzaldehyde-ethylsemicarbazone (Compound 1.1 of table C.1)

Step 1: Synthesis of 4-bromo-3-methyl-N-trimethylsilanylmethyl-benzamide

To a suspension of 4-bromo-3-methylbenzoic acid (25.00 g, 116.3 mmol) in CH$_2$Cl$_2$ (300 mL) was added N,N-dimethyl aminopyridine (2.13 g, 17.4 mmol), followed by N-ethyl-N-dimethylamine propylcarbodiimide hydrochloride (22.39 g) in small portions. After 30 min at room temperature, amonimethyl trimethylsilane (12.2 g, 8.62 mL, 118 mmol) was added while maintaining the temperature at 20° C. After stirring over night, water was added and the organic layer was separated. The aqueous layer was extracted twice with CH$_2$Cl$_2$ and the combined organic phases were dried and evaporated in vacuum. The residue was purified by flash chromatography on silica gel to give the title compound (32.75 g, 94%).

Characterization by $^1$H-NMR (400 MHz, CDCl$_3$):

δ [delta]=0.15 (s, 9H), 2.45 (s, 3H), 2.97 (m, 2H), 6.17 (br. s, 1H), 7.39 (m, 1H), 7.59 (m, 1H), 7.63 (m, 1H) ppm.

Step 2: Synthesis of 4-bromo-3-methyl-N-trimethylsilanylmethyl-thiobenzamide

To a suspension of 4-bromo-3-methyl-N-trimethylsilanylmethyl-benzamide (32.75 g, 109.1 mmol) in toluene (250 mL) was added Lawesson's reagent (31.32 g, 77.44 mmol) at room temperature. The mixture was heated at reflux for 1 h and cooled to ambient temperature. After adsorption of the reaction mixture on silica gel, the solvents were distilled off in vacuum. The residue was purified by flash chromatography on silica gel to give the title compound (30.3 g, 88%).

Characterization by $^1$H-NMR (400 MHz, CDCl$_3$):

δ [delta]=0.15 (s, 9H), 2.40 (s, 3H), 3.47 (m, 2H), 7.28 (m, 1H), 7.51 (m, 1H), 7.58 (m, 1H) ppm.

Step 3: Synthesis of 4-bromo-3-methyl-N-trimethyl-silanylmethyl-thiobenzimidic acid methyl ester To a solution of 4-bromo-3-methyl-N-trimethylsilanylm-ethyl-thiobenzamide (5.00 g, 15.8 mmol) in THF (30 mL) was added methyl iodide (1.97 mL, 4.49 g, 31.6 mmol) and Cs$_2$CO$_3$ (10.3 g, 31.6 mmol) at −5° C. After 1 h at this temperature, the mixture was allowed to reach room temperature and stirred over night. Water was added and the mixture was extracted three times with MTBE. The combined organic phases were dried over Na$_2$SO$_4$, filtered and concentrated in vacuum. The residue was purified by filtration over a short plug of silica gel to give the title compound (4.4 g), which was used in the next step without further purification.

Step 4: Synthesis of 5-(4-bromo-3-methyl-phenyl)-3-(3,5-dichloro-phenyl)-3-trifluoromethyl-3,4-dihydro-2H-pyrrole To a solution of 4-bromo-3-methyl-N-trimethylsilanylm-ethyl-thiobenzimidic acid methyl ester (4.40 g, 13.3 mmol) in dry THF (60 mL) was added 2-(3,5-dichlorophenyl)-1,1,1-trifluoro-2-propene (4.35 g, 16.25 mmol) at −7° C. A solution of tetrabutyl ammoniumfluoride (5.32 mL, 1 M in THF, 5.33 mmol) was added at this temperature and the mixture was allowed to warm to room temperature over night. All volatiles were removed in vacuum. The residue was purified by flash chromatography on silica gel to give the title compound (4.50 g, 75%).

Characterization by HPLC-MS: 4.643 min, M=451.95

Characterization by $^1$H-NMR (400 MHz, CDCl$_3$):

δ [delta]=2.45 (s, 3H), 3.44 (d, 1H), 3.76 (d, 1H), 4.42 (d, 1H), 4.88 (d, 1H), 7.26 (s, 2H), 7.38 (m, 1H), 7.50 (m, 1H) 7.61 (d, 1H), 7.72 (s, 1H) ppm.

Step 5: Synthesis of 4-[4-(3,5-dichloro-phenyl)-4-trifluoromethyl-4,5-dihydro-3H-pyrrol-2-yl]-2-methyl-benzaldehyde A mixture of 5-(4-bromo-3-methyl-phenyl)-3-(3,5-dichloro-phenyl)-3-trifluoromethyl-3,4-dihydro-2H-pyrrole (2.00 g, 4.43 mmol), dichloro[1,1'-bis(diphenylphosphino)ferrocene]palladium(II) (162 mg, 0.229 mmol), triethylsilane (1.42 mL, 1.03 g, 8.87 mmol) and Na$_2$CO$_3$ (587 mg, 5.54 mmol) in DMF (30 mL) were purged with CO gas at 65° C. The mixture was stirred over night at 65° C. and then cooled to room temperature. The residue was purified by flash chromatography on silica gel to give the title compound (1.316 g, 74%).

Characterization by $^1$H-NMR (400 MHz, CDCl$_3$):

δ [delta]=2.72 (s, 3H), 3.49 (d, 1H), 3.83 (d, 1H), 4.48 (d, 1H), 4.92 (d, 1H), 7.27 (s, 2H), 7.39 (s, 1H), 7.79 (s, 1H) 7.81 (d, 1H), 7.90 (m, 1H), 10.34 (s, 1H) ppm.

Step 6: Synthesis of 4-[4-(3,5-dichloro-phenyl)-4-trifluoromethyl-4,5-dihydro-3H-pyrrol-2-yl]-2-methyl-benzaldehyde-ethylsemicarbazone A mixture of 4-[4-(3,5-dichloro-phenyl)-4-trifluoromethyl-4,5-dihydro-3H-pyrrol-2-yl]-2-methyl-benzaldehyde (208 mg, 0.520 mmol) and ethyl semicarbazide hydrochloride (109 mg 0.780 mmol) in ethanol (5 mL) and glacial acetic acid (0.1 mL) was heated at 70° C. for 4 h. After cooling, the mixture was concentrated in vacuum. The residue was purified by flash chromatography on silica gel to give the title compound (151 mg, 60%).

Characterization by HPLC-MS: 3.741 min, M=485.00

Characterization by $^1$H-NMR (400 MHz, DMSO-d$_6$):

δ [delta]=1.09 (t, 3H), 2.43 (s, 3H), 3.19 (m, 2H), 3.70 (d, 1H), 3.88 (d, 1H), 4.40 (d, 1H), 4.82 (d, 1H), 7.07 (m, 1H), 7.58 (s, 2H), 7.71 (s, 1H), 7.75 (m, 2H), 8.09 (d, 1H), 8.14 (s, 1H), 10.36 (s, 1H) ppm.

S.2 Synthesis of 4-[4-(3,5-dichloro-phenyl)-4-trifluoromethyl-4,5-dihydro-3H-pyrrol-2-yl]-2-methyl-benzaldehyde-ethylthiosemicarbazone (Compound 1.2 of table C.1)

A mixture of 4-[4-(3,5-dichloro-phenyl)-4-trifluoromethyl-4,5-dihydro-3H-pyrrol-2-yl]-2-methyl-benzaldehyde (208 mg, 0.520 mmol) and ethyl thiosemicarbazide (93 mg 0.12 mmol) in ethanol (5 mL) and glacial acetic acid (0.1 mL) was heated at 70° C. for 4 h. After cooling, the resulting precipitate was filtered and dried to give the title compound (198 mg, 76%).

Characterization by HPLC-MS: 4.141 min, M=501.05

Characterization by $^1$H-NMR (400 MHz, DMSO-d$_6$):

δ [delta]=1.14 (t, 3H), 2.43 (s, 3H), 3.60 (m, 2H), 3.70 (d, 1H), 3.89 (d, 1H), 4.42 (d, 1H), 4.82 (d, 1H), 7.59 (s, 1H), 7.62 (s, 1H), 7.78 (m, 2H), 8.18 (m, 1H), 8.42 (s, 1H), 8.60 (m, 1H), 11.42 (s, 1H) ppm.

S.3 Synthesis of 4-[4-(3,5-dichloro-phenyl)-4-trifluoromethyl-4,5-dihydro-3H-pyrrol-2-yl]-2-chloro-benzaldehyde-ethylsemicarbazone (Compound 2.1 of table C.2)

Step 1: Synthesis of 4-bromo-3-chloro-N-trimethyl-silanylmethyl-benzamide

To a suspension of 4-bromo-3-chlorobenzoic acid (25.00 g, 106.2 mmol) in CH$_2$Cl$_2$ (320 mL) was added N,N-dimethyl aminopyridine (1.95 g), followed by N-ethyl-N-dimethy-lamine propylcarbodiimide hydrochloride (22.39 g) in small portions. After 30 min at room temperature, aminomethyl trimethylsilane (11.2 g, 7.87 mL, 108 mmol) was added while maintaining the temperature at 20° C. After stirring over night, water was added and the organic layer was separated. The aqueous layer was extracted twice with CH$_2$Cl$_2$ and the combined organic phases were dried and evaporated in vacuum. The residue was purified by flash chromatography on silica gel to give the title compound (34.00 g, 100%).

Characterization by $^1$H-NMR (400 MHz, CDCl$_3$):

δ [delta]=0.15 (s, 9H), 2.96 (m, 2H), 6.07 (br. s, 1H), 7.50 (m, 1H), 7.69 (m, 1H), 7.86 (m, 1H) ppm.

Step 2: Synthesis of 4-bromo-3-chloro-N-trimethyl-silanylmethyl-thiobenzamide

To a suspension of 4-bromo-3-chloro-N-trimethylsilanyl-methyl-benzamide (34.00 g, 106.0 mmol) in toluene (250 mL) was added Lawesson's reagent (30.45 g, 75.28 mmol) at room temperature. The mixture was heated at reflux for 1 h and cooled to ambient temperature. After adsorption of the reaction mixture on silica gel the solvents were distilled off in vacuum. The residue was purified by flash chromatography on silica gel to give the title compound (31.3 g, 88%).

Characterization by ¹H-NMR (400 MHz, CDCl₃):
δ [delta]=0.15 (s, 9H), 3.47 (m, 2H), 7.36 (m, 1H), 7.50-7.64 (m, 2H), 7.77 (d, 1H) ppm.

Step 3: Synthesis of 4-bromo-3-chloro-N-trimethyl-silanylmethyl-thiobenzimidic acid methyl ester To a solution of 4-bromo-3-chloro-N-trimethylsilanylmethyl-thiobenzamide (10.40 g, 30.88 mmol) in THF (200 mL) was added methyl iodide (5.77 mL, 13.15 g, 92.7 mmol) and Cs₂CO₃ (30.19 g, 92.7 mmol) at −5° C. After 1 h at this temperature, the mixture was heated at 40° C. and stirred over night. Water was added and the mixture was extracted three times with MTBE. The combined organic phases were dried over Na₂SO₄, filtered and concentrated in vacuum. The residue was purified by filtration over a short plug of silica gel to give the title compound (8.25 g), which was used in the next step without further purification.

Step 4: Synthesis of 5-(4-bromo-3-chloro-phenyl)-3-(3,5-dichloro-phenyl)-3-trifluoromethyl-3,4-dihydro-2H-pyrrole To a solution of 4-bromo-3-chloro-N-trimethylsilanylmethyl-thiobenzimidic acid methyl ester (9.60 g, 27.4 mmol) in dry THF (100 mL) was added 2-(3,5-dichlorophenyl)-1,1,1-trifluoro-2-propene (8.94 g, 33.4 mmol) at −7° C. A solution of tetrabutyl ammoniumfluoride (5.32 mL, 1 M in THF, 5.33 mmol) was added at this temperature and the mixture was allowed to warm to room temperature over night. All volatiles were removed in vacuum. The residue was purified by flash chromatography on silica gel to give the title compound (9.50 g, 74%).
Characterization by HPLC-MS: 4.944 min, M=471.90
Characterization by ¹H-NMR (400 MHz, CDCl₃):
δ [delta]=3.43 (d, 1H), 3.76 (d, 1H), 4.43 (d, 1H), 4.90 (d, 1H), 7.26 (s, 3H), 7.59 (m, 1H), 7.70 (m, 1H) 7.92 (s, 1H) ppm.

Step 5: Synthesis of 4-[4-(3,5-dichloro-phenyl)-4-trifluoromethyl-4,5-dihydro-3H-pyrrol-2-yl]-2-chloro-benzoic acid methyl ester A mixture of 5-(4-bromo-3-chloro-phenyl)-3-(3,5-dichloro-phenyl)-3-trifluoromethyl-3,4-dihydro-2H-pyrrole (10.60 g), dichloro[1,1'-bis(diphenylphosphino)ferrocene]palladium(II) (1.645 mg), sodium acetate (2.748 g) and methanol (100 mL) was placed in an autoclave and purged with CO gas. The pressure was adjusted to 5 bar and the mixture was heated at 80° C. for 16 h. After cooling the pressure was released and the solvents were distilled off in vacuum. The residue was purified by flash chromatography on silica gel to give the title compound (10.00 g, 99%).
Characterization by ¹H-NMR (400 MHz, CDCl₃):
δ [delta]=3.47 (d, 1H), 3.80 (d, 1H), 3.96 (s, 3H), 4.48 (d, 1H), 4.93 (d, 1H), 7.26 (s, 3H), 7.80 (m, 1H) 7.90-7.98 (m, 2H) ppm.

Step 6: Synthesis of 4-[4-(3,5-dichloro-phenyl)-4-trifluoromethyl-4,5-dihydro-3H-pyrrol-2-yl]-2-chloro-benzaldehyde To a solution of 4-[4-(3,5-dichloro-phenyl)-4-trifluoromethyl-4,5-dihydro-3H-pyrrol-2-yl]-2-chloro-benzoic acid methyl ester (807 mg, 1.79 mmol) in CH₂Cl₂ (100 mL) was added a solution of DIBAL (1.97 mL, 1 M in CH₂Cl₂, 1.97 mmol) with a syringe pump at −75° C. The mixture was stirred for 25 min at this temperature, before methanol (1 mL) was added and warmed to room temperature. Saturared aqueous Na/K-tartrate solution was added and the mixture was extracted three times with CH₂Cl₂. The organic layers were combined, dried over Na₂SO₄ and concentrated in vacuum. The residue was purified by flash chromatography on silica gel to give the title compound (190 mg, 25%).
Characterization by ¹H-NMR (400 MHz, CDCl₃):
δ [delta]=3.48 (d, 1H), 3.80 (d, 1H), 4.49 (d, 1H), 4.95 (d, 1H), 7.27 (s, 3H), 7.85 (m, 1H) 7.95-8.06 (m, 2H), 10.51 (s, 1H) ppm.

Step 7: Synthesis of 4-[4-(3,5-dichloro-phenyl)-4-trifluoromethyl-4,5-dihydro-3H-pyrrol-2-yl]-2-chloro-benzaldehyde-ethylsemicarbazone A mixture of 4-[4-(3,5-dichloro-phenyl)-4-trifluoromethyl-4,5-dihydro-3H-pyrrol-2-yl]-2-chloro-benzaldehyde (121 mg, 0.29 mmol) and ethyl semicarbazide hydrochloride (60 mg 0.43 mmol) in ethanol (5 mL) and glacial acetic acid (0.1 mL) was heated at 70° C. for 4 h. Then, water was added and cooled, upon which a precipitate formed. The latter was collected by filtration and dried in vacuum to obtain the title compound (137 mg, 93%).
Characterization by HPLC-MS: 4.159 min, M=505.05
Characterization by ¹H-NMR (400 MHz, DMSO-d₆):
δ [delta]=1.09 (t, 3H), 3.19 (m, 2H), 3.75 (d, 1H), 3.91 (d, 1H), 4.43 (d, 1H), 4.85 (d, 1H), 7.27 (m, 1H), 7.60 (s, 2H), 7.71 (s, 1H), 7.90 (d, 1H), 7.96 (s, 1H), 8.27 (s, 1H), 8.34 (s, 1H), 10.69 (s, 1H) ppm.

S.4 Synthesis of 1-[(E)-[4-[3-(3,5-dichlorophenyl)-3-(trifluoromethyl)-2,4-dihydropyrrol-5-yl]-2-methyl-phenyl]methyleneamino]-3-(2,2,2-trifluoroethyl)urea
(Compound 1-3 of table C.1)

Step 1: Synthesis of 4-bromo-3-methyl-N-(trimethylsilylmethyl)benzamide

To a suspension of 4-bromo-3-methylbenzoic acid (25 g) and 4-(dimethylamino)pyridine ("DMAP", 2.1 g) in CH₂Cl₂ (320 mL) was added N-(3-dimethylaminopropyl)-N'-ethyl-carbodiimide ("EDC", 22.4 g) portionwise. Then, (aminomethyl)trimethylsilane (8.6 mL) was added, while cooling to keep the internal temperature below 20° C. The reaction was stirred at room temperature overnight. Water was added under vigorous stirring, and the layers were separated. The aqueous layer was extracted twice with CH₂Cl₂, and the combined organic phase dried (Na₂SO₄), and filtered over silica gel using CH₂Cl₂ and methyl tert-butyl ether (MTBE) to afford the title compound (32.8 g, 94%).
Characterization by HPLC-MS: 3.628 min, M=302.00.

Step 2: Synthesis of 4-bromo-3-methyl-N-(trimethylsilylmethyl)benzenecarbothioamide To a suspension of 4-bromo-3-methyl-N-(trimethylsilylmethyl)benzamide (i.e. the product of Step 1, 32.8 g) in toluene (250 mL) was added 2,4-bis(4-methoxyphenyl)-2,4-dithioxo-1,3,2,4-dithiadiphosphetane ("Lawesson's reagent", 31.3 g). The mixture was heated at reflux for 1 h, cooled to room temperature and concentrated. Purification by flash chromatography on silica gel afforded the title compound (30.3 g, 88%).
Characterization by HPLC-MS: 4.184 min, M=317.90.

Step 3: Synthesis of methyl (1Z)-4-bromo-3-methyl-N-(trimethylsilylmethyl)benzenecarboximidothioate At −5° C., 4-bromo-3-methyl-N-(trimethylsilylmethyl)benzenecarbothioamide (i.e. the product of Step 2, 1.0 g) in THF (15 mL) was treated with methyliodide (0.30 mL). NaHCO$_3$ (0.80 g) was added portionwise and the reaction was stirred at room temperature for 72 h. Then, MTBE and brine were added. The aqueous phase was extracted three times with MTBE and the combined organic layers washed with brine, dried (Na$_2$SO$_4$), filtered and concentrated. Purification by flash chromatography on silica gel afforded the title compound (0.735 g, 70%).
Characterization by HPLC-MS: 2.890 min, M=330.00.

Step 4: Synthesis of 5-(4-bromo-3-methyl-phenyl)-3-(3,5-dichlorophenyl)-3-(trifluoromethyl)-2,4-dihydropyrrole To methyl (1Z)-4-bromo-3-methyl-N-(trimethylsilylmethyl)benzenecarboximidothioate (i.e. the product of Step 3, 4.4 g) in THF (100 mL) was added 1,3-dichloro-5-[1-(trifluoromethyl)vinyl]benzene (8.9 g). Between −7° C. and -5°C., a solution of tetrabutylammoniumfluoride (1 M in THF, 10.9 mL) was added. The reaction was allowed to warm to room temperature and was stirred for 72 h. The reaction was concentrated and the crude product purified by flash chromatography on silica gel and subsequently recrystallized from petrolether to afford the title compound (9.5 g, 74%).
Characterization by HPLC-MS: 4.944 min, M=471.90.

Step 5: Synthesis of 4-[3-(3,5-dichlorophenyl)-3-(trifluoromethyl)-2,4-dihydropyrrol-5-yl]-2-methyl-benzaldehyde To a solution of 5-(4-bromo-3-methyl-phenyl)-3-(3,5-dichlorophenyl)-3-(trifluoromethyl)-2,4-dihydropyrrole (i.e. the product of Step 4, 2.0 g) in dimethylformamide (DMF) (50 mL) was added [1,1'-bis(diphenylphosphino)ferrocene]dichloropalladium(II) ("Pd(dppf)Cl$_2$", 0.16 g), Na$_2$CO$_3$ (0.59 g) and triethylsilane (1.4 mL). The mixture was purged twice with N$_2$, then purged three times with CO and stirred under an atmosphere of CO overnight at 65° C. Then, the reaction was concentrated in vacuum and purified by flash chromatography on silica gel to afford the title compound (1.32 g, 74%).
Characterization by HPLC-MS: 4.322 min, M=400.00

Step 6: Synthesis of 1-[(E)-[4-[3-(3,5-dichlorophenyl)-3-(trifluoromethyl)-2,4-dihydropyrrol-5-yl]-2-methyl-phenyl]methyleneamino]-3-(2,2,2-trifluoroethyl)urea A mixture of 4-[3-(3,5-dichlorophenyl)-3-(trifluoromethyl)-2,4-dihydropyrrol-5-yl]-2-methyl-benzaldehyde (i.e. the product of Step 5, 200 mg), 1-amino-3-(2,2,2-trifluoroethyl)urea (145 mg) and acetic acid (0.1 mL) in EtOH (5 mL) was heated at 70° C. for 4 h. Water was added, the reaction cooled to room temperature and the solid was collected by filtration. Recrystallization from diisopropylether yielded the title compound (198 mg, 73%).
Characterization by HPLC-MS: 3.967 min, M=539.05
The following examples were synthesized analogously.

C. COMPOUND EXAMPLES

The following examples were synthesized in analogy to the Synthesis examples.

C.1 Compound Examples 1

Compound examples 1-1 to 1-10 correspond to compounds of formula C.1:

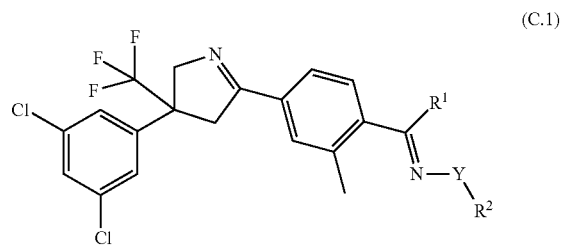

(C.1)

wherein $R^1$, $R^2$ and Y of each synthesized compound is defined in one row of table C.1 below.

TABLE C.1

| Compound Ex. | $R^1$ | $R^2$ | Y | $R_t$ (min) | [M + H] |
|---|---|---|---|---|---|
| 1-1 | H | C(=O)NH—CH$_2$CH$_3$ | NH | 3.741 | 485.00 |
| 1-2 | H | C(=S)NH—CH$_2$CH$_3$ | NH | 4.141 | 501.05 |
| 1-3 | H | C(=O)NH—CH$_2$CF$_3$ | NH | 3.967 | 539.05 |
| 1-4 | H | C(=O)NH—CH$_3$ | NH | 3.573 | 471.00 |
| 1-5 | H | C(=O)—NH-cyclopropyl | NH | 3.772 | 497.00 |
| 1-6 | H | C(=O)—NH—CH$_2$-cyclopropyl | NH | 3.948 | 511.10 |
| 1-7 | H | C(=O)NH—CH$_2$CH$_3$ | NH | 3.796 | 499.00 |
| 1-8 | H | C(=O)NH—CH$_2$CH$_2$CF$_3$ | NH | 3.993 | 553.00 |
| 1-9 | H | C(=O)NH—CH$_2$CHF$_2$ | NH | 3.834 | 521.05 |
| 1-10 | H | C(=O)NH$_2$ | NH | 3.324 | 457.00 |

C.2 Compound Examples 2

Compound example 2-1 to 2-10 corresponds to compound formula C.2:

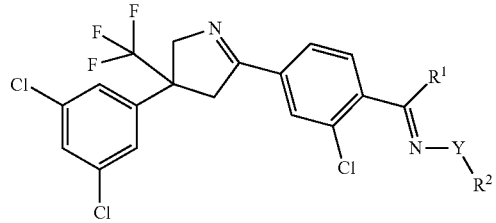

(formula C.2)

wherein $R^1$, $R^2$, and Y of each synthesized compound is defined in one row of table C.2 below.

TABLE C.2

| Compound Ex. | $R^1$ | $R^2$ | Y | $R_t$ (min) | [M + H] |
|---|---|---|---|---|---|
| 2-1 | H | C(=O)NH—CH$_2$CH$_3$ | NH | 4.159 | 505.05 |
| 2-2 | H | C(=S)NH—CH$_2$CH$_3$ | NH | 4.452 | 522.90 |
| 2-3 | H | C(=O)NH—CH$_2$CF$_3$ | NH | 4.307 | 559.25 |
| 2-4 | H | C(=O)NH—CH$_3$ | NH | 4.011 | 491.45 |
| 2-5 | H | C(=O)—NH-cyclopropyl | NH | 4.176 | 516.95 |
| 2-6 | H | C(=O)—NH—CH$_2$-cyclopropyl | NH | 4.336 | 531.05 |
| 2-7 | H | C(=O)NH—CH$_2$CH$_2$CH$_3$ | NH | 4.314 | 519.05 |

TABLE C.2-continued

| Compound Ex. | R$^1$ | R$^2$ | Y | R$_t$ (min) | [M + H] |
|---|---|---|---|---|---|
| 2-8 | H | C(=O)NH—CH$_2$CH$_2$CF$_3$ | NH | 4.336 | 572.90 |
| 2-9 | H | C(=O)NH—CH$_2$CHF$_2$ | NH | 4.164 | 540.90 |
| 2-10 | H | C(=O)NH$_2$ | NH | 3.837 | 476.90 |

II. Evaluation Of Pesticidal Activity:

The activity of the compounds of formula I of the present invention can be demonstrated and evaluated by the following biological test.

B.1 Cotton Aphid (*Aphis Gossypii*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic) was included in the solution at a volume of 0.01% (v/v).

Cotton plants at the cotyledon stage were infested with aphids prior to treatment by placing a heavily infested leaf from the main aphid colony on top of each cotyledon. Aphids were allowed to transfer overnight to accomplish an infestation of 80-100 aphids per plant and the host leaf was removed. The infested plants were then sprayed by an automated electrostatic plant sprayer equipped with an atomizing spray nozzle. The plants were dried in the sprayer fume hood, removed from the sprayer, and then maintained in a growth room under fluorescent lighting in a 24-hr photoperiod at 25° C. and 20-40% relative humidity. Aphid mortality on the treated plants, relative to mortality on untreated control plants, was determined after 5 days.

In this test, the compounds 1-4, 1-5, 2-1 and 2-5, respectively, at 300 ppm showed a mortality of at least 75% in comparison with untreated controls.

B.2 Cowpea Aphid (*Aphis Craccivora*)

Potted cowpea plants colonized with approximately 100-150 aphids of various stages were sprayed after the pest population had been recorded. Population reduction was assessed after 24, 72, and 120 hours.

In this test, the compounds 1-2, 1-3, 1-5, 1-8, 2-3 and 2-5, respectively, at 500 ppm showed a mortality of at least 75% in comparison with untreated controls.

B.3 Diamond Back Moth (*Plutella Xylostella*)

Leaves of Chinese cabbage were dipped in test solution and air-dried. Treated leaves were placed in petri dished lined with moist filter paper. Mortality was recorded 24, 72, and 120 hours after treatment.

In this test, the compounds 1-1, 1-3, 1-4, 1-5, 1-6, 1-7, 1-8, 1-9, 2-1, 2-3, 2-4, 2-5, 2-6, 2-7, 2-8 and 2-9, respectively, at 500 ppm showed a mortality of at least 75% in comparison with untreated controls.

B.4 Green Peach Aphid (*Myzus Persicae*)

For evaluating control of green peach aphid (*Myzus persicae*) through systemic means the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications.

After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed.

In this test, the compounds 1-1, 1-3, 1-4, 1-5, 1-6, 1-7, 1-8, 1-9, 2-1, 2-3, 2-4, 2-5, 2-6, 2-7, 2-8 and 2-9, respectively, at 2500 ppm showed a mortality of at least 75% in comparison with untreated controls.

B.5 Mediterranean Fruitfly (*Ceratitis Capitata*)

For evaluating control of Mediterranean fruitfly (*Ceratitis capitata*) the test unit consisted of microtiter plates containing an insect diet and 50-80 *C. capitata* eggs.

The compounds were formulated using a solution containing 75% v/v water and 25% v/v DMSO. Different concentrations of formulated compounds were sprayed onto the insect diet at 5 µl, using a custom built micro atomizer, at two replications.

After application, microtiter plates were incubated at about 28±1° C. and about 80±5% relative humidity for 5 days. Egg and larval mortality was then visually assessed.

In this test, the compounds 1-1, 1-2, 1-3, 1-4, 1-5, 1-6, 1-7, 1-8, 1-9, 1-10, 2-1, 2-2, 2-3, 2-4, 2-5, 2-6, 2-7, 2-8, 2-9 and 2-10, respectively, at 2500 ppm showed a mortality of at least 75% in comparison with untreated controls.

B.6 Orchid Thrips (*Dichromothrips corbetti*)

*Dichromothrips corbetti* adults used for bioassay were obtained from a colony maintained continuously under laboratory conditions. For testing purposes, the test compound was diluted to a concentration of 500 ppm (wt compound: vol diluent) in a 1:1 mixture of acetone:water (vol:vol), plus 0.01% vol/vol Kinetic® surfactant.

Thrips potency of each compound was evaluated by using a floral-immersion technique. Plastic petri dishes were used as test arenas. All petals of individual, intact orchid flowers were dipped into treatment solution and allowed to dry. Treated flowers were placed into individual petri dishes along with 10-15 adult thrips. The petri dishes were then covered with lids. All test arenas were held under continuous light and a temperature of about 28° C. for duration of the assay. After 4 days, the numbers of live thrips were counted on each flower, and along inner walls of each petri dish. The level of thrips mortality was extrapolated from pre-treatment thrips numbers.

In this test, the compounds 1-1, 1-3, 1-4, 1-5, 1-6, 1-8, 1-9, 2-1, 2-3, 2-4, 2-5, 2-7 and 2-8, respectively, at 500 ppm showed a mortality of at least 75% in comparison with untreated controls.

B.7 Rice Green Leafhopper (*Nephotettix Virescens*)

Rice seedlings were cleaned and washed 24 hours before spraying. The active compounds were formulated in 50:50 acetone:water (vol:vol), and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, the compounds 1-4, 2-3, 2-4 and 2-5, respectively, at 500 ppm showed a mortality of at least 75% in comparison with untreated controls.

B.8 Silverleaf Whitefly (*Bemisia Argentifolii*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic) was included in the solution at a volume of 0.01% (v/v).

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and about 10 to 12 whitefly adults (approximately 3-5 days old) were introduced. The insects were collected using an aspirator and a nontoxic Tygon® tubing connected to a barrier pipette tip. The tip, containing the collected insects, was then gently inserted into the soil containing the treated plant, allowing insects to crawl out of the tip to reach the foliage for feeding. Cups were covered with a reusable screened lid. Test plants were maintained in a growth room at about 25° C. and about 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, the compound 2-3, at 300 ppm showed a mortality of at least 75% in comparison with untreated controls.

B.9 Southern Armyworm (*Spodoptera Eridania*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Lima bean plants (variety Sieva) were grown 2 plants to a pot and selected for treatment at the $1^{st}$ true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 armyworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding was assessed 4 days after treatment, compared to untreated control plants.

In this test, the compounds 1-1, 1-3, 1-4, 1-5, 1-6, 1-7, 1-8, 1-9, 2-1, 2-2, 2-3, 2-4, 2-5, 2-6, 2-8 and 2-9, respectively, at 1 ppm showed a mortality of at least 75% in comparison with untreated controls.

B.10 Vetch Aphid (*Megoura Viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 µl, using a custom built micro atomizer, at two replications.

After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, the compounds 1-1, 1-3, 1-4, 1-5, 1-6, 1-7, 1-8, 1-9, 2-1, 2-2, 2-3, 2-4, 2-5, 2-6, 2-7, 2-8 and 2-9, respectively, at 2500 ppm, showed a mortality of at least 75% in comparison with untreated controls.

B.11 Tobacco Budworm (*Heliothis Virescens*) I

For evaluating control of tobacco budworm (*Heliothis virescens*) the test unit consisted of 96-well-microtiter plates containing an insect diet and 15-25 *H. virescens* eggs. The compounds were formulated using a solution containing 75% v/v water and 25% v/v DMSO. Different concentrations of formulated compounds were sprayed onto the insect diet at 10 µl, using a custom built micro atomizer, at two replications.

After application, microtiter plates were incubated at about 28±1° C. and about 80±5% relative humidity for 5 days. Egg and larval mortality was then visually assessed.

In this test, the compounds 1-1, 1-2, 1-3, 1-4, 1-5, 1-6, 1-8, 1-9, 1-10, 2-1, 2-2, 2-3, 2-4, 2-5, 2-6, 2-7, 2-8, 2-9 and 2-10, respectively, at 2500 ppm, showed a mortality of at least 75% in comparison with untreated controls.

B.12 Boll Weevil (*Anthonomus Grandis*)

For evaluating control of boll weevil (*Anthonomus grandis*) the test unit consisted of 24-well-microtiter plates containing an insect diet and 20-30 *A. grandis* eggs.

The compounds were formulated using a solution containing 75% v/v water and 25% v/v DMSO. Different concentrations of formulated compounds were sprayed onto the insect diet at 20 µl, using a custom built micro atomizer, at two replications. After application, microtiter plates were incubated at about 23±1° C. and about 50±5% relative humidity for 5 days. Egg and larval mortality was then visually assessed.

In this test, the compounds 1-1, 1-2, 1-3, 1-4, 1-5, 1-6, 1-8, 1-9, 1-10, 2-1, 2-2, 2-3, 2-4, 2-5, 2-6, 2-7, 2-8, 2-9 and 2-10, respectively, at 2500 ppm, showed a mortality of at least 75% in comparison with untreated controls.

B.13 Colorado Potato Beetle (*Leptinotarsa Decemlineata*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Eggplants were grown 2 plants to a pot and were selected for treatment at the $1^{st}$ true leaf stage. Test solutions were sprayed onto the foliage by an automated electrostatic plant sprayer equipped with an atomizing spray nozzle. The plants were dried in the sprayer fume hood and then removed from the sprayer. The treated foliage was then cut and removed from the pot and placed in a 5-inch Petri dish lined with moistened filter paper. Five beetle larvae were introduced into each Petri dish and the dish was covered by a Petri dish lid. Petri dishes were maintained in a growth room at 25° C. and 20-40% relative humidity for 4 days, avoiding direct exposure to fluorescent light (24 hour photoperiod) to prevent trapping of heat inside the dishes. Mortality and reduced feeding were assessed 4 days after treatment, compared to untreated control plants.

In this test, the compound 2-4, at 10 ppm showed a mortality of at least 75% in comparison with untreated controls.

B.14 Red Spider Mite (*Tetranychus Kanzawai*)

The active compound was dissolved at the desired concentration in a mixture of 1:1 (v/v) distilled water:acetone. A surfactant (Alkamuls® EL 620) was added at the rate of 0.1% (v/v).

Potted cowpea beans of 7-10 days of age were cleaned with tap water and sprayed with 5 ml of the test solution using air driven hand atomizer. The treated plants were allowed to air dry and afterwards inculated with 20 or more mites by clipping a cassaya leaf section with known mite population. Treated plants were placed inside a holding room at about 25-27° C. and about 50-60% relative humidity.

Mortality was determined by counting the live mites 72 HAT. Percent mortality was assessed after 72 h.

In this test, the compounds 1-1, 1-3, 1-5, 1-7, 1-8, 2-1, 2-4, 2-5 and 2-8, respectively, at 500 ppm showed a mortality of at least 75% in comparison with untreated controls.

We claim:

1. A compound of formula (I)

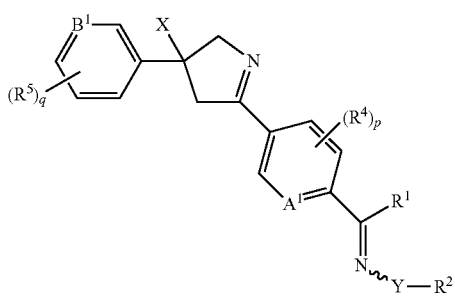

wherein
$A^1$ is N or CH;
$B^1$ is N or CH;
X is selected from the group consisting of $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl and $C_3$-$C_6$-halocycloalkyl;
Y is O, N—$R^3$, S(O)$_n$ or a chemical bond;
$R^1$ is selected from the group consisting of hydrogen; cyano; $C_1$-$C_{10}$-alkyl which may be partially or fully halogenated and/or may be substituted by one or more radicals $R^6$; $C_1$-$C_{10}$-alkoxy; $C_1$-$C_{10}$-haloalkoxy; $C_1$-$C_{10}$-alkylthio; $C_1$-$C_{10}$-haloalkylthio; $C_1$-$C_{10}$-alkylsulfinyl; $C_1$-$C_{10}$-haloalkylsulfinyl; $C_1$-$C_{10}$-alkylsulfonyl; $C_1$-$C_{10}$-haloalkylsulfonyl; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; phenyl which may be substituted by 1, 2, 3, 4 or 5 radicals $R^1$; and a C-bound 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals $R^{10}$;
$R^2$ is selected from the group consisting of hydrogen; cyano; $C_1$-$C_{10}$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —N($R^8$)$R^9$; —N($R^8$)C(=O)$R^6$; —Si($R^{14}$)$_2$$R^{13}$; —O$R^7$; —S$R^7$; —S(O)$_m$$R^7$; —S(O)$_n$N($R^8$)$R^9$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; —C(=N$R^8$)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals $R^{10}$;
with the proviso that $R^2$ is not —O$R^7$ if Y is O;
$R^3$ is selected from the group consisting of hydrogen; cyano; $C_1$-$C_{10}$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —N($R^8$)$R^9$; —Si($R^{14}$)$_2$$R^{13}$; —O$R^7$; —S$R^7$; —S(O)$_m$$R^7$; —S(O)$_n$N($R^8$)$R^9$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; —C(=N$R^8$)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals $R^{10}$;
or $R^2$ and $R^3$ together form a group =C$R^{11}$$R^{12}$; =S(O)$_m$$R^7$; =S(O)$_m$N($R^8$)$R^9$; =N$R^8$; or =NO$R^7$;
or $R^2$ and $R^3$ together form a $C_2$-$C_7$ alkylene chain, thus forming, together with the nitrogen atom to which they are bound, a 3-, 4-, 5-, 6-, 7- or 8-membered ring, where the alkylene chain may be interrupted by 1 or 2 O, S and/or N$R^{18}$ and/or 1 or 2 of the CH$_2$ groups of the alkylene chain may be replaced by a group C=O, C=S and/or C=N$R^{18}$; and/or the alkylene chain may be substituted by one or more radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals $R^{10}$;
each $R^4$ is independently selected from the group consisting of halogen; cyano; azido; nitro; —SCN; SF$_5$; $C_1$-$C_6$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_6$-alkenyl which may be partially or fully halogenated and/or may be substituted by one or more radicals $R^6$; $C_2$-$C_6$-alkynyl which may be partially or fully halogenated and/or may be substituted by one or more radicals $R^6$;
—Si($R^{14}$)$_2$$R^{13}$; —O$R^7$; —OS(O)$_n$$R^7$; —S$R^7$; —S(O)$_m$$R^7$; —S(O)$_n$N($R^8$)$R^9$; —N($R^8$)$R^9$; —N($R^8$)C(=O)$R^6$; C(=O)$R^6$; —C(=O)O$R^7$; —C(=N$R^8$)H; —C(=N$R^8$)$R^6$; —C(=O)N($R^8$)$R^9$; C(=S)N($R^8$)$R^9$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

or two radicals $R^4$ bound on adjacent carbon atoms may be together a group selected from the group consisting of —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=CHCH_2—, —$CH_2OCH_2CH_2$—, —$OCH_2CH_2O$—, —$OCH_2OCH_2$—, —$CH_2CH_2CH_2$—, —CH=CHCH_2—, —$CH_2CH_2O$—, —CH=CHO—, —$CH_2OCH_2$—, —$CH_2C$(=O)O—, —C(=O)$OCH_2$—, —$O(CH_2)O$—, —$SCH_2CH_2CH_2$—, —SCH=CHCH_2—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C$(=S)S—, —C(=S)$SCH_2$—, —$S(CH_2)S$—, —$CH_2CH_2NR^8$—, —$CH_2CH$=N—, —CH=CH—$NR^8$—, —OCH=N— and —SCH=N—, thus forming, together with the carbon atoms to which they are bound, a 5- or 6-membered ring, where the hydrogen atoms of the above groups may be replaced by one or more substituents selected from the group consisting of halogen, methyl, halomethyl, hydroxyl, methoxy and halomethoxy or one or more $CH_2$ groups of the above groups may be replaced by a C=O group;

each $R^5$ is independently selected from the group consisting of halogen, cyano, azido, nitro, —SCN, $SF_5$, $C_1$-$C_6$-alkyl which may be partially or fully halogenated and/or may be substituted by one or more radicals $R^6$, $C_3$-$C_8$-cycloalkyl which may be partially or fully halogenated and/or may be substituted by one or more radicals $R^6$, $C_2$-$C_6$-alkenyl which may be partially or fully halogenated and/or may be substituted by one or more radicals $R^6$, $C_2$-$C_6$-alkynyl which may be partially or fully halogenated and/or may be substituted by one or more radicals $R^6$, —Si$(R^{14})_2R^{13}$, —$OR^7$, —$OS(O)_nR^7$, —$SR^7$, —$S(O)_mR^7$, —$S(O)_nN(R^5)R^9$, —$N(R^8)R^9$, $N(R^8)$C(=O)$R^6$, —C(=O)$R^6$, —C(=O)$OR^7$, —C(=S)$R^6$, —C(=S)$OR^7$, —C(=$NR^8$)$R^6$, —C(=O)N(R)$R^9$, —C(=S)N($R^8$)$R^9$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

each $R^6$ is independently selected from the group consisting of cyano, azido, nitro, —SCN, $SF_5$, $C_3$-$C_8$-cycloalkyl, $C_3$-$C_8$-halocycloalkyl, —Si$(R^{14})_2R^{13}$, —$OR^7$, —$OSO_2R^7$, —$SR^7$, —$S(O)_mR^7$, —$S(O)_nN(R^8)R^9$, —$N(R^8)R^9$, —C(=O)N($R^8$)$R^9$, —C(=S)N($R^8$)$R^9$, —C(=O)$OR^7$, —C(=O)$R^{19}$, —C(=$NR^8$)$R^{19}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

and, in case $R^6$ is bound to a cycloalkyl group, $R^6$ may additionally be selected from the group consisting of $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl and benzyl which may be substituted by 1, 2, 3, 4 or 5 radicals $R^{10}$;

and in groups —C(=O)$R^6$, —C(=S)$R^6$, —C(=$NR^8$)$R^6$ and —N($R^8$)C(=O)$R^6$, $R^6$ may additionally be selected from the group consisting of hydrogen, halogen, $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl and benzyl which may be substituted by 1, 2, 3, 4 or 5 radicals $R^{10}$;

or two geminally bound radicals $R^6$ together form a group selected from the group consisting of =$CR^{11}R^{12}$, =$S(O)_mR^7$, =$S(O)_mN(R^8)R^9$, =$NR^8$, =$NOR^7$ and =$NNR^8$;

or two radicals $R^6$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from the group consisting of N, O, S, NO, SO and $SO_2$, as ring members;

each $R^7$ is independently selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si$(R^{14})_2R^{13}$, —$SR^8$, —$S(O)_mR^7$, —$S(O)_nN(R^8)R^9$, —$N(R^8)R^9$, —N=$CR^{15}R^{16}$, —C(=O)$R^{17}$, —C(=O)N($R^8$)$R^9$, —C(=S)N($R^8$)$R^9$, —C(=O)$OR^7$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

with the proviso that $R^7$ is not $C_1$-$C_6$-alkoxy or $C_1$-$C_6$-haloalkoxy if it is bound to an oxygen atom;

each $R^8$ is independently selected from the group consisting of hydrogen, cyano, $C_1$-$C_6$-alkyl which may be partially or fully halogenated and/or may be substituted by one or more radicals $R^{19}$, $C_1$-$C_6$-alkoxy, $C_1$-$C_6$-haloalkoxy, $C_1$-$C_6$-alkylthio, $C_1$-$C_6$-haloalkylthio, where the alkyl moiety in the four last-mentioned radicals may be substituted by one or more radicals $R^{19}$, $C_3$-$C_8$-cycloalkyl which may be partially or fully halogenated and/or may be substituted by one or more radicals $R^{19}$, $C_3$-$C_8$-cycloalkyl-$C_1$-$C_4$-alkyl where the cycloalkyl moiety may be partially or fully halogenated and/or may be substituted by one or more radicals $R^{19}$, $C_2$-$C_6$-alkenyl which may be partially or fully halogenated and/or may be substituted by one or more radicals $R^{19}$, $C_2$-$C_6$-alkynyl which may be partially or fully halogenated and/or may be substituted by one or more radicals $R^9$, —$S(O)_mR^{20}$, —$S(O)_nN(R^{21})R^{22}$, phenyl which may be substituted by 1, 2, 3, 4 or 5 radicals $R^{10}$, benzyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

each $R^9$ is independently selected from the group consisting of hydrogen, cyano, $C_1$-$C_6$-alkyl which may be partially or fully halogenated and/or may be substituted by one or more radicals $R^{19}$, $C_1$-$C_6$-alkoxy, $C_1$-$C_6$-haloalkoxy, $C_1$-$C_6$-alkylthio, $C_1$-$C_6$-haloalkylthio, where the alkyl moiety in the four last-mentioned radicals may be substituted by one or more radicals $R^{19}$, $C_3$-$C_8$-cycloalkyl which may be partially or fully halogenated and/or may be substituted by one or more radicals $R^{19}$, $C_3$-$C_8$-cycloalkyl-$C_1$-$C_4$-alkyl where the cycloalkyl moiety may be partially or fully halogenated and/or may be substituted by one or more radicals $R^{19}$, $C_2$-$C_6$-alkenyl which may be partially or fully halogenated and/or may be substituted by one or more radicals $R^{19}$, $C_2$-$C_6$-alkynyl which may be partially or fully halogenated and/or may be substituted by one or more radicals $R^{19}$, —S(O)$_m$R$^{20}$, —S(O)$_n$N(R$^{21}$)R$^{22}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals $R^{10}$;

or $R^8$ and $R^9$ together form a group =CR$^{11}$R$^{12}$;

or $R^8$ and $R^9$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from the group consisting of N, O, S, NO, SO and SO$_2$, as ring members, where the heterocyclic ring may be substituted by one or more radicals $R^{10}$;

each $R^{10}$ is independently selected from the group consisting of halogen, cyano, azido, nitro, —SCN, SF$_5$, $C_1$-$C_{10}$-alkyl which may be partially or fully halogenated and/or may be substituted by one or more radicals $R^{19}$, $C_3$-$C_8$-cycloalkyl which may be partially or fully halogenated and/or may be substituted by one or more radicals $R^{19}$, $C_2$-$C_{10}$-alkenyl which may be partially or fully halogenated and/or may be substituted by one or more radicals $R^{19}$, $C_2$-$C_{10}$-alkynyl which may be partially or fully halogenated and/or may be substituted by one or more radicals $R^9$, —Si(R$^{14}$)$_2$R$^{13}$, —OR$^{20}$, —OS(O)$_n$R$^{20}$, —SR$^{20}$, —S(O)$_m$R$^{20}$, —S(O)$_n$N(R$^{21}$)R$^{22}$, —N(R$^{21}$)R$^{22}$, —C(=O)R$^{19}$, —C(=O)OR$^{20}$, —C(=NR$^{21}$)R$^{22}$, —C(=O)N(R$^{21}$)R$^{22}$, —C(=S)N(R$^{21}$)R$^{22}$, phenyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy; and a 3-, 4-, 5-, 6- or 7-membered saturated or unsaturated heterocyclic ring containing 1, 2 or 3 heteroatoms or heteroatom groups selected from the group consisting of N, O, S, NO, SO and SO$_2$, as ring members, which may be substituted by one or more radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy;

or two radicals $R^{10}$ bound on adjacent atoms together form a group selected from the group consisting of
—CH$_2$CH$_2$CH$_2$CH$_2$—, —CH=CH—CH=CH—, —N=CH—CH=CH—, —CH=N—CH=CH—, —N=CH—N=CH—, —OCH$_2$CH$_2$CH$_2$—, —OCH=CHCH$_2$—, —CH$_2$OCH$_2$CH$_2$—, —OCH$_2$CH$_2$O—, —OCH$_2$OCH$_2$—, —CH$_2$CH$_2$CH$_2$—, —CH=CHCH$_2$—, —CH$_2$CH$_2$O—, —CH=CHO—, —CH$_2$OCH$_2$—, —CH$_2$C(=O)O—, —C(=O)OCH$_2$—, —O(CH$_2$)O—, —SCH$_2$CH$_2$CH$_2$—, —SCH=CHCH$_2$—, —CH$_2$SCH$_2$CH$_2$—, —SCH$_2$CH$_2$S—, —SCH$_2$SCH$_2$—, —CH$_2$CH$_2$S—, —CH=CHS—, —CH$_2$SCH$_2$—, —CH$_2$C(=S)S—, —C(=S)SCH$_2$—, —S(CH$_2$)S—, —CH$_2$CH$_2$NR$^{21}$—, —CH$_2$CH=N—, —CH=CH—NR$^{21}$—, —OCH=N— and —SCH=N—, thus forming, together with the atoms to which they are bound, a 5- or 6-membered ring, where the hydrogen atoms of the above groups may be replaced by one or more substituents selected from the group consisting of halogen, methyl, halomethyl, hydroxyl, methoxy and halomethoxy or one or more CH$_2$ groups of the above groups may be replaced by a C=O group;

$R^{11}$, $R^{12}$ are, independently of each other and independently of each occurrence, selected from the group consisting of hydrogen, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy, $C_1$-$C_6$-haloalkoxy, —C(=O)R$^{19}$, —C(=O)OR$^{20}$, —C(=NR$^{21}$)R$^{22}$, —C(=O)N(R$^{21}$)R$^{22}$, —C(=S)N(R$^{21}$)R$^{22}$, phenyl which may be substituted by 1, 2, 3, 4, or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, which may be substituted by one or more radicals $R^{10}$;

$R^{13}$, $R^{14}$ are, independently of each other and independently of each occurrence, selected from the group consisting of $C_1$-$C_4$-alkyl, $C_3$-$C_6$-cycloalkyl, $C_1$-$C_4$-alkoxy-$C_1$-$C_4$-alkyl, phenyl and benzyl;

$R^{15}$, $R^{16}$ are, independently of each other and independently of each occurrence, selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, phenyl which may be substituted by 1, 2, 3, 4, or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, which may be substituted by one or more radicals $R^{10}$;

each $R^{17}$ is independently selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, phenyl and benzyl;

each $R^{18}$ is independently defined like $R^3$;

each $R^{19}$ is independently selected from the group consisting of cyano, azido, nitro, —SCN, SF$_5$, $C_3$-$C_8$-cycloalkyl, $C_3$-$C_8$-halocycloalkyl, —Si(R$^{14}$)$_2$R$^{13}$, —OR$^{20}$, —OSO$_2$R$^{20}$, —SR$^{20}$, —S(O)$_m$R$^{20}$, —S(O)$_n$N(R$^{21}$)R$^{22}$, —N(R$^{21}$)R$^{22}$, —C(=O)N(R$^{21}$)R$^{22}$, —C(=S)N(R$^{21}$)R$^{22}$, —C(=NR$^{21}$)R$^{20}$, —C(=OO)OR$^{20}$, —C(=O)R$^{20}$, phenyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy;

and, in case $R^{19}$ is bound to a cycloalkyl group, $R^{19}$ may additionally be selected from the group consisting of $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl and $C_2$-$C_6$-haloalkynyl; and in groups —C(=O)$R^{19}$, $R^{19}$ may additionally be selected from the group consisting of hydrogen, halogen, $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, and $C_2$-$C_6$-haloalkynyl;

or two geminally bound radicals $R^{19}$ together form a group selected from the group consisting of =$CR^{11}R^{12}$, =S(O)$_m R^{20}$, =S(O)$_m N(R^{21})R^{22}$, =$R^{21}$, =$NOR^{20}$ and =$NNR^{21}$;

or two radicals $R^{19}$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from the group consisting of N, O, S, NO, SO and $SO_2$, as ring members;

each $R^{20}$ is independently selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si($R^{14}$)$_2 R^{13}$, $C_1$-$C_6$-alkylaminosulfonyl, amino, $C_1$-$C_6$-alkylamino, di-($C_1$-$C_6$-alkyl)-amino, $C_1$-$C_6$-alkylcarbonyl, $C_1$-$C_6$-haloalkylcarbonyl, aminocarbonyl, $C_1$-$C_6$-alkylaminocarbonyl, di-($C_1$-$C_6$-alkyl)aminocarbonyl, $C_1$-$C_6$-alkoxycarbonyl, $C_1$-$C_6$-haloalkoxycarbonyl, phenyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy;

with the proviso that $R^{20}$ is not $C_1$-$C_6$-alkoxy or $C_1$-$C_6$-haloalkoxy if it is bound to an oxygen atom;

$R^{21}$ and $R^{22}$ are independently of each other and independently of each occurence selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_3$-$C_8$-cycloalkyl-$C_1$-$C_4$-alkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy;

or $R^{21}$ and $R^{22}$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from the group consisting of N, O, S, NO, SO and $SO_2$, as ring members, where the heterocyclic ring may be substituted by one or more radicals selected from the group consisting of halogen, $C_1$-$C_6$-alkyl, $C_1$-$C_6$-haloalkyl, $C_1$-$C_6$-alkoxy and $C_1$-$C_6$-haloalkoxy;

each m is independently 1 or 2;
each n is independently 0, 1 or 2;
p is 0, 1, 2, 3 or 4; and
q is 0, 1, 2, 3, 4 or 5;
or an stereoisomer or an agriculturally or veterinarily acceptable salt thereof.

2. The compound of claim 1, wherein $B^1$ is CH.

3. The compound of claim 1, wherein $A^1$ is CH.

4. The compound of claim 1, wherein X is selected from the group consisting of $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_3$-$C_6$-cycloalkyl and $C_3$-$C_6$-halocycloalkyl.

5. The compound of claim 4, wherein X is selected from the group consisting of $CF_3$, $CHF_2$ and $CF_2Cl$.

6. The compound of claim 1, wherein R' is selected from the group consisting of hydrogen; cyano; $C_1$-$C_{10}$-alkyl which may be partially or fully halogenated and/or may be substituted by one or more radicals $R^6$; $C_1$-$C_{10}$-alkoxy; $C_1$-$C_{10}$-haloalkoxy; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —C(=O)$R^6$; —C(=O)$OR^7$; —C(=O)$N(R^8)R^9$; —C(=S)$R^6$; —C(=S)$OR^7$; —C(=S)$N(R^8)R^9$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$.

7. The compound of claim 6, wherein $R^1$ is selected from the group consisting of hydrogen; cyano; $C_1$-$C_{10}$-alkyl which may be partially or fully halogenated and/or may be substituted by one or more radicals $R^6$; $C_1$-$C_{10}$-alkoxy; $C_1$-$C_{10}$-haloalkoxy; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$;

$C_2$-$C_{10}$-alkynyl which may be partially or fully halogenated and/or may be substituted by one or more radicals $R^6$; —C(═O)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$.

8. The compound of claim 7, wherein $R^1$ is selected from the group consisting of hydrogen; cyano; $C_1$-$C_6$-alkyl; $C_1$-$C_4$-haloalkyl; $C_1$-$C_4$-alkoxy; $C_1$-$C_4$-haloalkoxy; and —C(═O)$R^6$.

9. The compound of claim 1, wherein $R^3$ is selected from the group consisting of hydrogen; cyano; $C_1$-$C_{10}$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —N($R^8$)$R^9$; —Si($R^{14}$)$_2R^{13}$; —$OR^7$; —$SR^7$; —S(O)$_mR^7$; —S(O)$_m$N(R)$R^9$; —C(═O)$R^6$; —C(═O)$OR^7$; —C(═O)N($R^8$)$R^9$; —C(═S)$R^6$; —C(═S)$OR^7$; —C(═S)N($R^8$)$R^9$; —C(═N$R^8$)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

or $R^2$ and $R^3$ together form a group ═$CR^{11}$, $R^{12}$; ═S(O)$_m$ $R^7$; ═S(O)$_m$N($R^8$)$R^9$; ═$NR^8$; or ═$NOR^7$;

or $R^2$ and $R^3$ together form a $C_2$-$C_7$ alkylene chain, thus forming, together with the nitrogen atom to which they are bound, a 3-, 4-, 5-, 6-, 7- or 8-membered ring, where the alkylene chain may be interrupted by 1 or 2 O, S and/or $NR^{18}$ and/or 1 or 2 of the $CH_2$ groups of the alkylene chain may be replaced by a group C═O, C═S and/or C═$NR^{18}$; and/or the alkylene chain may be substituted by one or more radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals R'.

10. The compounds according claim 9, wherein $R^3$ is selected from the group consisting of hydrogen; $C_1$-$C_{10}$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —C(═O)$R^6$; —C(═O)$OR^7$; —C(═O)N($R^8$)$R^9$; —C(═S)$R^6$; —C(═S)$OR^7$; —C(═S)N($R^8$)$R^9$; —C(═N$R^8$)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$.

11. The compounds according claim 10, wherein $R^3$ is selected from the group consisting of hydrogen; $C_1$-$C_6$-alkyl and $C_1$-$C_4$-haloalkyl.

12. The compound of claim 1, wherein each $R^4$ is independently selected from the group consisting of halogen; cyano; nitro; —SCN; $SF_5$; $C_1$-$C_6$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_6$-alkenyl which may be partially or fully halogenated and/or may be substituted by one or more radicals $R^6$; $C_2$-$C_6$-alkynyl which may be partially or fully halogenated and/or may be substituted by one or more radicals $R^6$; —Si($R^{14}$)$_2R^{13}$; —$OR^7$; —OS(O)$_nR^7$; —$SR^7$; —S(O)$_mR^7$; —S(O)$_n$N($R^8$)$R^9$; —N($R^8$)$R^9$; —N($R^8$)C(═O)$R^6$; C(═O)$R^6$; —C(═O)$OR^7$; —C(═$NR^8$)H; —C(═$NR^8$)$R^6$; —C(═O)N($R^8$)$R^9$; C(═S)N($R^8$)$R^9$; phenyl which may be substituted by 1, 2, 3, 4 or 5 radicals Ro$^1$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

or two radicals $R^4$ bound on adjacent carbon atoms may be together a group selected from the group consisting of —$CH_2CH_2CH_2CH_2$—, —CH═CH—CH═CH—, —N═CH—CH═CH—, —CH═N—CH═CH—, —N═CH—N═CH—, —$OCH_2CH_2CH_2$—, —OCH═$CHCH_2$—, —$CH_2OCH_2CH_2$—, —$OCH_2CH_2$O—, —$OCH_2OCH_2$—, —$CH_2CH_2CH_2$—, —CH═$CHCH_2$—, —$CH_2CH_2$O—, —CH═CHO—, —$CH_2OCH_2$—, —$CH_2$C(═O)O—, —C(═O)$OCH_2$—, —O($CH_2$)O—, —$SCH_2CH_2CH_2$—, —SCH═$CHCH_2$—, —$CH_2SCH_2CH_2$—, —$SCH_2CH_2$S—, —$SCH_2SCH_2$—, —$CH_2CH_2$S—, —CH═CHS—, —$CH_2SCH_2$—, —$CH_2$C(═S)S—, —C(═S)$SCH_2$—, —S($CH_2$)S—, —$CH_2CH_2NR^8$—, —$CH_2$CH═N—, —CH═CH—$NR^8$—, —OCH═N—, and —SCH═N—, thus forming, together with the carbon atoms to which they are bound, a 5- or 6-membered ring, where the hydrogen atoms of the above groups may be replaced by one or more substituents selected from the group consisting of halogen, methyl, halomethyl, hydroxyl, methoxy and halomethoxy or one or more $CH_2$ groups of the above groups may be replaced by a C═O group.

13. The compound of claim 12, wherein each $R^4$ is independently selected from the group consisting of halogen; cyano; nitro; —SCN; $C_1$-$C_6$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; —$OR^7$; —OS(O)$_nR^7$; —$SR^7$; —S(O)$_mR^7$; —S(O)$_n$N($R^8$)$R^9$; —N($R^8$)$R^9$; C(═O)$R^6$; —C(═O)$OR^7$; —C(═$NR^8$)$R^6$; —C(═O)N($R^8$)$R^9$; and —C(═S)N($R^8$)$R^9$.

14. The compounds according claim 13, wherein $R^4$ is selected from the group consisting of halogen, cyano, $C_1$-$C_4$-alkyl and $C_1$-$C_4$-haloalkyl.

15. The compound of claim 1, wherein each $R^5$ is independently selected from the group consisting of halogen, cyano, nitro, —SCN, $SF_5$, $C_1$-$C_6$-alkyl, $C_1$-$C_6$-alkyl which may be partially or fully halogenated and/or may be substituted by one or more radicals $R^6$, $C_3$-$C_8$-cycloalkyl which may be partially or fully halogenated and/or may be substituted by one or more radicals $R^6$, $C_2$-$C_6$-alkenyl which may be partially or fully halogenated and/or may be substituted by one or more radicals $R^6$, $C_2$-$C_6$-alkynyl which may be partially or fully halogenated and/or may be substituted by one or more radicals $R^6$, $Si(R^{14})_2R^{13}$, $OR^7$, $OS(O)_nR^7$, $S(O)_mR^7$, $NR^8R^9$, $N(R^8)C(=O)R^6$, $C(=O)R^6$, $C(=O)OR^7$, $C(=NR^8)R^6$, $C(=S)NR^6$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$.

16. The compounds according claim 15, wherein $R^5$ is selected from the group consisting of halogen and $C_1$-$C_4$-haloalkyl.

17. The compound of claim 1, wherein $R^2$ is selected from the group consisting of hydrogen; $C_1$-$C_{10}$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —$C(=O)R^6$; —$C(=O)OR^7$; —$C(=O)N(R^s)R^9$; —$C(=S)R^6$; —$C(=S)OR^7$, —$C(=S)N(R^8)R^9$; —$C(=NR^8)R^6$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$.

18. The compounds according claim 17, wherein $R^2$ is selected from the group consisting of $C_1$-$C_4$-alkyl; $C_1$-$C_4$-haloalkyl; a methyl group substituted by a radical $R^{6a}$; —$C(=O)R^{6c}$; —$C(=O)N(R^8)R^9$; —$C(=O)OR^7$; —$C(=S)R^{6c}$; —$C(=S)N(R^8)R^9$; —$C(=S)OR^7$; and —$C(=NR^8)R^{6d}$, where $R^{6a}$ is selected from the group consisting of CN, phenyl which may carry 1, 2 or 3 substituents $R^{10}$, —$C(=O)R^{6b}$; —$C(=O)N(R^8)R^9$ and —$C(=OO)OR^7$;

$R^{6b}$ and $R^{6c}$ are independently selected from the group consisting of $C_1$-$C_4$-alkyl, $C_1$-$C_4$-haloalkyl, phenyl, benzyl and a 5- or 6-membered saturated, partially unsaturated or aromatic heterocyclic ring containing 1, 2 or 3 heteroatoms or heteroatom groups selected from the group consisting of N, O, S, NO, SO and $SO_2$, as ring members, where the phenyl or heterocyclyl rings in the three last-mentioned radicals may carry 1, 2 or 3 substituents selected from the group consisting of halogen, CN, $C_1$-$C_4$-alkyl, $C_1$-$C_4$-haloalkyl, $C_1$-$C_4$-alkoxy and $C_1$-$C_4$-haloalkoxy;

$R^{6d}$ is selected from $N(R^8)R^9$;

$R^7$ is selected from the group consisting of hydrogen, $C_1$-$C_4$-alkyl, $C_1$-$C_4$-haloalkyl, phenyl, benzyl and a 5- or 6-membered saturated, partially unsaturated or aromatic heterocyclic ring containing 1, 2 or 3 heteroatoms or heteroatom groups selected from the group consisting of N, O, S, NO, SO and $SO_2$, as ring members, where the phenyl or heterocyclyl rings in the three last-mentioned radicals may carry 1, 2 or 3 substituents selected from the group consisting of halogen, CN, $C_1$-$C_4$-alkyl, $C_1$-$C_4$-haloalkyl, $C_1$-$C_4$-alkoxy and $C_1$-$C_4$-haloalkoxy;

each $R^8$ is independently selected from the group consisting of hydrogen, cyano, $C_1$-$C_6$-alkyl which may be partially or fully halogenated and/or may be substituted by one or more radicals $R^{19}$, $C_2$-$C_4$-alkenyl which may be partially or fully halogenated and/or may be substituted by one or more radicals $R^{19}$, $C_3$-$C_6$-cycloalkyl, $C_3$-$C_6$-halocycloalkyl, $C_3$-$C_6$-cycloalkyl-$C_1$-$C_4$-alkyl, $C_3$-$C_6$-halocycloalkyl-$C_1$-$C_4$-alkyl, —$S(O)_mR^{20}$, —$S(O)_nN(R^{21})R^{22}$, phenyl, benzyl and a 5- or 6-membered saturated, partially unsaturated or aromatic heterocyclic ring containing 1, 2 or 3 heteroatoms or heteroatom groups selected from the group consisting of N, O, S, NO, SO and $SO_2$, as ring members, where the phenyl or heterocyclyl rings in the three last-mentioned radicals may carry 1, 2 or 3 substituents selected from the group consisting of halogen, CN, $C_1$-$C_4$-alkyl, $C_1$-$C_4$-haloalkyl, $C_1$-$C_4$-alkoxy and $C_1$-$C_4$-haloalkoxy;

each $R^9$ is independently selected from the group consisting of hydrogen, cyano, $C_1$-$C_6$-alkyl which may be partially or fully halogenated and/or may be substituted by one or more radicals $R^{19}$, $C_2$-$C_4$-alkenyl which may be partially or fully halogenated and/or may be substituted by one or more radicals $R^{19}$, $C_3$-$C_6$-cycloalkyl, $C_3$-$C_6$-halocycloalkyl, $C_3$-$C_6$-cycloalkyl-$C_1$-$C_4$-alkyl, $C_3$-$C_6$-halocycloalkyl-$C_1$-$C_4$-alkyl, —$S(O)_mR^{20}$, —$S(O)_nN(R^{21})R^{22}$, phenyl, benzyl and a 5- or 6-membered saturated, partially unsaturated or aromatic heterocyclic ring containing 1, 2 or 3 heteroatoms or heteroatom groups selected from the group consisting of N, O, S, NO, SO and $SO_2$, as ring members, where the phenyl or heterocyclyl rings in the three last-mentioned radicals may carry 1, 2 or 3 substituents selected from the group consisting of halogen, CN, $C_1$-$C_4$-alkyl, $C_1$-$C_4$-haloalkyl, $C_1$-$C_4$-alkoxy and $C_1$-$C_4$-haloalkoxy; and $R^{10}$ is selected from the group consisting of halogen, CN, $C_1$-$C_4$-alkyl, $C_1$-$C_4$-haloalkyl, $C_1$-$C_4$-alkoxy and $C_1$-$C_4$-haloalkoxy;

where $R^{19}$ is as defined in claim 1; or $R^8$ and $R^9$ together form a group $=CR^{11}R^{12}$; or $R^8$ and $R^9$, together with the nitrogen atom to which they are bound, form a 3-, 4-, 5-, 6- or 7-membered saturated, partially unsaturated or aromatic heterocyclic ring which may additionally containing 1 or 2 further heteroatoms or heteroatom groups selected from the group consisting of N, O, S, NO, SO and $SO_2$, as ring members, where the heterocyclic ring may be substituted by one or more radicals $R^{10}$.

19. The compounds according claim 18, wherein $R^2$ is selected from the group consisting of —$C(=O)N(R^8)R^9$ and —$C(=S)N(R^8)R^9$;

wherein $R^8$ is selected from the group consisting of hydrogen and $C_1$-$C_6$-alkyl which may be partially or fully halogenated and/or may be substituted by one or more radicals $R^{19}$;

$R^9$ is selected from the group consisting of hydrogen, $C_1$-$C_6$-alkyl which may be partially or fully halogenated and/or may be substituted by one or more radicals $R^{19}$, $C_3$-$C_6$-cycloalkyl, $C_3$-$C_6$-halocycloalkyl, $C_3$-$C_6$-cycloalkyl-$C_1$-$C_4$-alkyl and $C_3$-$C_6$-halocycloalkyl-$C_1$-$C_4$-alkyl.

20. The compounds according claim 19, where $R^8$ is hydrogen; and $R^9$ is selected from the group consisting of hydrogen, $C_1$-$C_6$-alkyl; $C_1$-$C_6$-haloalkyl, $C_3$-$C_6$-cycloalkyl, $C_3$-$C_6$-halocycloalkyl, $C_3$-$C_6$-cycloalkyl-$C_1$-$C_4$-alkyl and $C_3$-$C_6$-halocycloalkyl-$C_1$-$C_4$-alkyl.

21. The compound of claim 1, wherein Y is O, $NR^3$ or a chemical bond.
22. The compound of claim 1, wherein Y is $NR^3$.
23. The compound of claim 1, wherein p is 0, 1 or 2.
24. The compound of claim 1, wherein q is 0, 1, 2 or 3.
25. The compound of claim 1, of formula I-1

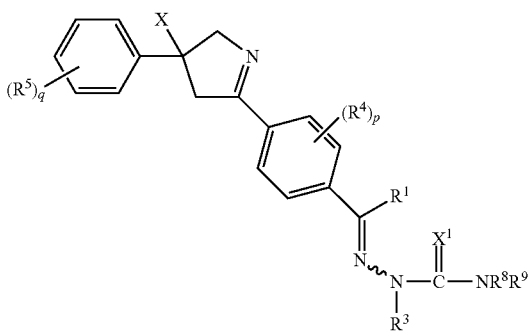

(I-1)

where

X is selected from the group consisting of $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl and $C_3$-$C_6$-halocycloalkyl;

$R^1$ is selected from the group consisting of hydrogen; cyano; $C_1$-$C_{10}$-alkyl which may be partially or fully halogenated and/or may be substituted by one or more radicals $R^6$; $C_1$-$C_{10}$-alkoxy; $C_1$-$C_{10}$-haloalkoxy; $C_1$-$C_{10}$-alkylthio; $C_1$-$C_{10}$-haloalkylthio; $C_1$-$C_{10}$-alkylsulfinyl; $C_1$-$C_{10}$-haloalkylsulfinyl; $C_1$-$C_{10}$-alkylsulfonyl; $C_1$-$C_{10}$-haloalkylsulfonyl; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —C(=O)$R^6$; —C(=O)$OR^7$; —C(=O)N($R^8$)$R^9$; —C(=S)$R^6$; —C(=S)$OR^7$; —C(=S)N($R^8$)$R^9$; phenyl which may be substituted by 1, 2, 3, 4 or 5 radicals $R^{10}$; and a C-bound 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

$R^3$ is selected from the group consisting of hydrogen; cyano; $C_1$-$C_{10}$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —N($R^8$)$R^9$; —Si($R^{14}$)$_2R^{13}$; —$OR^7$; —$SR^7$; —S(O)$_mR^7$; —S(O)$_nN(R^8)R^9$; —C(=O)$R^6$; —C(=O)$OR^7$; —C(=O)N($R^8$)$R^9$; —C(=S)$R^6$; —C(=S)$OR^7$; —C(=S)N($R^8$)$R^9$; —C(=N$R^8$)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

each $R^4$ is independently selected from the group consisting of halogen; cyano; azido; nitro; —SCN; $SF_5$; $C_1$-$C_6$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_6$-alkenyl which may be partially or fully halogenated and/or may be substituted by one or more radicals $R^6$; $C_2$-$C_6$-alkynyl which may be partially or fully halogenated and/or may be substituted by one or more radicals $R^6$; —Si($R^{14}$)$_2R^{13}$; —$OR^7$; —OS(O)$_nR^7$; —$SR^7$; —S(O)$_mR^7$; —S(O)$_nN(R^8)R^9$; —N($R^8$)$R^9$; —N($R^8$)C(=O)$R^6$; C(=O)$R^6$; —C(=O)$OR^7$; —C(=N$R^8$)H; —C(=N$R^8$)$R^6$; —C(=O)N($R^8$)$R^9$; C(=S)N($R^5$)$R^9$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

or two radicals $R^4$ bound on adjacent carbon atoms may be together a group selected from the group consisting of —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C(=O)$O—, —C(=O)$OCH_2$—, —O($CH_2$)O—, —$SCH_2CH_2CH_2$—, —SCH=$CHCH_2$—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C(=S)S$—, —C(=S)$SCH_2$—, —S($CH_2$)S—, —$CH_2CH_2NR^8$—, —$CH_2CH=N$—, —CH=CH—$NR^8$—, —OCH=N— and —SCH=N—, thus forming, together with the carbon atoms to which they are bound, a 5- or 6-membered ring, where the hydrogen atoms of the above groups may be replaced by one or more substituents selected from the group consisting of halogen, methyl, halomethyl, hydroxyl, methoxy and halomethoxy or one or more $CH_2$ groups of the above groups may be replaced by a C=O group;

each $R^5$ is independently selected from the group consisting of halogen, cyano, azido, nitro, —SCN, $SF_5$, $C_1$-$C_6$-alkyl which may be partially or fully halogenated and/or may be substituted by one or more radicals $R^6$, $C_3$-$C_8$-cycloalkyl which may be partially or fully halogenated and/or may be substituted by one or more radicals $R^6$, $C_2$-$C_6$-alkenyl which may be partially or fully halogenated and/or may be substituted by one or more radicals $R^6$, $C_2$-$C_6$-alkynyl which may be partially or fully halogenated and/or may be substituted by one or more radicals $R^6$, —Si($R^{14}$)$_2R^{13}$, —$OR^7$, —OS(O)$_nR^7$, —$SR^7$, —S(O)$_mR^7$, —S(O)$_nN(R^8)R^9$, —N($R^8$)$R^9$, N($R^8$)C(=O)$R^6$, —C(=O)$R^6$, —C(=O)$OR^7$, —C(=S)$R^6$, —C(=S)OR$^7$, —C(=NR$^8$)R$^6$, —C(=O)N(R$^8$)R$^9$, —C(=S)N(R$^8$)R$^9$, phenyl which may be substituted by 1, 2, 3, 4 or 5 radicals R$^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals R$^{10}$;

each R$^8$ is independently selected from the group consisting of hydrogen, cyano, C$_1$-C$_6$-alkyl which may be partially or fully halogenated and/or may be substituted by one or more radicals R$^{19}$, C$_1$-C$_6$-alkoxy, C$_1$-C$_6$-haloalkoxy, C$_1$-C$_6$-alkylthio, C$_1$-C$_6$-haloalkylthio, where the alkyl moiety in the four last-mentioned radicals may be substituted by one or more radicals R$^{19}$, C$_3$-C$_8$-cycloalkyl which may be partially or fully halogenated and/or may be substituted by one or more radicals R$^{19}$, C$_3$-C$_8$-cycloalkyl-C$_1$-C$_4$-alkyl where the cycloalkyl moiety may be partially or fully halogenated and/or may be substituted by one or more radicals R$^{19}$, C$_2$-C$_6$-alkenyl which may be partially or fully halogenated and/or may be substituted by one or more radicals R$^{19}$, C$_2$-C$_6$-alkynyl which may be partially or fully halogenated and/or may be substituted by one or more radicals R$^{19}$, —S(O)$_m$R$^{20}$, —S(O)$_n$N(R$^{21}$)R$^{22}$, phenyl which may be substituted by 1, 2, 3, 4 or 5 radicals R$^{10}$, benzyl which may be substituted by 1, 2, 3, 4 or 5 radicals R$^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals R$^{10}$;

each R$^9$ is independently selected from the group consisting of hydrogen, cyano, C$_1$-C$_6$-alkyl which may be partially or fully halogenated and/or may be substituted by one or more radicals R$^{19}$, C$_1$-C$_6$-alkoxy, C$_1$-C$_6$-haloalkoxy, C$_1$-C$_6$-alkylthio, C$_1$-C$_6$-haloalkylthio, where the alkyl moiety in the four last-mentioned radicals may be substituted by one or more radicals R$^{19}$, C$_3$-C$_8$-cycloalkyl which may be partially or fully halogenated and/or may be substituted by one or more radicals R$^{19}$, C$_3$-C$_8$-cycloalkyl-C$_1$-C$_4$-alkyl where the cycloalkyl moiety may be partially or fully halogenated and/or may be substituted by one or more radicals R$^{19}$, C$_2$-C$_6$-alkenyl which may be partially or fully halogenated and/or may be substituted by one or more radicals R$^{19}$, C$_2$-C$_6$-alkynyl which may be partially or fully halogenated and/or may be substituted by one or more radicals R$^{19}$, —S(O)$_m$R$^{20}$, —S(O)$_n$N(R$^{21}$)R$^{22}$, phenyl which may be substituted by 1, 2, 3, 4 or 5 radicals R$^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals R$^{10}$;

or R$^8$ and R$^9$ together form a group =CR$^{11}$R$^{12}$;

or R$^8$ and R$^9$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from the group consisting of N, O, S, NO, SO and SO$_2$, as ring members, where the heterocyclic ring may be substituted by one or more radicals R$^{10}$;

each R$^{10}$ is independently selected from the group consisting of halogen, cyano, azido, nitro, —SCN, SF$_5$, C$_1$-C$_{10}$-alkyl which may be partially or fully halogenated and/or may be substituted by one or more radicals R$^{19}$, C$_3$-C$_8$-cycloalkyl which may be partially or fully halogenated and/or may be substituted by one or more radicals R$^{19}$, C$_2$-C$_{10}$-alkenyl which may be partially or fully halogenated and/or may be substituted by one or more radicals R$^{19}$, C$_2$-C$_{10}$-alkynyl which may be partially or fully halogenated and/or may be substituted by one or more radicals R$^{19}$, —Si(R$^{14}$)$_2$R$^{13}$, —OR$^{20}$, —OS(O)$_n$R$^{20}$, —SR$^{20}$, —S(O)$_m$R$^{20}$, —S(O)$_n$N(R$^{21}$)R$^{22}$, —N(R$^{21}$)R$^{22}$, C(=O)R$^{19}$, —C(=O)OR$^{20}$, —C(=NR$^{21}$)R$^{22}$, —C(=O)N(R$^{21}$)R$^{22}$, —C(=S)N(R$^{21}$)R$^{22}$, phenyl which may be substituted by 1, 2, 3, 4 or 5 radicals independently selected from the group consisting of halogen, cyano, nitro, C$_1$-C$_6$-alkyl, C$_1$-C$_6$-haloalkyl, C$_1$-C$_6$-alkoxy and C$_1$-C$_6$-haloalkoxy; and a 3-, 4-, 5-, 6- or 7-membered saturated or unsaturated heterocyclic ring containing 1, 2 or 3 heteroatoms or heteroatom groups selected from the group consisting of N, O, S, NO, SO and SO$_2$, as ring members, which may be substituted by one or more radicals independently selected from the group consisting of halogen, cyano, nitro, C$_1$-C$_6$-alkyl, C$_1$-C$_6$-haloalkyl, C$_1$-C$_6$-alkoxy and C$_1$-C$_6$-haloalkoxy;

or two radicals R$^{10}$ bound on adjacent atoms together form a group selected from the group consisting of —CH$_2$CH$_2$CH$_2$CH$_2$—, —CH=CH—CH=CH—, —N=CH—CH=CH—, —CH=N—CH=CH—, —N=CH—N=CH—, —OCH$_2$CH$_2$CH$_2$—, —OCH=CHCH$_2$—, —CH$_2$OCH$_2$CH$_2$—, —OCH$_2$CH$_2$O—, —OCH$_2$OCH$_2$—, —CH$_2$CH$_2$CH$_2$—, —CH=CHCH$_2$—, —CH$_2$CH$_2$O—, —CH=CHO—, —CH$_2$OCH$_2$—, —CH$_2$C(=O)O—, —C(=O)OCH$_2$—, —O(CH$_2$)O—, —SCH$_2$CH$_2$CH$_2$—, —SCH=CHCH$_2$—, —CH$_2$SCH$_2$CH$_2$—, —SCH$_2$CH$_2$S—, —SCH$_2$SCH$_2$—, —CH$_2$CH$_2$S—, —CH=CHS—, —CH$_2$SCH$_2$—, —CH$_2$C(=S)S—, —C(=S)SCH$_2$—, —S(CH$_2$)S—, —CH$_2$CH$_2$NR$^{21}$—, —CH$_2$CH=N—, —CH=CH—NR$^{21}$—, —OCH=N— and —SCH=N—, thus forming, together with the atoms to which they are bound, a 5- or 6-membered ring, where the hydrogen atoms of the above groups may be replaced by one or more substituents selected from the group consisting of halogen, methyl, halomethyl, hydroxyl, methoxy and halomethoxy or one or more CH$_2$ groups of the above groups may be replaced by a C=O group;

R$^{11}$, R$^{12}$ are, independently of each other and independently of each occurrence, selected from the group consisting of hydrogen, halogen, C$_1$-C$_6$-alkyl, C$_1$-C$_6$-haloalkyl, C$_2$-C$_6$-alkenyl, C$_2$-C$_6$-haloalkenyl, C$_2$-C$_6$-alkynyl, C$_2$-C$_6$-haloalkynyl, C$_3$-C$_8$-cycloalkyl, C$_3$-C$_8$-halocycloalkyl, C$_1$-C$_6$-alkoxy-C$_1$-C$_6$-alkyl, C$_1$-C$_6$-haloalkoxy-C$_1$-C$_6$-alkyl, C$_1$-C$_6$-alkoxy, C$_1$-C$_6$-haloalkoxy, —C(=O)R$^{19}$, —C(=O)OR$^{20}$, —C(=NR$^{21}$)R$^{22}$, —C(=O)N(R$^{21}$)R$^{22}$, —C(=S)N(R$^{21}$)R$^{22}$, phenyl which may be substituted by 1, 2, 3, 4, or 5 radicals R$^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, which may be substituted by one or more radicals R$^{10}$;

$R^{13}$, $R^{14}$ are, independently of each other and independently of each occurrence, selected from the group consisting of $C_1$-$C_4$-alkyl, $C_3$-$C_6$-cycloalkyl, $C_1$-$C_4$-alkoxy-$C_1$-$C_4$-alkyl, phenyl and benzyl;

$R^{15}$, $R^{16}$ are, independently of each other and independently of each occurrence, selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, phenyl which may be substituted by 1, 2, 3, 4, or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, which may be substituted by one or more radicals $R^{10}$;

each $R^{17}$ is independently selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, phenyl and benzyl;

each $R^{18}$ is independently defined like $R^3$;

each $R^{19}$ is independently selected from the group consisting of cyano, azido, nitro, —SCN, $SF_5$, $C_3$-$C_8$-cycloalkyl, $C_3$-$C_8$-halocycloalkyl, —Si$(R^{14})_2R^{13}$, —$OR^{20}$, —$OSO_2R^{20}$, —$SR^{20}$, —$S(O)_mR^{20}$, —$S(O)_nN(R^{21})R^{22}$, —$N(R^{21})R^{22}$, —$C(=O)N(R^{21})R^{22}$, —$C(=S)N(R^{21})R^{22}$, —$C(=NR^{21})R^{20}$, —$C(=O)OR^{20}$, —$C(=O)R^{20}$, phenyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy;

and, in case $R^{19}$ is bound to a cycloalkyl group, $R^{19}$ may additionally be selected from the group consisting of $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl and $C_2$-$C_6$-haloalkynyl; and in groups —$C(=O)R^{19}$, $R^{19}$ may additionally be selected from the group consisting of hydrogen, halogen, $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, and $C_2$-$C_6$-haloalkynyl;

or two geminally bound radicals $R^{19}$ together form a group selected from the group consisting of =$CR^{11}R^{12}$, =$S(O)_mR^{20}$, =$S(O)_mN(R^{21})R^{22}$, =$NR^{21}$, =$NOR^{20}$ and =$NNR^{21}$;

or two radicals $R^{19}$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from the group consisting of N, O, S, NO, SO and $SO_2$, as ring members;

each $R^{20}$ is independently selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si$(R^{14})_2R^{13}$, $C_1$-$C_6$-alkylaminosulfonyl, amino, $C_1$-$C_6$-alkylamino, di-($C_1$-$C_6$-alkyl)-amino, $C_1$-$C_6$-alkylcarbonyl, $C_1$-$C_6$-haloalkylcarbonyl, aminocarbonyl, $C_1$-$C_6$-alkylaminocarbonyl, di-($C_1$-$C_6$-alkyl)aminocarbonyl, $C_1$-$C_6$-alkoxycarbonyl, $C_1$-$C_6$-haloalkoxycarbonyl, phenyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy;

with the proviso that $R^{20}$ is not $C_1$-$C_6$-alkoxy or $C_1$-$C_6$-haloalkoxy if it is bound to an oxygen atom;

$R^{21}$ and $R^{22}$ are independently of each other and independently of each occurrence selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_3$-$C_8$-cycloalkyl-$C_1$-$C_4$-alkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals independently selected from the group consisting of halogen, cyano, nitro, $C_1$-$C_6$-alkyl, $C_1$-$C_6$-haloalkyl, $C_1$-$C_6$-alkoxy and $C_1$-$C_6$-haloalkoxy;

or $R^{21}$ and $R^{22}$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from the group consisting of N, O, S, NO, SO and $SO_2$, as ring members, where the heterocyclic ring may be substituted by one or more radicals selected from the group consisting of halogen, $C_1$-$C_6$-alkyl, $C_1$-$C_6$-haloalkyl, $C_1$-$C_6$-alkoxy and $C_1$-$C_6$-haloalkoxy;

each m is independently 1 or 2;
each n is independently 0, 1 or 2;
$X^1$ is O or S;
p is 0, 1 or 2; and
q is 0, 1, 2 or 3.

26. The compound of claim 1, of formula I-A

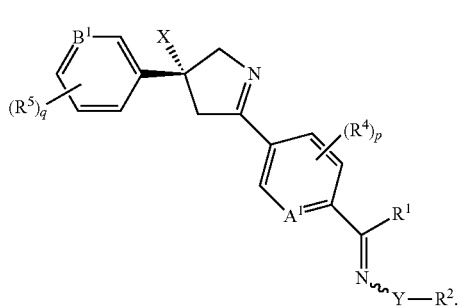

(I-A)

27. A compound of formula (II)

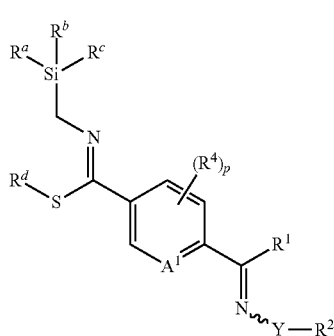

(II)

wherein $R^a$, $R^b$ and $R^c$, independently of each other, are selected from $C_1$-$C_{12}$-alkyl which may be partially or fully halogenated and/or may be substituted by one or more radicals $R^6$, and phenyl which may be substituted by 1, 2, 3, 4 or 5 radicals $R^{10}$; and $R^d$ is selected from the group consisting of hydrogen, $C_1$-$C_{12}$-alkyl which may be partially or fully halogenated and/or may be substituted by one or more radicals $R^6$, $C_2$-$C_{12}$-alkenyl which may be partially or fully halogenated and/or may be substituted by one or more radicals $R^6$, $C_2$-$C_{12}$-alkynyl which may be partially or fully halogenated and/or may be substituted by one or more radicals $R^6$, and benzyl where the phenyl moiety may be substituted by 1, 2, 3, 4 or 5 radicals $R^{10}$;

$A^1$ is N or CH;

Y is O, N—$R^3$, S(O)$_n$, or a chemical bond;

$R^1$ is selected from the group consisting of hydrogen; cyano; $C_1$-$C_{10}$-alkyl which may be partially or fully halogenated and/or may be substituted by one or more radicals $R^6$; $C_1$-$C_{10}$-alkoxy; $C_1$-$C_{10}$-haloalkoxy; $C_1$-$C_{10}$-alkylthio; $C_1$-$C_{10}$-haloalkylthio; $C_1$-$C_{10}$-alkylsulfinyl; $C_1$-$C_{10}$-haloalkylsulfinyl; $C_1$-$C_{10}$-alkylsulfonyl; $C_1$-$C_{10}$-haloalkylsulfonyl; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; phenyl which may be substituted by 1, 2, 3, 4 or 5 radicals $R^{10}$;

and a C-bound 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals $R^{10}$;

$R^2$ is selected from the group consisting of hydrogen; cyano; $C_1$-$C_{10}$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —N($R^8$)$R^9$; —N($R^8$)C(=O)$R^6$; —Si($R^{14}$)$_2$$R^{13}$; —O$R^7$; —S$R^7$; —S(O)$_m$$R^7$; —S(O)$_n$N($R^8$)$R^9$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; —C(=N$R^8$)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals $R^{10}$;

with the proviso that $R^2$ is not —O$R^7$ if Y is O;

each $R^4$ is independently selected from the group consisting of halogen; cyano; azido; nitro; —SCN; SF$_5$; $C_1$-$C_6$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_6$-alkenyl which may be partially or fully halogenated and/or may be substituted by one or more radicals $R^6$; $C_2$-$C_6$-alkynyl which may be partially or fully halogenated and/or may be substituted by one or more radicals $R^6$; —Si($R^{14}$)$_2$$R^{13}$; —O$R^7$; —OS(O)$_n$$R^7$; —S$R^7$; —S(O)$_m$$R^7$; —S(O)$_n$N($R^8$)$R^9$; —N($R^8$)$R^9$; —N(R)C(=O)$R^6$; C(=O)$R^6$; —C(=O)O$R^7$; —C(=N$R^8$)H; —C(=N$R^8$)$R^6$; —C(=O)N($R^8$)$R^9$; C(=S)N($R^8$)$R^9$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals $R^{10}$;

or two radicals $R^4$ bound on adjacent carbon atoms may be together a group selected from the group consisting of —CH$_2$CH$_2$CH$_2$CH$_2$—, —CH=CH—CH=CH—, —N=CH—CH=CH—, —CH=N—CH=CH—, —N=CH—N=CH—, —OCH$_2$CH$_2$CH$_2$—, —OCH=CHCH$_2$—, —CH$_2$OCH$_2$CH$_2$—, —OCH$_2$CH$_2$O—, —OCH$_2$OCH$_2$—, —CH$_2$CH$_2$CH$_2$—, —CH=CHCH$_2$—, —CH$_2$CH$_2$O—, —CH=CHO—, —CH$_2$OCH$_2$—, —CH$_2$C(=O)O—, —C(=O)OCH$_2$—, —O(CH$_2$)O—, —SCH$_2$CH$_2$CH$_2$—, —SCH=CHCH$_2$—, —CH$_2$SCH$_2$CH$_2$—, —SCH$_2$CH$_2$S—, —SCH$_2$SCH$_2$—, —CH$_2$CH$_2$S—, —CH=CHS—, —CH$_2$SCH$_2$—, —CH$_2$C(=S)S—, —C(=S)SCH$_2$—, —S(CH$_2$)S—, —CH$_2$CH$_2$NR$^8$—, —CH$_2$CH=N—, —CH=CH—NR$^8$—, —OCH=N— and —SCH=N—, thus forming, together with the carbon atoms to which they are bound, a 5- or 6-membered ring, where the hydrogen atoms of the above groups may be replaced by one or more substituents selected from the group consisting of halogen, methyl, halomethyl, hydroxyl, methoxy and halomethoxy or one or more $CH_2$ groups of the above groups may be replaced by a $C=O$ group;

p is 0, 1, 2, 3 or 4;

or a tautomer, stereoisomer or an agriculturally or veterinarily acceptable salt thereof.

28. The compounds of formula II according to claim 27, wherein $R^a$, $R^b$ and $R^c$, independently of each other, are selected from $C_1$-$C_4$-alkyl; and $R^d$ is selected from the group consisting of hydrogen, $C_1$-$C_4$-alkyl and $C_1$-$C_4$-haloalkyl.

29. An agricultural composition comprising a compound of claim 1 and at least one inert liquid and/or solid agriculturally acceptable carrier.

30. A veterinary composition comprising a compound of claim 1 and/or at least one veterinarily acceptable salt thereof, and at least one inert liquid and/or solid veterinarily acceptable carrier.

31. A method for controlling invertebrate pests which method comprises treating the pests, their food supply, their habitat or their breeding ground or a plant, plant propagation material, soil, area, material or environment in which the pests are growing or may grow, or the materials, plants, plant propagation material, soils, surfaces or spaces to be protected from invertebrate pest attack or infestation with a pesticidally effective amount of a compound of claim 1.

32. The method as claimed in claim 31, wherein plants are protected from attack or infestation by invertebrate pests.

33. The method as claimed in claim 31, for protecting plant propagation material and/or the plants which grow therefrom from attack or infestation by invertebrate pests, which method comprises treating the plant propagation material with a pesticidally effective amount of a compound of claim 1.

34. Plant propagation material treated with a composition comprising a compound of claim 1.

35. A method for treating or protecting an animal from infestation or infection by invertebrate pests which comprises bringing the animal in contact with a pesticidally effective amount of a compound of claim 1.

* * * * *